US011421032B2

(12) United States Patent
Ferrari de Andrade et al.

(10) Patent No.: US 11,421,032 B2
(45) Date of Patent: Aug. 23, 2022

(54) COMPOSITIONS AND METHODS FOR INHIBITION OF MICA/B SHEDDING

(71) Applicant: Dana-Farber Cancer Institute, Inc., Boston, MA (US)

(72) Inventors: Lucas Ferrari de Andrade, Boston, MA (US); Kai W. Wucherpfennig, Brookline, MA (US)

(73) Assignee: DANA-FARBER CANCER INSTITUTE, INC., Boston, MA (US)

( * ) Notice: Subject to any disclaimer, the term of this patent is extended or adjusted under 35 U.S.C. 154(b) by 0 days.

(21) Appl. No.: 16/612,932

(22) PCT Filed: May 22, 2018

(86) PCT No.: PCT/US2018/033793
§ 371 (c)(1),
(2) Date: Nov. 12, 2019

(87) PCT Pub. No.: WO2018/217688
PCT Pub. Date: Nov. 29, 2018

(65) Prior Publication Data
US 2020/0165343 A1 May 28, 2020

Related U.S. Application Data

(60) Provisional application No. 62/509,671, filed on May 22, 2017.

(51) Int. Cl.
| | | |
|---|---|---|
| A61K 39/395 | (2006.01) | |
| C07K 16/24 | (2006.01) | |
| C07K 16/28 | (2006.01) | |
| A61P 35/04 | (2006.01) | |
| G01N 33/574 | (2006.01) | |
| A61K 31/4164 | (2006.01) | |
| A61K 31/4965 | (2006.01) | |
| A61K 45/06 | (2006.01) | |
| A61K 39/00 | (2006.01) | |

(52) U.S. Cl.
CPC .......... *C07K 16/2833* (2013.01); *A61P 35/04* (2018.01); *G01N 33/574* (2013.01); *A61K 31/4164* (2013.01); *A61K 31/4965* (2013.01); *A61K 45/06* (2013.01); *A61K 2039/505* (2013.01); *C07K 2317/21* (2013.01); *C07K 2317/24* (2013.01); *C07K 2317/54* (2013.01); *C07K 2317/55* (2013.01); *C07K 2317/565* (2013.01); *C07K 2317/622* (2013.01); *C07K 2317/624* (2013.01); *C07K 2317/73* (2013.01); *C07K 2317/76* (2013.01); *G01N 2333/70539* (2013.01)

(58) Field of Classification Search
None
See application file for complete search history.

(56) References Cited

U.S. PATENT DOCUMENTS

| | | | |
|---|---|---|---|
| 5,225,539 A | 7/1993 | Winter | |
| 5,530,101 A | 6/1996 | Queen et al. | |
| 5,585,089 A | 12/1996 | Queen et al. | |
| 5,693,762 A | 12/1997 | Queen et al. | |
| 6,180,370 B1 | 1/2001 | Queen et al. | |
| 8,182,809 B1 | 5/2012 | Wu | |
| 9,114,131 B2 * | 8/2015 | Watanabe | .......... C07K 16/2803 |
| 2003/0153043 A1 | 8/2003 | Carr et al. | |
| 2010/0183618 A1* | 7/2010 | Hasegawa | .......... C07K 16/2866 424/139.1 |
| 2010/0260752 A1 | 10/2010 | Tang | |
| 2012/0315287 A1 | 12/2012 | Wu | |
| 2013/0315928 A1 | 11/2013 | Maurel et al. | |
| 2015/0320859 A1 | 11/2015 | Maecker et al. | |

FOREIGN PATENT DOCUMENTS

WO    WO2013/117647    8/2013

OTHER PUBLICATIONS

Paul, Fundamental Immunology, 3rd Edition, 1993, pp. 292-295.*
Casset et al (Biochemical and Biophysical Research Communications, 307:198-205, 2003.*
Wang et al. (Nuc. Acids Res. 27: 4609-4618, 1999; p. 4617.*
Wigley et al. Reprod Fert Dev 6: 585-588, 1994.*
Campbell et al. Theriology 47(1): 63-72, 1997.*
International Search Report and Written Opinion for International Application No. PCT/US18/33797 dated Sep. 21, 2018.
Lanier, Lewis L. "NKG2D receptor and its ligands in host defense." Cancer immunology research 3.6 (2015): 575-582.
Lee, June-Chul, et al. "Elevated TGF-b1 Secretion and Downmodulation of NKG2D Underlies Impaired NK Cytotoxicity in Cancer Patients." Journal of Immunotherapy 27.6 (2004): S50.
Leong, Jeffrey W., et al. "Preactivation with IL-12, IL-15, and IL-18 induces CD25 and a functional high-affinity IL-2 receptor on human cytokine-induced memory-like natural killer cells." Biology of Blood and Marrow Transplantation 20.4 (2014): 463-473.
Li, Pingwei, et al. "Complex structure of the activating immunoreceptor NKG2D and its MHC class I—like ligand MICA." Nature immunology 2.5 (2001): 443-451.
Liu, Gang, et al. "Perturbation of NK cell peripheral homeostasis accelerates prostate carcinoma metastasis." The Journal of clinical investigation 123.10 (2013): 4410-4422.
Lonberg, Nils. "Human antibodies from transgenic animals." Nature biotechnology 23.9 (2005): 1117-1125.
Long, Eric O., et al. "Controlling natural killer cell responses: integration of signals for activation and inhibition." Annual review of immunology 31 (2013): 227-258.

(Continued)

*Primary Examiner* — Bridget E Bunner
*Assistant Examiner* — Fozia M Hamud
(74) *Attorney, Agent, or Firm* — Baker Donelson

(57) ABSTRACT

The present invention is based, in part, on the discovery of monoclonal antibodies, and antigen-binding fragments thereof, that specifically bind to MICA/B α3 domain, as well as immunoglobulins, polypeptides, nucleic acids thereof, and methods of using such antibodies for diagnostic, prognostic, and therapeutic purposes.

16 Claims, 51 Drawing Sheets
Specification includes a Sequence Listing.

(56) References Cited

OTHER PUBLICATIONS

Maccallum, Robert M., Andrew CR Martin, and Janet M. Thornton. "Antibody-antigen interactions: contact analysis and binding site topography" Journal of molecular biology 262.5 (1996): 732-745.
Makabe, Koki, et al. "Thermodynamic consequences of mutations in vernier zone residues of a humanized anti-human epidermal growth factor receptor murine antibody, 528." Journal of Biological Chemistry 283.2 (2008): 1156-1166.
Martinet, Ludovic, et al. "DNAM-1 expression marks an alternative program of NK cell maturation." Cell reports 11.1 (2015): 85-97.
Moldenhauer, G., et al. "Identity of HML-1 Antigen on Intestinal Intraepithelial T Cells and of B-ly7 Antigen on Hairy Cell Leukaemia." Scandinavian journal of immunology 32.2 (1990): 77-82.
Morel, Guillemette A., et al. "Monoclonal antibodies to bovine serum albumin: affinity and specificity determinations." Molecular immunology 25.1 (1988): 7-15.
Morris, Glenn. "Epitope Mapping Protocols" in Methods in Molecular Biology. vol. 66 (1996).
Myers, Eugene W., and Webb Miller. "Optimal alignments in linear space." Bioinformatics 4.1 (1988): 11-17.
Needleman, Saul B., and Christian D. Wunsch. "A general method applicable to the search for similarities in the amino acid sequence of two proteins " Journal of molecular biology 48.3 (1970): 443-453.
Nimmerjahn, Falk, and Jeffrey V. Ravetch. "Divergent immunoglobulin g subclass activity through selective Fc receptor binding." Science 310.5753 (2005): 1510-1512.
Pende, Daniela, et al. "Major histocompatibility complex class I-related chain A and UL16-binding protein expression on tumor cell lines of different histotypes: analysis of tumor susceptibility to NKG2D-dependent natural killer cell cytotoxicity." Cancer research 62.21 (2002): 6178-6186.
Queen, Cary, et al. "A humanized antibody that binds to the interleukin 2 receptor." Proceedings of the National Academy of Sciences 86.24 (1989): 10029-10033.
Raffaghello, Lizzia, et al. "Downregulation and/or release of NKG2D ligands as immune evasion strategy of human neuroblastoma." Neoplasia 6.5 (2004): 558-568.
Raulet, David H., et al. "Regulation of ligands for the NKG2D activating receptor." Annual review of immunology 31 (2013): 413-441.
Riechmann, Lutz, et al. "Reshaping human antibodies for therapy." Nature 332.6162 (1988): 323-327.
Rothman, K. J. and S. Greenland. "Modern epidemiology. Lippincott Williams & Wilkins." Philadelphia, PA (1998).
Roux, Kenneth H., et al. "Comparisons of the ability of human IgG3 hinge mutants, IgM, IgE, and IgA2, to form small immune complexes: a role for flexibility and geometry." The Journal of Immunology 161.8 (1998): 4083-4090.
Salih, Helmut R., Hans-Georg Rammensee, and Alexander Steinle. "Cutting edge: down-regulation of MICA on human tumors by proteolytic shedding." The Journal of Immunology 169.8 (2002): 4098-4102.
Sambrook, J., E. F. Fritsch, and T. Maniatis. "Molecular cloning, A laboratory manual 3rd edition, Book 2." (2001).
Seton-Rogers, Sarah. "Stop the shedding." Nature Reviews Cancer 18.6 (2018): 338-339.
Songsivilai, S., and P. J. Lachmann. "Bispecific antibody: a tool for diagnosis and treatment of disease." Clinical & Experimental Immunology 79.3 (1990): 315-321.
Stahli. "Methods in Enzymology." (1983).
Tomlinson, Ian M., et al. "The repertoire of human germline VH sequences reveals about fifty groups of VH segments with different hypervariable loops." Journal of molecular biology 227.3 (1992): 776-798.
Vantourout, P., et al. Immunological visibility : Posttranscriptional regulation of human NKG2D ligands by the EGF receptor pathway . Sci . Transl . Med . 6, 231ra49 (2014 ).
Vetter, Claudia S., et al. "Expression of stress-induced MHC class I related chain molecules on human melanoma." Journal of Investigative Dermatology 118.4 (2002): 600-605.
Von Lilienfeld-Toal, Marie, et al. "Reduced immune effector cell NKG2D expression and increased levels of soluble NKG2D ligands in multiple myeloma may not be causally linked." Cancer immunology, immunotherapy 59.6 (2010): 829-839.
Waldhauer, Inja, et al. "Tumor-associated MICA is shed by ADAM proteases." Cancer research 68.15 (2008): 6368-6376.
Nang, Xuanjun, et al. "An six-amino acid motif in the a3 domain of MICA is the cancer therapeutic target to inhibit shedding." Biochemical and biophysical research communications 387.3 (2009): 476-481.
Ward, E. Sally, et al. "Binding activities of a repertoire of single immunoglobulin variable domains secreted from *Escherichia coli*." Nature 341.6242 (1989): 544-546.
Westfall, Peter H., et al. Multiple comparisons and multiple tests using SAS. SAS Institute, 1999.
Wiemann, Katrin, et al. "Systemic NKG2D down-regulation impairs NK and CD8 T cell responses in vivo." The Journal of Immunology 175.2 (2005): 720-729.
Written Opinion of the International Searching Authority for PCT/US18/33793, dated Sep. 21, 2018.
Wu, Jennifer D., et al. "Prevalent expression of the immunostimulatory MHC class I chain-related molecule is counteracted by shedding in prostate cancer." The Journal of clinical investigation 114.4 (2004): 560-568.
Yang, F. Q., et al. "Matrix metallopeptidase 2 (MMP2) mediates MHC class I polypeptide-related sequence A (MICA) shedding in renal cell carcinoma." Aetas Urologicas Espaholas (English Edition) 38.3 (2014): 172-178.
Zhang, Jinyu, Fahmin Basher, and Jennifer D. Wu. "NKG2D ligands in tumor immunity: two sides of a coin." Frontiers in immunology 6 (2015): 97.
Altschul SF, et al. Basic local alignment search tool. J Mol Biol. Oct. 5, 1990;215(3):403-10 doi: 10.1016/S0022-2836(05)80360-2.
Altschul SF, et al. Gapped BLAST and PSI-BLAST: a new generation of protein database search programs. Nucleic Acids Res. Sep. 1, 1997;25(17):3389-402.
Ausubel, et al . Current Protocols in Molecular Biology , Greene Publishing and Wiley Interscience , New York ( 2003).
Balazs AB, et al. Antibody-based protection against HIV infection by vectored immunoprophylaxis. Nature. Nov. 30, 2011;481(7379):81-4.
Bauer, Stefan, et al. "Activation of NK cells and T cells by NKG2D, a receptor for stress-inducible MICA." Science 285.5428 (1999): 727-729.
Benjamini, Yoav, and Yosef Hochberg. "Controlling the false discovery rate: a practical and powerful approach to multiple testing." Journal of the Royal statistical society: series B (Methodological) 57.1 (1995): 289-300.
Bird, Robert E., et al. "Single-chain antigen-binding proteins." Science 242.4877 (1988): 423-426.
Boutet, Philippe, et al. "Cutting edge: the metalloproteinase ADAM17/TNF-a-converting enzyme regulates proteolytic shedding of the MHC class I-related chain B protein." The Journal of Immunology 182.1 (2009): 49-53.
Brummell, David A., et al. "Probing the combining site of an anti-carbohydrate antibody by saturation-mutagenesis: role of the heavy-chain CDR3 residues." Biochemistry 32.4 (1993): 1180-1187.
Bryceson, Yenan T., et al. "Synergy among receptors on resting NK cells for the activation of natural cytotoxicity and cytokine secretion." Blood 107.1 (2006): 159-166.
Burks, Elizabeth A., et al. "In vitro scanning saturation mutagenesis of an antibody binding pocket." Proceedings of the National Academy of Sciences 94.2 (1997): 412-417.
Chan, Christopher J., Mark J. Smyth, and Ludovic Martinet. "Molecular mechanisms of natural killer cell activation in response to cellular stress." Cell Death & Differentiation 21.1 (2014): 5-14.
Cheung, Ramsey C., et al. "Epitope-specific antibody response to the surface antigen of duck hepatitis B virus in infected ducks." Virology 176.2 (1990): 546-552.

(56) References Cited

OTHER PUBLICATIONS

Chitadze, Guranda, et al. "Shedding of endogenous MHC class I-related chain molecules A and B from different human tumor entities: heterogeneous involvement of the "a disintegrin and metalloproteases" 10 and 17." International journal of cancer 133.7 (2013): 1557-1566.

Chothia, Cyrus, et al. "Conformations of immunoglobulin hypervariable regions." Nature 342.6252 (1989): 877-883.

Clayton, Aled, et al. "Human tumor-derived exosomes downmodulate NKG2D expression." The Journal of Immunology 180.11 (2008): 7249-7258.

Cox, Jonathan PL, Ian M. Tomlinson, and Greg Winter. "A directory of human germ-line V? segments reveals a strong bias in their usage." European journal of immunology 24.4 (1994): 827-836.

Deng, Weiwen, et al. "A shed NKG2D ligand that promotes natural killer cell activation and tumor rejection." Science 348.6230 (2015): 136-139.

Draper, Norman R., and Harry Smith. Applied regression analysis. vol. 326. John Wiley & Sons, 1998.

FDA CDER Data Standards Manual: Exemplary methods are described in the FDA's CDER Data Standards Manual, version No. 004, Feb. 12, 2021.

Ferrari De Andrade, Lucas, et al. "Antibody-mediated inhibition of MICA and MICB shedding promotes NK cell-driven tumor immunity." Science 359.6383 (2018): 1537-1542.

Ferrari De Andrade, Lucas, et al. "Natural killer cells are essential for the ability of BRAF inhibitors to control BRAFV600E-mutant metastatic melanoma." Cancer research 74.24 (2014): 7298-7308.

Gao, Yulong, et al. "Tumor immunoevasion by the conversion of effector NK cells into type 1 innate lymphoid cells." Nature immunology 18.9 (2017): 1004-1015.

Gasser, Stephan, et al. "The DNA damage pathway regulates innate immune system ligands of the NKG2D receptor." Nature 436.7054 (2005): 1186-1190.

Ghadially, Hormas, et al. "MHC class I chain-related protein A and B (MICA and MICB) are predominantly expressed intracellularly in tumour and normal tissue." British journal of cancer 116.9 (2017): 1208-1217.

Groh, Veronika, et al. "Costimulation of CD8αβ T cells by NKG2D via engagement by MIC induced on virus-infected cells" Nature immunology 2.3 (2001): 255-260.

Groh, Veronika, et al. "Recognition of stress-induced MHC molecules by intestinal epithelial ?d T cells." Science 279.5357 (1998): 1737-1740.

Groh, Veronika, et al. "Tumour-derived soluble MIC ligands impair expression of NKG2D and T-cell activation." Nature 419.6908 (2002): 734-738.

Guerra, Nadia, et al. "NKG2D-deficient mice are defective in tumor surveillance in models of spontaneous malignancy." Immunity 28.4 (2008): 571-580.

Harlow, E. D., and David Lane. "Antibodies: A laboratory manual." New York: Cold Spring Harbor Laboratory 579 (1988).

Harlow, Ed and David Lane. Using Antibodies: A Laboratory Manual. Cold Spring Harbor Laboratory Press, 1999.

Harlow, Ed, and David Lane. "Epitope Mapping by Competition Assay." Cold Spring Harbor Protocols (1999).

Hastie, Trevor. "The Elements of Statistical Learning/Hastie T., Tibshirani R., Priedman JH." (2001).

Hayakawa, Yoshihiro, et al. "Cutting edge: tumor rejection mediated by NKG2D receptor-ligand interaction is dependent upon perforin." The Journal of Immunology 169.10 (2002): 5377-5381.

Holdenrieder, Stefan, et al. "Soluble MICA in malignant diseases." International journal of cancer 118.3 (2006): 684-687.

Huergo-Zapico, Leticia, et al. "Expression of ERp5 and GRP78 on the membrane of chronic lymphocytic leukemia cells: association with soluble MICA shedding." Cancer Immunology, Immunotherapy 61.8 (2012): 1201-1210.

Huston, James S., et al. "Protein engineering of antibody binding sites: recovery of specific activity in an anti-digoxin single-chain Fv analogue produced in *Escherichia coli*." Proceedings of the National Academy of Sciences 85.16 (1988): 5879-5883.

Ikeshita, Shunji, et al. "MICA/B expression in macrophage foam cells infiltrating atherosclerotic plaques." Experimental and molecular pathology 97.1 (2014): 171-175.

International Search Report for PCT/US18/33793, dated Sep. 21, 2018.

Izar, Benjamin, et al. "Bidirectional cross talk between patient-derived melanoma and cancer-associated fibroblasts promotes invasion and proliferation" Pigment cell & melanoma research 29.6 (2016): 656-668.

Jefferis, Roy, and Marie-Paule Lefranc. "Human immunoglobulin allotypes: possible implications for immunogenicity." MAbs vol. 1 No. 4. Taylor & Francis, 2009.

Jinushi, Masahisa, et al. "MHC class I chain-related protein A antibodies and shedding are associated with the progression of multiple myeloma." Proceedings of the National Academy of Sciences 105.4 (2008): 1285-1290.

Jones, Peter T., et al. "Replacing the complementarity-determining regions in a human antibody with those from a mouse." Nature 321.6069 (1986): 522-525.

Kabat, E. A., et al. "Sequences of proteins of immunological interest (Fifth)." US Dept Public Health Service, US Dept Public Health Service, National Institutes of Health, Washington, DC (1991).

Kaiser, Brett K., et al. "Disulphide-isomerase-enabled shedding of tumour-associated NKG2D ligands." Nature 447.7143 (2007): 482-486.

Kang, Sang-Mo, et al. "Transactivation by AP-1 is a molecular target of T cell clonal anergy." Science 257.5073 (1992): 1134-1138.

Kirkland, Theo N., et al. "Analysis of the fine specificity and cross-reactivity of monoclonal anti-lipid A antibodies." The Journal of Immunology 137.11 (1986): 3614-3619.

Kobayashi H, et al. Tryptophan H33 plays an important role in pyrimidine (6-4) pyrimidone photoproduct binding by a high-affinity antibody. Protein Eng. Oct. 1999;12(10):879-84.

Koguchi, Yoshinobu, et al. "Serum immunoregulatory proteins as predictors of overall survival of metastatic melanoma patients treated with ipilimumab." Cancer research 75.23 (2015): 5084-5092.

Kostelny, Sheri A., et al. "Formation of a bispecific antibody by the use of leucine zippers." The Journal of Immunology 148.5 (1992): 1547-1553.

* cited by examiner

FIG. 3 (cont.)
G
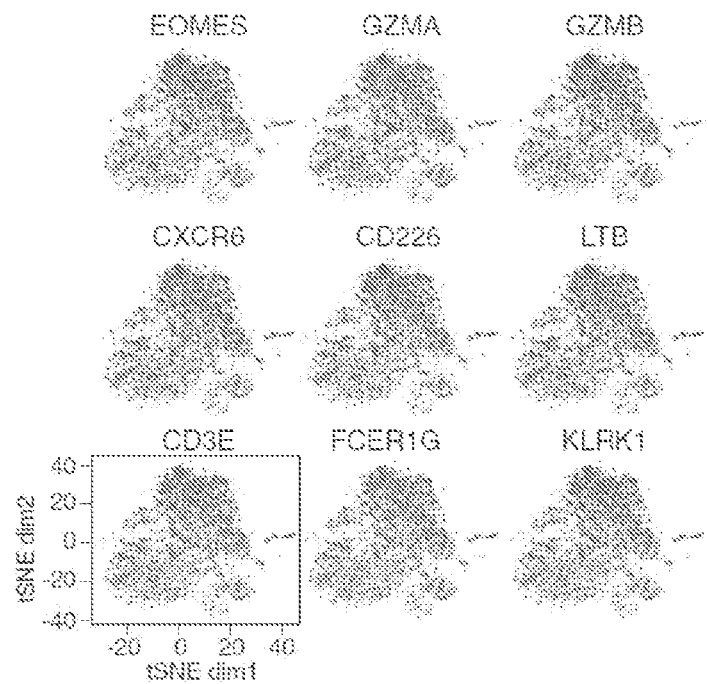
H
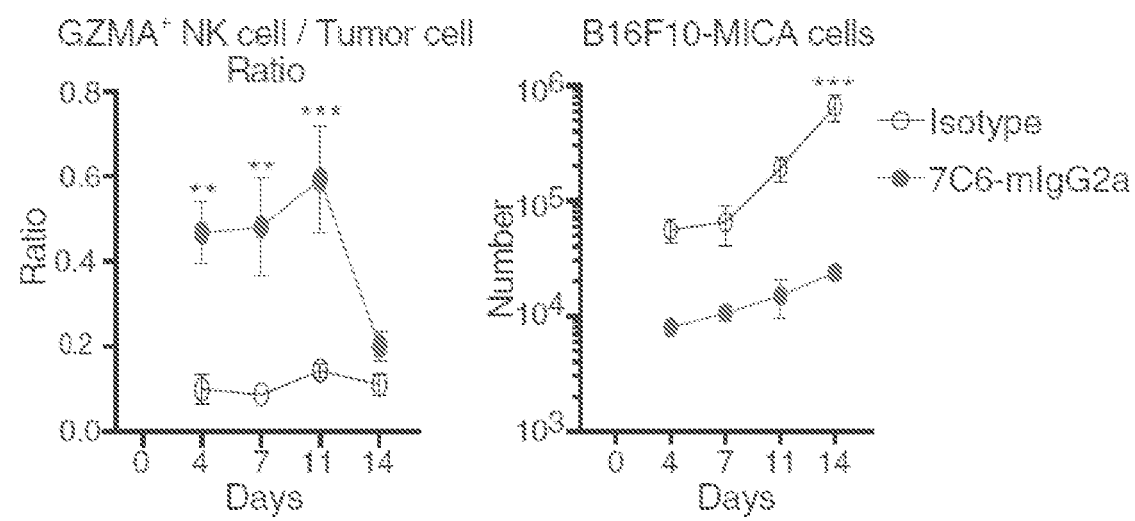

FIG. 4
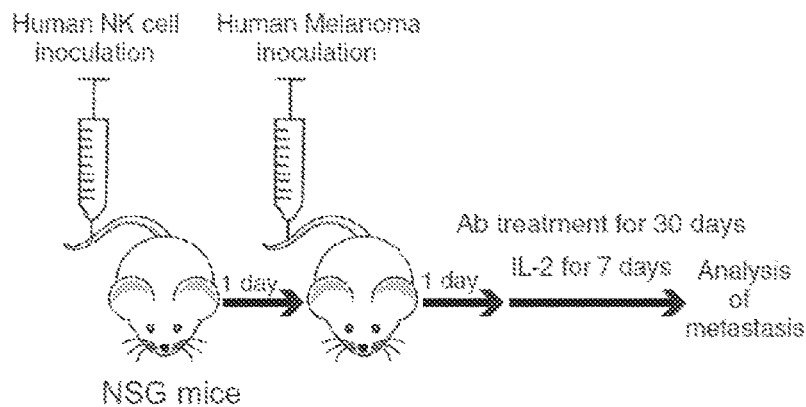
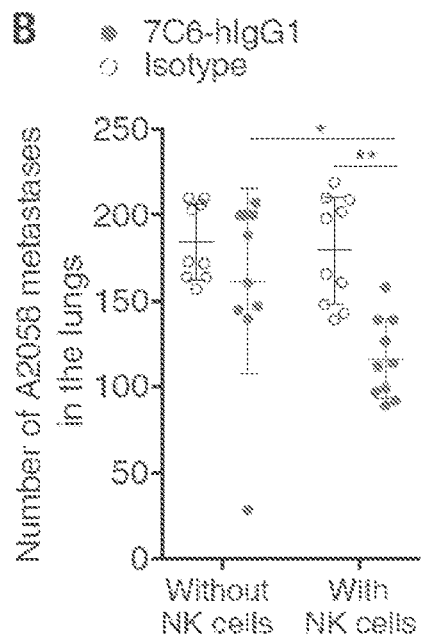
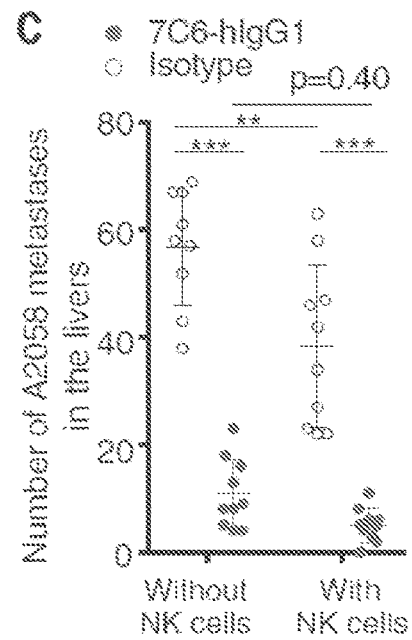
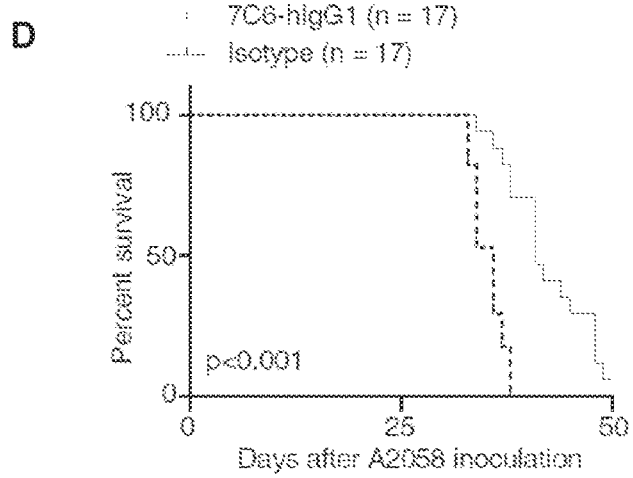

FIG. 4 (cont.)
E
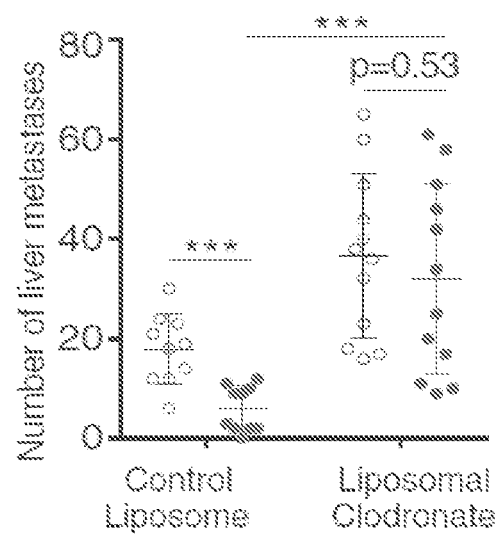
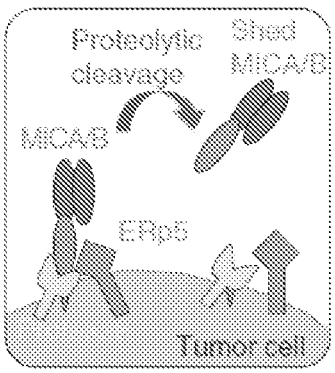 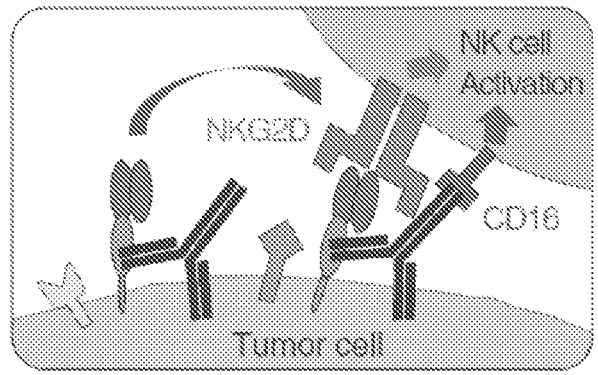
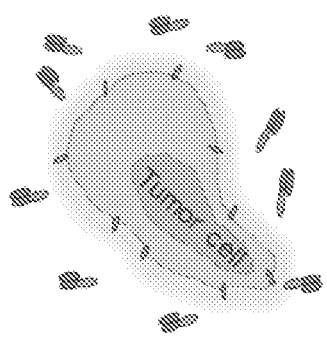 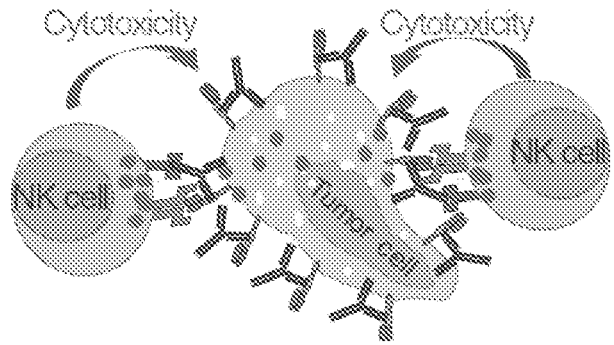

FIG. 5
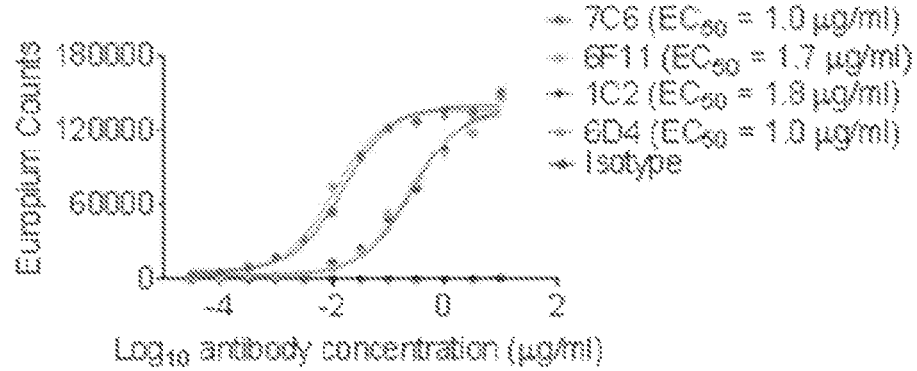
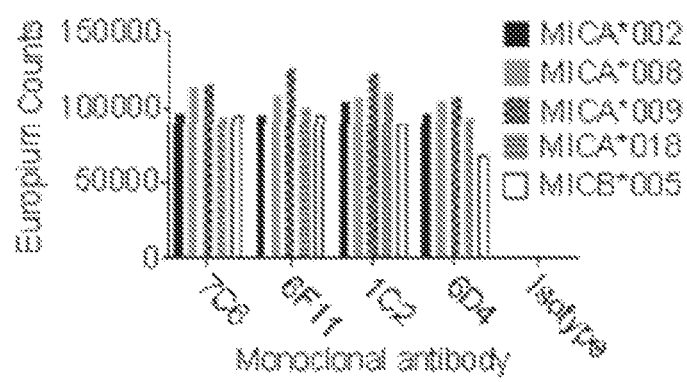
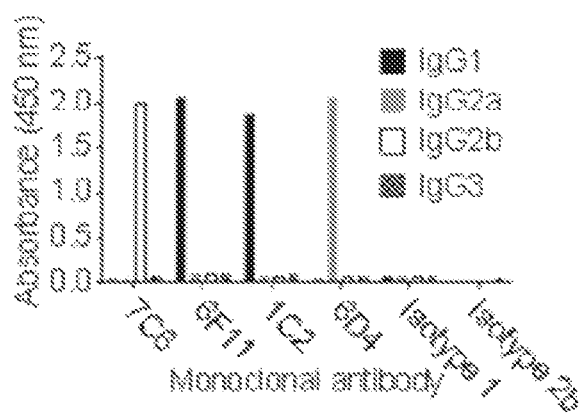

α3 Domain Sequences:

```
MICA*002  VPPMVNVTRSEASEGNITVTCRASGFYPWNITLSWRQDGVSLSHDTQQWGDVLPDGNGTYQTWVATRICQGEEQRFTCYMEHSGNHSTHPVPSGKVLVLQSH
MICA*008  ---------------------------------S---R--I-T------------------------------------R-------------------
MICA*009  ---------------------------------S---R----T----------------------------------------------------------
MICA*018  --------------------------------------------------------N-----------------------R--------G--------A-----
MICB*005  ------------C--V-----------------S---R---T---------------------------------------R--------G--------A-----Q
```

FIG. 8 (cont.)
C
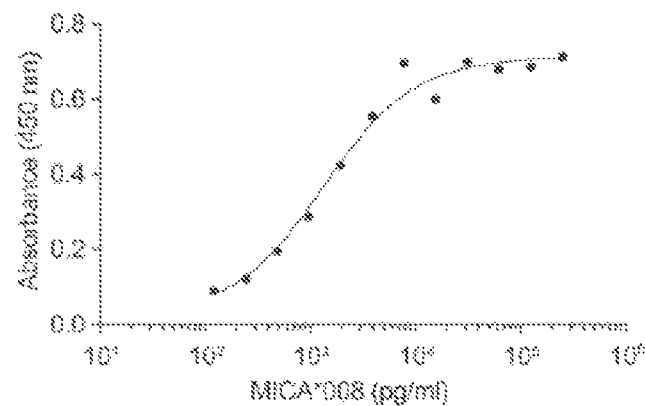
D
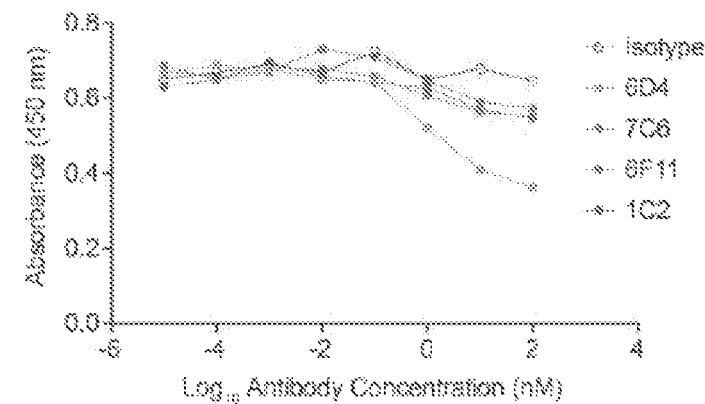
FIG. 9
A
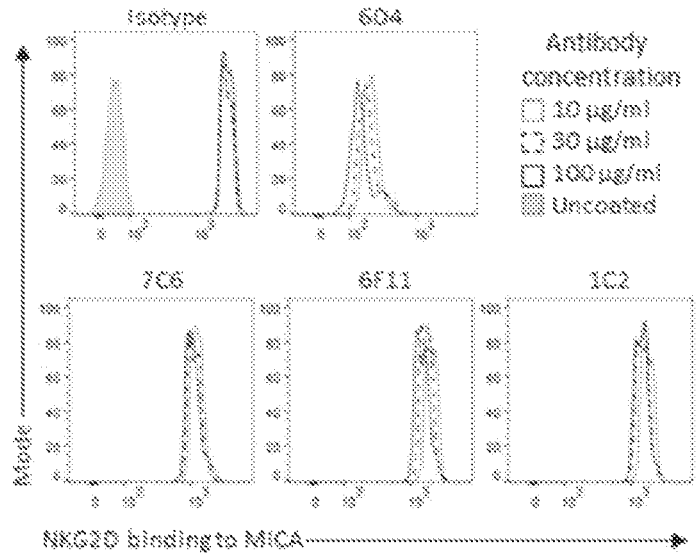

FIG. 9 (cont.)
B
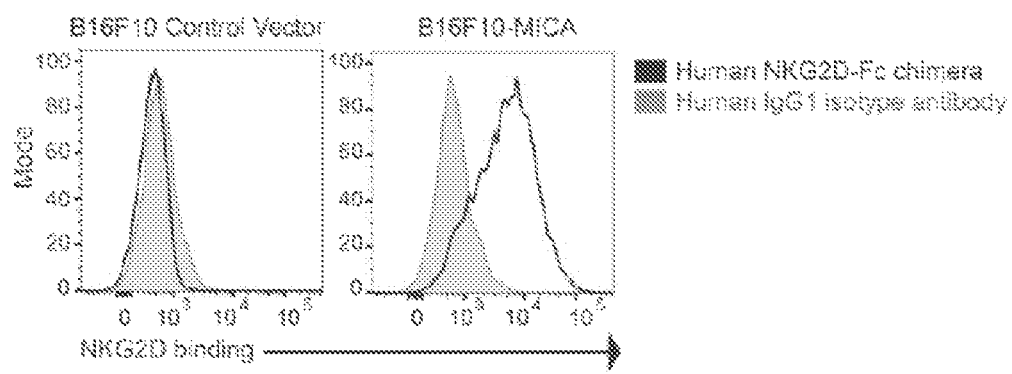
C
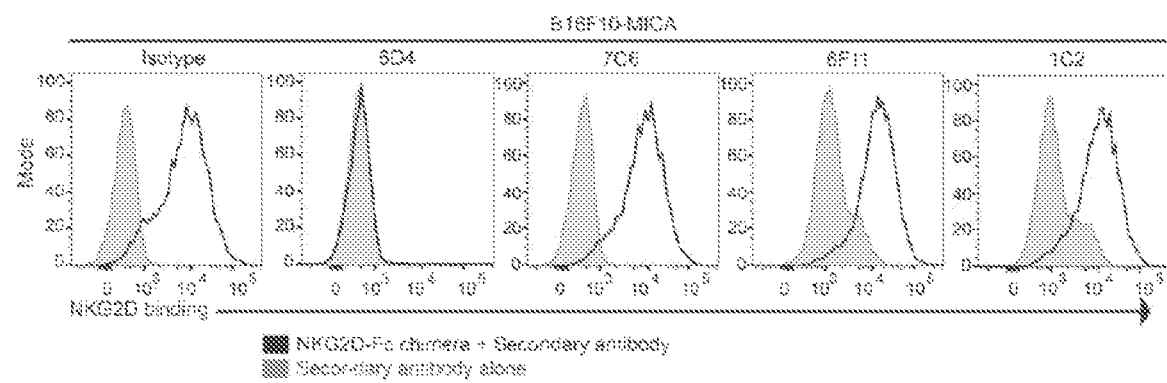

FIG. 12 (cont.)
F
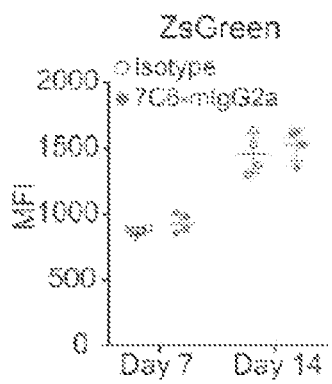
G
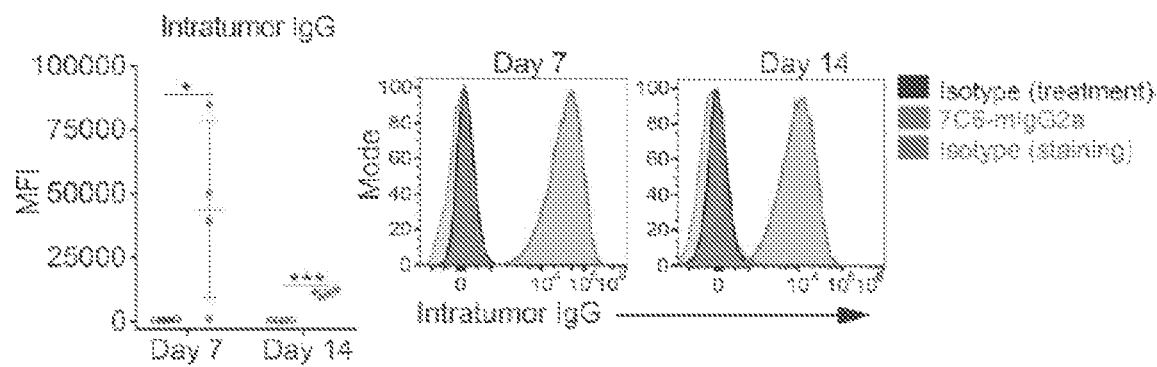
H
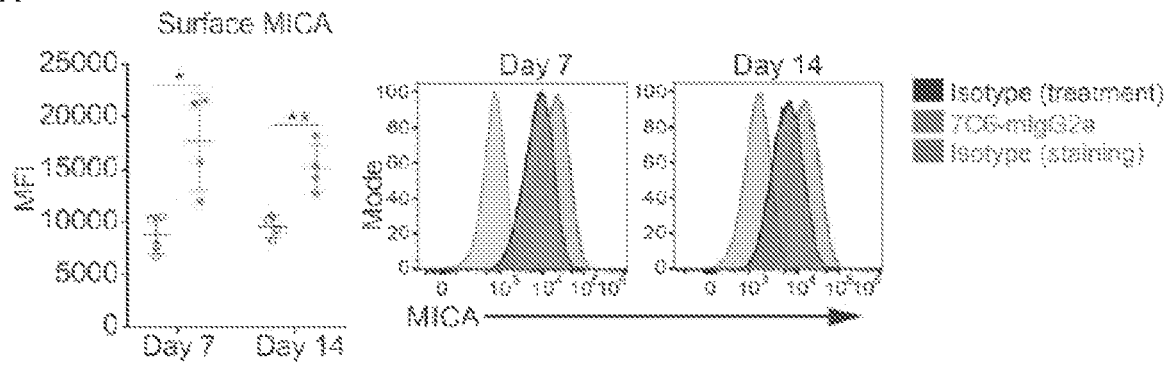
I
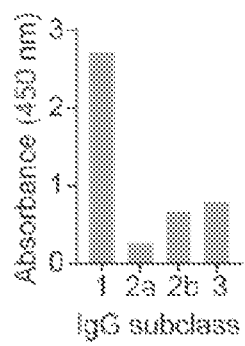
J
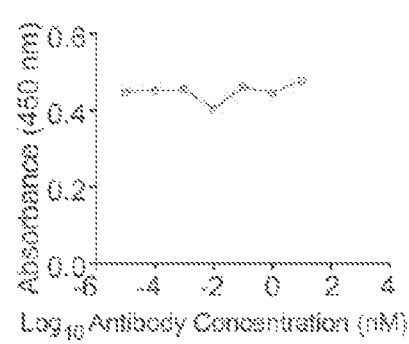

FIG. 14
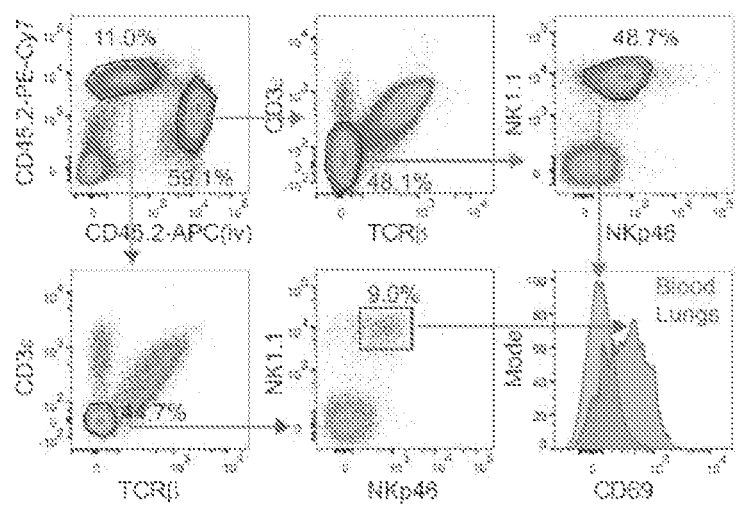
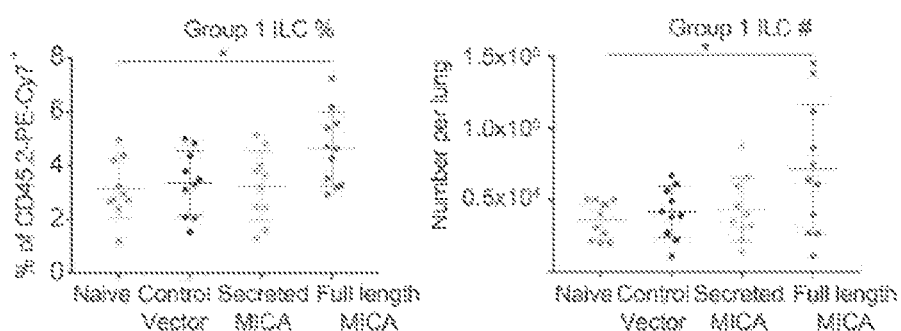
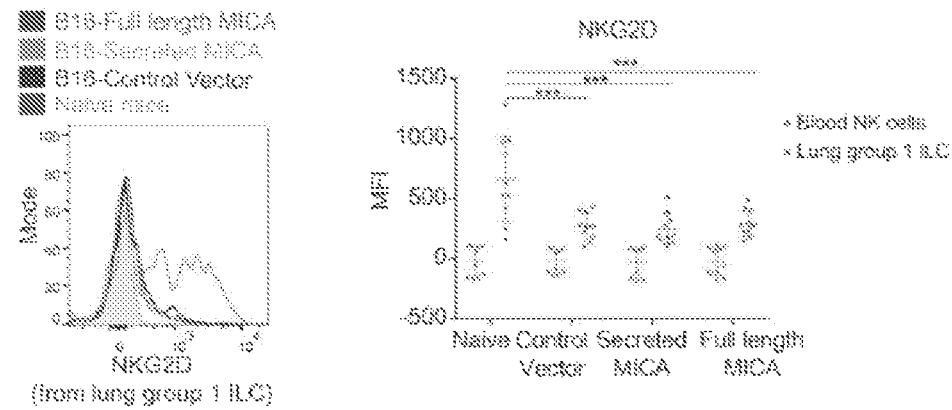

FIG. 15
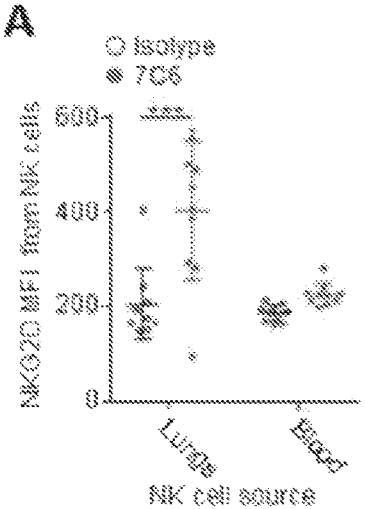
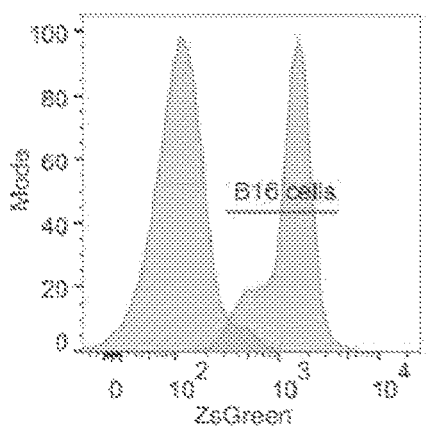
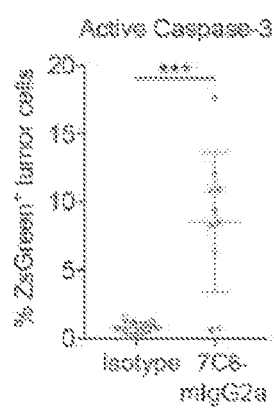
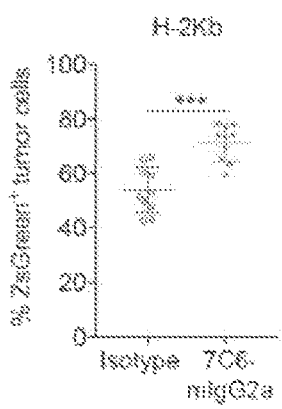
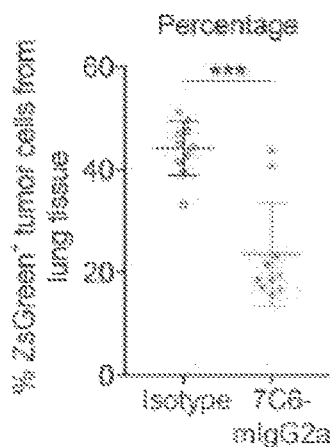
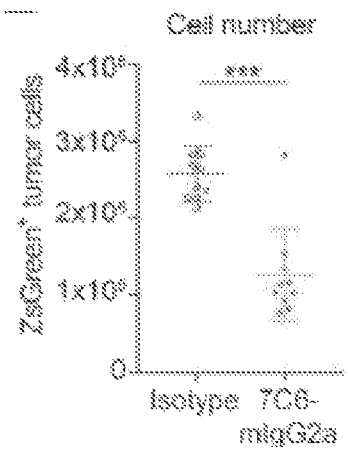

FIG. 17
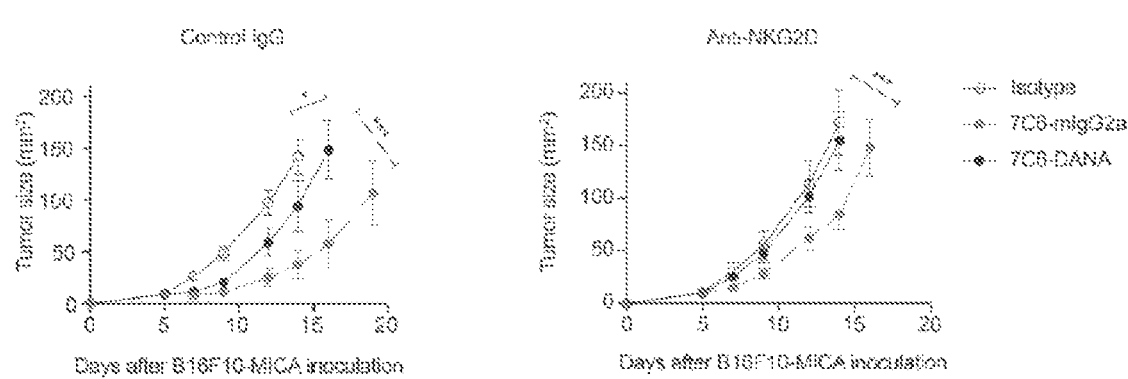
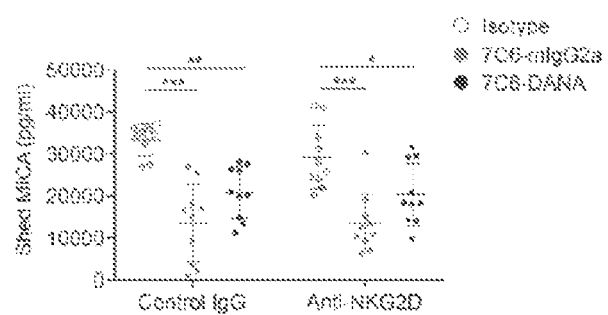

FIG. 19
A
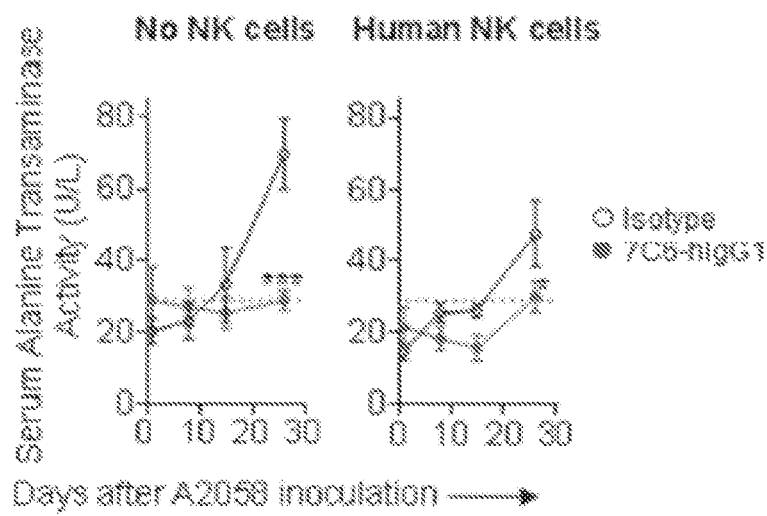
B
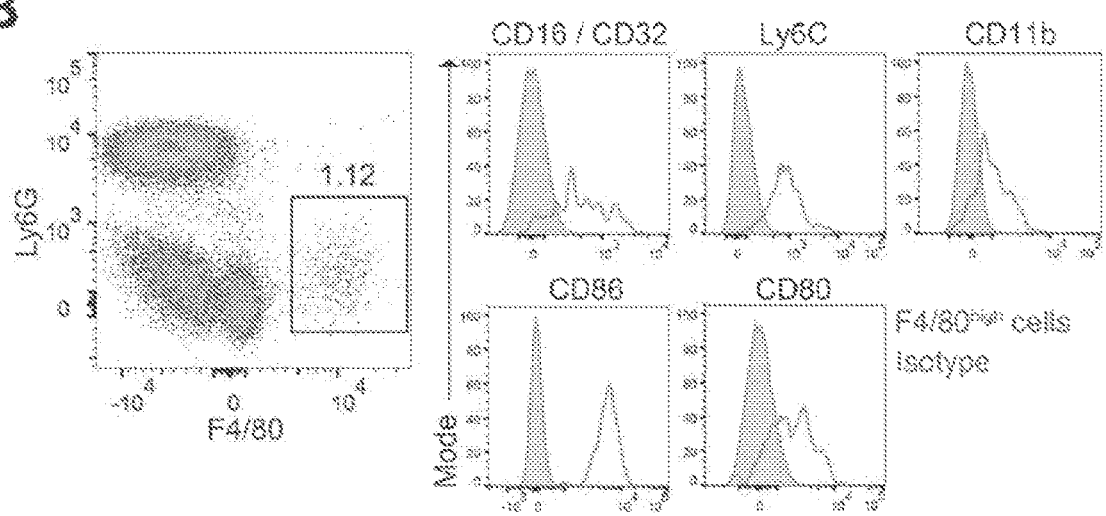
C
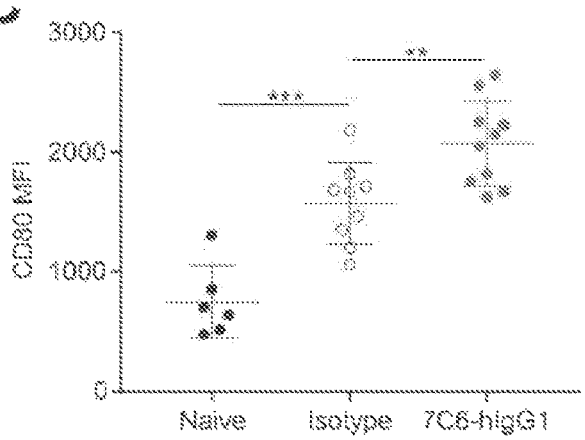

7C6-mIg2a-2a-LC

```
1     ATGGTACCGGTCACGGCTGCTCCTGCTGTTGGCGGCCGCCCTG
1     M  V  P  C  L  L  L  L  L  A  A  A  L

61    GCTCCGACTCAGACCCGGGCGCAGATCCAGTTGGTGCAGTCTGGACCTGAGCTGAAGAAG
21    A  P  T  Q  T  R  A  Q  I  Q  L  V  Q  S  G  P  E  L  K  K

121   CCTGGAGAGACAGTCAAGGTCTCCTGCAAGGCTTCTGGGTATATGTTCACAAACTATGCA
41    P  G  E  T  V  K  V  S  C  K  A  S  G  Y  M  F  T  N  Y  A

181   ATGAACTGGGTGAAGCAGGCTCCAGAAAAGGGTTTAAAGTGGATGGGCTGGATAAACACC
61    M  N  W  V  K  Q  A  P  E  K  G  L  K  W  M  G  W  I  N  T

241   CACACTGGAGAGCCAACATATGCTGATGACTTCAAGGGACGAATTGCCTTCTCTTTGGAA
81    H  T  G  E  P  T  Y  A  D  D  F  K  G  R  I  A  F  S  L  E

301   ACCTCTGCCAGCACTGCCTATTTGCAGATCAACAACCTCAAAAATGAGGACACGGCTACA
101   T  S  A  S  T  A  Y  L  Q  I  N  N  L  K  N  E  D  T  A  T

361   TATTTCTGTGTAAGAACTTATGGTAATTACGCTATGGACTACTGGGGTCAAGGAACCTCA
121   Y  F  C  V  R  T  Y  G  N  Y  A  M  D  Y  W  G  Q  G  T  S

421   GTCACCGTCTCCTCAGCCAAAACAACAGCCCCATCGGTCTATCCACTGGCCCCTGTGTGT
141   V  T  V  S  S  A  K  T  T  A  P  S  V  Y  P  L  A  P  V  C

481   GGAGATACAACTGGCTCCTCGGTTGACTCTAGGATGCCTGGTCAAGGGTTATTTCCCTGAG
161   G  D  T  T  G  S  S  V  T  L  G  C  L  V  K  G  Y  F  P  E

541   CCAGTGACCTTGACCTGGAACTCTGGATCCCTGTCCAGTGGTGTGCACACCTTCCCAGCT
181   P  V  T  L  T  W  N  S  G  S  L  S  S  G  V  H  T  F  P  A

601   GTCCTGCAGTCTGACCTCTACACCCTCAGCAGCTCAGTGACTGTAACCTCGAGCACCTGG
201   V  L  Q  S  D  L  Y  T  L  S  S  S  V  T  V  T  S  S  T  W

661   CCCAGCCAGTCCATCACCTGCAATGTGGCCCACCCGGCAAGCAGCACCAAGGTGGACAAG
221   P  S  Q  S  I  T  C  N  V  A  H  P  A  S  S  T  K  V  D  K

721   AAAATTGAGCCCAGAGGGCCCACAATCAAGCCCTGTCCTCCATGCAAATGCCCAGCACCT
241   K  I  E  P  R  G  P  T  I  K  P  C  P  P  C  K  C  P  A  P

781   GAACTCCTGGGGGGACCGTCAGTCTTCCTCTTCCCCCCAAAACCCAAGGACACCCTCATG
261   E  L  L  G  G  P  S  V  F  L  F  P  P  K  P  K  D  T  L  M

841   ATCTCCCGGACCCCTGAGGTCACATGCGTGGTGGTGGACGTGAGCCACGAAGACCCTGAG
281   I  S  R  T  P  E  V  T  C  V  V  V  D  V  S  H  E  D  P  E

901   GTCAAGTTCAACTGGTACGTGGACGGCGTGGAGGTGCATAATGCCAAGACAAAGCCGCGG
301   V  K  F  N  W  Y  V  D  G  V  E  V  H  N  A  K  T  K  P  R

961   GAGGAGCAGTACAACAGCACGTACCGTGTGGTCAGCGTCCTCACCGTCCTGCACCAGGAC
321   E  E  Q  Y  N  S  T  Y  R  V  V  S  V  L  T  V  L  H  Q  D

1021  TGGCTGAATGGCAAGGAGTACAAGTGCAAGGTCTCCAACAAAGCCCTCCCAGCCCCCATC
341   W  L  N  G  K  E  Y  K  C  K  V  S  N  K  A  L  P  A  P  I

1081  GAGAAAACCATCTCCAAAGCCAAAGGGCAGCCCCGAGAACCACAGGTGTACACCCTGCCC
361   E  K  T  I  S  K  A  K  G  Q  P  R  E  P  Q  V  Y  T  L  P
```

FIG. 21 (cont.) B

```
1141    CCATCCCGGGATGAGCTGACCAAGAACCAGGTCAGCCTGACCTGCCTGGTCAAAGGCTTC
381       P  S  R  D  E  L  T  K  N  Q  V  S  L  T  C  L  V  K  G  F

1201    TATCCCAGCGACATCGCCGTGGAGTGGGAGAGCAATGGGCAGCCGGAGAACAACTACAAG
401       Y  P  S  D  I  A  V  E  W  E  S  N  G  Q  P  E  N  N  Y  K

1261    ACCACGCCTCCCGTGCTGGACTCCGACGGCTCCTTCTTCCTCTACAGCAAGCTCACCGTG
421       T  T  P  P  V  L  D  S  D  G  S  F  F  L  Y  S  K  L  T  V

1321    GACAAGAGCAGGTGGCAGCAGGGGAACGTCTTCTCATGCTCCGTGATGCATGAGGCTCTG
441       D  K  S  R  W  Q  Q  G  N  V  F  S  C  S  V  M  H  E  A  L

1381    CACAACCACTACACGCAGAAGAGCCTCTCCCTGTCTCCGGGTAAAGAGGGCAGAGGCAGC
461       H  N  H  Y  T  Q  K  S  L  S  L  S  P  G  K  E  G  R  G  S

1441    CTGCTGACCTGCGGCGACGTGGAGGAGAACCCCGGCCCCATGGTACCGTGCACGCTGCTC
481       L  L  T  C  G  D  V  E  E  N  P  G  P  M  V  P  C  T  L  L

1501    CTGCTGTTGGCGGCCGCCCTGGCTCCGACTCAGACCCGCGCGGATATCCAGATGACACAG
501       L  L  L  A  A  A  L  A  P  T  Q  T  R  A  D  I  Q  M  T  Q

1561    ACCACATCCTCCCTGTCTGCCTCTCTGGGAGACAGAGTCACCATCAGTTGCAGTGCAAGT
521       T  T  S  S  L  S  A  S  L  G  D  R  V  T  I  S  C  S  A  S

1621    CAGGACATTAGCAATTATTTAAACTGGTATCAGCAGAAACCAGATGGAACTGTTAAACTC
541       Q  D  I  S  N  Y  L  N  W  Y  Q  Q  K  P  D  G  T  V  K  L

1681    CTGATCTATGACACATCAATTTTACACTTAGGAGTCCCATCAAGGTTCAGTGGCAGTGGG
561       L  I  Y  D  T  S  I  L  H  L  G  V  P  S  R  F  S  G  S  G

1741    TCTGGGACAGATTATTCTCTCACCATCAGTAACCTGGAACCTGAAGATATTGCCACTTAC
581       S  G  T  D  Y  S  L  T  I  S  N  L  E  P  E  D  I  A  T  Y

1801    TATTGTCAGCAGTATAGTAAATTTCCTCGGACGTTCGGTGGAGGCACCACGCTGGAAATC
601       Y  C  Q  Q  Y  S  K  F  P  R  T  F  G  G  G  T  L  E  I

1861    AAACGGGCTGATGCTGCACCAACTGTATCCATCTTCCCACCATCCAGTGAGCAGTTAACA
621       K  R  A  D  A  A  P  T  V  S  I  F  P  P  S  S  E  Q  L  T

1921    TCTGGAGGTGCCTCAGTCGTGTGCTTCTTGAACAACTTCTACCCCAAAGACATCAATGTC
641       S  G  G  A  S  V  V  C  F  L  N  N  F  Y  P  K  D  I  N  V

1981    AAGTGGAAGATTGATGGCAGTGAACGACAAAATGGCGTCCTGAACAGTTGGACTGATCAG
661       K  W  K  I  D  G  S  E  R  Q  N  G  V  L  N  S  W  T  D  Q

2041    GACAGCAAAGACAGCACCTACAGCATGAGCAGCACCCTCACGTTGACCAAGGACGAGTAT
681       D  S  K  D  S  T  Y  S  M  S  S  T  L  T  L  T  K  D  E  Y

2101    GAACGACATAACAGCTATACCTGTGAGGCCACTCACAAGACATCAACTTCACCCATTGTC
701       E  R  H  N  S  Y  T  C  E  A  T  H  K  T  S  T  S  P  I  V

2161    AAGAGCTTCAACAGGAATGAGTGTTGA
721       K  S  F  N  R  N  E  C  *
```

FIG. 22

7C6MICA-mIgG2b DANA

[Illegible sequence data - low resolution scan]

FIG. 23A

7C6-hIgG1-DANA

```
1    ATGGTACCGTGCACGCTGCTCCTGCTGTTGGCGGCCGCCCTG
1     M  V  P  C  T  L  L  L  L  A  A  A  L

61   GCTCCGACTCAGACCCGCGCCCAGATCCAGTTGGTGCAGTCTGGACCTGAGCTGAAGAAG
21    A  P  T  Q  T  R  A  Q  I  Q  L  V  Q  S  G  P  E  L  K  K

121  CCTGGAGAGACAGTCAAGGTCTCCTGCAAGGCTTCTGGGTATATGTTCACAAACTATGCA
41    P  G  E  T  V  K  V  S  C  K  A  S  G  Y  M  F  T  N  Y  A

181  ATGAACTGGGTGAAGCAGGCTCCAGAAAAGGGGTTTAAAGTGGATGGGCTGGATAAACACC
61    M  N  W  V  K  Q  A  P  E  K  G  L  K  W  M  G  W  I  N  T

241  CTCACTGGAGACCCAACATATGCTGATGACTTCAAGGGACGAATTGCCTTCTCTTTGGAA
81    S  T  G  D  P  T  Y  A  D  D  F  K  G  R  I  A  F  S  L  E

301  ACCTCTGCCAGCACTGCCTATTTGCAGATCAACAACCTCAAAAATGAGGACACGGCTACA
101   T  S  A  S  T  A  Y  L  Q  I  N  N  L  K  N  E  D  T  A  T

361  TATTTCTGTGTAAGAACTTATGGTAATTACGCTATGGACTACTGGGGTCAAGGAACCTCA
121   Y  F  C  V  R  T  Y  G  N  Y  A  M  D  Y  W  G  Q  G  T  S

421  GTCACCGTCTCCTCAGCCAAAACAACAGCCCCATCGGTCTATCCACTGGCCCCTGTGTGT
141   V  T  V  S  S  A  K  T  T  A  P  S  V  Y  P  L  A  P  V  C

481  GGAGATACAACTGGCTCCTCGGTGACTCTAGGATGCCTGGTCAAGGGTTATTTCCCTGAG
161   G  D  T  T  G  S  S  V  T  L  G  C  L  V  K  G  Y  F  P  E

541  CCAGTGACCTTGACCTGGAACTCTGGATCCCTGTCCAGTGGTGTGCACACCTTCCCAGCT
181   P  V  T  L  T  W  N  S  G  S  L  S  S  G  V  H  T  F  P  A

601  GTCCTGCAGTCTGACCTCTACACCCTCAGCAGCTCAGTTACTGTAACCTCGAGCACCTGG
201   V  L  Q  S  D  L  Y  T  L  S  S  S  V  T  V  T  S  S  T  W

661  CCCAGCCAGTCCATCACCTGCAATGTGGCCCACCCGGCAAGCAGCACCAAGGTGGACAAG
221   P  S  Q  S  I  T  C  N  V  A  H  P  A  S  S  T  K  V  D  K

721  AAAATTGAGCCCAGAGGGCCCACAATCAAGCCCTGTCCTCCATGCAAATGCCCAGCACCT
241   K  I  E  P  R  G  P  T  I  K  P  C  P  P  C  K  C  P  A  P

781  GAACTCCTGGGGGGACCGTCAGTCTTCCTCTTCCCCCCAAAACCCAAGGACACCCTCATG
261   E  L  L  G  G  P  S  V  F  L  F  P  P  K  P  K  D  T  L  M

841  ATCTCCCGGACCCCTGAGGTCACATGCGTGGTGGTGGCCGTGAGCCACGAAGACCCTGAG
281   I  S  R  T  P  E  V  T  C  V  V  V  A  V  S  H  E  D  P  E

901  GTCAAGTTCAACTGGTACGTGGACGGCGTGGAGGTGCATAATGCCAAGACAAAGCCGCGG
301   V  K  F  N  W  Y  V  D  G  V  E  V  H  N  A  K  T  K  P  R

961  GAGGAGCAGTACAACAGCACGTACCGTGTGGTCAGCGTCCTCACCGTCCTGCACCAGGAC
321   E  E  Q  Y  N  S  T  Y  R  V  V  S  V  L  T  V  L  H  Q  D

1021 TGGCTGAATGGCAAGGAGTACAAGTGCAAGGTCTCCAACAAAGCCCTCCCAGCCCCCATC
341   W  L  N  G  K  E  Y  K  C  K  V  S  N  K  A  L  P  A  P  I
```

FIG. 23 (cont.) B

```
1081    GAGAAAACCATCTCCAAAGCCAAAGGGCAGCCCCGAGAACCACAGGTTTACACCCTGCCC
361      E  K  T  I  S  K  A  K  G  Q  P  R  E  P  Q  V  Y  T  L  P

1141    CCATCCCGGGAGGAGATGACCAAGAACCAGGTCAGCCTGACCTGCCTGGTCAAAGGCTTC
381      P  S  R  E  E  M  T  K  N  Q  V  S  L  T  C  L  V  K  G  F

1201    TATCCCAGCGACATCGCCGTGGAGTGGGAGAGCAATGGGCAGCCGGAGAACAACTACAAG
401      Y  P  S  D  I  A  V  E  W  E  S  N  G  Q  P  E  N  N  Y  K

1261    ACCACGCCTCCCGTGCTGGACTCCGACGGCTCCTTCTTCCTCTACAGCAAGCTCACCGTG
421      T  T  P  P  V  L  D  S  D  G  S  F  F  L  Y  S  K  L  T  V

1321    GACAAGAGCAGGTGGCAGCAGGGGAACGTCTTCTCATGCTCCGTGATGCATGAGGCTCTG
441      D  K  S  R  W  Q  Q  G  N  V  F  S  C  S  V  M  H  E  A  L

1381    CACAACCACTACACGCAGAAGAGCCTCTCCCTGTCTCCGGGTAAAGAGGGCAGAGGCAGC
461      H  N  H  Y  T  Q  K  S  L  S  L  S  P  G  K  E  G  R  G  S

1441    CTGCTGACCTGCGGCGACGTGGAGGAGAACCCCGGCCCCATGGTACCTGCACGCTGCTC
481      L  L  T  C  G  D  V  E  E  N  P  G  P  M  V  P  C  T  L  L

1501    CTGCTGTTGGCGGCCGCCCTGGCTCCGACTCAGACCCGCGCGGATATCCAGATGACACAG
501      L  L  L  A  A  A  L  A  P  T  Q  T  R  A  D  I  Q  M  T  Q

1561    ACCACATCCTCCCTGTCTGCCTCTCTGGGAGACAGAGTCACCATCAGTTGCAGTGCAAGT
521      T  T  S  S  L  S  A  S  L  G  D  R  V  T  I  S  C  S  A  S

1621    CAGGACATTAGCAATTATTTAAACTGGTATCAGCAGAAACCAGATGGAACTGTTAAACTC
541      Q  D  I  S  N  Y  L  N  W  Y  Q  Q  K  P  D  G  T  V  K  L

1681    CTGATCTATGACACATCAATTTTACACTTAGGAGTCCCATCAAGGTTCAGTGGCAGTGGG
561      L  I  Y  D  T  S  I  L  H  L  G  V  P  S  R  F  S  G  S  G

1741    TCTGGGACAGATTATTCTCTCACCATCAGTAACCTGGAACCTGAAGATATTGCCACTTAC
581      S  G  T  D  Y  S  L  T  I  S  N  L  E  P  E  D  I  A  T  Y

1801    TATTGTCAACAGTATAGTAAATTTCCTCGGACGTTCGGTGGAGGCACCAAGCTGGAAATC
601      Y  C  Q  Q  Y  S  K  F  P  R  T  F  G  G  G  T  K  L  E  I

1861    AAACGGGCTGATGCTGCACCAACTGTATCCATCTTCCCACCATCCAGTGAGCAGTTAACA
621      K  R  A  D  A  A  P  T  V  S  I  F  P  P  S  S  E  Q  L  T

1921    TCTGGAGGTGCCTCAGTCGTGTGCTTCTTGAACAACTTCTACCCCAAAGACATCAATGTC
641      S  G  G  A  S  V  V  C  F  L  N  N  F  Y  P  K  D  I  N  V

1981    AAGTGGAAGATTGATGGCAGTGAACGACAAAATGGCGTCCTGAACAGTTGGACTGATCAG
661      K  W  K  I  D  G  S  E  R  Q  N  G  V  L  N  S  W  T  D  Q

2041    GACAGCAAAGACAGCACCTACAGCATGAGCAGCACCCTCACGTTGACCAAGGACGAGTAT
681      D  S  K  D  S  T  Y  S  M  S  S  T  L  T  L  T  K  D  E  Y

2101    GAACGACATAACAGCTATACCTGTGAGGCCACTCACAAGACATCAACTTCACCCATTGTC
701      E  R  H  N  S  Y  T  C  E  A  T  H  K  T  S  T  S  P  I  V

2161    AAGAGCTTCAACAGGAATGAGTGTTGA
721      K  S  F  N  R  N  E  C  *
```

FIG. 24
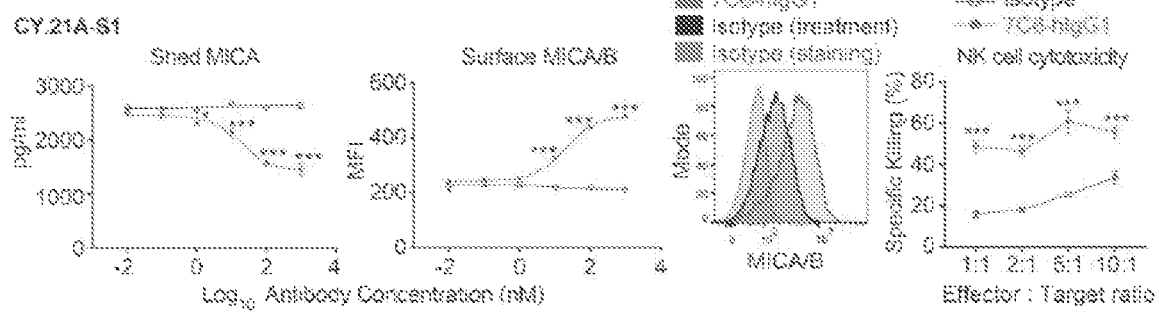
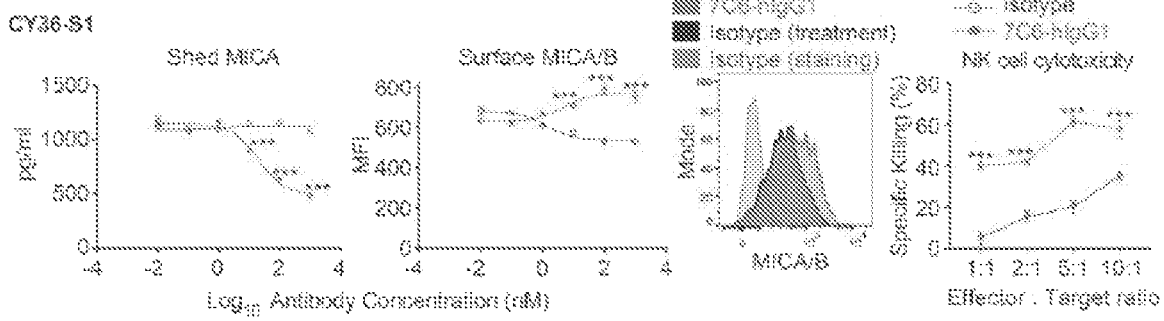
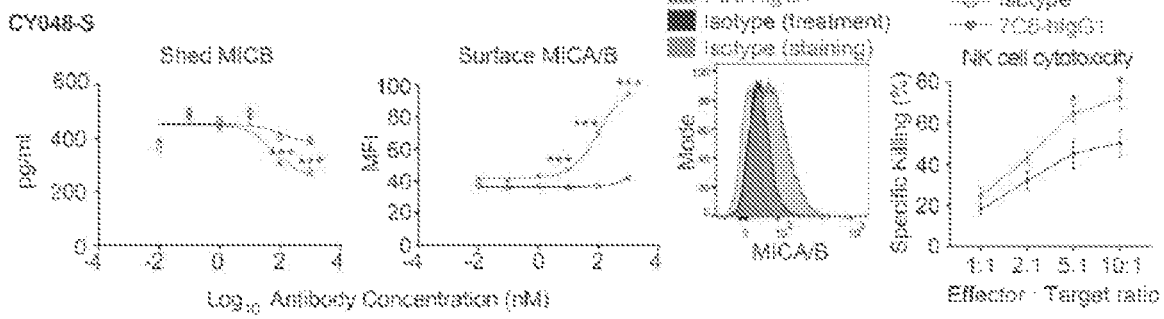

FIG. 26 (cont.)B
B
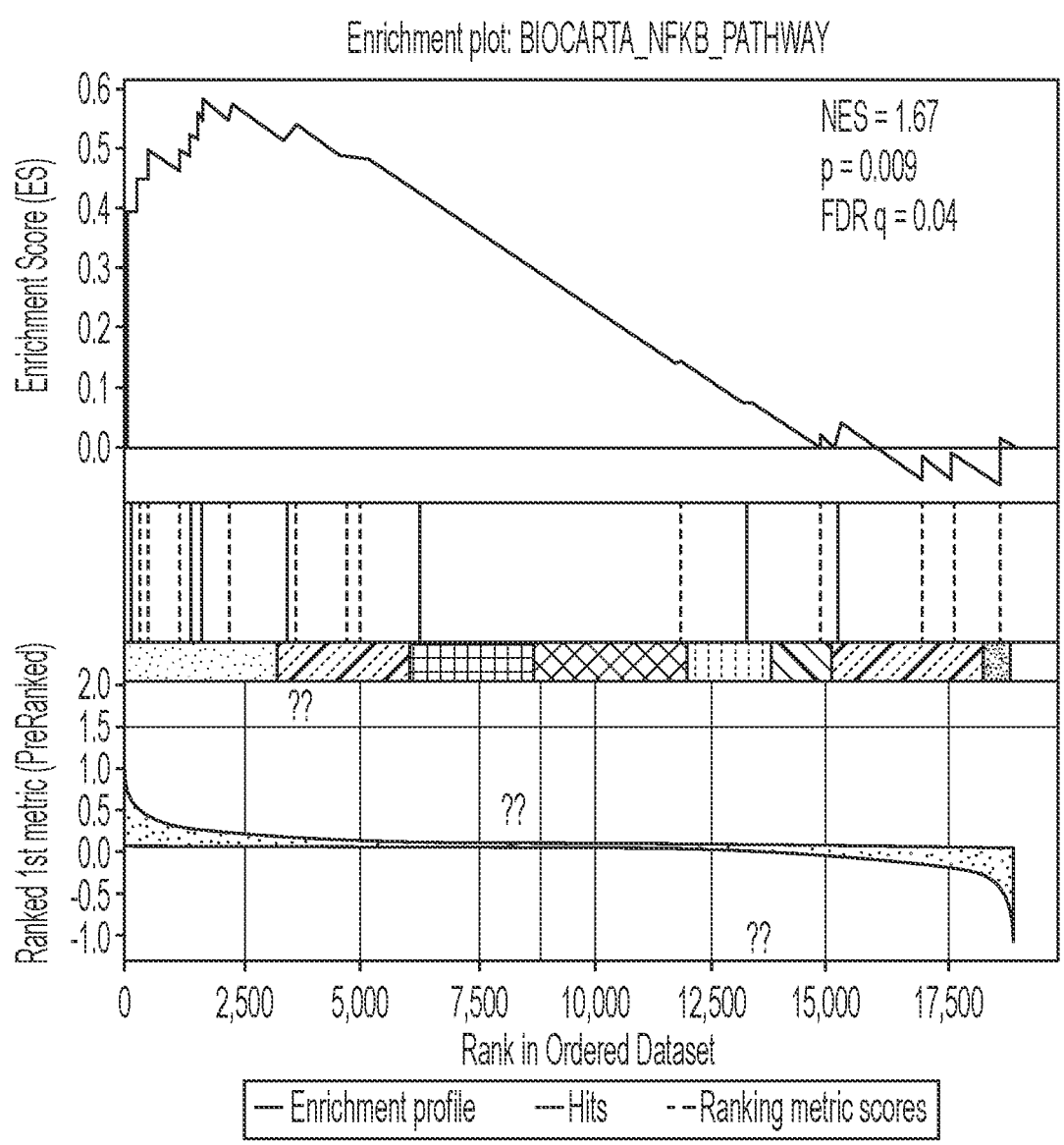

FIG. 26 (cont.)C
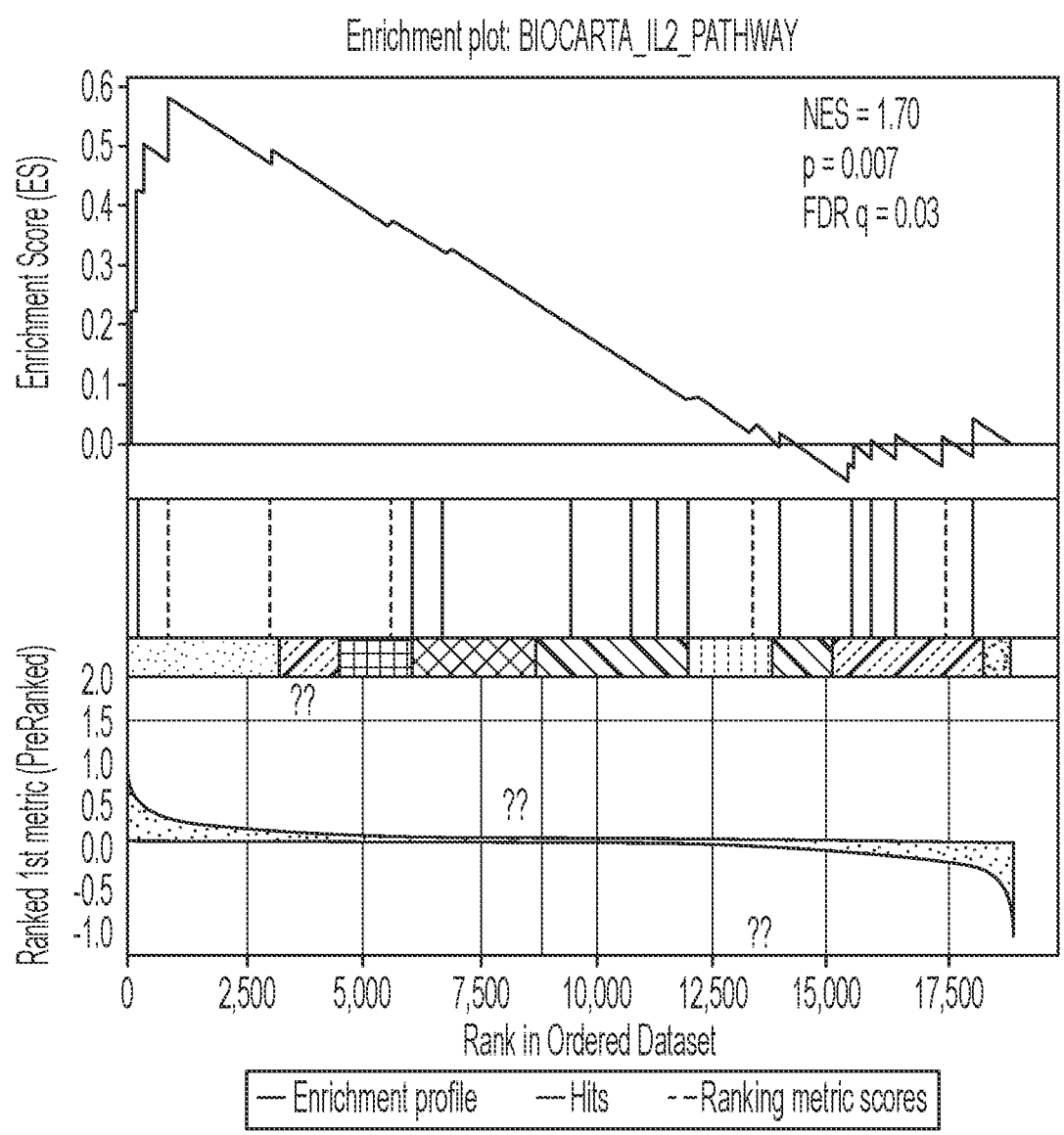

FIG. 26 (cont.)D
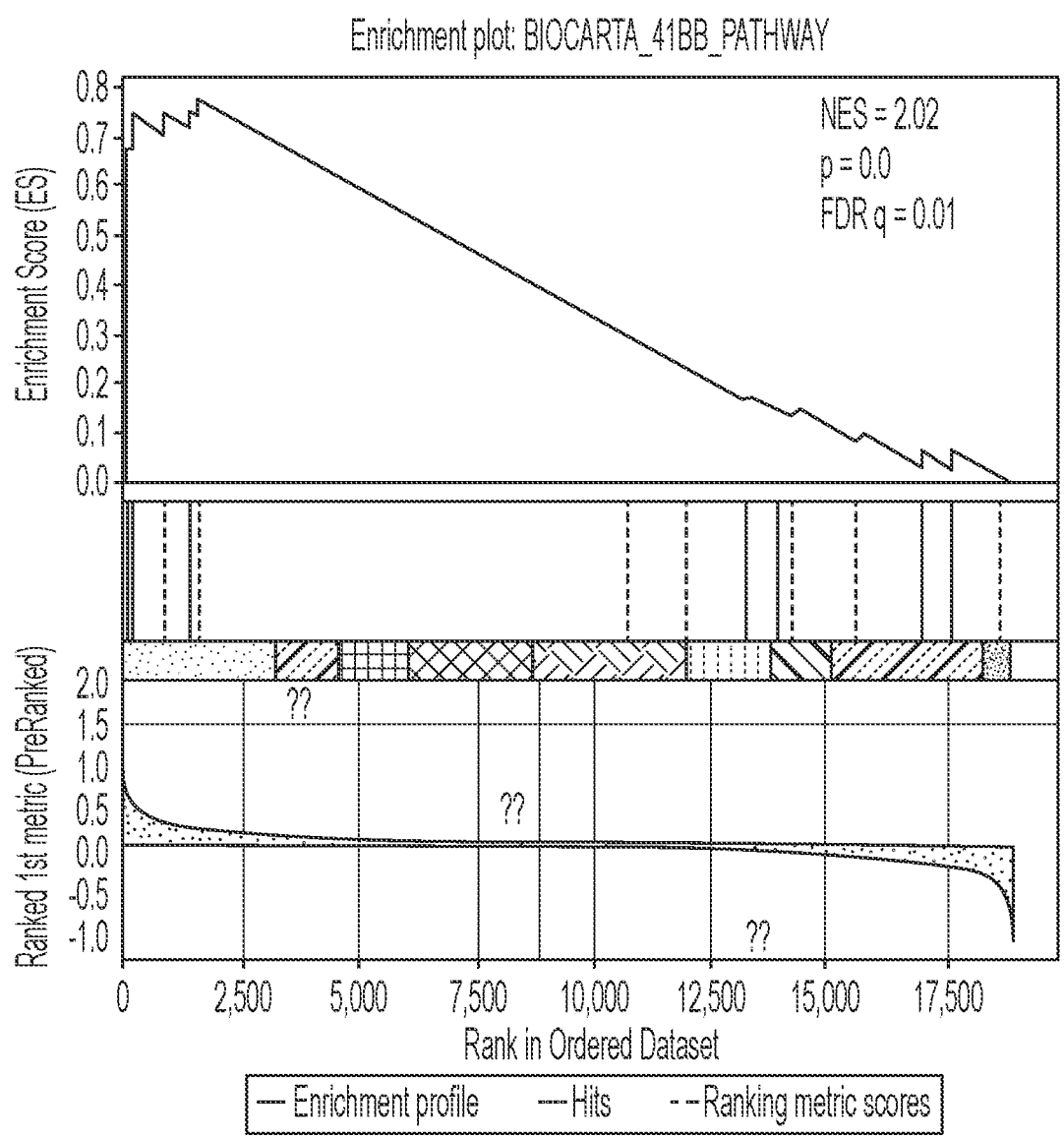

FIG. 26 (cont.)E
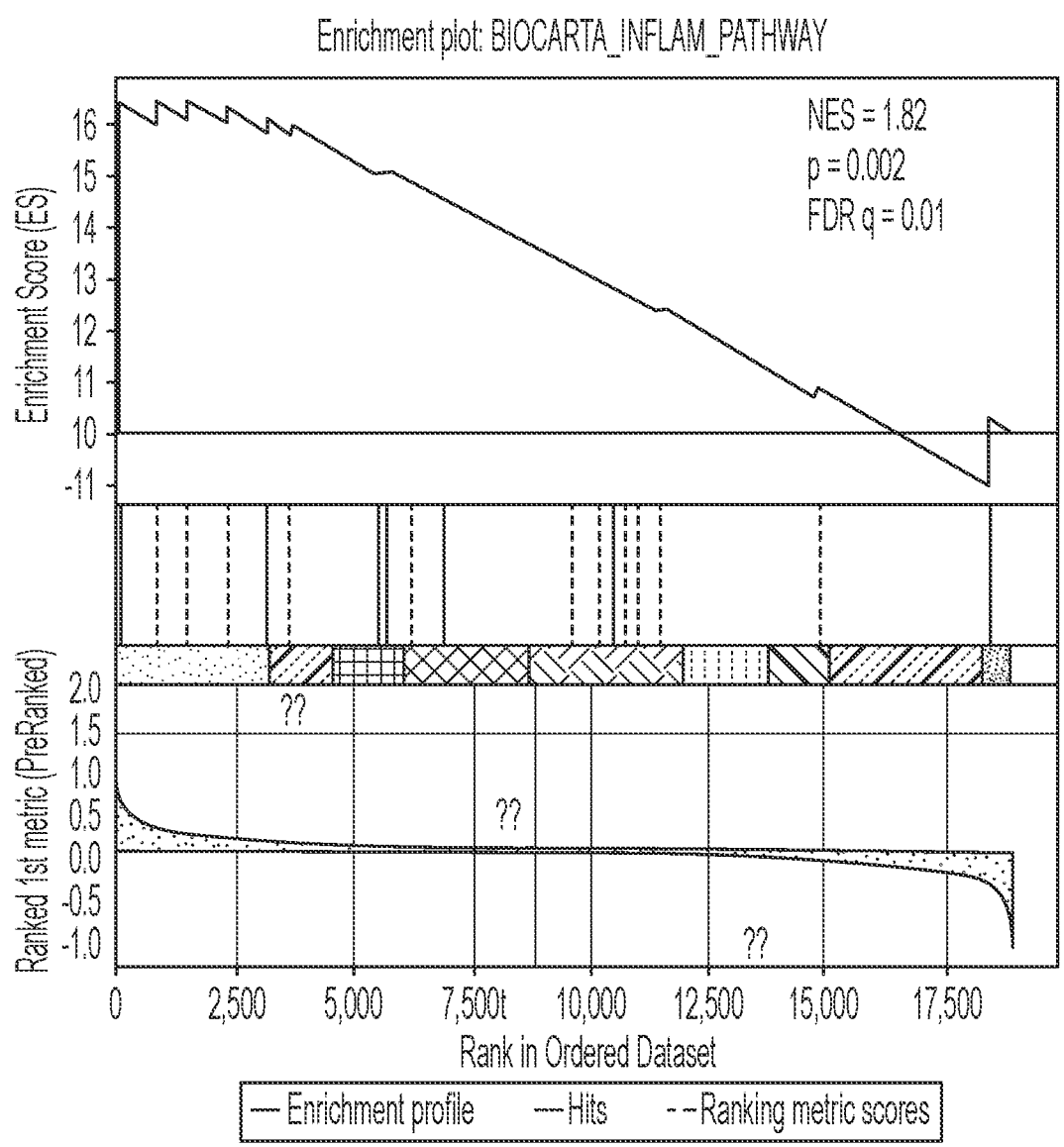

FIG. 27 (cont.)B
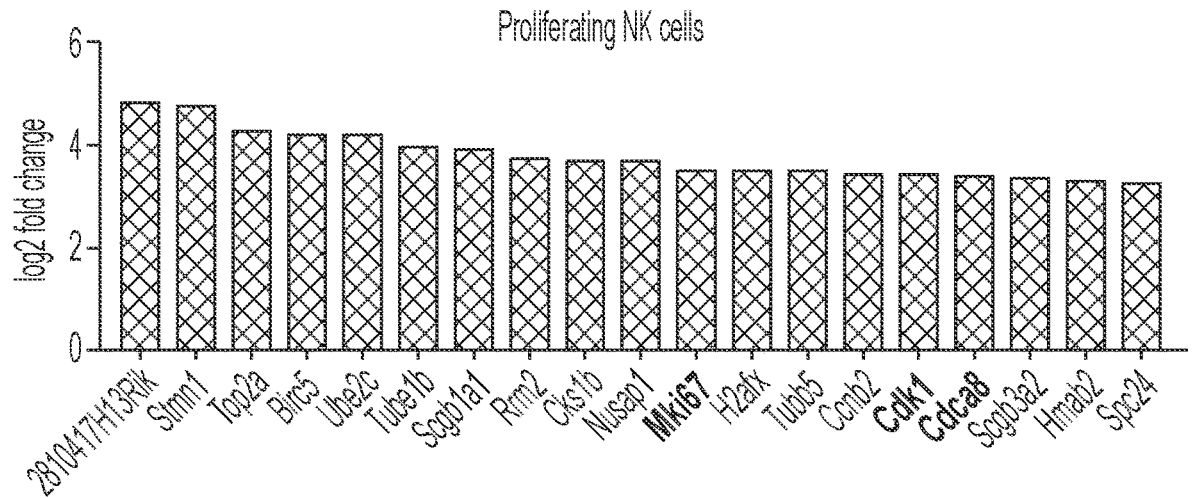
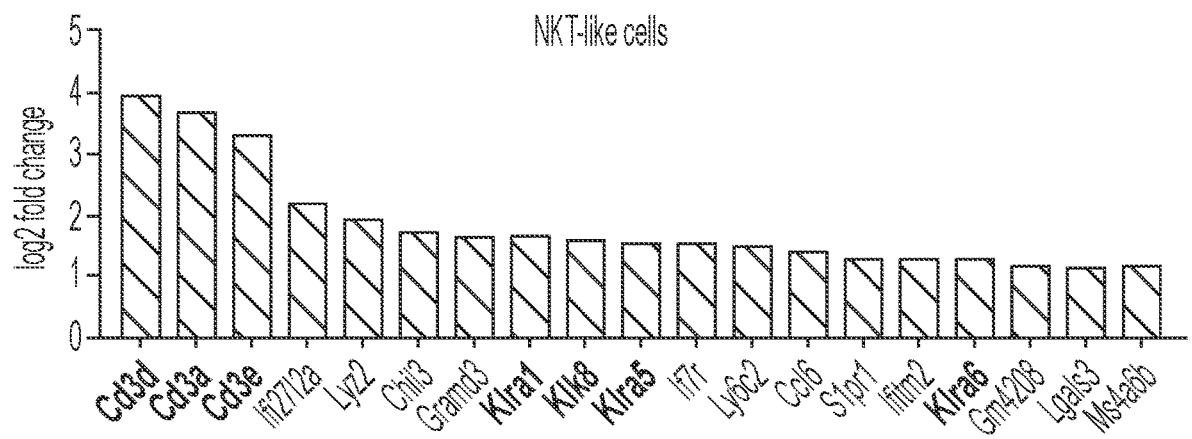
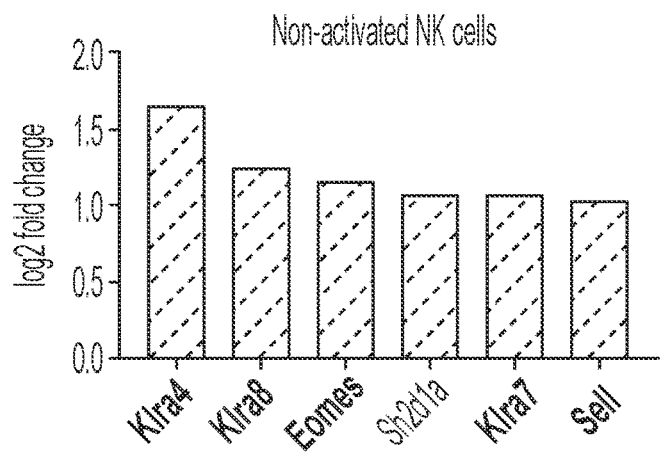

FIG. 27 (cont.) C
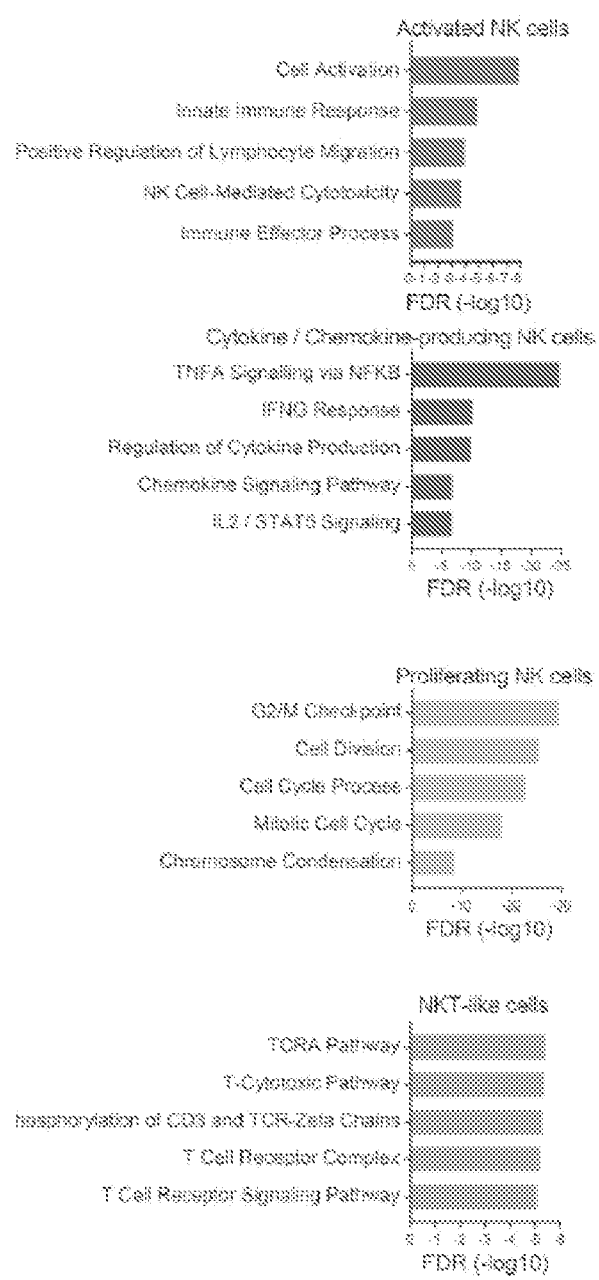

FIG. 28
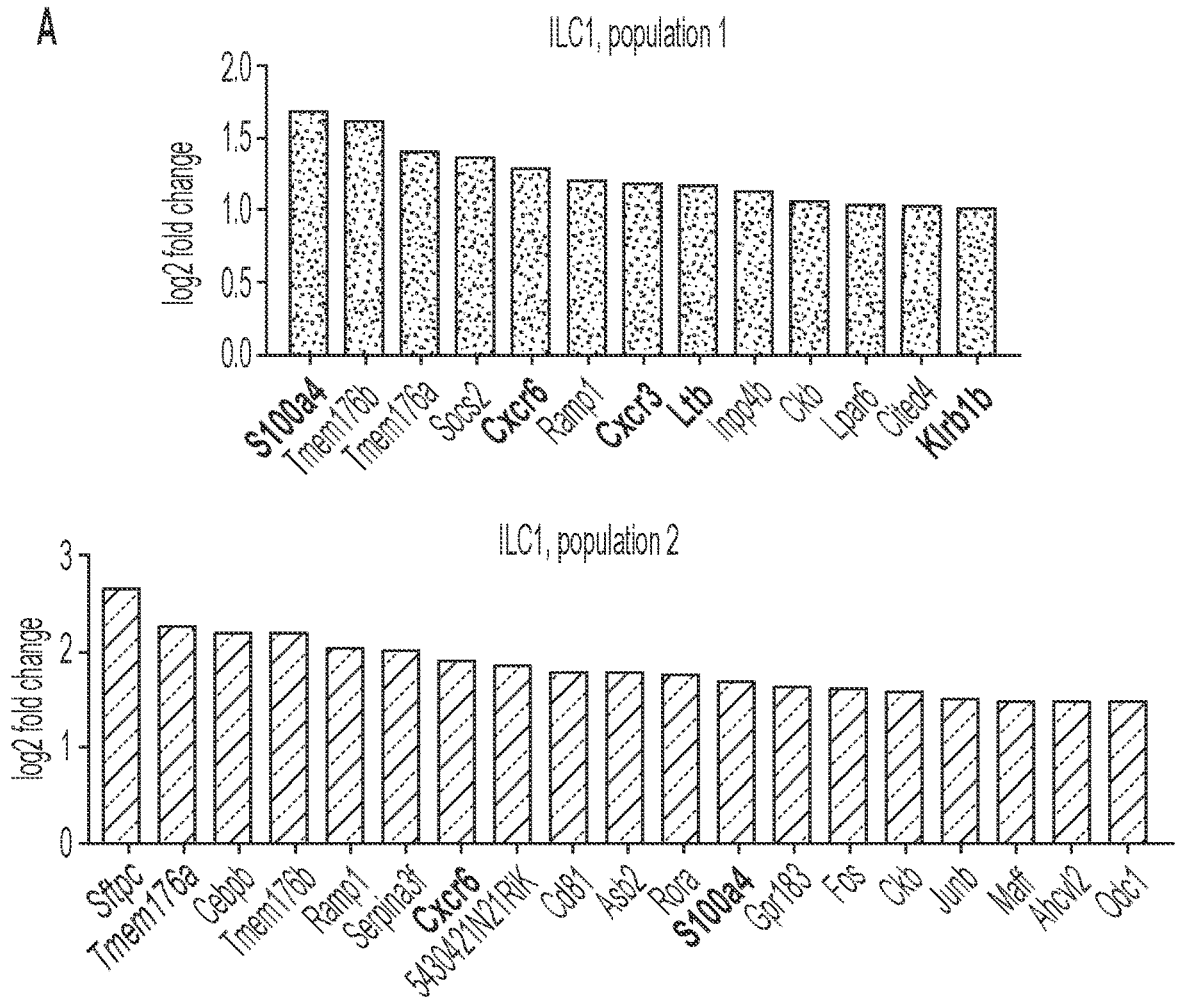
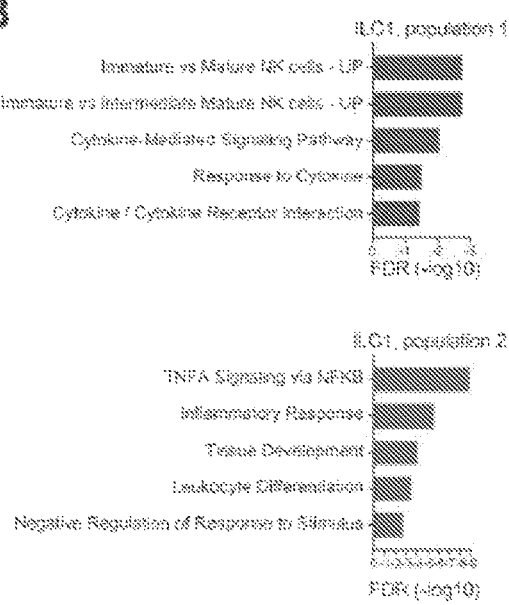

FIG. 29 (cont.)B
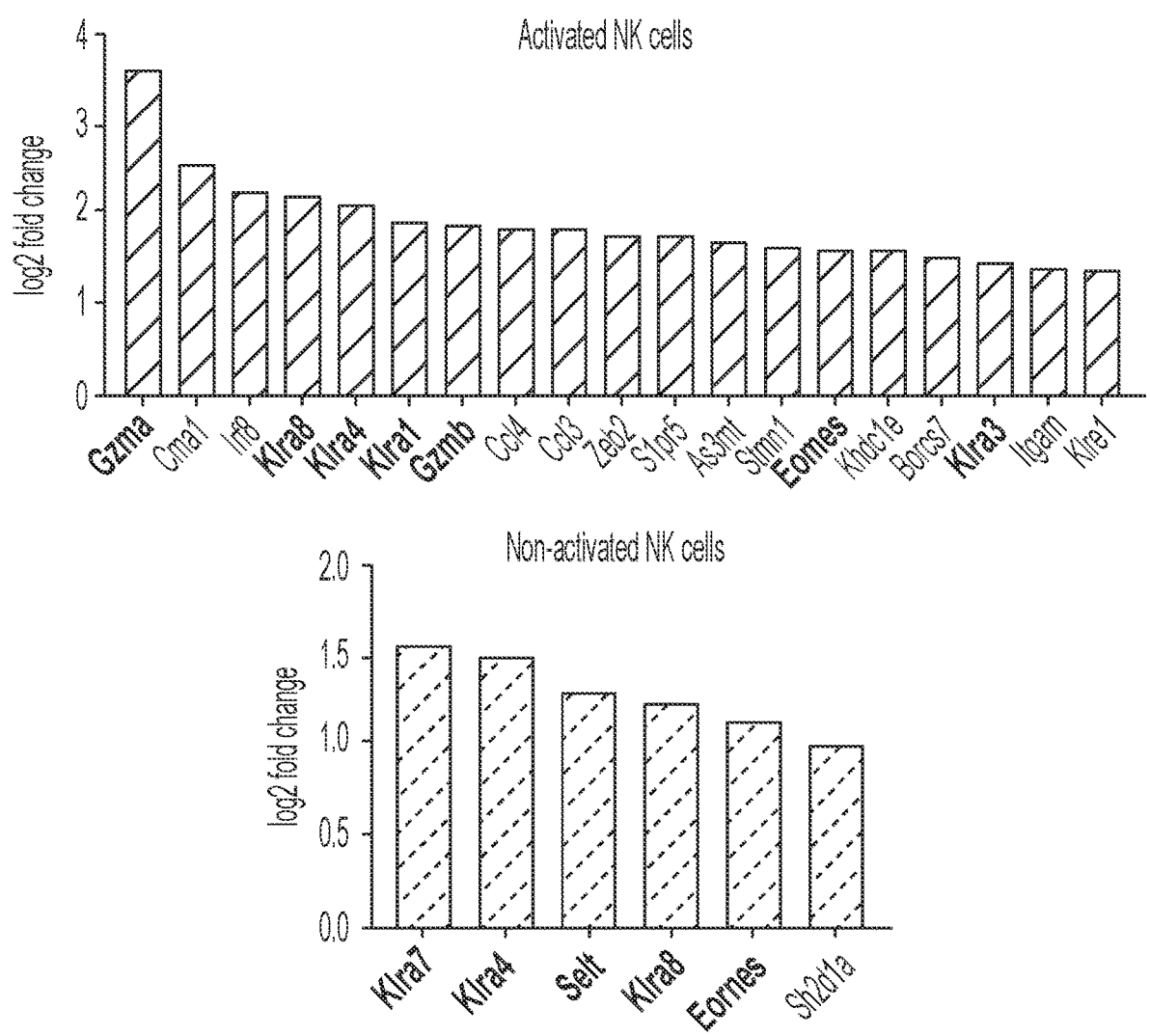

FIG. 29 (cont.)C
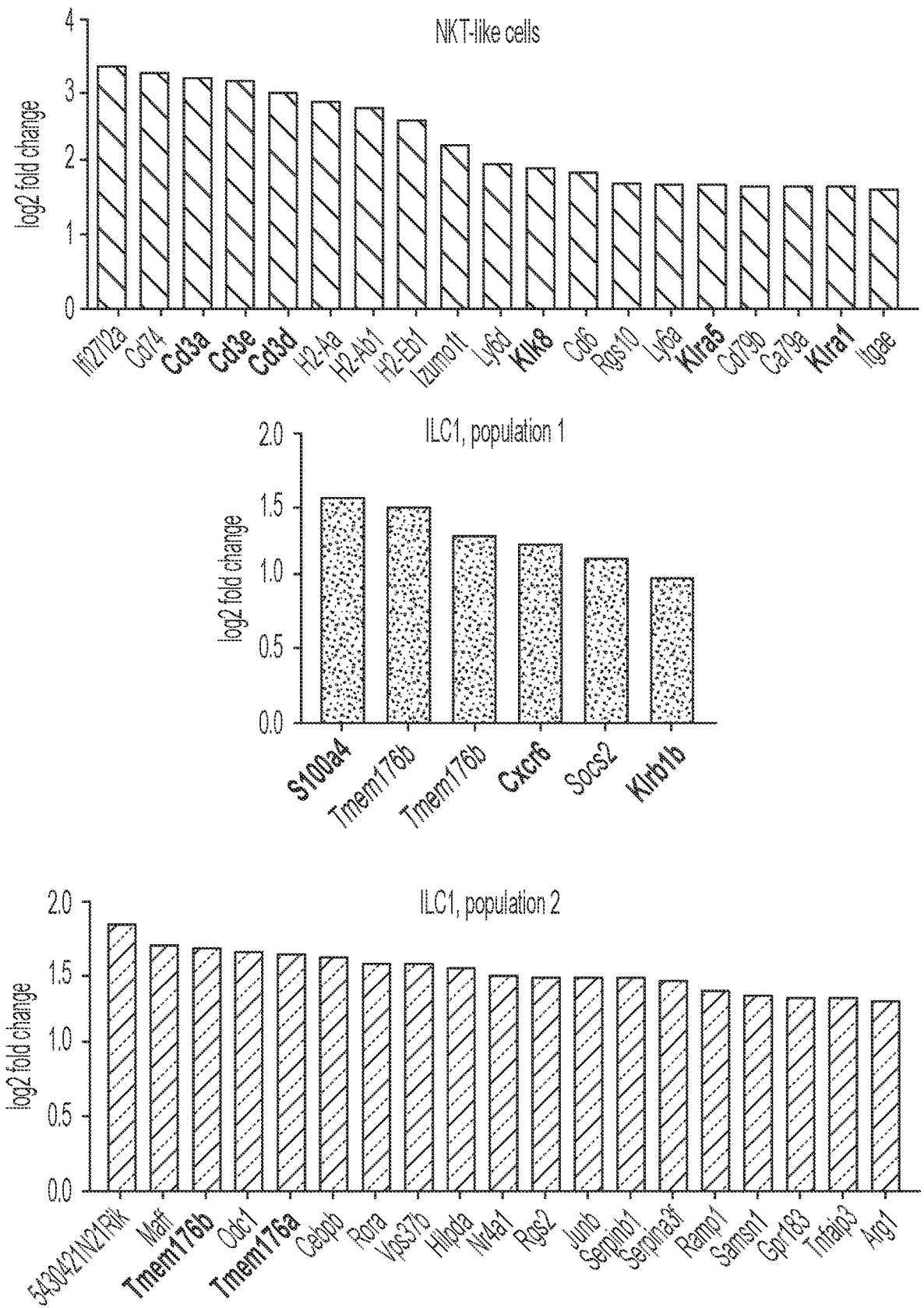

FIG. 30
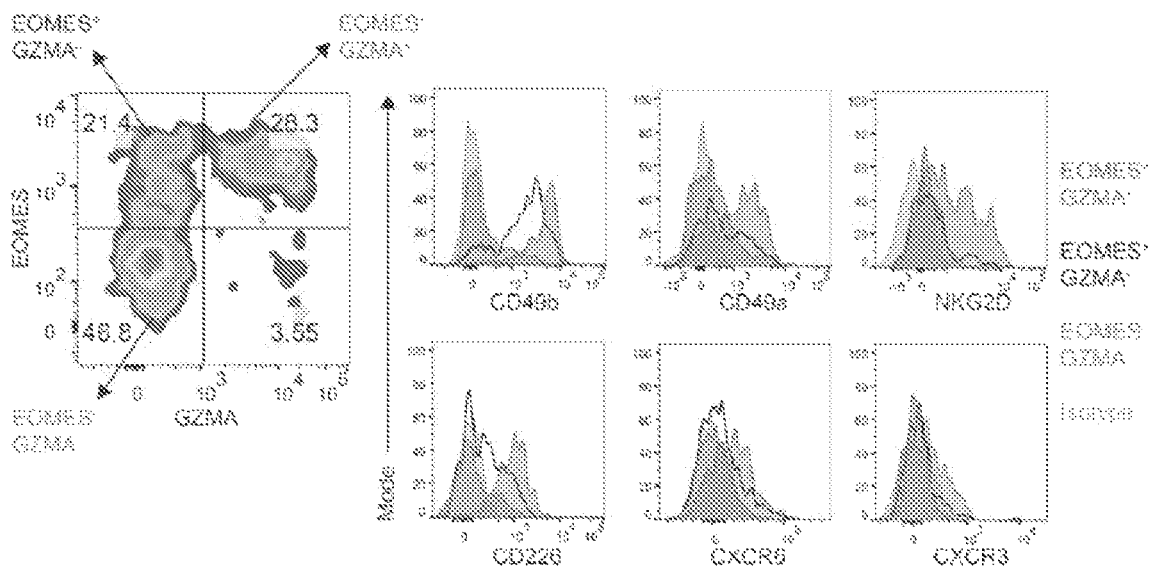
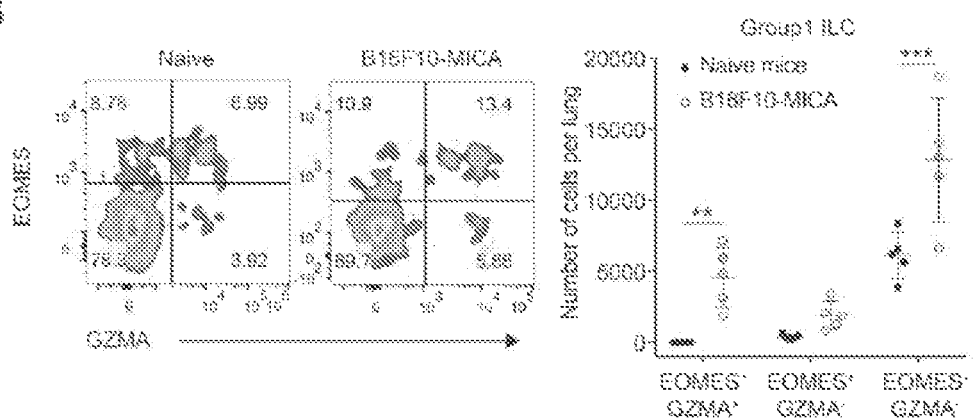
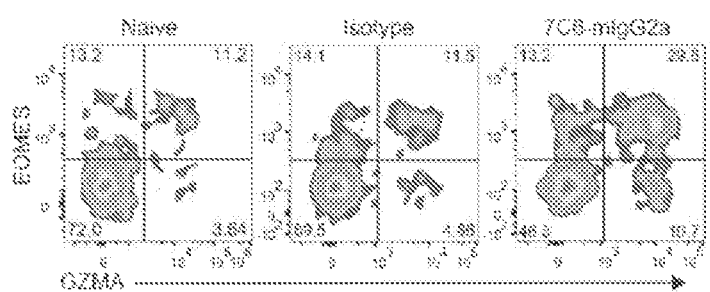

FIG. 31
A
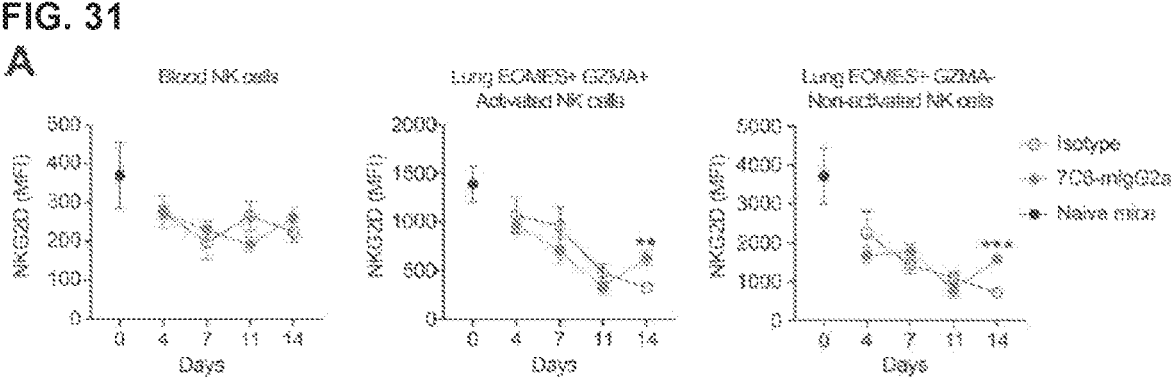
B
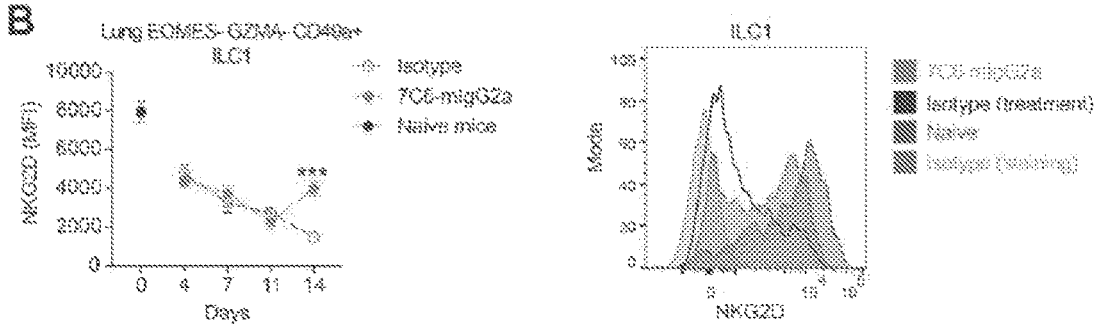

FIG. 32
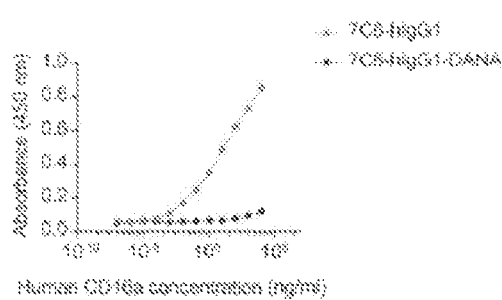
A
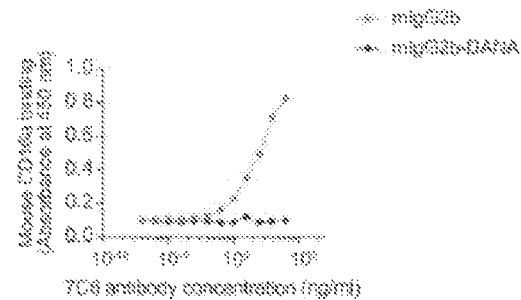
B
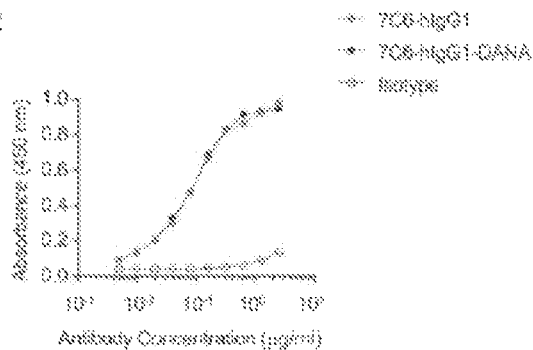
C
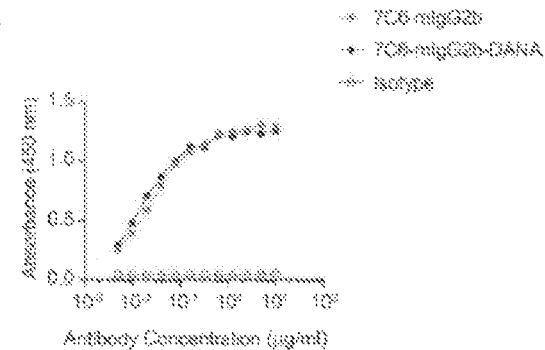
D

FIG. 36
A
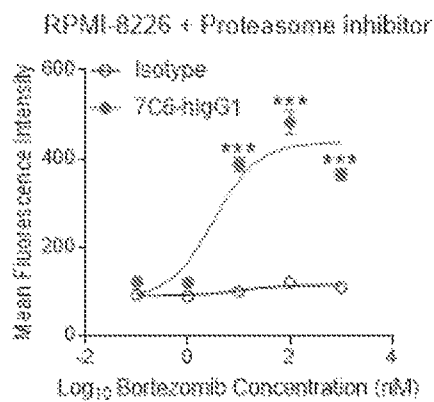
B
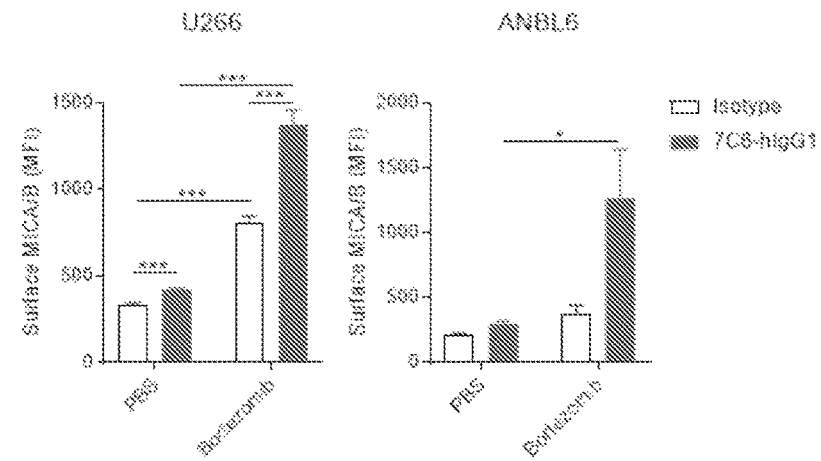
C
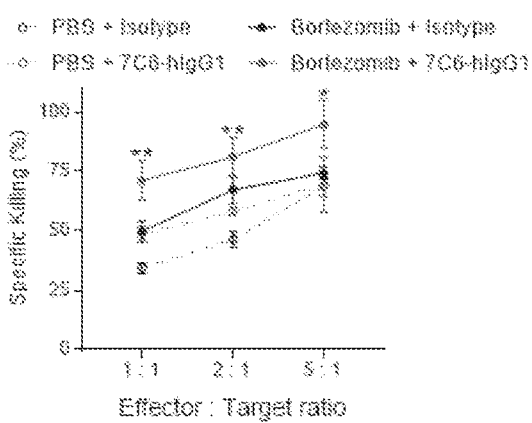

COMPOSITIONS AND METHODS FOR INHIBITION OF MICA/B SHEDDING

CROSS-REFERENCE TO RELATED APPLICATIONS

This application is the U.S. national phase of International Patent Application No. PCT/US2019/0333793, filed on 22 May 2018, which claims the benefit of U.S. Provisional Application Ser. No. 62/509,671, filed on 22 May 2017; the entire contents of each of said applications are incorporated herein in their entirety by this reference.

GOVERNMENT SUPPORT

This invention was made with government support under P30 CA06516 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 26, 2021, is named 5031461-83US2_SL.txt and is 55,947 bytes in size.

TECHNICAL FIELD

This invention relates to therapeutic compositions (e.g., antibodies and antibody fragments) related to human subjects.

BACKGROUND

The stress proteins MICA and MICB (MICA/B) are expressed by many human cancers due to genomic damage, STING pathway activation and aberrant signaling by growth factor receptors (1, 4, 33). Expression of these proteins tags stressed or infected cells for elimination by cytotoxic lymphocytes that express the NKG2D receptor (2, 3, 34). Engagement of the NKG2D receptor triggers NK cell mediated cytotoxicity and provides a costimulatory signal for CD8 T cells and γδ T cells (5, 35). NKG2D-deficient mice have impaired tumor immunity, highlighting the importance of this pathway (6). However, advanced cancers frequently escape from this immune mechanism by proteolytic shedding of MICA/B through the coordinated action of a disulfide isomerase (ERp5) and several different proteases belonging to the ADAM and MMP families (7-9, 36-37). Serum levels of shed MICA are associated with disease progression in many human cancers, including prostate cancer, multiple myeloma, neuroblastoma, kidney cancer, chronic lymphocytic leukemia and melanoma (10-14, 38-41).

It is difficult to block MICA/B shedding in vivo with small molecule inhibitors because multiple proteases with broad substrate specificities contribute to this process (9, 36-37). The membrane-proximal α3 domain is the site of proteolytic shedding, while the membrane-distal α1-α2 domains bind to the NKG2D receptor (15, 16).

Accordingly, there is a need for therapeutic agents which effectively block MICA/B shedding in vivo as an immune-based cancer therapy. Such agents would be useful for diagnostic screening and therapeutic intervention in disease states that are associated with tumor development.

SUMMARY

Provided herein are antibodies, such as monoclonal antibodies, in particular human monoclonal antibodies, that specifically bind WIC class I polypeptide-related sequence A (MICA) and/or B (MICB) α3 domain, the site of proteolytic shedding and have desirable functional properties. These properties include inhibition of MICA/B shedding by human cancer cells, stabilization of cell surface MICA/B for NK cell recognition, and activation of both NKG2D and CD16 Fc receptors on NK cells. MICA antibodies with these properties restore immune activation by stress molecules that activate cytotoxic lymphocytes.

In some embodiments, the monoclonal antibodies, or antigen binding portions thereof, which bind to MICA and/or MICB comprise heavy and light chain variable regions, wherein the heavy chain CDR1, CDR2, and CDR3 sequences comprise SEQ ID NOs: 1-3, respectively. In some embodiments, the monoclonal antibodies, or antigen binding portions thereof, comprise heavy and light chain variable regions wherein light chain CDR1, CDR2, and CDR3 sequences comprise SEQ ID NOs: 4-6, respectively. In some embodiments, the monoclonal antibodies, or antigen binding portions thereof, which bind to MICA and/or MICB comprise heavy and light chain variable regions, the heavy chain CDR1, CDR2, and CDR3 sequences comprising SEQ ID NOs: 1-3, respectively, and the light chain CDR1, CDR2 and CDR3 sequences comprising SEQ ID NOs: 4-6.

Provided herein are isolated monoclonal antibodies, or antigen binding portions thereof, which bind to MICA and/or MICB and comprise a heavy and light chain variable regions, wherein the heavy chain variable region comprises an amino acid sequence which is at least 90%, 95%, 96%, 97%, 98%, 99%, or 100% identical to the amino acid sequence set forth in SEQ ID NO: 7.

Provided herein are isolated monoclonal antibodies, or antigen binding portions thereof, which bind to MICA and/or MICB and comprise heavy and light chain variable regions, wherein the light chain variable region comprises an amino acid sequence which is at least 90%, 95%, 96%, 97%, 98%, 99%, or 100% identical to the amino acid sequence set forth in SEQ ID NO: 8.

In certain embodiments, the anti-MICA and/or anti-MICB antibodies, or antigen binding portions thereof, do not bind to Fc receptors. In certain embodiments, the anti-MICA and/or anti-MICB antibodies, or antigen binding portions thereof, bind to one or more FcγRs, e.g., activating or inhibitory, FcγRs.

In a related aspect, provided herein are nucleic acids encoding the heavy and/or light chain variable regions of the anti-MICA and/or anti-MICB antibodies, or antigen binding portions thereof, expression vectors comprising the nucleic acid molecules, and cells transformed with the expression vectors. Also provided herein is a method of preparing the anti-MICA and/or anti-MICB antibodies, comprising expressing an anti-MICA and/or anti-MICB antibody in a cell and isolating the antibody from the cell.

Also provided herein are compositions comprising anti-MICA and/or anti-MICB antibodies, or antigen binding portions thereof, and a carrier. Also provided herein are immunoconjugates comprising the anti-MICA and/or anti-MICB antibodies described herein, linked to an agent. Also provided herein are kits comprising the anti-MICA and/or anti-MICB antibodies, or antigen binding portions thereof, and instructions for use.

In another aspect, provided herein is a method of stimulating an antigen-specific T cell response comprising contacting the T cell with an anti-MICA and/or anti-MICB antibody, or antigen binding portion thereof, such that an antigen-specific T cell response is stimulated.

Also provided herein is a method of treating cancer, e.g., by immunotherapy, comprising administering to a subject in need thereof a therapeutically effective amount an anti-MICA and/or anti-MICB antibody, or antigen binding portion thereof, bispecific molecule or conjugate comprising the anti-MICA and/or anti-MICB antibody, or composition comprising the anti-MICA and/or anti-MICB antibody, to treat the cancer. In certain embodiments, the cancer is bladder cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and virus-related cancer. In certain embodiments, the cancer is a metastatic cancer, refractory cancer, or recurrent cancer. In certain embodiments, the methods described herein further comprise administering one or more additional therapeutics with an anti-MICA and/or anti-MICB antibody.

In one aspect, a monoclonal antibody, or antigen-binding fragment thereof, wherein the monoclonal antibody comprises a) a heavy chain sequence with at least about 95% identity to a heavy chain sequence selected from the group consisting of the sequences listed in Table 2; and/or b) a light chain sequence with at least about 95% identity to a light chain sequence selected from the group consisting of the sequences listed in Table 2, is provided.

In another aspect, a monoclonal antibody, or antigen-binding fragment thereof, wherein the monoclonal antibody comprises a) a heavy chain CDR sequence with at least about 95% identity to a heavy chain CDR sequence selected from the group consisting of the sequences listed in Table 2; and/or b) a light chain CDR sequence with at least about 95% identity to a light chain CDR sequence selected from the group consisting of the sequences listed in Table 2, is provided.

In still another aspect, a monoclonal antibody, or antigen-binding fragment thereof, wherein the monoclonal antibody comprises a) a heavy chain sequence selected from the group consisting of the sequences listed in Table 2; and/or b) a light chain sequence selected from the group consisting of the sequences listed in Table 2, is provided.

In yet another aspect, a monoclonal antibody, or antigen-binding fragment thereof, wherein the monoclonal antibody comprises a) a heavy chain CDR sequence selected from the group consisting of the sequences listed in Table 2; and/or b) a light chain CDR sequence selected from the group consisting the sequences listed in Table 2, is provided.

Numerous embodiments are further provided that can be applied to any aspect of the present invention described herein. For example, in one embodiment, the monoclonal antibody, or antigen-binding fragment thereof, is chimeric, humanized, composite, murine, or human. In another embodiment, the monoclonal antibody, or antigen-binding fragment thereof, is detectably labeled, comprises an effector domain, comprises an Fc domain, and/or is selected from the group consisting of Fv, Fav, F(ab')2, Fab', dsFv, scFv, sc(Fv)2, and diabodies fragments. In still another embodiment, the monoclonal antibody, or antigen-binding fragment thereof, inhibits the shedding of MICA and/or MICB. In yet another embodiment, the monoclonal antibody, or antigen-binding fragment thereof, increases the cell surface density of MICA and/or MICB. The cell may be a cancer cell. In another embodiment, the monoclonal antibody, or antigen-binding fragment thereof, reduces serum concentrations of shed MICA and/or MICB. In still another embodiment, the monoclonal antibody, or antigen-binding fragment thereof, restores immune activation by stress molecules that activate cytotoxic lymphocytes. In yet another embodiment, the monoclonal antibody, or antigen-binding fragment thereof, enhances the tumor immunity mediated by the cytotoxic lymphocytes. The tumor immunity may be enhanced through activation of NKG2D receptor and/or CD16 Fc receptor on the cytotoxic lymphocytes. The cytotoxic lymphocytes may be NK cells or macrophages. In another embodiment, the monoclonal antibody, or antigen-binding fragment thereof, specifically binds MICA α3 domain and/or MICB α3 domain. In still another embodiment, the monoclonal antibody, or antigen-binding fragment thereof, does not interfere with NKG2D binding to MICA and/or MICB.

In yet another embodiment, the monoclonal antibody, or antigen-binding fragment thereof, does not bind to Fc receptors. In another embodiment, the monoclonal antibody, or antigen-binding fragment thereof, binds to one or more FcγRs, e.g., activating or inhibitory FcγRs In another aspect, an immunoglobulin heavy and/or light chain selected from the group consisting of immunoglobulin heavy and light chain sequences listed in Table 2, is provided.

In still another aspect, an isolated nucleic acid molecule that hybridizes, under stringent conditions, with the complement of a nucleic acid encoding a polypeptide selected from the group consisting of polypeptide sequences listed in Table 2, or a sequence with at least about 95% homology to a nucleic acid encoding a polypeptide selected from the group consisting of the polypeptide sequences listed in Table 2, is provided.

In yet another aspect, a vector comprising the isolated nucleic acid described herein, is provided.

In another aspect, a host cell which comprises the isolated nucleic acid described herein, comprises the vector described herein, expresses the antibody, or antigen-binding fragment thereof, described herein, is provided.

In still another aspect, a device or kit comprising at least one monoclonal antibody, or antigen-binding fragment thereof, described herein, the device or kit optionally comprising a label to detect the at least one monoclonal antibody, or antigen-binding fragment thereof, or a complex comprising the monoclonal antibody, or antigen-binding fragment thereof, is provided.

In yet another aspect, a composition comprising at least one monoclonal antibody, or antigen-binding fragment thereof, described herein, and a carrier, is provided.

In another aspect, a method of producing at least one monoclonal antibody, or antigen-binding fragment thereof, described herein, which method comprises the steps of: (i) culturing a transformed host cell which has been transformed by a nucleic acid comprising a sequence encoding at least one monoclonal antibody described herein under conditions suitable to allow expression of said monoclonal antibody, or antigen-binding fragment thereof; and (ii) recovering the expressed monoclonal antibody, or antigen-binding fragment thereof, is provided.

In still another aspect, an immune-conjugate comprising at least one monoclonal antibody, or antigen-binding fragment thereof, described herein, linked to an agent, is provided. In one embodiment, the agent is a cytotoxic agent, e.g., a chemotherapeutic agent, a biologic agent, a toxin, and a radioactive isotope.

In yet another aspect, a method of stimulating an antigen-specific T cell response comprising contacting the T-cell with at least one monoclonal antibody, or antigen-binding fragment thereof, described herein, such that an antigen-specific T cell response is stimulated.

In another aspect, a method of detecting the presence or level of an MICA and/or MICB polypeptide comprising obtaining a sample and detecting said polypeptide in the sample by use of at least one monoclonal antibody, or antigen-binding fragment thereof, described herein.

As described above, certain embodiments are applicable to any method described herein. For example, in one embodiment, the at least one monoclonal antibody, or antigen-binding fragment thereof, forms a complex with an MICA and/or MICB polypeptide and the complex is detected in the form of an enzyme linked immunosorbent assay (ELISA), radioimmune assay (MA), immunochemically, Western blot, or using an intracellular flow assay.

In still another aspect, a method for monitoring the progression of a disorder associated with aberrant MICA and/or MICB expression in a subject, the method comprising a) detecting in a subject sample at a first point in time the level of MICA and/or MICB using at least one monoclonal antibody, or antigen-binding fragment thereof, described herein; b) repeating step a) at a subsequent point in time; and c) comparing the level of MICA and/or MICB detected in steps a) and b) to monitor the progression of the disorder in the subject, is provided.

As described above, certain embodiments are applicable to any method described herein. For example, in one embodiment, between the first point in time and the subsequent point in time, the subject has undergone treatment to ameliorate the disorder.

In yet another aspect, a method for predicting the clinical outcome of a subject afflicted with a disorder associated with aberrant MICA and/or MICB expression, the method comprising a) determining the level of MICA and/or MICB in a subject sample using at least one monoclonal antibody, or antigen-binding fragment thereof, described herein; b) determining the level of MICA and/or MICB in a sample from a control subject having a good clinical outcome using the at least one monoclonal antibody, or antigen-binding fragment thereof; and c) comparing the level of MICA and/or MICB in the subject sample and in the sample from the control subject; wherein a significantly lower level of MICA and/or MICB in the subject sample as compared to the level in the sample from the control subject is an indication that the subject has a poor clinical outcome, is provided.

In another aspect, a method of assessing the efficacy of a therapy for a disorder associated with aberrant MICA and/or MICB expression in a subject, the method comprising a) determining the level of MICA and/or MICB using at least one monoclonal antibody, or antigen-binding fragment thereof, described herein, in a first sample obtained from the subject prior to providing at least a portion of the therapy to the subject, and b) determining the level of MICA and/or MICB in a second sample obtained from the subject following provision of the portion of the therapy, wherein a significantly higher level of MICA and/or MICB in the second sample, relative to the first sample, is an indication that the therapy is efficacious for inhibiting the disorder in the subject, is provided.

In still another aspect, a method of assessing the efficacy of a test compound for inhibiting a disorder associated with aberrant MICA and/or MICB expression in a subject, the method comprising a) determining the level of MICA and/or MICB using at least one monoclonal antibody, or antigen-binding fragment thereof, described herein, in a first sample obtained from the subject and exposed to the test compound; and b) determining the level of MICA and/or MICB in a second sample obtained from the subject, wherein the second sample is not exposed to the test compound, and a significantly higher level of MICA and/or MICB, relative to the second sample, is an indication that the test compound is efficacious for inhibiting the disorder in the subject, is provided.

As described above, certain embodiments are applicable to any method described herein. For example, in one embodiment, the first and second samples are portions of a single sample obtained from the subject or portions of pooled samples obtained from the subject. In another embodiment, the disorder is a cancer. In still another embodiment, the cancer is selected from the group consisting of bladder cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and virus-related cancer. In yet another embodiment, the sample comprises cells, serum, peritumoral tissue, and/or intratumoral tissue obtained from the subject. In another embodiment, the significantly lower level of MICA and/or MICB comprises an at least twenty percent increase between the level of MICA and/or MICB in the subject sample relative to the normal level of MICA and/or MICB in the sample from the control subject. In still another embodiment, the significantly higher level of MICA and/or MICB comprises an at least twenty percent decrease of the level of MICA and/or MICB. In yet another embodiment, the subject is a human.

In yet another aspect, a method of treating a subject afflicted with cancer comprising administering to the subject at least one monoclonal antibody, or antigen-binding fragment thereof, described herein, is provided.

In another aspect, a method of treating a subject afflicted with cancer comprising administering to the subject at least one monoclonal antibody, or antigen-binding fragment thereof, described herein, in combination with an agent that enhances MICA and/or MICB expression. In one embodiment, the agent enhances MICA and/or MICB expression through genomic damage pathways. In another embodiment, the agent is selected from the group consisting of radiation therapy, antibody-drug conjugate, HDAC inhibitor, proteasome inhibitor, chemotherapy, alkylating agent, and topoisomerase inhibitor. In still another embodiment, the HDAC inhibitor is selected from the group consisting of hydroxamic acid, vorinostat, suberoylanilide hydroxamic acid, trichostatin A, LAQ824, panobinostat, belinostat, ITF2357, cyclic tetrapeptide, depsipeptide, benzamide, Eetinostat, MGCD0103, short-chain aliphatic acids, valproic acid, phenyl butyrate, AN-9, pivanex, CHR-3996, and CHR-2845. In yet another embodiment, the proteasome inhibitor is selected from the group consisting of bortezomib, NPI-0052, carfilzomib, CEP 18770, and MLN9708, e.g., bortezomib. In another embodiment, the chemotherapy agent is dacarbazine. In still another embodiment, the agent administered before, after, or concurrently with the at least one monoclonal antibody, or antigen-binding fragment thereof. In yet another embodiment, the at least one monoclonal antibody, or antigen-binding fragment thereof, and the agent, have a synergistic effect on reducing the number of proliferating cells in the cancer and/or reduces the volume or size of a tumor of the cancer. In another embodiment, the at least one monoclonal antibody, or antigen-binding fragment thereof, and the agent, have a synergistic effect on reducing the metastases of cancer cells. In still another embodiment, the at least monoclonal antibody, or antigen-binding fragment thereof, and the agent, have a synergistic effect on enhancing the infiltration of NK cells into a tumor. In yet another embodiment, the infiltrating NK cells are activated and cytotoxic. In another embodiment, the infiltrating NK cells express cytotoxicity genes selected from the group consisting of eomesodermin, granzyme A, granzyme B, and perforin 1.

As described above, certain embodiments are applicable to any method described herein. For example, in one embodiment, the at least one monoclonal antibody, or antigen-binding fragment thereof, is conjugated to a cytotoxic agent. In another embodiment, the cytotoxic agent is selected from the group consisting of a chemotherapeutic agent, a biologic agent, a toxin, and a radioactive isotope. In yet another embodiment, the at least one monoclonal antibody, or antigen-binding fragment thereof, reduces the number of proliferating cells in the cancer and/or reduces the volume or size of a tumor of the cancer. In another embodiment, the at least one monoclonal antibody, or antigen-binding fragment thereof, reduces the metastases of cancer cells. In still another embodiment, the at least monoclonal antibody, or antigen-binding fragment thereof, enhances the infiltration of NK cells into a tumor. In yet another embodiment, the infiltrating NK cells are activated and cytotoxic. In another embodiment, the infiltrating NK cells express cytotoxicity genes selected from the group consisting of eomesodermin, granzyme A, granzyme B, and perforin 1. In still another embodiment, the at least one monoclonal antibody, or antigen-binding fragment thereof, and/or the agent is administered in a pharmaceutically acceptable formulation. In yet another embodiment, the method described herein, further comprising administering to the subject a therapeutic agent or regimen for treating cancer. In another embodiment, the method described herein, further comprising administering to the subject an additional therapy selected from the group consisting of immunotherapy, checkpoint blockade, cancer vaccines, chimeric antigen receptors, chemotherapy, radiation, target therapy, and surgery. In another embodiment, cancer cells in the subject express MICA and/or MICB. In still another embodiment, the cancer is selected from the group consisting of bladder cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and virus-related cancer. In yet another embodiment, the cancer is a metastatic cancer, refractory cancer, or recurrent cancer. In another embodiment, the subject is an animal model of cancer. In still another embodiment, the animal model is a mouse model, optionally wherein the mouse model is a humanized mouse model. In yet another embodiment, the subject is a mammal. In another embodiment, the mammal is a humanized mouse or a human. In still another embodiment, the mammal is a human.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

BRIEF DESCRIPTION OF THE DRAWINGS

FIG. 4. Depicts data indicating that MICA antibody shows therapeutic activity in metastasis model with human tumor cells and human NK cells. NSG mice were reconstituted with IL-2 pre-treated human NK cells. NK cell survival was supported by injection of human IL-2 on alternate days, until day 8. One day after NK cell transfer, human A2058 melanoma cells were injected intravenously into all mice. 7C6-hIgG1 or isotype control antibodies were administered on days 1 and 2 following tumor inoculation and then once per week. On day 30, mice were euthanized, and metastases were counted in different organs. (A) Outline of the experimental procedure. (B) MICA antibody (7C6-hIgG1) reduces number of lung metastases in the presence of human NK cells. Data are mean±SD of pooled data from two independent experiments. (C) Quantification of liver metastases by stereomicroscopy. MICA antibody shows significant therapeutic activity against liver metastases even in the absence of NK cells; this activity is enhanced by NK cells. Data are mean±SD of pooled data from two independent experiments. (D) MICA antibody treatment increases the survival of mice that were reconstituted with human NK cells and inoculated with human melanoma. Same conditions as in (A). Data are pooled from two independent experiments. (E) Liposomal clodronate (or control liposomes) were injected intravenously to deplete liver macrophages (same day as tumor cell inoculation and then once per week). Liver metastases were quantified by stereomicroscopy 3 weeks after tumor inoculation. Tumor cell inoculation and antibody treatments were done as shown in (A) but without NK cell reconstitution and with analysis of metastases a week earlier. Data are mean±SD of pooled data from two independent experiments. (F) Cartoon illustrating proposed therapeutic mechanism. *P<0.05, P<0.01, and *P<0.001, calculated by two-way ANOVA with Bonferroni's post hoc test (B) and (C) or multiple two-tailed unpaired Student's t test (E). In (D), the comparison of survival curves is by Mantel-Cox test.

FIG. 5. Depicts data indicating the specificity of MICA antibodies. (A) Comparison of MICA binding by antibodies 7C6, 1C2 and 6F11. Binding by antibody 6D4 (specific for MICA α1-α2 domains) is shown for comparison. Antibody binding to immobilized MICA extracellular domain was quantified using a biotinylated anti-mouse IgG antibody followed by Europium-labeled streptavidin. One representative of three independent experiments. (B) Antibodies bind to all tested MICA alleles (alleles 002, 008, 009 and 018) as well as to MICB (allele 005). One representative of three independent experiments. (C) Definition of antibody isotypes using secondary antibodies specific for the indicated heavy chain Fc regions by ELISA. One representative of three independent experiments. (D) Alignment of α3 domain protein sequences for tested MICA and MICB alleles. FIG. 5 Panel D discloses SEQ ID NOS 17-20 and 31, respectively, in order of appearance.

FIG. 9. Depicts data demonstrating that antibodies specific for the MICA/B α3 domain do not inhibit NKG2D receptor binding. (A) Streptavidin-coated beads were incubated with mono-biotinylated MICA (allele 008). Binding of Alexa488-conjugated human NKG2D-Fc dimer (10 μg/ml) was assessed in the presence of MICA α3 domain-specific antibodies (1C2, 7C6, 6F11). Antibody 6D4 which binds to the MICA α1-α2 domains was used as a positive control for NKG2D blockade. Data representative of two independent experiments. (B) Human NKGD2 binding to B16F10-MICA. B16F10 cells were transduced with a control vector or with a vector that drives MICA expression. $1\times10^5$ cells were stained with 10 μg/ml human NKG2D-Fc chimera or a human IgG1 isotype control antibody and binding was measured using an APC-conjugated anti-human IgG antibody. Data representative of two independent experiments. (C) MICA α3 domain specific antibodies did not inhibit NKG2D binding to B16F10-MICA cells. The indicated antibodies and human NKG2D-Fc chimeric proteins were added simultaneously at 10 g/ml, with exception of 'secondary alone' samples that were incubated only with the APC-conjugated human IgG1 antibody used to detect NKG2D binding to B16F10-MICA cells. Data representative of two independent experiments.

The endogenous MICA antibodies were analyzed by ELISA using secondary antibodies specific for the indicated IgG isotypes. Data representative of two independent experiments. (J) Analysis of potential interference by endogenous MICA antibodies on detection of shed MICA by ELISA. Detection of 2000 pg/ml MICA allele 008 with increasing concentrations of endogenous antibodies isolated using protein G beads. Data representative of two independent experiments. Statistics are as follows: *p<0.05, p<0.01, *p<0.001, calculated by two-way ANOVA with Bonferroni's post-hoc test (D-E) or multiple two-tailed unpaired Student's t test (F and H).

Figure 13:
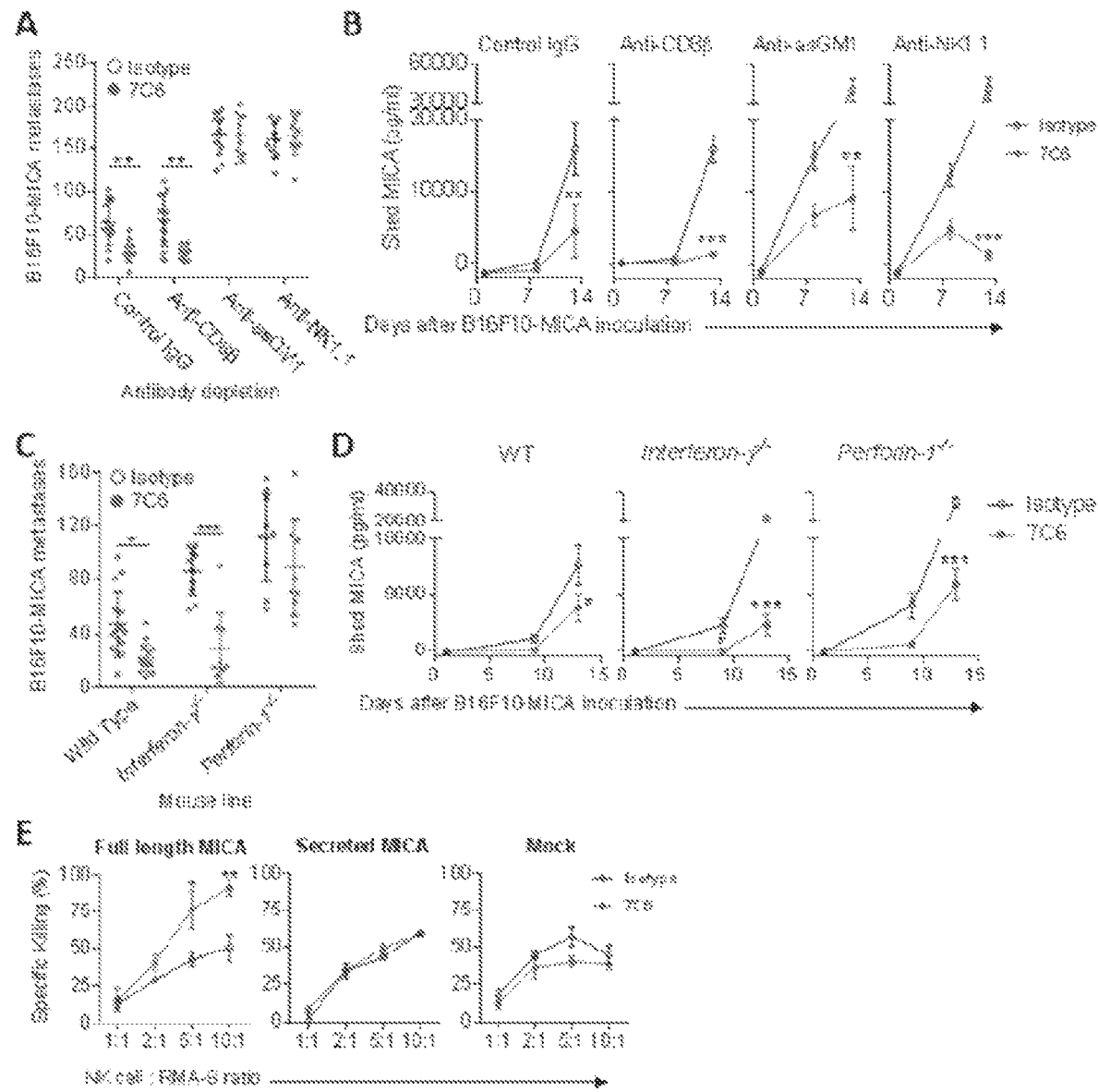

FIG. 13. Depicts data indicating that NK cell mediated cytotoxicity is essential for the therapeutic activity of MICA antibody. (A) Quantification of pulmonary metastases in mice that were CD8 T cell depleted (α-CD8β) or NK cell depleted (α-NK1.1 and α-asGM1). Data indicate mean±SD pooled from two independent experiments. NK cell (anti-asGM1 or anti-NK1.1) but not CD8 T cell (anti-CD8(3) depletion abrogated the therapeutic activity of the 7C6-mIgG2b MICA antibody. B16F10-MICA tumor cells were injected iv, mice were treated with 7C6 or isotype control antibodies and lung metastases were counted on day 14. (B) 7C6 antibody reduced shed MICA in the sera of wild-type C57BL/6 mice that were inoculated intravenously with B16F10-MICA cells. Mice were also treated with a control IgG antibody, anti-CD8β, anti-NK1.1 and anti-asGM1 antibodies, which were administered on days −1, 0 and 7 relative to tumor cell inoculation (to deplete either CD8 T cells or NK cells). 7C6 or isotype control antibodies were given on days 1, 2, 7, and 10. Mean±SEM for 5 mice per group; data are representative of two independent experiments. (C) Perforin but not interferon-γ expression is required for therapeutic activity of 7C6 MICA antibody. B16F10-MICA tumor cells were injected i.v. into WT, $Prf1^{-/-}$ and $Ifng^{-/-}$ mice. Mice were treated with 7C6 MICA or isotype control antibodies and lung metastases were quantified on day 14. (D) Analysis of shed MICA for experiment shown in (C) for at least 5 mice per group; mean±SEM are shown. Data are representative of two independent experiments. (E) 7C6-mIgG2b antibody enhances NK cell-mediated cytotoxicity against tumor cells that express full-length MICA, but not against tumor cells that release MICA by exocytosis. $^{51}Cr$ release assay with murine NK cells against RMA-S cell lines transduced with different lentiviruses. Mean±SEM of three replicates (full-length MICA) and four replicates (secreted MICA, mock) per condition. *P<0.05, p<0.01 and *p<0.001, calculated by two-way ANOVA with Bonferroni's post-hoc test. Representative of three independent experiments.

FIG. 14. Depicts the analysis of group 1 ILCs in lung tissue. (A, B) C57BL/6 mice received an i.v. injection of B16F10-MICA cells. On day 7, intravascular immune cells were labeled by i.v. injection of an APC-conjugated anti-CD45.2 antibody ~1-3 minutes prior to euthanasia. Lungs were then dissociated to obtain single cell suspensions, followed by labeling with a PE-Cy7-conjugated CD45.2 antibody as well as other antibodies for analysis by flow cytometry. (A) APC-CD45.2 labeling identified intravascular immune cells, while PE-Cy7-CD45.2 labeling was used to define tissue-infiltrating cells. Group 1 ILCs were identified as NK1.1 and NKp46 positive cells that were CD3ε and TCRβ negative. Blood NK cells were CD69 negative, while lung group 1 ILCs expressed CD69, a marker of tissue residency, confirming that this labeling approach identified distinct NK cell populations. Doublets and dead cells were gated out prior to analysis of leukocyte populations. (B) Percentages and absolute numbers of tissue-infiltrating group 1 ILCs based on the gating strategy described in (A). A larger number of tissue-resident group 1 ILCs were present following i.v. injection of B16F10 tumor cells that expressed full-length MICA while group 1 ILCs were not increased following injection of B16F10 cells that secreted MICA or were transduced with the control lentiviral vector (mock). Data are mean+/−SD from pooled data of two independent experiments. *p<0.05 calculated by one-way ANOVA with Dunnett's post-hoc test. (C) NKG2D expression on the cell surface of lung group 1 ILCs and intravascular NK cells. NKG2D expression was reduced on tissue-resident group 1 ILCs in all groups that received i.v. injection of B16F10 tumor cells. NKG2D expression was low on intravascular NK cells, compared to the lung-resident group 1 ILCs. Data are mean+/−SD from pooled data of two independent experiments. ***P<0.001, calculated by one-way ANOVA with Dunnett's post-hoc test.

FIG. 15. Depicts the impact of MICA antibody treatment on NKG2D expression by NK cells as well as B16F10 tumor cells within lung metastases. (A) The CD45.2 labeling approach (APC vs. PE-Cy7) described in FIG. 14 was used to examine the impact of MICA antibody treatment on NKG2D expression by NK cells. 7C6-mIgG2a antibody treatment increased NKG2D levels on lung-infiltrating NK cells compared to the isotype control antibody. 7C6-mIgG2a treatment had no effect on NKG2D levels on intravascular NK cells. (B-F) The ZsGreen marker expressed by B16F10-MICA cells was used to examine the impact of MICA antibody treatment on the tumor population within lung metastases. (B) Tumor cells were defined as ZsGreen$^+$ cells, after gating out leukocytes, in single cell suspensions from dissociated lung tissue. (C) 7C6-mIgG2a treatment increased apoptosis of tumor cells based on labeling with an antibody specific for active caspase-3. Data are mean+/−SD and are representative of two independent experiments. *P<0.001, calculated by unpaired Student's t test. (D) 7C6-mIgG2a treatment also increased expression of $H2$-$K^b$, potentially due to interferon-γ secretion by NK cells or other immune cells. Data are mean+/−SD and are representative of two independent experiments. *P<0.001, calculated by unpaired Student's t test. (E, F) 7C6-mIgG2a treatment also reduced the percentage (E) as well as absolute numbers (F) of B16F10-MICA tumor cells within lung tissue. (E, F) Data are mean+/−SD and are representative of two independent experiments. ***P<0.001, calculated by unpaired Student's t test.

Figure 16:
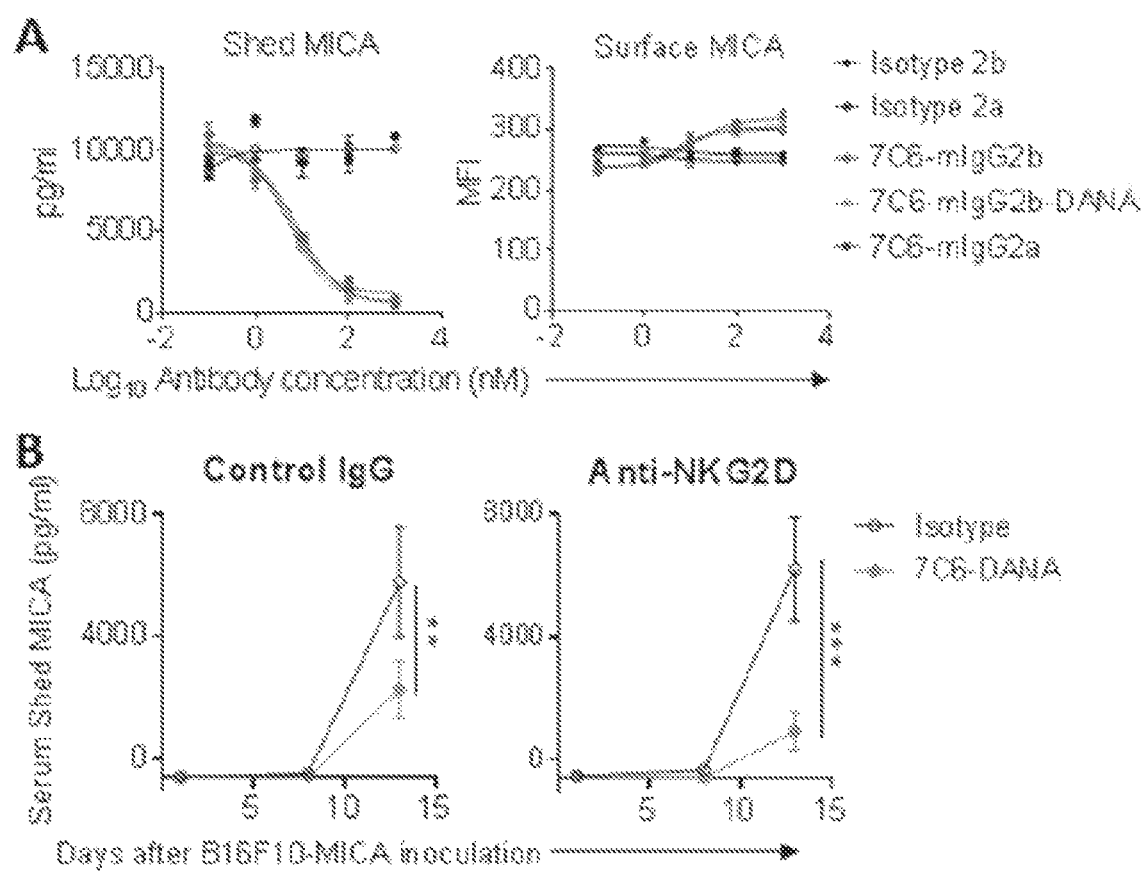

FIG. 16. Depicts data demonstrating that the IgG Fc region does not alter the ability of MICA antibody to inhibit MICA shedding. (A) B16F10-MICA cells were incubated for 24 hours with the indicated doses of 7C6 antibody with distinct Fc regions (7C6-mIgG2a, 7C6-mIgG2b, 7C6-mIgG2b-DANA) or appropriate isotype control antibodies. Shed MICA in the supernatant was analyzed by ELISA (left), and surface MICA levels (right) were determined by flow cytometry following staining with 6D4-PE antibody. Mean±SEM for triplicates per condition were used for non-linear regression analysis. Data are representative of three independent experiments. (B) 7C6 antibody with mutated Fc region can inhibit MICA shedding in vivo. Analysis of shed MICA in the sera of mice following injection of B16F10-MICA cells and treatment with 7C6-mIgG2b-DANA or isotype control antibodies. Data are mean±SEM of at least 5 mice per group and are representative of two independent experiments. p<0.01, *P<0.001, calculated by two-way ANOVA with Bonferroni's post-hoc test.

FIG. 17. Depicts data showing the contribution of NKG2D and Fc receptors to the therapeutic activity of MICA antibody in subcutaneous melanoma model. B16F10-MICA tumor cells were implanted subcutaneously into Igh$^{-/-}$ mice. Mice were treated with 200 µg of 7C6-mIgG2a, 7C6-DANA mutant or isotype control antibody at days 5, 7 and 9. Mice also received an NKG2D blocking antibody clone HMG2D (200 µg) or appropriate isotype control antibody. (A) Analysis of tumor growth in the six experimental groups. Asterisks indicate statistical significance for comparison of tumor size on day 14 for either version of 7C6 antibody (7C6-mIgG2a or 7C6-DANA mutant) versus the isotype control antibody. Data are mean±SEM of at least 5 mice per group and are representative of two independent experiments. *$p<0.05$, ***$p<0.001$, calculated by two-way ANOVA with Bonferroni's post-hoc test. The asterisks indicate the p values on day 14. (B) Shed MICA in the serum on day 9. Data are mean+/−SD and are pooled from two independent experiments. *$p<0.05$, $p<0.01$, *$p<0.001$, calculated by two-way ANOVA with Bonferroni's post-hoc test.

Figure 18:
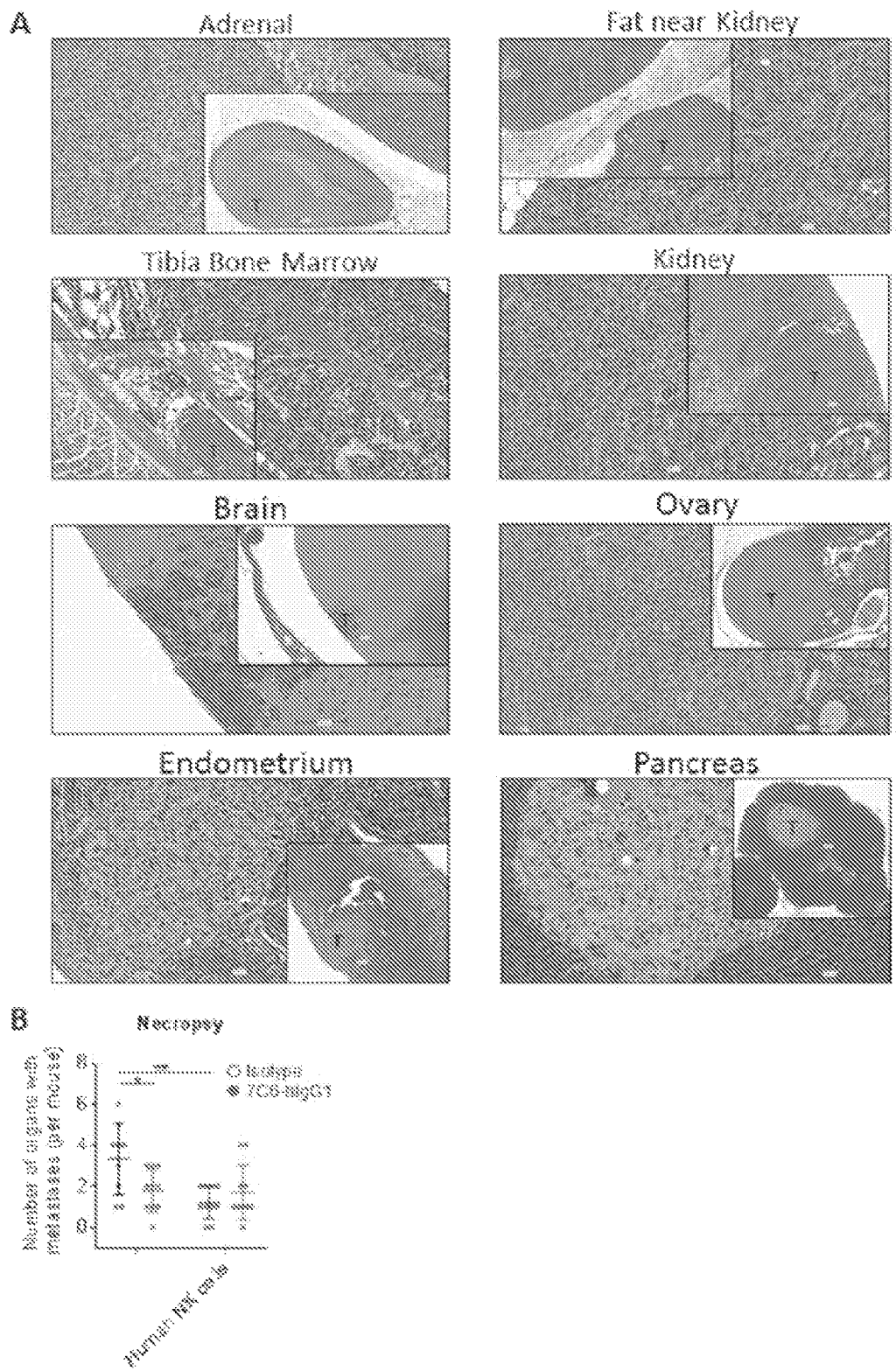
Figure 18:
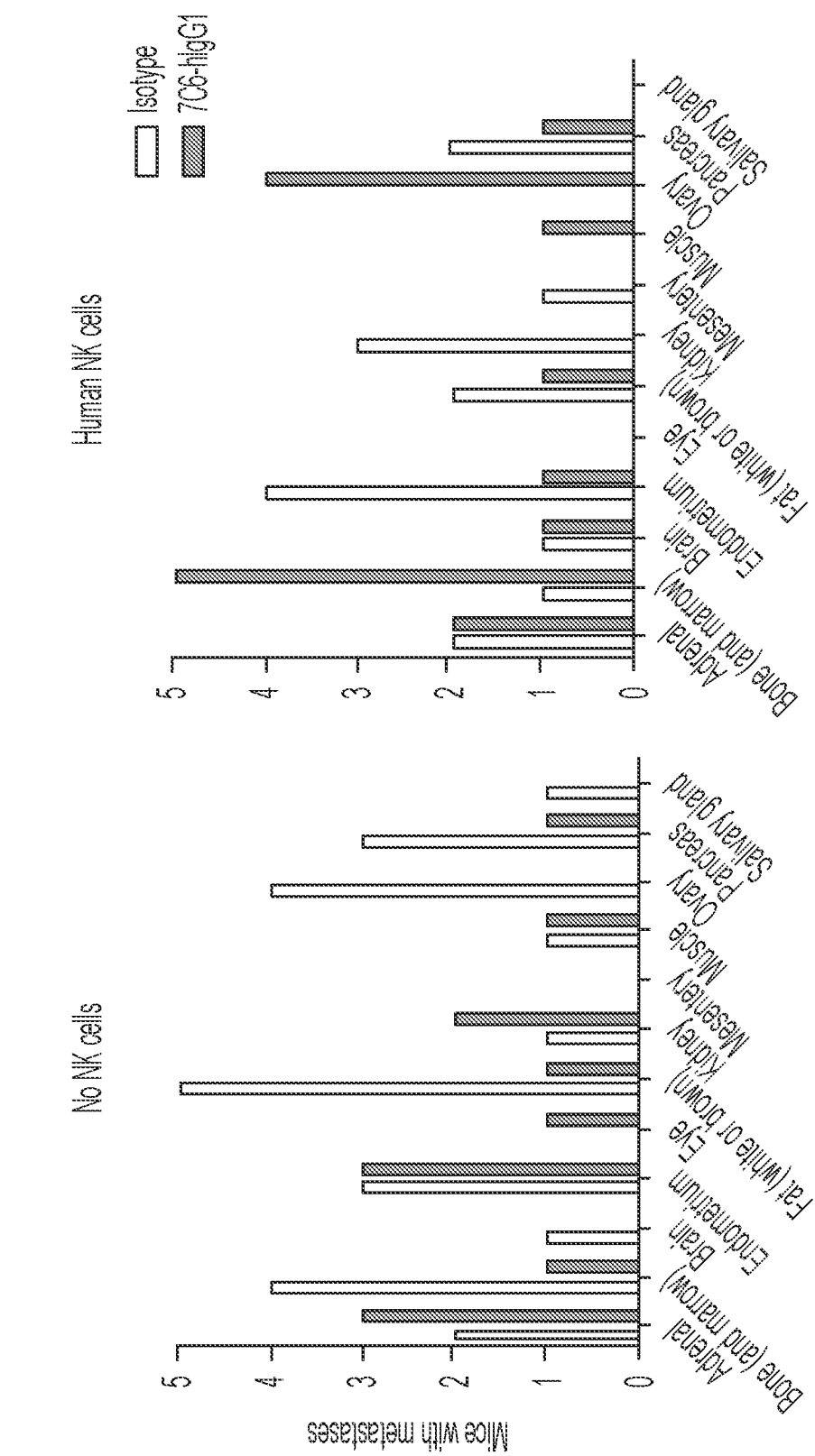
Figure 18:
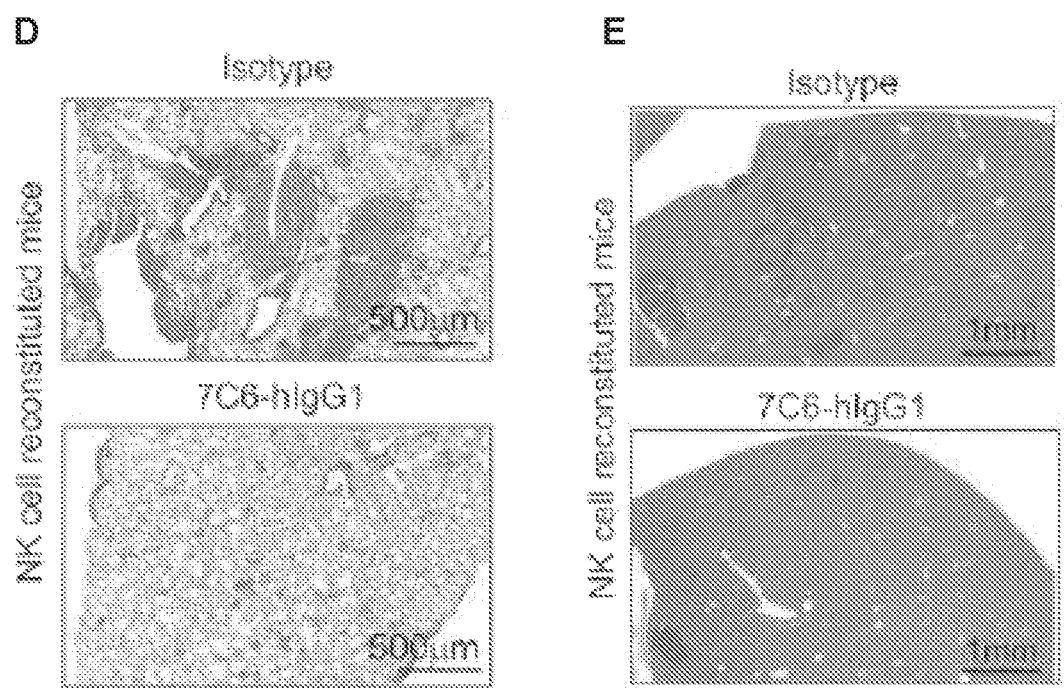

FIG. 18. Depicts data demonstrating that the MICA antibody inhibits metastases by human melanoma cell line in NSG mice. NSG mice were reconstituted with human NK cells or did not receive NK cells (naïve). One day later, mice were inoculated i.v. with human A2058 melanoma cells and treated with 7C6-hIgG1 or isotype control antibodies (days 1, 2, 7, 14, and 21). Euthanasia and analysis of metastases by necropsy were performed on day 30. (A) Human A2058 melanoma cells form widespread metastases, as analyzed by H&E staining (magnification of 15× and 4×). (B) Quantification of the number of organs bearing metastases. 7C6-hIgG1 antibody significantly reduced metastatic load in the absence of transferred NK cells; reconstitution with human NK cells also significantly reduced the number of organs with metastases. (C) Summary of organs affected by metastases in relationship with treatment conditions, excluding liver and lung. Data are pooled from two independent experiments. (D) Histological analysis (H&E staining) of lung metastases in isotype and 7C6-hIgG1 treatment groups with NK cell transfer (2× magnification). Data are representative of three mice per group. (E) Liver histology (H&E staining) of mice reconstituted with NK cells, inoculated with human melanoma cells and treated with the indicated antibodies. 2× magnification. Data are representative of three mice per group.

FIG. 19. Depicts data showing that the MICA antibody induces activation of liver macrophages. (A) Serum alanine transaminase activity was quantified at four different time points in NSG mice that had or had not been reconstituted with human NK cells and received either 7C6-hIgG1 or isotype control antibodies. Data are mean+/−SEM and are pooled from two independent experiments (total of 10 mice per group). (B-C) Analysis of liver macrophages (Kupffer cells) three weeks after tumor cell inoculation. (B) Analysis of surface markers of Kupffer cells (Ly6Gnegative F4/80high), including CD16/32 (activating Fc receptor) and CD80 (activation marker). (C) 7C6-hIgG1 treatment increased expression of CD80 by Kupffer cells from tumor-bearing mice. Data are mean+/−SD and are pooled from two independent experiments. Statistics are as follows: *$p<0.05$, $p<0.01$, and *$p<0.001$, as calculated by two-way ANOVA, Bonferroni's post-hoc test (A) and multiple two-tailed unpaired Student's t tests (C).

Figure 20:
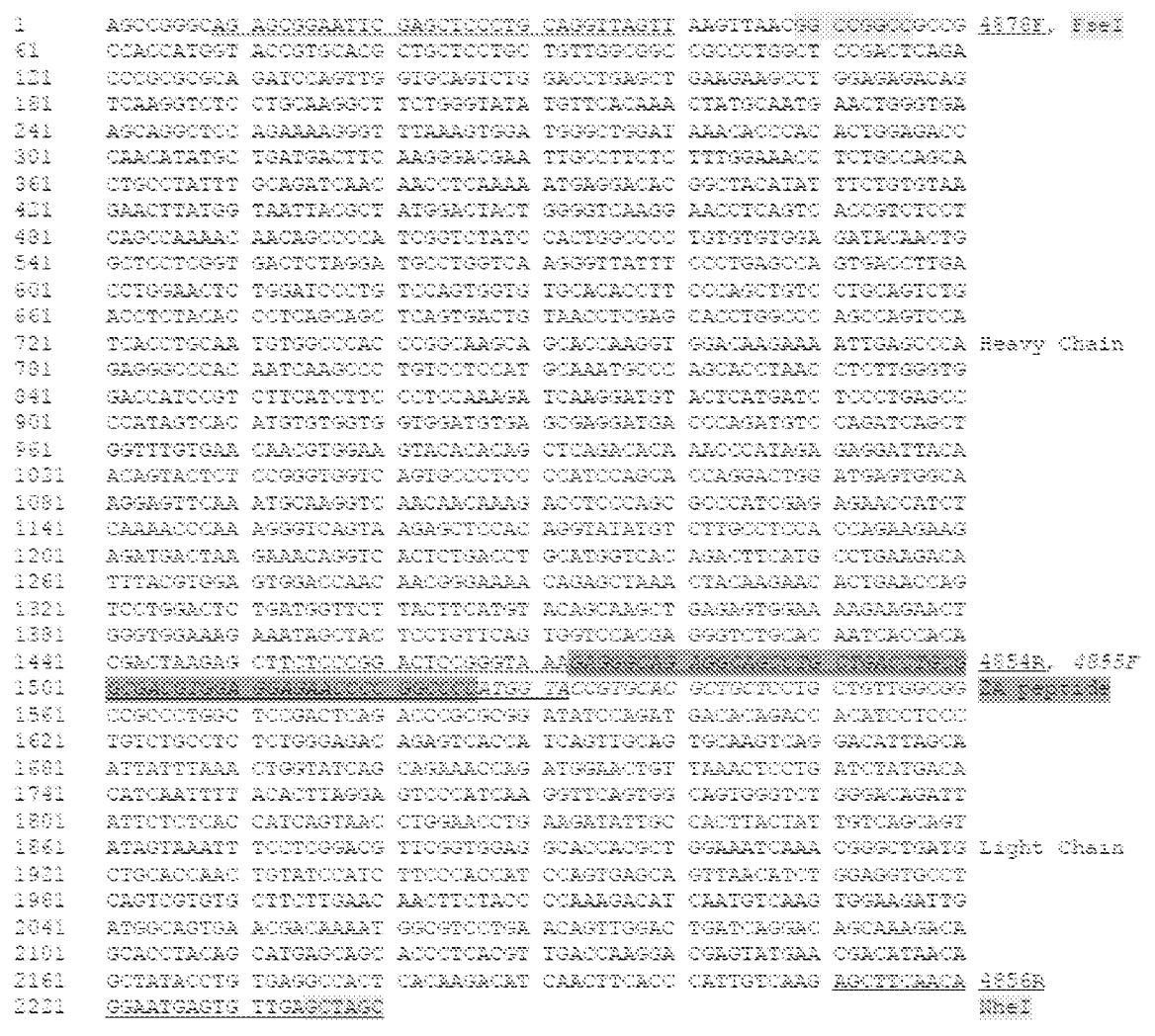

FIG. 20. Depicts the nucleotide sequence of the vector insert of 7C6-mIg2a-2A-LC. Oligonucleotide primer sequences, restriction sites, the 2A peptide sequence, heavy chain sequence, and light chain sequences are indicated. FIG. 20 discloses SEQ ID NO: 22.

FIGS. 21A and 21B. Depicts the amino acid sequence of 7C6 mAb heavy and light chain sequences linked by the 2A peptide. The heavy and light chain CDR sequences are highlighted in light grey FIG. 21A and 21B discloses SEQ ID NOS 23 and 32, respectively, in order of appearance. FIGS. 21A and 21B are continuous.

FIG. 22. Depicts the nucleotide sequence of the vector insert of 7C6-mIg2b-DANA-2A-LC. Oligonucleotide primer sequences, restriction sites, the 2A peptide sequence, heavy chain sequence, and light chain sequences are indicated. FIG. 22 discloses SEQ ID NO: 24.

FIGS. 23A and 23B. Depicts the amino acid sequence of 7C6-DANA mAb heavy and light chain sequences linked by the 2A peptide. The altered residues in the Fc are indicated highlighted and in bold. FIG. 23A and 23B discloses SEQ ID NOS 25 and 33, respectively, in order of appearance. FIGS. 23A and 23B are continuous.

FIG. 24. Depicts the analysis of short-term human melanoma cell lines in terms of MICA shedding and NK cell-mediated killing. (A-C) The indicated short-term human melanoma cell lines were cultured for 24-72 hours with different concentrations of 7C6-hIgG1 or isotype control antibodies. Subsequently, shed MICA (A and B) and shed MICB (C) were quantified in supernatants by ELISA. Surface MICA/B was quantified by FACS using PE-labelled 6D4 antibody (A-C). For analysis of NK cell-mediated cytotoxicity, human NK cells were isolated from heathy donors and activated with 1,000 U/ml IL-2 for 1-5 days prior to use in a 4 hour 51Cr release assay; isotype control or 7C6-hIgG1 antibodies (66.7 nM) were added to cytotoxicity assay (A-C). *$p<0.05$ and ***$p<0.001$, as calculated by two-way ANOVA, Bonferroni's post-hoc test. Mean±SEM of quadruplicates. Data representative of three independent experiments for shed and surface MICA/B analyses, and two independent experiments for NK cell cytotoxicity assays.

Figure 25:
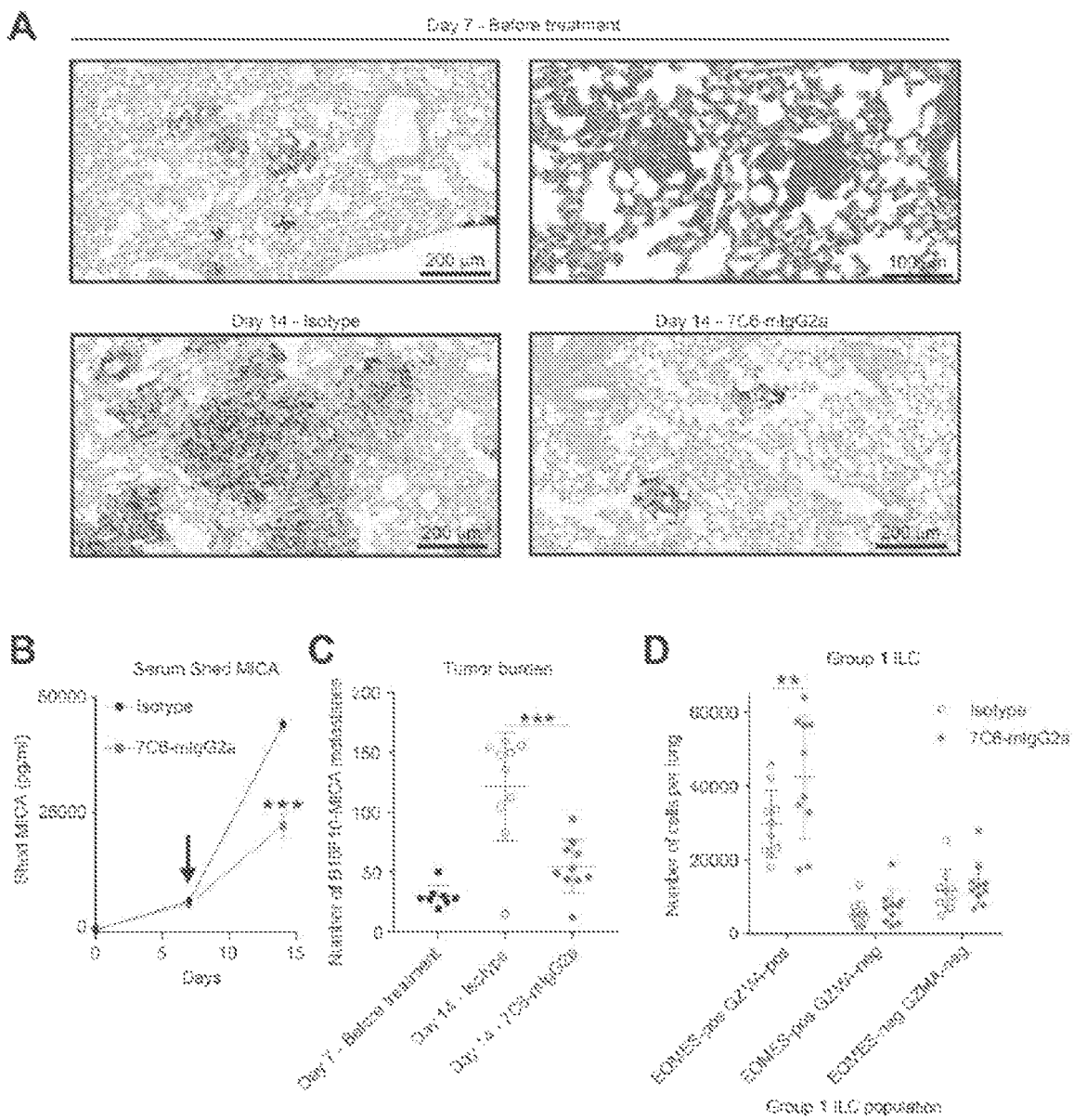
Figure 26A:
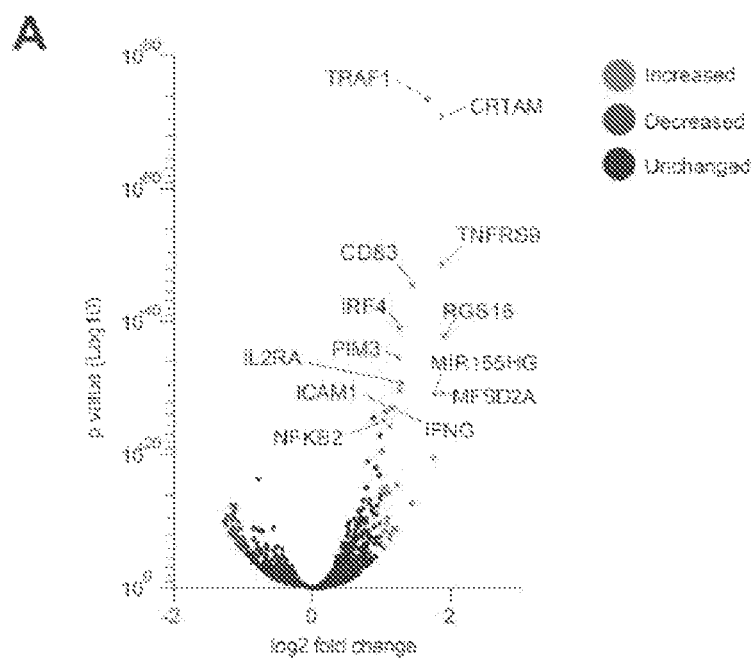

FIG. 25 Depicts the treatment of established metastases with MICA antibody. (A-D) Igh$^{-/-}$ mice were injected i.v. with B16F10-MICA cells. On day 7 following tumor cell inoculation, a group of mice was euthanized for analysis of lung metastases, while other mice were divided between 7C6-mIgG2a or isotype antibody treatment groups. Antibodies were administered at 200 µg/injection on days 7, 8 and 11. (A) Histological analysis (Fontana-Masson and H&E staining) demonstrating pre-existing metastases on days 7, before antibody treatment, and lung metastases on day 14 in isotype and 7C6-mIgG2a treated mice. In these mice, antibody treatment was started on day 7. Data representative of 4 mice per group. (B) Serum levels of shed MICA. The arrow indicates the start of antibody treatment. Data are mean+/−SEM of 10 mice per group. Data are pooled from two independent experiments. (C) Analysis of metastasis load on day 7 (no antibody treatment) and on day 14 (following treatment with indicated antibodies) by visual inspection of the lung surface under a stereomicroscope. Data are mean+/−SD and are pooled from two independent experiments. (D) Analysis of lung-infiltrating ILC1 on day 14 as described in FIG. 14A and FIG. 30A. Data are mean+/−SD and are pooled from two independent experiments. Statistics are as follows: $p<0.01$ and *$p<0.001$ as calculated by two-way ANOVA, Bonferroni's post-hoc test (B and D), or unpaired Student's t test (C).

FIGS. 26A, 26B, 26C, 26D, and 26E Depict the effect of MICA antibody on gene expression by human NK cells. (FIGS. 26A-26E) RNA-seq analysis of human NK cells 6 hours after co-culture with tumor cells that were pre-treated with the indicated antibodies for 48 hours. (FIG. 26A) Volcano plot comparing differential NK cell gene expression between 7C6-hIgG1 and isotype control groups with a 1 Log 2 fold change cut-off. (FIGS. 26B-26E) Pathway analysis for genes overexpressed in NK cells from the 7C6-hIgG1 group compared to the isotype control group. FIGS. 26A, 26B, 26C, 26D, and 26E are continuous.

Figure 27A:
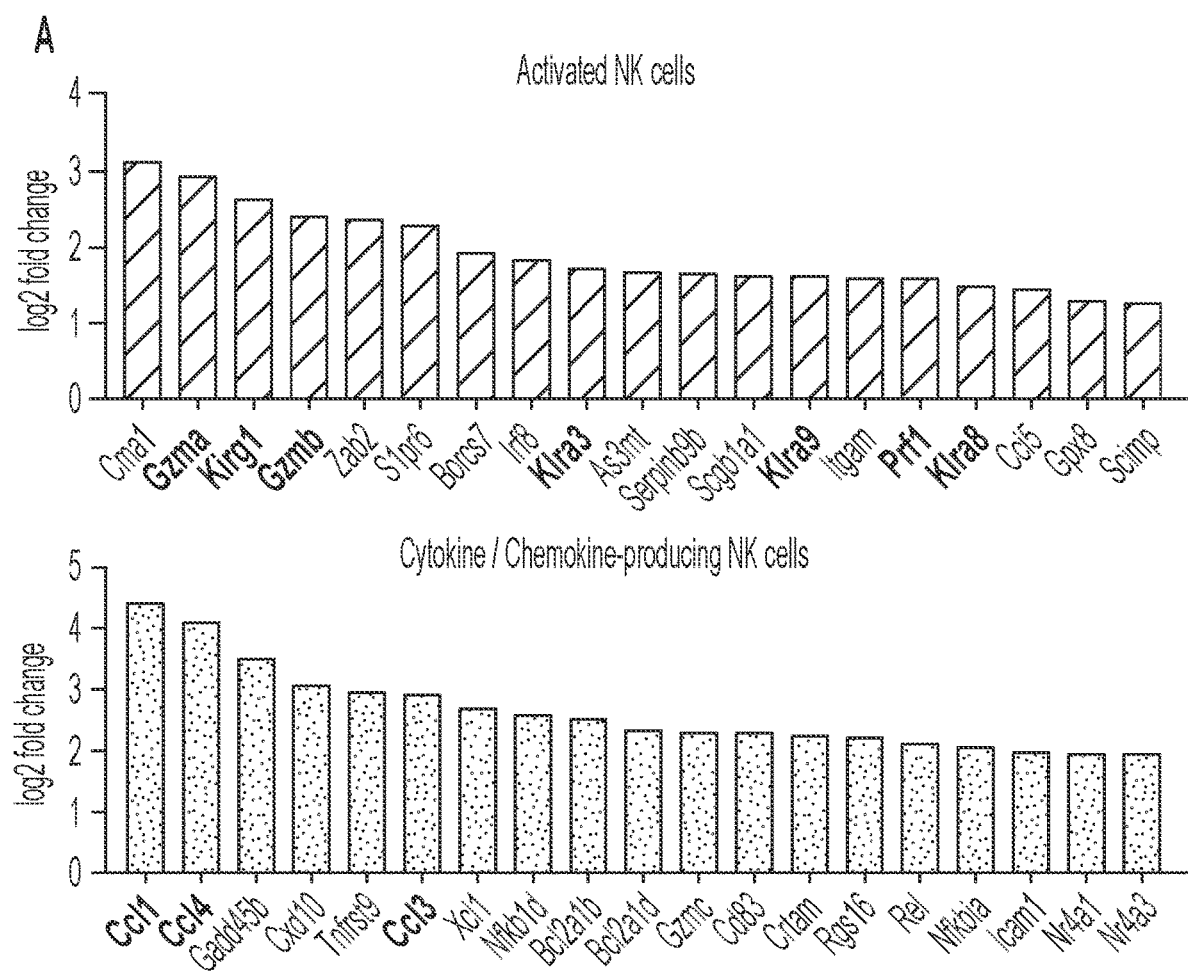

FIGS. 27A, 27B, and 27C Depicts the gene expression analysis of lung-resident NK cells and NKT-like cells. (FIGS. 27A-27C) C57BL/6 mice were inoculated i.v. with B16F10-MICA and treated twice with 7C6-mIgG2a or isotype control antibodies 24 and 48 hours later. On day 7 following tumor cell inoculation, lung-resident group 1 ILCs were isolated using the strategy described in FIG. 14A; cells were pooled from multiple mice per group (9 mice for isotype control and 8 mice for 7C6-mIgG2a groups). Gene expression was analyzed by single cell RNA-seq. The data from the two groups were pooled for identification of the different NK cell and NKT-like cell populations. The colors of the clusters in FIG. 3F match with the colors in 'A' and 'B'. (FIGS. 27A and 27B) The twenty most differentially expressed genes in each cluster relative to all other cell populations are shown. Key genes are in bold. (FIGS. 27C) Pathway analysis was performed based on the 30 most differentially expressed genes for each cluster; the top pathways are shown for each cell population. FDR=False Discovery Rate. FIGS. 27A, 27B, and 27C are continuous.

FIG. 28 Depicts the gene expression analysis for lung-resident ILC1. (A-B) Analysis of ILC1 using the procedure described in FIG. 27A-B. The colors of the clusters in FIG. 3A match with the colors in 'A' and 'B'. (A) The twenty most differentially expressed genes relative to all other cell populations are indicated for each identified cell population. Key genes are in bold. (B) Pathway analysis of differentially expressed genes for each cell population. FDR=False Discovery Rate.

Figure 29A:
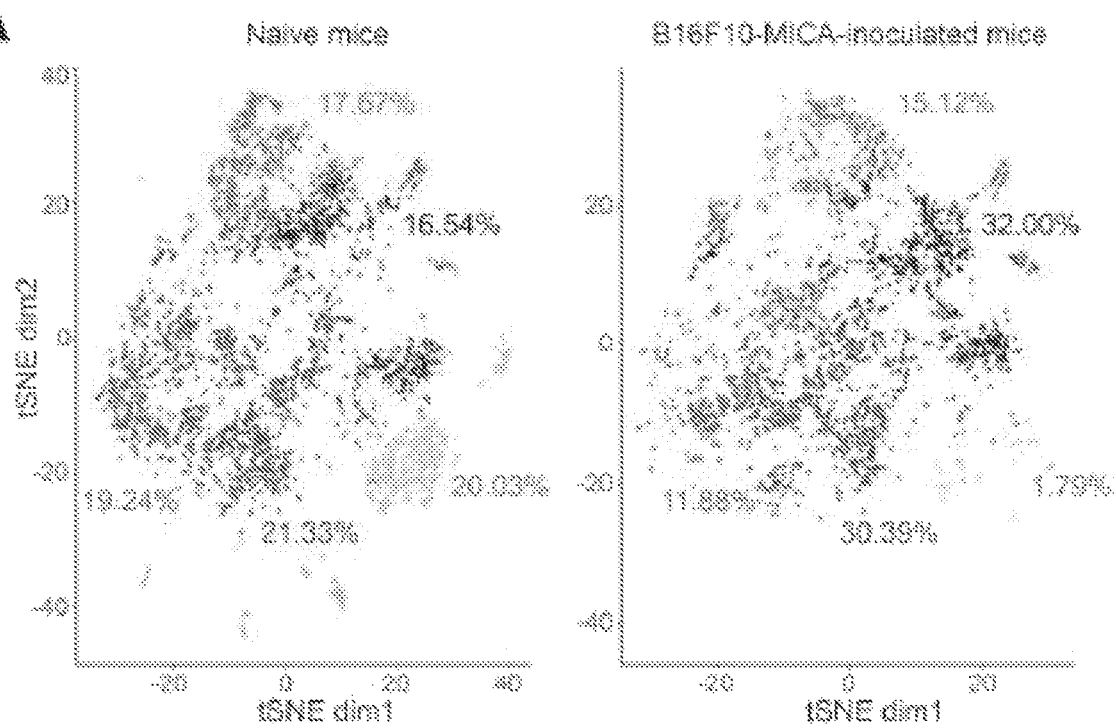

FIGS. 29A-29C Depicts the single cell RNA-seq analysis of group 1 ILC from naïve mice versus tumor-bearing mice. (FIGS. 29A-29C) Group 1 ILCs were isolated by FACS as described in FIG. 14A and single-cell RNA-seq was performed. The resulting data were analyzed together with data from B16F10-MICA-inoculated mice treated with isotype control antibody (the latter data are also part of FIG. 3A-B and FIG. 27-28). (FIG. 29A) Comparison of identified cell populations in naïve (n=7) and tumor-inoculated mice. Colors represent clusters calculated using k-means (k=10) on these two samples. Note that while cell types roughly correspond to those in FIG. 3A-B, tSNE produces visually distinct clusters each time the procedure is performed. Data therefore cannot be superimposed with FIG. 3. (FIG. 29B and FIG. 29C) The most differentially expressed genes from each cluster are shown, relative to all other cell populations in naïve mice and B16F10-MICA-inoculated mice. Key genes are in bold. FIGS. 29A, 29B, and 29C are continuous.

FIG. 30 Depicts the validation of single cell RNA-seq data by flow cytometry. (A-B) C57BL/6 mice were inoculated i.v. with B16F10-MICA cells and lung-infiltrating group 1 ILCs were identified based on the strategy shown in FIG. 14A. (A) FACS analysis of group 1 ILCs (NK1.1$^+$ NKp46$^+$ TCR3$^-$ CD3$\varepsilon^-$) on day 11 after tumor cell inoculation in a 7C6-mIgG2a-treated mouse identifying EOMES$^+$ GZMA$^+$ activated NK cells, EOMES+ GZMA− non-activated NK cells, and EOMES$^-$ GZMA$^-$ ILC1 (left). These three cell populations were analyzed further in terms of the indicated surface markers (right). Data are representative of five mice. (B) Analysis of lung infiltrating NK cells and ILC1 in tumor-bearing mice. Analysis done on day 7 following tumor cell inoculation. Naïve mice were not injected with tumor cells. Data are mean±SD and are representative of two independent experiments. p<0.01 and *p<0.001 as calculated by two-way ANOVA, Bonferroni's post-hoc test. (C) FACS analysis of lung-infiltrating activated NK cells (EOMES$^+$ GZMA$^+$) on day 7 following tumor inoculation. Mice were treated with isotype or 7C6-mIgG2a antibodies on days 1 and 2. Naïve mice did not receive antibody treatment or tumor cell inoculation. Data representative of 5 mice per group and two independent experiments.

FIG. 31 Depicts the NKG2D downregulation by group 1 ILCs. (A-B) C57BL/6 mice were inoculated i.v. with B16F10-MICA cells and treated with 7C6-mIgG2a or isotype control antibodies on days 1, 2, 7, and 10 after tumor cell injection. At the indicated time points, group 1 ILCs were analyzed as described in FIG. 14A and FIG. 30A. (A) Comparison of NKG2D surface levels by intravascular (CD45.2-APC+) and lung-resident NK cells. Data are mean+/−SEM of 5 mice per treatment condition for each time point of analysis (thus 40 mice total). Data on days 7 and 14 are representative of two independent experiments. p<0.01 and *p<0.001 as calculated by two-tailed unpaired Student's t tests, comparing isotype versus 7C6-mIgG2a for each individual time point. (B) NKG2D expression by ILC1. Data are mean+/−SEM of 5 mice per treatment condition for each time point (thus 40 mice total). Data on days 7 and 14 are representative of two independent experiments. ***p<0.001 as calculated by two-tailed unpaired Student's t tests, comparing isotype versus 7C6-mIgG2a for each individual time point.

FIG. 32 Depicts data showing that the DANA mutations do not affect MICA binding but abrogate Fc receptor binding. 7C6-hIgG1 or 7C6-mIgG2b antibodies were expressed with D265A and N297A (DANA) mutations in the Fc region of the antibody heavy chain. (A-B) DANA mutant 7C6 does not bind to CD16a Fc receptor expressed by NK cells. (A) 7C6-hIgG1 and 7C6-hIgG1-DANA antibodies were coated in different wells of an ELISA plate. Human recombinant His-tagged human CD16a was added at different concentrations and binding was detected using a HRP-conjugated anti-His tag antibody. Data representative of three independent experiments. (B) Recombinant murine CD16a was coated in wells of an ELISA plate to capture 7C6 antibodies. Subsequently, antibodies were added at different concentrations and capture by murine CD16a was detected with a HRP-conjugated antimouse IgG antibody with minimum cross-species reactivity. Data representative of three independent experiments. (C-D) DANA mutations do not interfere with the ability of 7C6 to bind MICA. (C) 7C6 with human Fc region binds to immobilized MICA independent of DANA mutations. Data representative of three independent experiments. (D) 7C6 with murine Fc region binds to immobilized MICA in a DANA mutation-independent manner. Data representative of three independent experiments.

Figure 33:
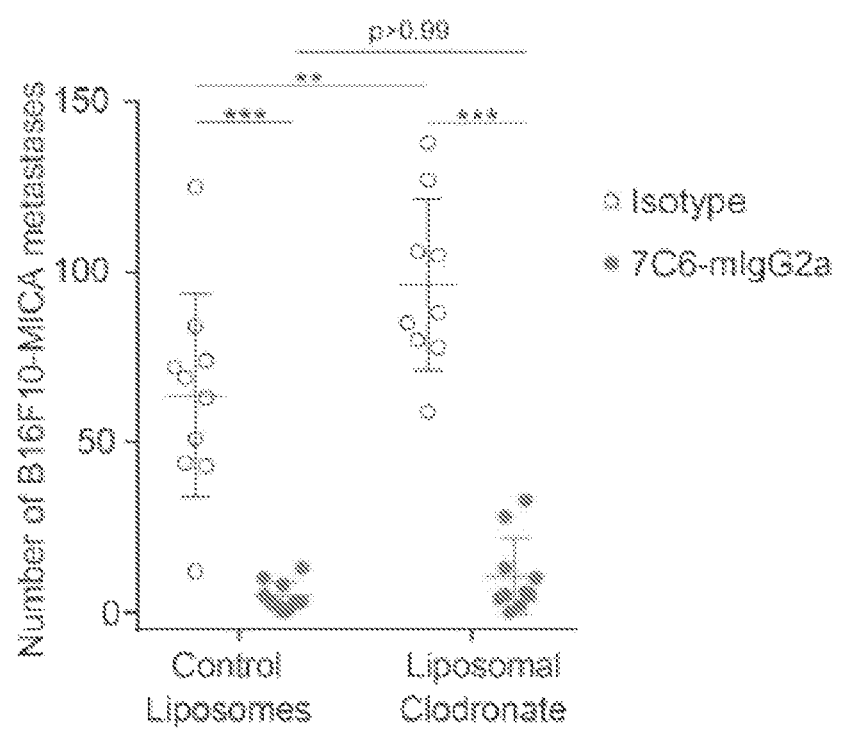

FIG. 33 Depicts data showing that macrophage depletion does not diminish treatment response in lung metastasis model in immunocompetent mice. C57BL/6 mice were injected i.v. with B16F10-MICA cells and treated with 7C6-mIgG2a or isotype control antibodies (days 1, 2, 7 and 10). Control liposomes or clodronate liposomes were injected i.v. on the day of tumor cell inoculation and again 7 days later. Analysis of metastases on day 14. Data pooled from two independent experiments. Data are mean±SD, p<0.01, and *p<0.001 calculated by two-way ANOVA, Bonferroni's post-hoc test.

Figure 34:
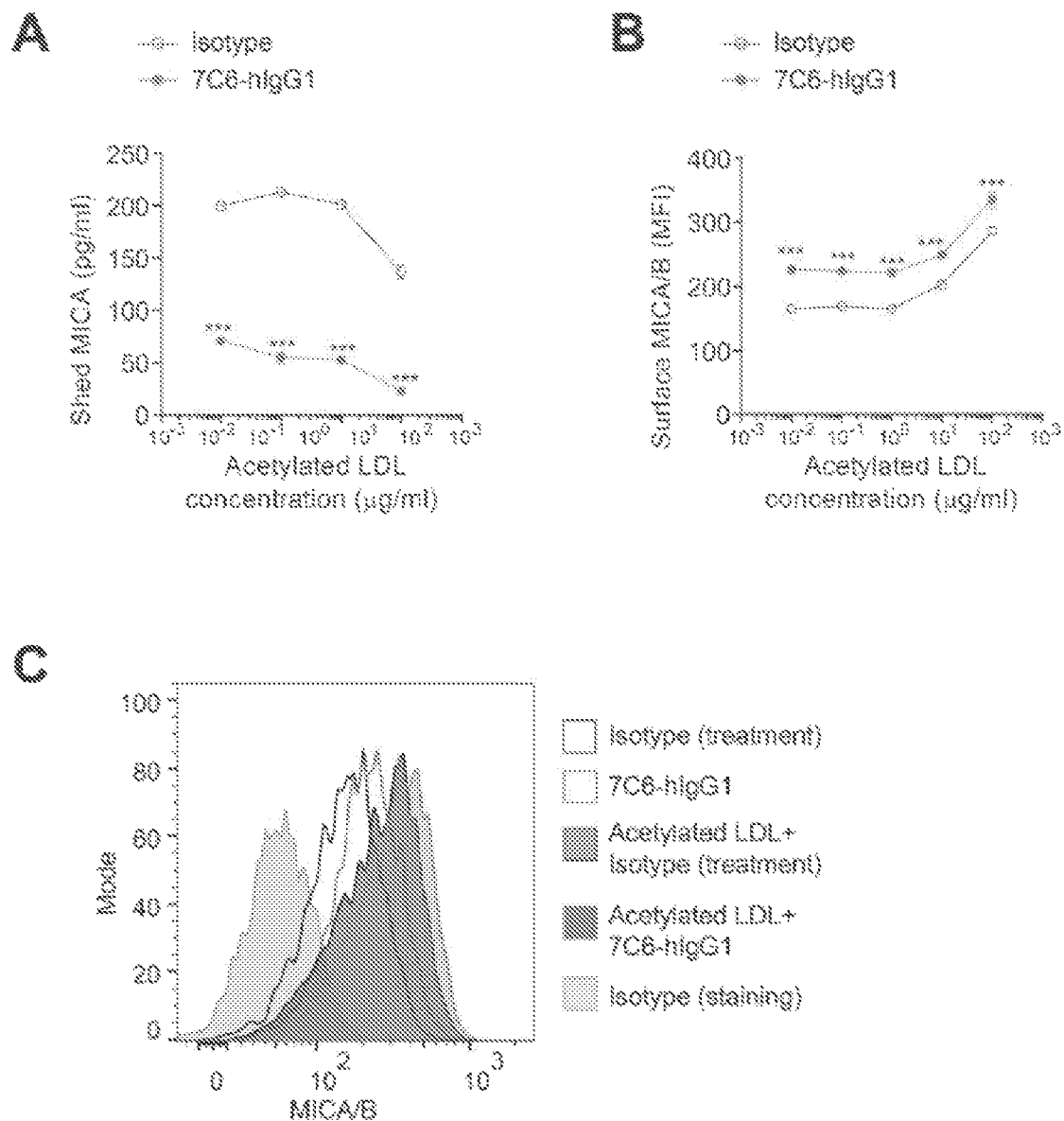

FIG. 34 Depicts the inhibition of MICA shedding by human macrophages. (A-C) Human monocytes were isolated from peripheral blood mononuclear cells of a healthy donor by cell adhesion to tissue culture plates and subsequently cultured for 5-7 days with 100 ng/ml M-CSF for generation of macrophages. Subsequently, macrophages were incubated for 24 hours with different concentrations of acetylated-LDL to increase MICAS expression. Isotype control or 7C6-hIgG1 antibodies were added at a concentration of 10 μg/ml. (A) Analysis of shed MICA in supernatants of macrophage cultures. Data are mean+/−SD of triplicates and are representative of three independent experiments. *p<0.001, as calculated by two-way ANOVA, Bonferroni's post-hoc test. (B-C) Surface MICA/B expression on macrophages. (B) Cells were labeled with PE-conjugated 6D4 antibody and analyzed by FACS. Data are mean+/−SD of triplicates and are representative of three independent experiments. *p<0.001, as calculated by twoway ANOVA, Bonferroni's post-hoc test. (C) Histograms from experiment shown in '13' with acetylated LDL concentration of 100 μg/ml.

Figure 35:
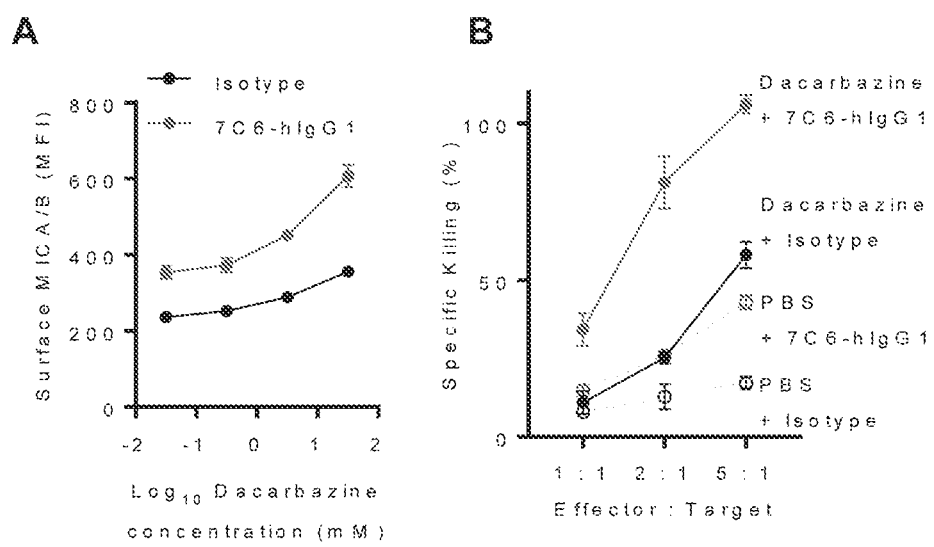

FIG. 35 Depicts data showing that Dacarbazine synergizes with MICA/B antibody in vitro against melanoma. The A375 human melanoma cell line was treated for 48 hours with the indicated doses of dacarbazine (A) or with 30 mM dacarbazine or equivalent PBS volume (B) and co-incubated with 10 μg/ml MICA/B antibodies (clone 7C6) or isotype control. (A) Dacarbazine increased MICA/B expression and 7C6 inhibited MICA/B shedding, as analyzed by 6D4-PE staining. (B) Human NK cell killing of A375 cells is increased by dacarbazine combination with MICA/B antibody. Data representative of three independent experiments.

FIG. 36 Depicts data showing that antibody-mediated inhibition of MICA/B shedding synergizes with proteasome inhibitor against multiple myeloma (MM). (A) The RPMI-8226 cell line expresses higher levels of surface MICA/B when treated for 24 hours with 10 mg/ml anti-MICA/B antibody clone 7C6 and the indicated doses of a proteasome inhibitor. Surface MICA/B was analyzed on viable MM cells after Zombie Yellow (BioLegend) exclusion by flow cytometry. (B) Analysis of surface MICA/B in the U266 and ANBL6 MM cell lines that were treated with isotype or anti-MICA/B antibodies. Bortezomib was given at 10 and 100 nM in the U266 and ANBL6 cultures, respectively. (C) Human NK cell cytotoxicity is increased against RPMI-8226 cells that were treated with 1 nM bortezomib and anti-MICA/B antibody, compared against 'PBS+Isotype' group. *p<0.05, p<0.01 and *p<0.001, as determined by two-way ANOVA with Bonferroni's test. Representative of two independent experiments.

For any figure showing a bar histogram, curve, or other data associated with a legend, the bars, curve, or other data presented from left to right for each indication correspond directly and in order to the boxes from top to bottom of the legend.

DETAILED DESCRIPTION

Described herein are isolated antibodies, particularly monoclonal antibodies, e.g., human monoclonal antibodies, which specifically bind to the MICA and/or MICB α3 domain, the site of proteolytic shedding. These antibodies inhibit MICA/B shedding by human cancer cells and stabilize cell surface MICA/B for NK cell recognition. The activity of these antibodies is mediated by activation of both NKG2D and CD16 Fc receptors on NK cells, and restore immune activation by stress molecules that activate cytotoxic lymphocytes. The antibodies described herein have further been shown to be have therapeutic activity against cancer (e.g., human melanoma metastases).

Accordingly, provided herein are isolated antibodies, methods of making such antibodies, immunoconjugates and bispecific molecules comprising such antibodies, and pharmaceutical compositions formulated to contain the antibodies. Also provided herein are methods of using the antibodies for alone or in combination with other immunostimulatory agents (e.g., antibodies) and/or cancer therapies. Accordingly, the anti-MICA and/or anti-MICB antibodies described herein may be used in a treatment in a wide variety of therapeutic applications, including, for example, inhibiting tumor growth.

Definitions

In order that the present description may be more readily understood, certain terms are first defined. Additional definitions are set forth throughout the detailed description.

MICA is a ligand for NKG2D, a C-type lectin-like, type II transmembrane receptor expressed on most human NK cells, γδ T cells, and CD8+ T cells. Upon ligation, NKG2D signals through the adaptor protein DAP10 to evoke perforin dependent cytolysis and to provide co-stimulation. In humans, the NKG2D ligands include MHC class I chain-related protein A (MICA), the closely related MICB, UL-16 binding proteins (ULBP) 1-4, and RAE-1G. While NKG2D ligands are not usually found on healthy tissues, various forms of cellular stress, including DNA damage, may upregulate ligand expression, resulting in their frequent detection in multiple solid and hematologic malignancies, including melanoma. NKG2D activation through ligand positive transformed cells contributes to extrinsic tumor suppression, since NKG2D deficient and wild type mice treated with anti-NKG2D blocking antibodies manifest enhanced tumor susceptibility. Immune escape may be achieved in patients, however, by the shedding of NKG2D ligands from tumor cells, which triggers internalization of surface NKG2D and impaired function of cytotoxic lymphocytes. Soluble NKG2D ligands may also stimulate the expansion of regulatory NKG2D$^+$CD4$^+$Foxp3$^-$ T cells that may antagonize anti-tumor cytotoxicity through Fas ligand, IL-10, and TGF-β. MICA is a NKG2D ligand shed from tumor cells, i.e., released from the cell surface into the surrounding medium, and sera from cancer patients typically contain elevated levels of the soluble form (sMICA). MICA shedding is accomplished in part through interactions with the protein disulfide isomerase ERp5, which forms a disulfide bond with a critical cysteine that results in unfolding of the α3 domain, rendering it susceptible to proteolysis by ADAM-10/17 and MMP14. The amino acid sequences of MHC class I polypeptide-related sequence A and B from various species are disclosed in the prior art (e.g., UniGene Hs.130838), and various alleles are commercially available (Luminex).

The term "antibody" as used to herein includes whole antibodies and any antigen binding fragments (i.e., "antigen-binding portions") or single chains thereof. An "antibody" refers, in one embodiment, to a glycoprotein comprising at least two heavy (H) chains and two light (L) chains interconnected by disulfide bonds, or an antigen binding portion thereof. Each heavy chain is comprised of a heavy chain variable region (abbreviated herein as V$_H$) and a heavy chain constant region. In certain naturally occurring antibodies, the heavy chain constant region is comprised of three domains, CH1, CH2 and CH3. In certain naturally occurring antibodies, each light chain is comprised of a light chain variable region (abbreviated herein as $V_L$) and a light chain constant region. The light chain constant region is comprised of one domain, CL. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

Antibodies typically bind specifically to their cognate antigen with high affinity, reflected by a dissociation constant ($K_D$) of $10^{-5}$ to $10^{-11}$ M or less. Any $K_D$ greater than about $10^{-4}$ M is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $5 \times 10^{-9}$M or less, and most preferably between $10^{-8}$M and $10^{-10}$M or less, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99% sequence identity to the sequence of the given antigen. By way of example, an antibody that binds specifically to human MICA and/or MICB may also have cross-reactivity with MICA and/or MICB antigens from certain primate species (e.g., cynomolgus MICA and/or MICB), but may not cross-react with MICA and/or MICB antigens from other species or with an antigen other than MICA and/or MICB.

An immunoglobulin may be from any of the commonly known isotypes, including but not limited to IgA, secretory IgA, IgG and IgM. The IgG isotype is divided in subclasses in certain species: IgG1, IgG2, IgG3 and IgG4 in humans, and IgG1, IgG2a, IgG2b and IgG3 in mice. In certain embodiments, the anti-MICA and/or anti-MICB antibodies described herein are of the IgG1 or IgG2 subtype. Immunoglobulins, e.g., IgG1, exist in several allotypes, which differ from each other in at most a few amino acids. "Antibody" includes, by way of example, both naturally occurring and non-naturally occurring antibodies; monoclonal and polyclonal antibodies; chimeric and humanized antibodies; human and nonhuman antibodies; wholly synthetic antibodies; and single chain antibodies.

The term "antigen-binding portion" of an antibody, as used herein, refers to one or more fragments of an antibody that retain the ability to specifically bind to an antigen (e.g., human MICA). Such "fragments" are, for example between about 8 and about 1500 amino acids in length, suitably between about 8 and about 745 amino acids in length, suitably about 8 to about 300, for example about 8 to about 200 amino acids, or about 10 to about 50 or 100 amino acids in length. It has been shown that the antigen-binding function of an antibody can be performed by fragments of a full-length antibody. Examples of binding fragments encompassed within the term "antigen-binding portion" of an antibody, e.g., an anti-MICA and/or anti-MICB antibody described herein, include (i) a Fab fragment, a monovalent fragment consisting of the $V_L$, $V_H$, CL and CH1 domains; (ii) a F(ab')$_2$ fragment, a bivalent fragment comprising two Fab fragments linked by a disulfide bridge at the hinge region; (iii) a Fd fragment consisting of the $V_H$ and CH1 domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; and (vi) an isolated complementarity determining region (CDR) or (vii) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies. Antigen-binding portions can be produced by recombinant DNA techniques, or by enzymatic or chemical cleavage of intact immunoglobulins.

A "CDR" of a variable domain are amino acid residues within the hypervariable region that are identified in accordance with the definitions of the Kabat, Chothia, the cumulation of both Kabat and Chothia, AbM, contact, and/or conformational definitions or any method of CDR determination well known in the art. Antibody CDRs may be identified as the hypervariable regions originally defined by Kabat et al. See, e.g., Kabat et al., 1992, Sequences of Proteins of Immunological Interest, 5th ed., Public Health Service, NIH, Washington D.C. The positions of the CDRs may also be identified as the structural loop structures originally described by Chothia and others. See, e.g., Chothia et al., 1989, Nature 342:877-883. Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding. See, e.g., Makabe et al., 2008, Journal of Biological Chemistry, 283:1156-1166. Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs may be defined in accordance with any of Kabat, Chothia, extended, AbM, contact, and/or conformational definitions.

A "bispecific" or "bifunctional antibody" is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann, *Clin. Exp. Immunol.* 79:315-321 (1990); Kostelny et al., *J. Immunol.* 148, 1547-1553 (1992).

The term "monoclonal antibody," as used herein, refers to an antibody that displays a single binding specificity and affinity for a particular epitope or a composition of antibodies in which all antibodies display a single binding specificity and affinity for a particular epitope. Accordingly, the term "human monoclonal antibody" refers to an antibody or antibody composition that display(s) a single binding specificity and which has variable and optional constant regions derived from human germline immunoglobulin sequences. In one embodiment, human monoclonal antibodies are produced by a hybridoma which includes a B cell obtained from a transgenic non-human animal, e.g., a transgenic mouse, having a genome comprising a human heavy chain transgene and a light chain transgene fused to an immortalized cell.

The term "recombinant human antibody," as used herein, includes all human antibodies that are prepared, expressed, created or isolated by recombinant means, such as (a) antibodies isolated from an animal (e.g., a mouse) that is transgenic or transchromosomal for human immunoglobulin genes or a hybridoma prepared therefrom, (b) antibodies isolated from a host cell transformed to express the antibody, e.g., from a transfectoma, (c) antibodies isolated from a recombinant, combinatorial human antibody library, and (d) antibodies prepared, expressed, created or isolated by any other means that involve splicing of human immunoglobulin gene sequences to other DNA sequences. Such recombinant human antibodies comprise variable and constant regions that utilize particular human germline immunoglobulin sequences are encoded by the germline genes, but include subsequent rearrangements and mutations which occur, for example, during antibody maturation. As known in the art (see, e.g., Lonberg (2005) Nature Biotech. 23(9):1117-1125), the variable region contains the antigen binding domain, which is encoded by various genes that rearrange to form an antibody specific for a foreign antigen. In addition to rearrangement, the variable region can be further modified by multiple single amino acid changes (referred to as somatic mutation or hypermutation) to increase the affinity of the antibody to the foreign antigen. The constant region will change in further response to an antigen (i.e., isotype switch). Therefore, the rearranged and somatically mutated nucleic acid molecules that encode the light chain and heavy chain immunoglobulin polypeptides in response to an antigen may not have sequence identity with the original nucleic acid molecules, but instead will be substantially identical or similar (i.e., have at least 80% identity).

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The antibodies described herein may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies are and are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

As used herein, "isotype" refers to the antibody class (e.g., IgG1, IgG2, IgG3, IgG4, IgM, IgA1, IgA2, IgD, and IgE antibody) that is encoded by the heavy chain constant region genes.

"Allotype" refers to naturally occurring variants within a specific isotype group, which variants differ in a few amino acids (see, e.g., Jefferis et al. (2009) mAbs 1:1). Antibodies described herein may be of any allotype. As used herein, antibodies referred to as "IgG1f" or "IgG1.1f" isotype are IgG1 and effectorless IgG1.1 antibodies, respectively, of the allotype "f," i.e., having 214R, 356E and 358M according to the EU index as in Kabat.

The phrases "an antibody recognizing an antigen" and "an antibody specific for an antigen" are used interchangeably herein with the term "an antibody which binds specifically to an antigen."

An "isolated antibody," as used herein, is intended to refer to an antibody which is substantially free of other antibodies having different antigenic specificities (e.g., an isolated antibody that specifically binds to MICA and/or MICB is substantially free of antibodies that specifically bind antigens other than MICA). An isolated antibody that specifically binds to an epitope of MICA and/or MICB may, however, have cross-reactivity to other MICA and/or MICB proteins from different species.

An "effector function" refers to the interaction of an antibody Fc region with an Fc receptor or ligand, or a biochemical event that results therefrom. Exemplary "effector functions" include C1q binding, complement dependent cytotoxicity (CDC), Fc receptor binding, FcγR-mediated effector functions such as ADCC and antibody dependent cell-mediated phagocytosis (ADCP), and downregulation of a cell surface receptor (e.g., the B cell receptor; BCR). Such effector functions generally require the Fc region to be combined with a binding domain (e.g., an antibody variable domain).

An "Fc receptor" or "FcR" is a receptor that binds to the Fc region of an immunoglobulin. FcRs that bind to an IgG antibody comprise receptors of the FcγR family, including allelic variants and alternatively spliced forms of these receptors. The FcγR family consists of three activating (FcγRI, FcγRIII, and FcγRIV in mice; FcγRIA, FcγRIIA, and FcγRIIIA in humans) and one inhibitory (FcγRIIB) receptor. Various properties of human FcγRs are summarized in Table 1. The majority of innate effector cell types coexpress one or more activating FcγR and the inhibitory FcγRIIB, whereas natural killer (NK) cells selectively express one activating Fc receptor (FcγRIII in mice and FcγRIIIA in humans) but not the inhibitory FcγRIIB in mice and humans. Human IgG1 binds to most human Fc receptors and is considered equivalent to murine IgG2a with respect to the types of activating Fc receptors that it binds to.

TABLE 1

Properties of human FcγRs

| Fcγ | Allelic variants | Affinity for human IgG | Isotype preference | Cellular distribution |
|---|---|---|---|---|
| FcγRI | None described | High ($K_D$ ~10 nM) | IgG1 = 3 > 4 >> 2 | Monocytes, macrophages, activated neutrophils, dentritic cells? |
| FcγRIIA | H131 | Low to medium | IgG1 > 3 > 2 > 4 | Neutrophils, monocytes, macrophages, eosinophils, dentritic cells, platelets |
| | R131 | Low | IgG1 > 3 > 4 > 2 | |
| FcγRIIIA | V158 | Medium | IgG1 = 3 >> 4 > 2 | NK cells, monocytes, macrophages, mast cells, eosinophils, dentritic cells? |
| | F158 | Low | IgG1 = 3 >> 4 > 2 | |
| FcγRIIB | I232 | Low | IgG1 = 3 = 4 > 2 | B cells, monocytes, macrophages, dentritic cells, mast cells |
| | T232 | Low | IgG1 = 3 = 4 > 2 | |

An "Fc region" (fragment crystallizable region) or "Fc domain" or "Fc" refers to the C-terminal region of the heavy chain of an antibody that mediates the binding of the immunoglobulin to host tissues or factors, including binding to Fc receptors located on various cells of the immune system (e.g., effector cells) or to the first component (C1q) of the classical complement system. Thus, an Fc region comprises the constant region of an antibody excluding the first constant region immunoglobulin domain (e.g., CH1 or CL). In IgG, IgA and IgD antibody isotypes, the Fc region comprises two identical protein fragments, derived from the second ($C_{H2}$) and third ($C_{H3}$) constant domains of the antibody's two heavy chains; IgM and IgE Fc regions comprise three heavy chain constant domains (CH domains 2-4) in each polypeptide chain. For IgG, the Fc region comprises immunoglobulin domains Cγ2 and Cγ3 and the hinge between Cγ1 and Cγ2. Although the boundaries of the Fc region of an immunoglobulin heavy chain might vary, the human IgG heavy chain Fc region is usually defined to stretch from an amino acid residue at position C226 or P230 (or amino acid between these two amino acids) to the carboxy-terminus of the heavy chain, wherein the numbering is according to the EU index as in Kabat. The $C_{H2}$ domain of a human IgG Fc region extends from about amino acid 231 to about amino acid 340, whereas the $C_{H3}$ domain is positioned on C-terminal side of a $C_{H2}$ domain in an Fc region, i.e., it extends from about amino acid 341 to about amino acid 447 of an IgG. As used herein, the Fc region may be a native sequence Fc, including any allotypic variant, or a variant Fc (e.g., a non-naturally occurring Fc). Fc may also refer to this region in isolation or in the context of an Fc-comprising protein polypeptide such as a "binding protein comprising an Fc region," also referred to as an "Fc fusion protein" (e.g., an antibody or immunoadhesin).

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fc include the various allotypes of Fcs (see, e.g., Jefferis et al. (2009) mAbs 1:1).

A "hinge", "hinge domain" or "hinge region" or "antibody hinge region" refers to the domain of a heavy chain constant region that joins the CH1 domain to the CH2 domain and includes the upper, middle, and lower portions of the hinge (Roux et al. J. Immunol. 1998 161:4083). The hinge provides varying levels of flexibility between the binding and effector regions of an antibody and also provides sites for intermolecular disulfide bonding between the two heavy chain constant regions. As used herein, a hinge starts at Glu216 and ends at Gly237 for all IgG isotypes (Roux et al., 1998 J Immunol 161:4083).

The term "hinge" includes wildtype hinges as well as variants thereof (e.g., non-naturally-occurring hinges or modified hinges). For example, the term "IgG2 hinge" includes wildtype IgG2 hinge and variants having 1, 2, 3, 4, 5, 1-3, 1-5, 3-5 and/or at most 5, 4, 3, 2, or 1 mutations, e.g., substitutions, deletions or additions. Exemplary IgG2 hinge variants include IgG2 hinges in which 1, 2, 3 or all 4 cysteines (C219, C220, C226 and C229) are changed to another amino acid. In a specific embodiment, an IgG2 comprises a C219S substitution. In certain embodiments, a hinge is a hybrid hinge that comprises sequences from at least two isotypes. For example, a hinge may comprise the upper, middle or lower hinge from one isotype and the remainder of the hinge from one or more other isotypes. For example, a hinge can be an IgG2/IgG1 hinge, and may comprise, e.g., the upper and middle hinges of IgG2 and the lower hinge of IgG1. A hinge may have effector function or be deprived of effector function. For example, the lower hinge of wildtype IgG1 provides effector function.

The term "CH1 domain" refers to the heavy chain constant region linking the variable domain to the hinge in a heavy chain constant domain. As used herein, a CH1 domain starts at A118 and ends at V215. The term "CH1 domain" includes wildtype CH1 domains as well as variants thereof (e.g., non-naturally-occurring CH1 domains or modified CH1 domains). For example, the term "CH1 domain" includes wildtype CH1 domains and variants having 1, 2, 3, 4, 5, 1-3, 1-5, 3-5 and/or at most 5, 4, 3, 2, or 1 mutations, e.g., substitutions, deletions or additions. Exemplary CH1 domains include CH1 domains with mutations that modify a biological activity of an antibody, such as ADCC, CDC or half-life. Modifications to the CH1 domain that affect a biological activity of an antibody are provided herein.

The term "CH2 domain" refers to the heavy chain constant region linking the hinge to the CH3 domain in a heavy chain constant domain. As used herein, a CH2 domain starts at P238 and ends at K340. The term "CH2 domain" includes wildtype CH2 domains, as well as variants thereof (e.g., non-naturally-occurring CH2 domains or modified CH2 domains). For example, the term "CH2 domain" includes wildtype CH2 domains and variants having 1, 2, 3, 4, 5, 1-3, 1-5, 3-5 and/or at most 5, 4, 3, 2, or 1 mutations, e.g., substitutions, deletions or additions. Exemplary CH2 domains include CH2 domains with mutations that modify a biological activity of an antibody, such as ADCC, CDC or half-life. In certain embodiments, a CH2 domain comprises the substitutions A330S/P331S that reduce effector function. Other modifications to the CH2 domain that affect a biological activity of an antibody are provided herein.

The term "CH3 domain" refers to the heavy chain constant region that is C-terminal to the CH2 domain in a heavy chain constant domain. As used herein, a CH3 domain starts at G341 and ends at K447. The term "CH3 domain" includes wildtype CH3 domains, as well as variants thereof (e.g., non-naturally-occurring CH3 domains or modified CH3 domains). For example, the term "CH3 domain" includes wildtype CH3 domains and variants having 1, 2, 3, 4, 5, 1-3, 1-5, 3-5 and/or at most 5, 4, 3, 2, or 1 mutations, e.g., substitutions, deletions or additions. Exemplary CH3 domains include CH3 domains with mutations that modify a biological activity of an antibody, such as ADCC, CDC or half-life. Modifications to the CH3 domain that affect a biological activity of an antibody are provided herein.

A "native sequence Fc region" or "native sequence Fc" comprises an amino acid sequence that is identical to the amino acid sequence of an Fc region found in nature. Native sequence human Fc regions include a native sequence human IgG1 Fc region; native sequence human IgG2 Fc region; native sequence human IgG3 Fc region; and native sequence human IgG4 Fc region as well as naturally occurring variants thereof. Native sequence Fc includes the various allotypes of Fcs (see, e.g., Jefferis et al. (2009) mAbs 1:1).

The term "epitope" or "antigenic determinant" refers to a site on an antigen (e.g., MICA) to which an immunoglobulin or antibody specifically binds. Epitopes can be formed both from contiguous amino acids (usually a linear epitope) or noncontiguous amino acids juxtaposed by tertiary folding of a protein (usually a conformational epitope). Epitopes formed from contiguous amino acids are typically, but not always, retained on exposure to denaturing solvents, whereas epitopes formed by tertiary folding are typically lost on treatment with denaturing solvents. An epitope typically includes at least 3, 4, 5, 6, 7, 8, 9, 10, 11, 12, 13, 14 or 15 amino acids in a unique spatial conformation. Methods for determining what epitopes are bound by a given antibody (i.e., epitope mapping) are well known in the art and include, for example, immunoblotting and immunoprecipitation assays, wherein overlapping or contiguous peptides from (e.g., from MICA) are tested for reactivity with a given antibody (e.g., anti-MICA and/or anti-MICB antibody). Methods of determining spatial conformation of epitopes include techniques in the art and those described herein, for example, x-ray crystallography, 2-dimensional nuclear magnetic resonance and HDX-MS (see, e.g., *Epitope Mapping Protocols in Methods in Molecular Biology*, Vol. 66, G. E. Morris, Ed. (1996)).

The term "epitope mapping" refers to the process of identification of the molecular determinants for antibody-antigen recognition.

The term "binds to the same epitope" with reference to two or more antibodies means that the antibodies bind to the same segment of amino acid residues, as determined by a given method. Techniques for determining whether antibodies bind to the "same epitope on MICA" with the antibodies described herein include, for example, epitope mapping methods, such as, x-ray analyses of crystals of antigen:antibody complexes which provides atomic resolution of the epitope and hydrogen/deuterium exchange mass spectrometry (HDX-MS). Other methods monitor the binding of the antibody to antigen fragments or mutated variations of the antigen where loss of binding due to a modification of an amino acid residue within the antigen sequence is often considered an indication of an epitope component. In addition, computational combinatorial methods for epitope mapping can also be used. These methods rely on the ability of the antibody of interest to affinity isolate specific short peptides from combinatorial phage display peptide libraries. Antibodies having the same VH and VL or the same CDR1, 2 and 3 sequences are expected to bind to the same epitope.

Antibodies that "compete with another antibody for binding to a target" refer to antibodies that inhibit (partially or completely) the binding of the other antibody to the target. Whether two antibodies compete with each other for binding to a target, i.e., whether and to what extent one antibody inhibits the binding of the other antibody to a target, may be determined using known competition experiments. In certain embodiments, an antibody competes with, and inhibits binding of another antibody to a target by at least 10%, 20%, 30%, 40%, 50%, 60%, 70%, 80%, 90% or 100%. The level of inhibition or competition may be different depending on which antibody is the "blocking antibody" (i.e., the cold antibody that is incubated first with the target). Competition assays can be conducted as described, for example, in Ed Harlow and David Lane, Cold Spring Harb Protoc; 2006; doi:10.1101/pdb.prot4277 or in Chapter 11 of "Using Antibodies" by Ed Harlow and David Lane, Cold Spring Harbor Laboratory Press, Cold Spring Harbor, N.Y., USA 1999. Competing antibodies bind to the same epitope, an overlapping epitope or to adjacent epitopes (e.g., as evidenced by steric hindrance).

Other competitive binding assays include: solid phase direct or indirect radioimmunoassay (MA), solid phase direct or indirect enzyme immunoassay (EIA), sandwich competition assay (see Stahli et al., *Methods in Enzymology* 9:242 (1983)); solid phase direct biotin-avidin EIA (see Kirkland et al., *J. Immunol.* 137:3614 (1986)); solid phase direct labeled assay, solid phase direct labeled sandwich assay (see Harlow and Lane, *Antibodies: A Laboratory Manual*, Cold Spring Harbor Press (1988)); solid phase direct label MA using 1-125 label (see Morel et al., *Mol. Immunol.* 25(1):7 (1988)); solid phase direct biotin-avidin EIA (Cheung et al., *Virology* 176:546 (1990)); and direct labeled MA. (Moldenhauer et al., *Scand. J. Immunol.* 32:77 (1990)).

As used herein, the terms "specific binding," "selective binding," "selectively binds," and "specifically binds," refer to antibody binding to an epitope on a predetermined antigen. Typically, the antibody (i) binds with an equilibrium dissociation constant ($K_D$) of approximately less than $10^{-7}$ M, such as approximately less than $10^{-8}$ M, $10^{-9}$M or $10^{-10}$ M or even lower when determined by, e.g., surface plasmon resonance (SPR) technology in a BIACORE 2000 instrument using the predetermined antigen, e.g., recombinant human MICA, as the analyte and the antibody as the ligand, or Scatchard analysis of binding of the antibody to antigen positive cells, and (ii) binds to the predetermined antigen with an affinity that is at least two-fold greater than its affinity for binding to a non-specific antigen (e.g., BSA, casein) other than the predetermined antigen or a closely-related antigen. Accordingly, an antibody that "specifically binds to human MICA and/or MICB" refers to an antibody that binds to soluble or cell bound human MICA and/or MICB with a $K_D$ of $10^{-7}$ M or less, such as approximately less than $10^{-8}$ M, $10^{-9}$M or $10^{-10}$ M or even lower. An antibody that "cross-reacts with cynomolgus MICA and/or MICB" refers to an antibody that binds to cynomolgus MICA and/or MICB with a $K_D$ of $10^{-7}$ M or less, such as approximately less than $10^{-8}$ M, $10^{-9}$M or $10^{-10}$ M or even lower. In certain embodiments, such antibodies that do not cross-react with MICA and/or MICB from a non-human species exhibit essentially undetectable binding against these proteins in standard binding assays.

The term "$k_{assoc}$" or "$k_a$", as used herein, is intended to refer to the association rate of a particular antibody-antigen interaction, whereas the term "$k_{dis}$" or "$k_d$," as used herein, is intended to refer to the dissociation rate of a particular antibody-antigen interaction. The term "$K_D$", as used herein, is intended to refer to the dissociation constant, which is obtained from the ratio of $k_d$ to $k_a$ (i.e., $k_d/k_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore® system or flow cytometry and Scatchard analysis.

As used herein, the term "high affinity" for an IgG antibody refers to an antibody having a $K_D$ of $10^{-8}$M or less, more preferably $10^{-9}$ M or less and even more preferably $10^{-10}$ M or less for a target antigen. However, "high affinity" binding can vary for other antibody isotypes. For example, "high affinity" binding for an IgM isotype refers to an antibody having a $K_D$ of $10^{-7}$ M or less, more preferably $10^{-8}$M or less.

The term "EC50" in the context of an in vitro or in vivo assay using an antibody or antigen binding fragment thereof, refers to the concentration of an antibody or an antigen-binding portion thereof that induces a response that is 50% of the maximal response, i.e., halfway between the maximal response and the baseline.

The term "binds to immobilized MICA and/or MICB," refers to the ability of an antibody described herein to bind to MICA and/or MICB, for example, expressed on the surface of a cell or which is attached to a solid support.

The term "cross-reacts," as used herein, refers to the ability of an antibody described herein to bind to MICA and/or MICB from a different species. For example, an antibody described herein that binds human MICA and/or MICB may also bind another species of MICA and/or MICB (e.g., cynomolgus MICA and/or MICB). As used herein, cross-reactivity may be measured by detecting a specific reactivity with purified antigen in binding assays (e.g., SPR, ELISA) or binding to, or otherwise functionally interacting with, cells physiologically expressing MICA and/or MICB. Methods for determining cross-reactivity include standard binding assays as described herein, for example, by Biacore™ surface plasmon resonance (SPR) analysis using a Biacore™ 2000 SPR instrument (Biacore AB, Uppsala, Sweden), or flow cytometric techniques.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring.

A "polypeptide" refers to a chain comprising at least two consecutively linked amino acid residues, with no upper limit on the length of the chain. One or more amino acid residues in the protein may contain a modification such as, but not limited to, glycosylation, phosphorylation or disulfide bond formation. A "protein" may comprise one or more polypeptides.

The term "nucleic acid molecule," as used herein, is intended to include DNA molecules and RNA molecules. A nucleic acid molecule may be single-stranded or double-stranded, and may be cDNA.

Also provided are "conservative sequence modifications" of the sequences set forth herein, e.g., in Table 2, i.e., nucleotide and amino acid sequence modifications which do not abrogate the binding of the antibody encoded by the nucleotide sequence or containing the amino acid sequence, to the antigen. Such conservative sequence modifications include conservative nucleotide and amino acid substitutions, as well as, nucleotide and amino acid additions and deletions. For example, modifications can be introduced into a sequence by standard techniques known in the art, such as site-directed mutagenesis and PCR-mediated mutagenesis. Conservative amino acid substitutions include ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, a predicted nonessential amino acid residue in an anti-MICA and/or anti-MICB antibody is preferably replaced with another amino acid residue from the same side chain family. Methods of identifying nucleotide and amino acid conservative substitutions which do not eliminate antigen binding are well-known in the art (see, e.g., Brummell et al., Biochem. 32:1180-1187 (1993); Kobayashi et al. Protein Eng. 12(10):879-884 (1999); and Burks et al. Proc. Natl. Acad. Sci. USA 94:412-417 (1997)). Alternatively, in another embodiment, mutations can be introduced randomly along all or part of an anti-MICA and/or anti-MICB antibody coding sequence, such as by saturation mutagenesis, and the resulting modified anti-MICA and/or anti-MICB antibodies can be screened for binding activity.

For nucleic acids, the term "substantial homology" indicates that two nucleic acids, or designated sequences thereof, when optimally aligned and compared, are identical, with appropriate nucleotide insertions or deletions, in at least about 80% of the nucleotides, usually at least about 90% to 95%, and more preferably at least about 98% to 99.5% of the nucleotides. Alternatively, substantial homology exists when the segments will hybridize under selective hybridization conditions, to the complement of the strand.

For polypeptides, the term "substantial homology" indicates that two polypeptides, or designated sequences thereof, when optimally aligned and compared, are identical, with appropriate amino acid insertions or deletions, in at least about 80% of the amino acids, usually at least about 90% to 95%, and more preferably at least about 98% to 99.5% of the amino acids.

The percent identity between two sequences is a function of the number of identical positions shared by the sequences (i.e., % homology=# of identical positions/total # of positions×100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package (available on the World Wide Web at gcg.com), using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (CABIOS, 4:11-17 (1989)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (*J. Mol. Biol.* (48):444-453 (1970)) algorithm which has been incorporated into the GAP program in the GCG software package (available at gcg.com), using either a Blossum 62 matrix or a PAM250 matrix, and a gap weight of 16, 14, 12, 10, 8, 6, or 4 and a length weight of 1, 2, 3, 4, 5, or 6.

The nucleic acid and protein sequences described herein can further be used as a "query sequence" to perform a search against public databases to, for example, identify related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to the nucleic acid molecules described herein. BLAST protein searches can be performed with the XBLAST program, score=50, wordlength=3 to obtain amino acid sequences homologous to the protein molecules described herein. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See World Wide Web at ncbi.nlm.nih.gov.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids (e.g., the other parts of the chromosome) or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

Nucleic acids, e.g., cDNA, may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

The term "vector," as used herein, is intended to refer to a nucleic acid molecule capable of transporting another nucleic acid to which it has been linked. One type of vector is a "plasmid," which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, also included are other forms of expression vectors, such as viral vectors (e.g., replication defective retroviruses, adenoviruses and adeno-associated viruses), which serve equivalent functions.

The term "recombinant host cell" (or simply "host cell"), as used herein, is intended to refer to a cell that comprises a nucleic acid that is not naturally present in the cell, and maybe a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

As used herein, the term "antigen" refers to any natural or synthetic immunogenic substance, such as a protein, peptide, or hapten. An antigen may be MICA and/or MICB, or a fragment thereof. An antigen may also be a tumor antigen, against which protective or therapeutic immune responses are desired, e.g., antigens expressed by a tumor cell (e.g., in a vaccine in combination with an anti-MICA and/or anti-MICB antibody).

An "immune response" refers to a biological response within a vertebrate against foreign agents, which response protects the organism against these agents and diseases caused by them. An immune response is mediated by the action of a cell of the immune system (for example, a T lymphocyte, B lymphocyte, natural killer (NK) cell, macrophage, eosinophil, mast cell, dendritic cell or neutrophil) and soluble macromolecules produced by any of these cells or the liver (including antibodies, cytokines, and complement) that results in selective targeting, binding to, damage to, destruction of, and/or elimination from the vertebrate's body of invading pathogens, cells or tissues infected with pathogens, cancerous or other abnormal cells, or, in cases of autoimmunity or pathological inflammation, normal human cells or tissues. An immune reaction includes, e.g., activation or inhibition of a T cell, e.g., an effector T cell or a Th cell, such as a CD4+ or CD8+ T cell, or the inhibition of a Treg cell.

An "immunomodulator" or "immunoregulator" refers to an agent, e.g., a component of a signaling pathway that may be involved in modulating, regulating, or modifying an immune response. "Modulating," "regulating," or "modifying" an immune response refers to any alteration in a cell of the immune system or in the activity of such cell (e.g., an effector T cell). Such modulation includes stimulation or suppression of the immune system which may be manifested by an increase or decrease in the number of various cell types, an increase or decrease in the activity of these cells, or any other changes which can occur within the immune system. Both inhibitory and stimulatory immunomodulators have been identified, some of which may have enhanced function in a tumor microenvironment. In preferred embodiments, the immunomodulator is located on the surface of a T cell. An "immunomodulatory target" or "immunoregulatory target" is an immunomodulator that is targeted for binding by, and whose activity is altered by the binding of, a substance, agent, moiety, compound or molecule. Immunomodulatory targets include, for example, receptors on the surface of a cell ("immunomodulatory receptors") and receptor ligands ("immunomodulatory ligands").

"Immunotherapy" refers to the treatment of a subject afflicted with, or at risk of contracting or suffering a recurrence of, a disease by a method comprising inducing, enhancing, suppressing or otherwise modifying an immune response.

"Immunostimulating therapy" or "immunostimulatory therapy" refers to a therapy that results in increasing (inducing or enhancing) an immune response in a subject for, e.g., treating cancer.

"Potentiating an endogenous immune response" means increasing the effectiveness or potency of an existing immune response in a subject. This increase in effectiveness and potency may be achieved, for example, by overcoming mechanisms that suppress the endogenous host immune response or by stimulating mechanisms that enhance the endogenous host immune response.

"T effector" ("$T_{eff}$") cells refers to T cells (e.g., CD4+ and CD8+ T cells) with cytolytic activities as well as T helper (Th) cells, which secrete cytokines and activate and direct other immune cells, but does not include regulatory T cells (Treg cells). Anti-MICA and/or anti-MICB antibodies described herein activate $T_{eff}$ cells, e.g., CD4+ and CD8+$T_{eff}$ cells.

An increased ability to stimulate an immune response or the immune system, can result from an enhanced agonist activity of T cell costimulatory receptors and/or an enhanced antagonist activity of inhibitory receptors. An increased ability to stimulate an immune response or the immune system may be reflected by a fold increase of the $EC_{50}$ or maximal level of activity in an assay that measures an immune response, e.g., an assay that measures changes in cytokine or chemokine release, cytolytic activity (determined directly on target cells or indirectly via detecting CD107a or granzymes) and proliferation. The ability to stimulate an immune response or the immune system activity may be enhanced by at least 10%, 30%, 50%, 75%, 2 fold, 3 fold, 5 fold or more.

As used herein, the term "linked" refers to the association of two or more molecules. The linkage can be covalent or non-covalent. The linkage also can be genetic (i.e., recombinantly fused). Such linkages can be achieved using a wide variety of art recognized techniques, such as chemical conjugation and recombinant protein production.

As used herein, "administering" refers to the physical introduction of a composition comprising a therapeutic agent to a subject, using any of the various methods and delivery systems known to those skilled in the art. Preferred routes of administration for antibodies described herein include intravenous, intraperitoneal, intramuscular, subcutaneous, spinal or other parenteral routes of administration, for example by injection or infusion. The phrase "parenteral administration" as used herein means modes of administration other than enteral and topical administration, usually by injection, and includes, without limitation, intravenous, intraperitoneal, intramuscular, intraarterial, intrathecal, intralymphatic, intralesional, intracapsular, intraorbital, intracardiac, intradermal, transtracheal, subcutaneous, subcuticular, intraarticular, subcapsular, subarachnoid, intraspinal, epidural and intrasternal injection and infusion, as well as in vivo electroporation. Alternatively, an antibody described herein can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

As used herein, the term "T cell-mediated response" refers to a response mediated by T cells, including effector T cells (e.g., CD8+ cells) and helper T cells (e.g., CD4+ cells). T cell mediated responses include, for example, T cell cytotoxicity and proliferation.

As used herein, the term "cytotoxic T lymphocyte (CTL) response" refers to an immune response induced by cytotoxic T cells. CTL responses are mediated primarily by CD8+ T cells.

As used herein, the terms "inhibits" or "blocks" (e.g., referring to inhibition/blocking of shedding of MICA and/or MICB on cells) are used interchangeably and encompass both partial and complete inhibition/blocking. In some embodiments, the anti-MICA and/or anti-MICB antibody inhibits shedding by at least about 50%, for example, about 60%, 70%, 80%, 90%, 95%, 99%, or 100%, determined, e.g., as further described herein. In some embodiments, the anti-MICA and/or anti-MICB antibody inhibits shedding by no more than 50%, for example, by about 40%, 30%, 20%, 10%, 5% or 1%, determined, e.g., as further described herein.

As used herein, the term "inhibits growth" of a tumor includes any measurable decrease in the growth of a tumor, e.g., the inhibition of growth of a tumor by at least about 10%, for example, at least about 20%, at least about 30%, at least about 40%, at least about 50%, at least about 60%, at least about 70%, at least about 80%, at least about 90%, at least about 99%, or 100%.

As used herein, "cancer" refers a broad group of diseases characterized by the uncontrolled growth of abnormal cells in the body. Unregulated cell division may result in the formation of malignant tumors or cells that invade neighboring tissues and may metastasize to distant parts of the body through the lymphatic system or bloodstream.

The terms "treat," "treating," and "treatment," as used herein, refer to any type of intervention or process performed on, or administering an active agent to, the subject with the objective of reversing, alleviating, ameliorating, inhibiting, or slowing down or preventing the progression, development, severity or recurrence of a symptom, complication, condition or biochemical indicia associated with a disease. Treatment can be of a subject having a disease or a subject who does not have a disease (e.g., for prophylaxis).

The term "effective dose" or "effective dosage" is defined as an amount sufficient to achieve or at least partially achieve a desired effect. A "therapeutically effective amount" or "therapeutically effective dosage" of a drug or therapeutic agent is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression or inhibit the development or recurrence of the disease can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent is a drug that promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms in the patient. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount or dosage of the drug preferably inhibits cell growth or tumor growth by at least about 20%, more preferably by at least about 40%, even more preferably by at least about 60%, and still more preferably by at least about 80% relative to untreated subjects. In the most preferred embodiments, a therapeutically effective amount or dosage of the drug completely inhibits cell growth or tumor growth, i.e., preferably inhibits cell growth or tumor growth by 100%. The ability of a compound to inhibit tumor growth can be evaluated using the assays described infra. Alternatively, this property of a composition can be evaluated by examining the ability of the compound to inhibit cell growth, such inhibition can be measured in vitro by assays known to the skilled practitioner. In other preferred embodiments described herein, tumor regression may be observed and continue for a period of at least about 20 days, more preferably at least about 40 days, or even more preferably at least about 60 days.

The term "patient" includes human and other mammalian subjects that receive either prophylactic or therapeutic treatment.

As used herein, the term "subject" includes any human or non-human animal. For example, the methods and compositions described herein can be used to treat a subject having cancer. The term "non-human animal" includes all vertebrates, e.g., mammals and non-mammals, such as non-human primates, sheep, dog, cow, chickens, amphibians, reptiles, etc.

As used herein, the terms "ug" and "uM" are used interchangeably with "μg" and "μM".

The articles "a" and "an" are used herein to refer to one or to more than one (i.e. to at least one) of the grammatical object of the article. By way of example, "an element" means one element or more than one element.

The amount of a biomarker in a subject is "significantly" higher or lower than the normal amount of the biomarker, if the amount of the biomarker is greater or less, respectively, than the normal or control level by an amount greater than the standard error of the assay employed to assess amount, and preferably at least 20%, 30%, 40%, 50%, 60%, 70%, 80%, 90%, 100%, 150%, 200%, 300%, 350%, 400%, 500%, 600%, 700%, 800%, 900%, 1000% or than that amount. Alternatively, the amount of the biomarker in the subject can be considered "significantly" higher or lower than the normal and/or control amount if the amount is at least about two, and preferably at least about 5%, 10%, 15%, 20%, 25%, 30%, 35%, 40%, 45%, 50%, 55%, 60%, 65%, 70%, 75%, 80%, 85%, 90%, 95%, 100%, 105%, 110%, 115%, 120%, 125%, 130%, 135%, 140%, 145%, 150%, 155%, 160%, 165%, 170%, 175%, 180%, 185%, 190%, 195%, two times, three times, four times, five times, or more, or any range in between, such as 5%-100%, higher or lower, respectively, than the normal and/or control amount of the biomarker. Such significant modulation values can be applied to any metric described herein, such as altered level of expression, altered activity, changes in cancer cell hyperproliferative growth, changes in cancer cell death, changes in biomarker inhibition, changes in test agent binding, and the like.

The "amount" of a marker, e.g., expression or copy number of a marker or MCR, or protein level of a marker, in a subject is "significantly" higher or lower than the normal amount of a marker, if the amount of the marker is greater or less, respectively, than the normal level by an amount greater than the standard error of the assay employed to assess amount, and preferably at least twice, and more preferably three, four, five, ten or more times that amount. Alternately, the amount of the marker in the subject can be considered "significantly" higher or lower than the normal amount if the amount is at least about two, and preferably at least about three, four, or five times, higher or lower, respectively, than the normal amount of the marker.

The term "altered level of expression" of a marker refers to an expression level or copy number of a marker in a test sample e.g., a sample derived from a subject suffering from cancer, that is greater or less than the standard error of the assay employed to assess expression or copy number, and is preferably at least twice, and more preferably three, four, five or ten or more times the expression level or copy number of the marker or chromosomal region in a control sample (e.g., sample from a healthy subject not having the associated disease) and preferably, the average expression level or copy number of the marker or chromosomal region in several control samples. The altered level of expression is greater or less than the standard error of the assay employed to assess expression or copy number, and is preferably at least twice, and more preferably three, four, five or ten or more times the expression level or copy number of the marker in a control sample (e.g., sample from a healthy subject not having the associated disease) and preferably, the average expression level or copy number of the marker in several control samples.

The term "control" refers to any reference standard suitable to provide a comparison to the expression products in the test sample. In one embodiment, the control comprises obtaining a "control sample" from which expression product levels are detected and compared to the expression product levels from the test sample. Such a control sample may comprise any suitable sample, including but not limited to a sample from a control cancer patient (can be stored sample or previous sample measurement) with a known outcome; normal tissue or cells isolated from a subject, such as a normal patient or the cancer patient, cultured primary cells/tissues isolated from a subject such as a normal subject or the cancer patient, adjacent normal cells/tissues obtained from the same organ or body location of the cancer patient, a tissue or cell sample isolated from a normal subject, or a primary cells/tissues obtained from a depository. In another preferred embodiment, the control may comprise a reference standard expression product level from any suitable source, including but not limited to housekeeping genes, an expression product level range from normal tissue (or other previously analyzed control sample), a previously determined expression product level range within a test sample from a group of patients, or a set of patients with a certain outcome (for example, survival for one, two, three, four years, etc.) or receiving a certain treatment (for example, standard of care cancer therapy). It will be understood by those of skill in the art that such control samples and reference standard expression product levels can be used in combination as controls in the methods of the present invention. In one embodiment, the control may comprise normal or non-cancerous cell/ tissue sample. In another preferred embodiment, the control may comprise an expression level for a set of patients, such as a set of cancer patients, or for a set of cancer patients receiving a certain treatment, or for a set of patients with one outcome versus another outcome. In the former case, the specific expression product level of each patient can be assigned to a percentile level of expression, or expressed as either higher or lower than the mean or average of the reference standard expression level. In another preferred embodiment, the control may comprise normal cells, cells from patients treated with combination chemotherapy, and cells from patients having benign cancer. In another embodiment, the control may also comprise a measured value for example, average level of expression of a particular gene in a population compared to the level of expression of a housekeeping gene in the same population. Such a population may comprise normal subjects, cancer patients who have not undergone any treatment (i.e., treatment naive), cancer patients undergoing standard of care therapy, or patients having benign cancer. In another preferred embodiment, the control comprises a ratio transformation of expression product levels, including but not limited to determining a ratio of expression product levels of two genes in the test sample and comparing it to any suitable ratio of the same two genes in a reference standard; determining expression product levels of the two or more genes in the test sample and determining a difference in expression product levels in any suitable control; and determining expression product levels of the two or more genes in the test sample, normalizing their expression to expression of housekeeping genes in the test sample, and comparing to any suitable control. In particularly preferred embodiments, the control comprises a control sample which is of the same lineage and/or type as the test sample. In another embodiment, the control may comprise expression product levels grouped as percentiles within or based on a set of patient samples, such as all patients with cancer. In one embodiment a control expression product level is established wherein higher or lower levels of expression product relative to, for instance, a particular percentile, are used as the basis for predicting outcome. In another preferred embodiment, a control expression product level is established using expression product levels from cancer control patients with a known outcome, and the expression product levels from the test sample are compared to the control expression product level as the basis for predicting outcome. As demonstrated by the data below, the methods of the invention are not limited to use of a specific cut-point in comparing the level of expression product in the test sample to the control.

The "normal" level of expression of a marker is the level of expression of the marker in cells of a subject, e.g., a human patient, not afflicted with a disease or disorder related to aberrant marker levels.

An "over-expression" or "significantly higher level of expression" of a marker refers to an expression level in a test sample that is greater than the standard error of the assay employed to assess expression, and is preferably at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more higher than the expression activity or level of the marker in a control sample (e.g., sample from a healthy subject not having the marker associated disease) and preferably, the average expression level of the marker in several control samples. A "significantly lower level of expression" of a marker refers to an expression level in a test sample that is at least twice, and more preferably 2.1, 2.2, 2.3, 2.4, 2.5, 2.6, 2.7, 2.8, 2.9, 3, 3.5, 4, 4.5, 5, 5.5, 6, 6.5, 7, 7.5, 8, 8.5, 9, 9.5, 10, 10.5, 11, 12, 13, 14, 15, 16, 17, 18, 19, 20 times or more lower than the expression level of the marker in a control sample (e.g., sample from a healthy subject not having the marker associated disease) and preferably, the average expression level of the marker in several control samples. Such "significance" levels can also be applied to any other measured parameter described herein, such as for expression, inhibition, cytotoxicity, cell growth, and the like.

Such antibodies, described herein, can be used in any one of well-known immunoassay forms, including, without limitation, a radioimmunoassay, a Western blot assay, an immunofluorescence assay, an enzyme immunoassay, an immunoprecipitation assay, a chemiluminescence assay, an immunohistochemical assay, a dot blot assay, or a slot blot assay. General techniques to be used in performing the various immunoassays noted above and other variations of the techniques, such as in situ proximity ligation assay (PLA), fluorescence polarization immunoassay (FPIA), fluorescence immunoassay (FIA), enzyme immunoassay (EIA), nephelometric inhibition immunoassay (MA), enzyme linked immunosorbent assay (ELISA), and radio-immunoassay (MA), ELISA, etc. alone or in combination or alternatively with NMR, MALDI-TOF, LC-MS/MS, are known to those of ordinary skill in the art.

Such reagents can also be used to monitor protein levels in a cell or tissue, e.g., white blood cells or lymphocytes, as part of a clinical testing procedure, e.g., in order to monitor an optimal dosage of an inhibitory agent. Detection can be facilitated by coupling (e.g., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Such reagents can also be used with any number of biological samples. Biological samples can be collected from a variety of sources from a patient including a body fluid sample, cell sample, or a tissue sample comprising nucleic acids and/or proteins. In a preferred embodiment, the subject and/or control sample is selected from the group consisting of cells, cell lines, histological slides, paraffin embedded tissues, biopsies, whole blood, nipple aspirate, serum, plasma, buccal scrape, saliva, cerebrospinal fluid, urine, stool, and bone marrow. In one embodiment, the sample is serum, plasma, or urine. In another embodiment, the sample is serum.

The samples can be collected from individuals repeatedly over a longitudinal period of time (e.g., once or more on the order of days, weeks, months, annually, biannually, etc.). Obtaining numerous samples from an individual over a period of time can be used to verify results from earlier detections and/or to identify an alteration in biological pattern as a result of, for example, disease progression, drug treatment, etc. For example, subject samples can be taken and monitored every month, every two months, or combinations of one, two, or three month intervals according to the present invention. In addition, the biomarker amount and/or activity measurements of the subject obtained over time can be conveniently compared with each other, as well as with those of normal controls during the monitoring period, thereby providing the subject's own values, as an internal, or personal, control for long-term monitoring.

Samples can contain live cells/tissue, fresh frozen cells, fresh tissue, biopsies, fixed cells/tissue, cells/tissue embedded in a medium, such as paraffin, histological slides, or any combination thereof.

Sample preparation and separation can involve any of the procedures, depending on the type of sample collected and/or analysis of biomarker measurement(s). Such procedures include, by way of example only, concentration, dilution, adjustment of pH, removal of high abundance polypeptides (e.g., albumin, gamma globulin, and transferrin, etc.), addition of preservatives and calibrants, addition of protease inhibitors, addition of denaturants, desalting of samples, concentration of sample proteins, extraction and purification of lipids.

The sample preparation can also isolate molecules that are bound in non-covalent complexes to other protein (e.g., carrier proteins). This process may isolate those molecules bound to a specific carrier protein (e.g., albumin), or use a more general process, such as the release of bound molecules from all carrier proteins via protein denaturation, for example using an acid, followed by removal of the carrier proteins.

Removal of undesired proteins (e.g., high abundance, uninformative, or undetectable proteins) from a sample can be achieved using high affinity reagents, high molecular weight filters, ultracentrifugation and/or electrodialysis. High affinity reagents include antibodies or other reagents (e.g., aptamers) that selectively bind to high abundance proteins. Sample preparation could also include ion exchange chromatography, metal ion affinity chromatography, gel filtration, hydrophobic chromatography, chromatofocusing, adsorption chromatography, isoelectric focusing and related techniques. Molecular weight filters include membranes that separate molecules on the basis of size and molecular weight. Such filters may further employ reverse osmosis, nanofiltration, ultrafiltration and microfiltration.

The term "predictive" includes the use of a biomarker nucleic acid and/or protein status, e.g., over- or under-activity, emergence, expression, growth, remission, recurrence or resistance of tumors before, during or after therapy, for determining the likelihood of response of a cancer to immunomodulatory therapy, such as MICA and/or MICB pathway modulator therapy (e.g., modulator of MICA and/or MICB shedding, either alone or in combination with an agent that enhances the expression of MICA and/or MICB, such as radiation therapy, chemotherapy, HDAC inhibitor, proteasome inhibitor, etc.). Such predictive use of the biomarker may be confirmed by, e.g., (1) increased or decreased copy number (e.g., by FISH, FISH plus SKY, single-molecule sequencing, e.g., as described in the art at least at J. Biotechnol., 86:289-301, or qPCR), overexpression or underexpression of a biomarker nucleic acid (e.g., by ISH, Northern Blot, or qPCR), increased or decreased biomarker protein (e.g., by IHC) and/or biomarker target, or increased or decreased activity, e.g., in more than about 5%, 6%, 7%, 8%, 9%, 10%, 11%, 12%, 13%, 14%, 15%, 20%, 25%, 30%, 40%, 50%, 60%, 70%, 80%, 90%, 95%, 100%, or more of assayed human cancers types or cancer samples; (2) its absolute or relatively modulated presence or absence in a biological sample, e.g., a sample containing tissue, whole blood, serum, plasma, buccal scrape, saliva, cerebrospinal fluid, urine, stool, or bone marrow, from a subject, e.g. a human, afflicted with cancer; (3) its absolute or relatively modulated presence or absence in clinical subset of patients with cancer (e.g., those responding to a particular immunomodulatory therapy (e.g., MICA and/or MICB pathway modulator therapy (e.g., modulator of MICA and/or MICB shedding, either alone or in combination with an agent that enhances the expression of MICA and/or MICB) or those developing resistance thereto).

The terms "prevent," "preventing," "prevention," "prophylactic treatment," and the like refer to reducing the probability of developing a disease, disorder, or condition in a subject, who does not have, but is at risk of or susceptible to developing a disease, disorder, or condition.

The term "prognosis" includes a prediction of the probable course and outcome of cancer or the likelihood of recovery from the disease. In some embodiments, the use of statistical algorithms provides a prognosis of cancer in an individual. For example, the prognosis can be surgery, development of a clinical subtype of cancer (e.g., solid tumors, such as lung cancer, melanoma, and renal cell carcinoma), development of one or more clinical factors, development of intestinal cancer, or recovery from the disease.

The term "response to therapy" relates to any response to therapy (e.g., MICA and/or MICB pathway modulator therapy (e.g., modulator of MICA and/or MICB shedding, either alone or in combination with an agent that enhances the expression of MICA and/or MICB), and, for cancer, preferably to a change in cancer cell numbers, tumor mass, and/or volume after initiation of neoadjuvant or adjuvant chemotherapy. Hyperproliferative disorder response may be assessed, for example for efficacy or in a neoadjuvant or adjuvant situation, where the size of a tumor after systemic intervention can be compared to the initial size and dimensions as measured by CT, PET, mammogram, ultrasound or palpation. Responses may also be assessed by caliper measurement or pathological examination of the tumor after biopsy or surgical resection. Response may be recorded in a quantitative fashion like percentage change in tumor volume or in a qualitative fashion like "pathological complete response" (pCR), "clinical complete remission" (cCR), "clinical partial remission" (cPR), "clinical stable disease" (cSD), "clinical progressive disease" (cPD) or other qualitative criteria. Assessment of hyperproliferative disorder response may be done early after the onset of neoadjuvant or adjuvant therapy, e.g., after a few hours, days, weeks or preferably after a few months. A typical endpoint for response assessment is upon termination of neoadjuvant chemotherapy or upon surgical removal of residual tumor cells and/or the tumor bed. This is typically three months after initiation of neoadjuvant therapy. In some embodiments, clinical efficacy of the therapeutic treatments described herein may be determined by measuring the clinical benefit rate (CBR). The clinical benefit rate is measured by determining the sum of the percentage of patients who are in complete remission (CR), the number of patients who are in partial remission (PR) and the number of patients having stable disease (SD) at a time point at least 6 months out from the end of therapy. The shorthand for this formula is CBR=CR+PR+SD over 6 months. In some embodiments, the CBR for a particular cancer therapeutic regimen is at least 25%, 30%, 35%, 40%, 45%, 50%, 55%, 60%, 65%, 70%, 75%, 80%, 85%, or more. Additional criteria for evaluating the response to cancer therapies are related to "survival," which includes all of the following: survival until mortality, also known as overall survival (wherein said mortality may be either irrespective of cause or tumor related); "recurrence-free survival" (wherein the term recurrence shall include both localized and distant recurrence); metastasis free survival; disease free survival (wherein the term disease shall include cancer and diseases associated therewith). The length of said survival may be calculated by reference to a defined start point (e.g., time of diagnosis or start of treatment) and end point (e.g., death, recurrence or metastasis). In addition, criteria for efficacy of treatment can be expanded to include response to chemotherapy, probability of survival, probability of metastasis within a given time period, and probability of tumor recurrence. For example, in order to determine appropriate threshold values, a particular cancer therapeutic regimen can be administered to a population of subjects and the outcome can be correlated to biomarker measurements that were determined prior to administration of any immunomodulatory therapy. The outcome measurement may be pathologic response to therapy given in the neoadjuvant setting. Alternatively, outcome measures, such as overall survival and disease-free survival can be monitored over a period of time for subjects following immunomodulatory therapy for whom biomarker measurement values are known. In certain embodiments, the doses administered are standard doses known in the art for cancer therapeutic agents. The period of time for which subjects are monitored can vary. For example, subjects may be monitored for at least 2, 4, 6, 8, 10, 12, 14, 16, 18, 20, 25, 30, 35, 40, 45, 50, 55, or 60 months.

The terms "response" or "responsiveness" refers to response to therapy. For example, an anti-cancer response includes reduction of tumor size or inhibiting tumor growth. The terms can also refer to an improved prognosis, for example, as reflected by an increased time to recurrence, which is the period to first recurrence censoring for second primary cancer as a first event or death without evidence of recurrence, or an increased overall survival, which is the period from treatment to death from any cause. To respond or to have a response means there is a beneficial endpoint attained when exposed to a stimulus. Alternatively, a negative or detrimental symptom is minimized, mitigated or attenuated on exposure to a stimulus. It will be appreciated that evaluating the likelihood that a tumor or subject will exhibit a favorable response is equivalent to evaluating the likelihood that the tumor or subject will not exhibit favorable response (i.e., will exhibit a lack of response or be non-responsive).

The term "tolerance" or "unresponsiveness" includes refractivity of cells, such as immune cells, to stimulation, e.g., stimulation via an activating receptor or a cytokine. Unresponsiveness can occur, e.g., because of exposure to immunosuppressants or exposure to high doses of antigen. Several independent methods can induce tolerance. One mechanism is referred to as "anergy," which is defined as a state where cells persist in vivo as unresponsive cells rather than differentiating into cells having effector functions. Such refractivity is generally antigen-specific and persists after exposure to the tolerizing antigen has ceased. For example, anergy in T cells is characterized by lack of cytokine production, e.g., IL-2. T cell anergy occurs when T cells are exposed to antigen and receive a first signal (a T cell receptor or CD-3 mediated signal) in the absence of a second signal (a costimulatory signal). Under these conditions, reexposure of the cells to the same antigen (even if reexposure occurs in the presence of a costimulatory polypeptide) results in failure to produce cytokines and, thus, failure to proliferate. Anergic T cells can, however, proliferate if cultured with cytokines (e.g., IL-2). For example, T cell anergy can also be observed by the lack of IL-2 production by T lymphocytes as measured by ELISA or by a proliferation assay using an indicator cell line. Alternatively, a reporter gene construct can be used. For example, anergic T cells fail to initiate IL-2 gene transcription induced by a heterologous promoter under the control of the 5' IL-2 gene enhancer or by a multimer of the AP1 sequence that can be found within the enhancer (Kang et al. (1992) Science 257:1134). Another mechanism is referred to as "exhaustion." T cell exhaustion is a state of T cell dysfunction that arises during many chronic infections and cancer. It is defined by poor effector function, sustained expression of inhibitory receptors and a transcriptional state distinct from that of functional effector or memory T cells.

The term "synergistic effect" refers to the combined effect of two or more cancer agents (e.g., an modulator of MICA and/or MICB shedding combined with an agent that induces or enhances the expression of MICA and/or MICB) can be greater than the sum of the separate effects of the cancer agents/therapies alone.

In addition, it is noted that in some embodiments of any aspect encompassed by the present invention, the term MICA and/or MICB can refer to a form of MICA and/or MICB comprising the extracellular domain having the ability to bind NKG2D (e.g., full-length MICA/MICB, full-length MICA/MICB extracellular domain, MICA/MICB extracellular domains having alpha 1 through alpha 3 domains, etc.).

Various aspects described herein are described in further detail in the following subsections.

Anti-MICA and/or Anti-MICB Antibodies

In some embodiments, the antibodies or antigen binding fragments thereof provided herein include (e.g., comprise, consist essentially of, or consist of at least one (e.g., one, two or three) variable heavy chain ($V_H$) complementarity determining region (CDR) set forth in SEQ ID NO: 1, 2 and 3, respectively. In some embodiments, the antibodies or antigen binding fragments thereof provided herein may also include (e.g., comprise, consist essentially of, or consist of at least one (e.g., one, two or three) light chain variable ($V_L$) complementarity determining region (CDR) variable light chain ($V_L$) set forth in SEQ ID NO: 4, 5 and 6, respectively.

In some embodiments, the antibodies or antigen binding fragments thereof provided herein include (e.g., comprise, consist essentially of, or consist of) the amino acid sequence of the $V_H$ shown in FIG. 21. In some embodiments, the antibodies or antigen binding fragments thereof provided herein also include the amino acid sequence of the $V_L$ shown in FIG. 21.

In some embodiments, the $V_H$ and/or $V_L$ of the antibodies or antigen binding fragments thereof comprise an amino acid sequence that is at least 90%, 95%, 97%, 98% or 99% identical to the amino acid sequences of the $V_H$ and/or $V_L$ set forth in FIG. 21.

In some embodiments, the antibodies or antigen binding fragments thereof provided herein include (e.g., comprise, consist essentially of, or consist of) the amino acid sequence of the heavy chain constant domain set forth in FIG. 21 or FIG. 23.

Also provided are modified antibodies and/or antigen binding fragments which can be prepared using an antibody having one or more of the $V_H$ and/or $V_L$ sequences disclosed herein as starting material to engineer a modified antibody which may have altered properties from the starting antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann, L. et al. (1998) *Nature* 332:323-327; Jones, P. et al. (1986) *Nature* 321:522-525; Queen, C. et al. (1989) *Proc. Natl. Acad. See. U.S.A.* 86:10029-10033; U.S. Pat. No. 5,225,539 to Winter, and U.S. Pat. Nos. 5,530,101; 5,585,089; 5,693,762 and 6,180,370 to Queen et al.)

Such framework sequences can be obtained from public DNA databases or published references that include germline antibody gene sequences. For example, germline DNA sequences for human heavy and light chain variable region genes can be found in the "VBase" human germline sequence database (available on the Internet at mrc-cpe.cam.ac.uk/vbase), as well as in Kabat, E. A., et al. (1991) Sequences of Proteins of Immunological Interest, Fifth Edition, U.S. Department of Health and Human Services, NIH Publication No. 91-3242; Tomlinson, I. M., et al. (1992) "The Repertoire of Human Germline $V_H$ Sequences Reveals about Fifty Groups of $V_H$ Segments with Different Hypervariable Loops" *J. Mol. Biol.* 227:776-798; and Cox, J. P. L. et al. (1994) "A Directory of Human Germ-line $V_H$ Segments Reveals a Strong Bias in their Usage" *Eur. J. Immunol.* 24:827-836; the contents of each of which are expressly incorporated herein by reference.

Preferred framework sequences for use in the antibodies described herein are those that are structurally similar to the framework sequences used by antibodies described herein. The $V_H$ CDR1, 2 and 3 sequences, and the $V_L$ CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Engineered antibodies described herein include those in which modifications have been made to framework residues within $V_H$ and/or $V_L$, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis or PCR-mediated mutagenesis. Such "backmutated" antibodies are also intended to be encompassed.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043 by Carr et al.

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Preferably conservative modifications (as discussed above) are introduced. The mutations may be amino acid substitutions, additions or deletions, but are preferably substitutions. Moreover, typically no more than one, two, three, four or five residues within a CDR region are altered.

Methionine residues in CDRs of antibodies can be oxidized, resulting in potential chemical degradation and consequent reduction in potency of the antibody. Accordingly, also provided are anti-MICA and/or anti-MICB antibodies which have one or more methionine residues in the heavy and/or light chain CDRs replaced with amino acid residues which do not undergo oxidative degradation. In one embodiment, the methionine residues in the CDRs of antibody 7C6 are replaced with amino acid residues which do not undergo oxidative degradation.

Similarly, deamidation sites may be removed from anti-MICA and/or anti-MICB antibodies, particularly in the CDRs.

Nucleic Acids

Also provided are nucleotide sequences corresponding to (e.g., encoding) the anti-MICA and/or anti-MICB antibodies and antigen binding fragments disclosed herein. These sequences include all degenerate sequences related to the disclosed antibodies, i.e., all nucleic acids having a sequence that encodes one particular peptide and variants and derivatives thereof. Thus, while each particular nucleic acid sequence may not be written out herein, it is understood that each and every sequence is in fact disclosed and described herein through the disclosed polypeptide sequences.

In some instances, nucleic acids of the disclosed can include expression vectors. Examples of suitable vectors include, but are not limited to, plasmids, artificial chromosomes, such as BACs, YACs, or PACs, and viral vectors.

The provided vectors also can include, for example, origins of replication and/or markers. A marker gene can confer a selectable phenotype, e.g., antibiotic resistance, on a cell. The marker product is used to determine if the vector has been delivered to the cell and once delivered is being expressed. Examples of selectable markers for mammalian cells are dihydrofolate reductase (DHFR), thymidine kinase, neomycin, neomycin analog G418, hygromycin, puromycin, and blasticidin. When such selectable markers are successfully transferred into a mammalian host cell, the transformed mammalian host cell can survive if placed under selective pressure. Examples of other markers include, for example, the *E. coli* lacZ gene, green fluorescent protein (GFP), and luciferase. In addition, an expression vector can include a tag sequence designed to facilitate manipulation or detection (e.g., purification or localization) of the expressed polypeptide. Tag sequences, such as GFP, glutathione S-transferase (GST), polyhistidine, c-myc, hemagglutinin, or FLAG™ tag (Kodak; New Haven, Conn.) sequences typically are expressed as a fusion with the encoded polypeptide. Such tags can be inserted anywhere within the polypeptide including at either the carboxyl or amino terminus.

In some instances, the disclosure includes cells comprising the nucleic acids (e.g., vectors) and/or peptides disclosed herein. Cells can include, for example, eukaryotic and/or prokaryotic cells. In general, cells that can be used herein are commercially available from, for example, the American Type Culture Collection (ATCC), P.O. Box 1549, Manassas, Va. 20108. See also F. Ausubel et al., Current Protocols in Molecular Biology, John Wiley & Sons, New York, N.Y., (1998). Transformation and transfection methods useful in the generation of the cells disclosed herein are described, e.g., in F. Ausubel et al., Current Protocols in Molecular Biology, John Wiley & Sons, New York, N.Y., (1998).

Vector-mediated gene transfer has been shown to engineer targeted delivery of antibodies. (Balazs et al., Nature. 2011 Nov. 30; 481(7379):81-4) Accordingly, in one aspect, methods and compositions are provided for delivering a polynucleotide encoding an antibody or antigen binding fragment binds to MICA and/or MICB to a target cell using a virus. In the context of gene therapy, nucleic acid sequences encoding the anti-MICA and/or anti-MICB antibody or antigen binding fragment thereof may be delivered into cells via a vector (e.g., a viral vector, including but not limited to adenovirus, vaccinia virus or adeno-associated virus). For example, a protein such as an antibody or antibody fragment having specificity for a particular cell surface molecule may be attached to the surface of the virus, allowing the virus to target specific cells. Further, the virus may be engineered to contain nucleic acid sequences, such as promoters, which allow the virus to function in only particular cells, such as cancer cells.

In some instances, the disclosed therapeutic compositions can include a vector (e.g., expression vector, a viral vector, an adeno-associated virus vector) comprising a nucleic acid encoding and anti-MICA and/or anti-MICB antibody or antigen binding fragment thereof. As described herein, antibodies and antibody fragments include, but are not limited to, monoclonal antibodies (including full-length monoclonal antibodies), polyclonal antibodies, multispecific antibodies formed from at least two different epitope binding fragments (e.g., bispecific antibodies), camelised antibodies, chimeric antibodies, single-chain Fvs (scFv), single-chain antibodies, single domain antibodies, domain antibodies, Fab fragments, F(ab')2 fragments, antibody fragments that exhibit the desired biological activity (e.g. the antigen binding portion), disulfide-linked Fvs (dsFv), and anti-idiotypic (anti-Id) antibodies (including, e.g., anti-Id antibodies to antibodies of the invention), intrabodies, and epitope-binding fragments of any of the above.

In some embodiments, the nucleic acids encode a $V_H$ comprising the CDR sequences set forth in SEQ ID NOs: 1-3. In some embodiments, the nucleic acids encode a $V_H$ comprising an amino acid that is at least about 90%, 95%, 99% or more, or the complete (100%) sequence of the $V_H$ set forth in FIG. 21. In some embodiments, the nucleic acids encode the $V_H$ of the anti-MICA and/or anti-MICB antibody set forth in FIG. 21.

In some embodiments, the nucleic acids encode a $V_L$ comprising the CDR sequences set forth in SEQ ID NOs: 4-6. In some embodiments, the nucleic acids encode a $V_L$ comprising an amino acid that is at least about 90%, 95%, 99% or more, or the complete (100%) sequence of the $V_H$ set forth in FIG. 21. In some embodiments, the nucleic acids encode the $V_L$ of the anti-MICA and/or anti-MICB antibody set forth in FIG. 21.

In some embodiments, the isolated nucleic acids comprising a nucleotide sequence at least about 75%, 80%, 90%, 95%, 99% or more, or complete (100%) sequence identity to the portion of the nucleotide sequence set forth in FIG. 21 encoding the $V_H$ amino acid sequence. In some embodiments, the isolated nucleic acids comprising a nucleotide sequence at least about 75%, 80%, 90%, 95%, 99% or more, or complete (100%) sequence identity to the portion of the nucleotide sequence set forth in FIG. 21 encoding the $V_L$ amino acid sequence. In some embodiments, the isolated nucleic acid encodes the nucleotide sequence set forth in FIG. 21 or FIG. 23.

Accordingly, also provided are vectors and cells which comprise a nucleotide sequence having at least about 75%, 80%, 90%, 95%, 99% or more, or complete (100%) sequence identity to the portion of the nucleotide sequence set forth in FIG. 21 encoding the $V_H$ amino acid sequence and/or the $V_L$ amino acid sequence. In some embodiments, vectors and cells which comprise a nucleotide sequence having at least about 75%, 80%, 90%, 95%, 99% or more, or complete (100%) sequence identity to the nucleotide sequence set forth in FIG. 21 or FIG. 23.

The term "nucleic acid" or "nucleic acid molecule", as used herein, is intended to include DNA molecules and RNA molecules. A nucleic acid molecule may be single-stranded or double-stranded, but preferably is double-stranded DNA.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, cDNA, or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

In calculating percent sequence identity, two sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align with more than one other sequence and hence, can have different percent sequence identity values over each aligned region. It is noted that the percent identity value is usually rounded to the nearest integer. For example, 78.1%, 78.2%, 78.3%, and 78.4% are rounded down to 78%, while 78.5%, 78.6%, 78.7%, 78.8%, and 78.9% are rounded up to 79%. It is also noted that the length of the aligned region is always an integer.

As used herein, the term "percent sequence identity" refers to the degree of identity between any given query sequence and a subject sequence. A percent identity for any query nucleic acid or amino acid sequence, e.g., a transcription factor, relative to another subject nucleic acid or amino acid sequence can be determined as follows.

The nucleic acids may be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques, including alkaline/SDS treatment, CsCl banding, column chromatography, agarose gel electrophoresis and others well known in the art. See, F. Ausubel, et al., ed. Current Protocols in Molecular Biology, Greene Publishing and Wiley Interscience, New York (1987).

The nucleic acid compositions of the present invention, while often in a native sequence (except for modified restriction sites and the like), from either cDNA, genomic or mixtures thereof may be mutated, in accordance with standard techniques to provide gene sequences. For coding sequences, these mutations, may affect amino acid sequence as desired. In particular, DNA sequences substantially homologous to or derived from native V, D, J, constant, switches and other such sequences described herein are contemplated (where "derived" indicates that a sequence is identical or modified from another sequence).

A nucleic acid is "operably linked" when it is placed into a functional relationship with another nucleic acid sequence. For instance, a promoter or enhancer is operably linked to a coding sequence if it affects the transcription of the sequence. With respect to transcription regulatory sequences, operably linked means that the DNA sequences being linked are contiguous and, where necessary to join two protein coding regions, contiguous and in reading frame. For switch sequences, operably linked indicates that the sequences are capable of effecting switch recombination.

The term "vector" as used herein refers to any molecule used to transfer a nucleic acid sequence to a host cell. In some aspects, an expression vector is utilized. An expression vector is a nucleic acid molecule that is suitable for transformation of a host cell and contains nucleic acid sequences that direct and/or control the expression of the transferred nucleic acid sequences. Expression includes, but is not limited to, processes such as transcription, translation, and splicing, if introns are present. In some aspects, a viral vector is utilized (e.g., a retrovirus, adenovirus, adeno-associated virus (AAV), herpes virus, and poxvirus, among others). It is understood in the art that many such viral vectors are available in the art. In yet other aspects, a non-viral plasmid vector may also be suitable in practicing the present invention. The vectors of the present invention may be constructed using standard recombinant techniques widely available to one skilled in the art. Such techniques may be found in common molecular biology references such as Sambrook et al., Molecular Cloning: A Laboratory Manual (2nd Edition, 1989).

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

Pharmaceutical Formulations

In some instances, the anti-MICA and/or anti-MICB antibodies and/or antigen-binding fragments disclosed herein can be formulated for use as or in pharmaceutical compositions. Such compositions can be formulated or adapted for administration to a subject via any route, e.g., any route approved by the Food and Drug Administration (FDA). Exemplary methods are described in the FDA's CDER Data Standards Manual, version number 004 (which is available at fda.give/cder/dsm/DRG/drg00301.htm).

The amount of active ingredient which can be combined with a carrier material to produce a single dosage form will vary depending upon the subject being treated, and the particular mode of administration. The amount of active ingredient which can be combined with a carrier material to produce a single dosage form will generally be that amount of the composition which produces a therapeutic effect. Generally, out of one hundred percent, this amount will range from about 0.01 percent to about ninety-nine percent of active ingredient, preferably from about 0.1 percent to about 70 percent, most preferably from about 1 percent to about 30 percent of active ingredient in combination with a pharmaceutically acceptable carrier.

In some instances, pharmaceutical compositions can include an effective amount of one or more peptides. The terms "effective amount" and "effective to treat," as used herein, refer to an amount or a concentration of one or more peptides disclosed herein (e.g., antibody or antibody fragment which binds MICA) for a period of time (including acute or chronic administration and periodic or continuous administration) that is effective within the context of its administration for causing an intended effect or physiological outcome.

In some instances, pharmaceutical compositions can include one or more peptides and any pharmaceutically acceptable carrier, adjuvant and/or vehicle. In some instances, pharmaceuticals can further include one or more additional therapeutic agents in amounts effective for achieving a modulation of disease or disease symptoms.

The term "pharmaceutically acceptable carrier or adjuvant" refers to a carrier or adjuvant that may be administered to a patient, together with a peptide of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-☐-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as ▯ -, ▯ -, and ▯ -cyclodextrin, may also be advantageously used to enhance delivery of compounds of the formulae described herein.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intra-articular, intraarterial, intrasynovial, intrasternal, intrathecal, intralesional and intracranial injection or infusion techniques.

Pharmaceutical compositions can be in the form of a solution or powder for inhalation and/or nasal administration. Such compositions may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

Pharmaceutical compositions can be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

Alternatively or in addition, pharmaceutical compositions can be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

In some embodiments, the present disclosure provides methods for using any one or more of the antibodies, fragments thereof or pharmaceutical compositions (indicated below as 'X') disclosed herein in the following methods: substance X for use as a medicament in the treatment of one or more diseases or conditions disclosed herein (e.g., cancer, referred to in the following examples as 'Y'). Use of substance X for the manufacture of a medicament for the treatment of Y; and substance X for use in the treatment of Y.

In some instances, therapeutic compositions disclosed herein can be formulated for sale in the US, import into the US, and/or export from the US.

Diagnostic Assays

The present invention provides, in part, methods, systems, and code for accurately classifying whether a biological sample expresses cell-restricted MICA/B and/or whether the levels of cell-restricted MICA/B are modulated (e.g., upregulated or downregulated), thereby indicative of the state of a disorder of interest, such as cancer. In some embodiments, the present invention is useful for classifying a sample (e.g., from a subject) as associated with or at risk for cancer or a subtype thereof, mediated by MICA and/or MICB using a statistical algorithm and/or empirical data (e.g., the presence, absence, or level of MICA and/or MICB).

An exemplary method for detecting the level of MICA and/or MICB or fragments thereof, and thus useful for classifying whether a sample is associated with a disease or disorder mediated by an aberrant expression (e.g., upregulation or downregulation) of MICA and/or MICB or a clinical subtype thereof involves obtaining a biological sample from a test subject and contacting the biological sample with an antibody or antigen-binding fragment thereof of the present invention capable of detecting MICA and/or MICB such that the level of MICA and/or MICB is detected in the biological sample. In some embodiments, at least one antibody or antigen-binding fragment thereof is used, wherein two, three, four, five, six, seven, eight, nine, ten, or more such antibodies or antibody fragments can be used in combination (e.g., in sandwich ELISAs) or in serial. In certain instances, the statistical algorithm is a single learning statistical classifier system. For example, a single learning statistical classifier system can be used to classify a sample as a MICA and/or MICB sample based upon a prediction or probability value and the presence or level of MICA and/or MICB. The use of a single learning statistical classifier system typically classifies the sample as a MICA and/or MICB sample with a sensitivity, specificity, positive predictive value, negative predictive value, and/or overall accuracy of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%.

Other suitable statistical algorithms are well-known to those of skill in the art. For example, learning statistical classifier systems include a machine learning algorithmic technique capable of adapting to complex data sets (e.g., panel of markers of interest) and making decisions based upon such data sets. In some embodiments, a single learning statistical classifier system such as a classification tree (e.g., random forest) is used. In other embodiments, a combination of 2, 3, 4, 5, 6, 7, 8, 9, 10, or more learning statistical classifier systems are used, preferably in tandem. Examples of learning statistical classifier systems include, but are not limited to, those using inductive learning (e.g., decision/ classification trees such as random forests, classification and regression trees (C&RT), boosted trees, etc.), Probably Approximately Correct (PAC) learning, connectionist learning (e.g., neural networks (NN), artificial neural networks (ANN), neuro fuzzy networks (NFN), network structures, perceptrons such as multi-layer perceptrons, multi-layer feed-forward networks, applications of neural networks, Bayesian learning in belief networks, etc.), reinforcement learning (e.g., passive learning in a known environment such as naive learning, adaptive dynamic learning, and temporal difference learning, passive learning in an unknown environment, active learning in an unknown environment, learning action-value functions, applications of reinforcement learning, etc.), and genetic algorithms and evolutionary programming. Other learning statistical classifier systems include support vector machines (e.g., Kernel methods), multivariate adaptive regression splines (MARS), Levenberg-Marquardt algorithms, Gauss-Newton algorithms, mixtures of Gaussians, gradient descent algorithms, and learning vector quantization (LVQ). In certain embodiments, the method of the present invention further comprises sending the MICA and/or MICB sample classification results to a clinician, e.g., a histopathologist or an oncologist.

In another embodiment, the method of the present invention further provides a diagnosis in the form of a probability that the individual has a condition or disorder associated with MICA and/or MICB. For example, the individual can have about a 0%, 5%, 10%, 15%, 20%, 25%, 30%, 35%, 40%, 45%, 50%, 55%, 60%, 65%, 70%, 75%, 80%, 85%, 90%, 95%, or greater probability of having the condition or disorder. In yet another embodiment, the method of the present invention further provides a prognosis of the condition or disorder in the individual. In some instances, the method of classifying a sample as a MICA and/or MICB sample is further based on the symptoms (e.g., clinical factors) of the individual from which the sample is obtained. The symptoms or group of symptoms can be, for example, lymphocyte count, white cell count, erythrocyte sedimentation rate, diarrhea, abdominal pain, cramping, fever, anemia, weight loss, anxiety, depression, and combinations thereof. In some embodiments, the diagnosis of an individual as having a condition or disorder associated with MICA and/or MICB is followed by administering to the individual a therapeutically effective amount of a drug useful for treating one or more symptoms associated with the condition or disorder (e.g., chemotherapeutic agents).

In one embodiment, the methods further involve obtaining a control biological sample (e.g., biological sample from a subject who does not have a condition or disorder mediated by MICA and/or MICB), a biological sample from the subject during remission or before developing a condition or disorder mediated by MICA and/or MICB, or a biological sample from the subject during treatment for developing a condition or disorder mediated by MICA and/or MICB.

An exemplary method for detecting the presence or absence of MICA and/or MICB polypeptide or fragments thereof is an antibody of the present invention, or fragment thereof, capable of binding to a MICA and/or MICB polypeptide, preferably an antibody with a detectable label. Antibodies can be polyclonal, or more preferably, monoclonal. Such agents can be labeled. The term "labeled", with regard to the antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody. The term "biological sample" is intended to include tissues, cells, and biological fluids isolated from a subject, such as serum, as well as tissues, cells, and fluids present within a subject. That is, the detection method of the present invention can be used to detect MICA and/or MICB, or fragments thereof, in a biological sample in vitro as well as in vivo. In vitro techniques for detection of MICA and/or MICB polypeptide include enzyme linked immunosorbent assays (ELISAs), Western blots, immunoprecipitations, immunohistochemistry (IHC), intracellular flow cytometry and related techniques, and immunofluorescence. Furthermore, in vivo techniques for detection of a MICA and/or MICB polypeptide or a fragment thereof include introducing into a subject a labeled anti-MICA and/or MICB antibody. For example, the antibody can be labeled with a radioactive, luminescent, fluorescent, or other similar marker whose presence and location in a subject can be detected by standard imaging techniques, either alone or in combination with imaging for other molecules, such as markers of cell type (e.g., CD8+ T cell markers).

In one embodiment, the biological sample contains polypeptide molecules from the test subject. A preferred biological sample is a serum, tumor microenvironment, peritumoral, or intratumoral, isolated by conventional means from a subject.

In another embodiment, the methods further involve obtaining a control biological sample from a control subject, contacting the control sample with a compound or agent capable of detecting MICA and/or MICB polypeptide, or fragments thereof, such that the presence of MICA and/or MICB polypeptide, or fragments thereof, is detected in the biological sample, and comparing the presence of MICA and/or MICB polypeptide, or fragments thereof, in the control sample with the presence of MICA and/or MICB polypeptide, or fragments thereof in the test sample.

In still other embodiments, the antibodies can be associated with a component or device for the use of the antibodies in an ELISA or MA. Non-limiting examples include antibodies immobilized on solid surfaces for use in these assays (e.g., linked and/or conjugated to a detectable label based on light or radiation emission as described above). In other embodiments, the antibodies are associated with a device or strip for detection of MICA and/or MICB by use of an immunochromatographic or immunochemical assay, such as in a "sandwich" or competitive assay, immunohistochemistry, immunofluorescence microscopy, and the like. Additional examples of such devices or strips are those designed for home testing or rapid point of care testing. Further examples include those that are designed for the simultaneous analysis of multiple analytes in a single sample. For example, an unlabeled antibody of the invention may be applied to a "capture" MICA and/or MICB polypeptides in a biological sample and the captured (or immobilized) MICA and/or MICB polypeptides may be bound to a labeled form of an anti-MICA and/or anti-MICB antibody of the invention for detection. Other standard embodiments of immunoassays are well-known the skilled artisan, including assays based on, for example, immunodiffusion, immuno-electrophoresis, immunohistopathology, immunohistochemistry, and histopathology.

Prognostic Assays

The diagnostic methods described herein can furthermore be utilized to identify subjects having or at risk of developing a disorder associated with MICA and/or MICB. As used herein, the term "aberrant" includes a MICA and/or MICB upregulation or downregulation which deviates from the normal MICA and/or MICB levels, or the increase or decrease of MICA and/or MICB shedding. Aberrant expression or shedding includes increased or decreased expression or shedding, as well as expression or shedding which does not follow the normal developmental pattern of expression or the subcellular pattern of expression. For example, aberrant MICA and/or MICB levels is intended to include the cases in which a mutation in the MICA and/or MICB gene or regulatory sequence, or amplification of the chromosomal MICA and/or MICB gene, thereof causes upregulation or downregulation of MICA and/or MICB. As used herein, the term "unwanted" includes an unwanted phenomenon involved in a biological response such as immune cell activation. For example, the term unwanted includes a MICA and/or MICB which is undesirable in a subject.

Many disorders associated with MICA and/or MICB are known to the skilled artisan, as explained further in the Examples. MICA and/or MICB is expressed by multiple tumor types, including select lymphoid malignancies, virally-induced cancers, and many solid tumors. Generally, MICA and/or MICB is a positive prognostic marker because it activates NKG2D receptor on cytotoxic lymphocytes (e.g., NK cells) that induce strong immune responses against conditions in need thereof. However, immunoinhibition is desired for downregulating immune responses in treating a number of disorders, such as autoimmune diseases, inflammatory diseases, and the like.

The assays described herein, such as the preceding diagnostic assays or the following assays, can be utilized to identify a subject having or at risk of developing a disorder associated with a misregulation of MICA and/or MICB shedding. Thus, the present invention provides a method for identifying a disorder associated with aberrant or unwanted MICA and/or MICB shedding in which a test sample is obtained from a subject and MICA and/or MICB is detected, wherein the presence of MICA and/or MICB polypeptide is diagnostic for a subject having or at risk of developing the disorder associated with aberrant or unwanted MICA and/or MICB shedding. As used herein, a "test sample" refers to a biological sample obtained from a subject of interest. For example, a test sample can be a biological fluid (e.g., cerebrospinal fluid or serum), cell sample, or tissue, such as a histopathological slide of the tumor microenvironment, peritumoral area, and/or intratumoral area. In a preferred embodiment, the sample comprises cells expressing mature membrane-bound MICA/B and/or MICA/B fragments.

Furthermore, the prognostic assays described herein can be used to determine whether a subject can be administered an agent (e.g., an agonist, antagonist, peptidomimetic, polypeptide, peptide, nucleic acid, small molecule, or other drug candidate) to treat such a disorder associated with aberrant or unwanted MICA and/or MICB shedding. For example, such methods can be used to determine whether a subject can be effectively treated with one or a combination of agents. Thus, the present invention provides methods for determining whether a subject can be effectively treated with one or more agents for treating a disorder associated with aberrant or unwanted MICA and/or MICB shedding in which a test sample is obtained and MICA and/or MICB is detected (e.g., wherein the abundance of MICA and/or MICB polypeptide is diagnostic for a subject that can be administered the agent to treat the disorder associated with aberrant or unwanted MICA and/or MICB shedding).

The methods described herein may be performed, for example, by utilizing pre-packaged diagnostic kits comprising at least one antibody reagent described herein, which may be conveniently used, e.g., in clinical settings to diagnose patients exhibiting symptoms or family history of a disease or illness involving MICA and/or MICB.

Furthermore, any cell type or tissue in which MICA and/or MICB is expressed may be utilized in the prognostic assays described herein.

Another aspect of the present invention includes uses of the compositions and methods described herein for association and/or stratification analyses in which the MICA and/or MICB in biological samples from individuals with a disorder associated with aberrant MICA and/or MICB shedding, are analyzed and the information is compared to that of controls (e.g., individuals who do not have the disorder; controls may be also referred to as "healthy" or "normal" individuals or at early timepoints in a given time lapse study) who are preferably of similar age and race. The appropriate selection of patients and controls is important to the success of association and/or stratification studies. Therefore, a pool of individuals with well-characterized phenotypes is extremely desirable. Criteria for disease diagnosis, disease predisposition screening, disease prognosis, determining drug responsiveness (pharmacogenomics), drug toxicity screening, etc. are described herein.

Different study designs may be used for genetic association and/or stratification studies (Modern Epidemiology, Lippincott Williams & Wilkins (1998), 609-622). Observational studies are most frequently carried out in which the response of the patients is not interfered with. The first type of observational study identifies a sample of persons in whom the suspected cause of the disease is present and another sample of persons in whom the suspected cause is absent, and then the frequency of development of disease in the two samples is compared. These sampled populations are called cohorts, and the study is a prospective study. The other type of observational study is case-control or a retrospective study. In typical case-control studies, samples are collected from individuals with the phenotype of interest (cases) such as certain manifestations of a disease, and from individuals without the phenotype (controls) in a population (target population) that conclusions are to be drawn from. Then the possible causes of the disease are investigated retrospectively. As the time and costs of collecting samples in case-control studies are considerably less than those for prospective studies, case-control studies are the more commonly used study design in genetic association studies, at least during the exploration and discovery stage.

After all relevant phenotypic and/or genotypic information has been obtained, statistical analyses are carried out to determine if there is any significant correlation between the presence of an allele or a genotype with the phenotypic characteristics of an individual. Preferably, data inspection and cleaning are first performed before carrying out statistical tests for genetic association. Epidemiological and clinical data of the samples can be summarized by descriptive statistics with tables and graphs well-known in the art. Data validation is preferably performed to check for data completion, inconsistent entries, and outliers. Chi-squared tests and t-tests (Wilcoxon rank-sum tests if distributions are not normal) may then be used to check for significant differences between cases and controls for discrete and continuous variables, respectively.

An important decision in the performance of genetic association tests is the determination of the significance level at which significant association can be declared when the p-value of the tests reaches that level. In an exploratory analysis where positive hits will be followed up in subsequent confirmatory testing, an unadjusted p-value <0.2 (a significance level on the lenient side), for example, may be used for generating hypotheses for significant association of a MICA and/or MICB level with certain phenotypic characteristics of a disease. It is preferred that a p-value <0.05 (a significance level traditionally used in the art) is achieved in order for the level to be considered to have an association with a disease. When hits are followed up in confirmatory analyses in more samples of the same source or in different samples from different sources, adjustment for multiple testing will be performed as to avoid excess number of hits while maintaining the experiment-wise error rates at 0.05. While there are different methods to adjust for multiple testing to control for different kinds of error rates, a commonly used but rather conservative method is Bonferroni correction to control the experiment-wise or family-wise error rate (Multiple comparisons and multiple tests, Westfall et al, SAS Institute (1999)). Permutation tests to control for the false discovery rates, FDR, can be more powerful (Benjamini and Hochberg, Journal of the Royal Statistical Society, Series B 57, 1289-1300, 1995, Resampling-based Multiple Testing, Westfall and Young, Wiley (1993)). Such methods to control for multiplicity would be preferred when the tests are dependent and controlling for false discovery rates is sufficient as opposed to controlling for the experiment-wise error rates.

Once individual risk factors, genetic or non-genetic, have been found for the predisposition to disease, a classification/prediction scheme can be set up to predict the category (for instance, disease or no-disease) that an individual will be in depending on his phenotype and/or genotype and other non-genetic risk factors. Logistic regression for discrete trait and linear regression for continuous trait are standard techniques for such tasks (Applied Regression Analysis, Draper and Smith, Wiley (1998)). Moreover, other techniques can also be used for setting up classification. Such techniques include, but are not limited to, MART, CART, neural network, and discriminant analyses that are suitable for use in comparing the performance of different methods (The Elements of Statistical Learning, Hastie, Tibshirani & Friedman, Springer (2002)).

Monitoring of Effects During Clinical Trials

Monitoring the influence of agents (e.g., compounds, drugs or small molecules) on the MICA and/or MICB polypeptide or a fragment thereof (e.g., the modulation of cell proliferation and/or migration) can be applied not only in basic drug screening, but also in clinical trials. For example, the effectiveness of an agent determined by a screening assay as described herein to increase MICA and/or MICB gene expression, polypeptide levels, or downregulate MICA and/or MICB shedding, can be monitored in clinical trials of subjects exhibiting increased MICA and/or MICB gene expression, polypeptide levels, or downregulated MICA and/or MICB shedding, or can be monitored in clinical trails of subjects exhibiting increased MICA and/or MICB expression, detectable by the anti-MICA and/or anti-MICB antibodies or fragments described herein. In such clinical trials, the expression or activity of a MICA and/or MICB gene and/or symptoms or markers of the disorder of interest, can be used as a "read out" or marker of the phenotype of a particular cell, tissue, or system. Similarly, the effectiveness of an agent determined by a screening assay as described herein to decrease MICA and/or MICB gene expression, polypeptide levels, or increase MICA and/or MICB shedding, can be monitored in clinical trials of subjects exhibiting increased MICA and/or MICB gene expression, polypeptide levels, or increased MICA and/or MICB shedding, or can be monitored in clinical trails of subjects exhibiting increased MICA and/or MICB, detectable by the anti-MICA and/or anti-MICB antibodies or fragments described herein. In such clinical trials, the expression or activity of a MICA and/or MICB gene and/or symptoms or markers of the disorder of interest, can be used as a "read out" or marker of the phenotype of a particular cell, tissue, or system, such as for an autoimmune disorder.

For example, and not by way of limitation, genes, including MICA and/or MICB, that are modulated in cells by treatment with an agent (e.g., compound, drug or small molecule) which modulates MICA and/or MICB shedding (e.g., identified in a screening assay as described herein) can be identified. Thus, to study the effect of agents on a disorder associated with aberrant MICA and/or MICB shedding, for example, in a clinical trial, cells can be isolated and nucleic acids and/or protein prepared and analyzed for the levels of MICA and/or MICB and/or other genes implicated in the disorder associated with aberrant MICA and/or MICB shedding. The levels of gene expression (e.g., a gene expression pattern) analyzed by measuring the amount of polypeptide produced, by one of the methods as described herein, or by measuring the levels of MICA and/or MICB or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, polypeptide, peptide, nucleic acid, small molecule, or other drug candidate identified by the screening assays described herein) including the steps of (i) obtaining a pre-administration sample from a subject prior to administration of the agent; (ii) detecting the level of MICA and/or MICB polypeptides, or fragments thereof, in the preadministration sample; (iii) obtaining one or more post-administration samples from the subject; (iv) detecting the level of MICA and/or MICB polypeptides, or fragments thereof, in the post-administration samples; (v) comparing the level of the MICA and/or MICB polypeptide, or fragments thereof, in the pre-administration sample with the MICA and/or MICB polypeptide in the post administration sample or samples; and (vi) altering the administration of the agent to the subject accordingly. For example, increased administration of the agent may be desirable to increase the cell surface density of MICA and/or MICB on the tumor cells, i.e., to increase the effectiveness of the agent. According to such an embodiment, MICA and/or MICB may be used as an indicator of the effectiveness of an agent, even in the absence of an observable phenotypic response. Similarly, MICA and/or MICB analysis, such as by immunohistochemistry (IHC), can also be used to select patients who will receive MICA and/or MICB immunotherapy to activate NK-cell mediated tumor immunity. Patients whose tumors having MICA and/or MICB expression and/or shedding are more likely to respond to MICA and/or MICB mAb immunotherapy, as described herein. Because MICA and/or MICB shedding is blocked by the anti-MICA and/or anti-MICB mAb as described herein, the immunotherapy will result in activation of cytotoxic lymphocytes (e.g., NK cells) and enhanced tumor immunity.

Therapeutic Methods

In some instances, methods can include selection of a human subject who has or had a condition or disease and who exhibits or exhibited a positive immune response towards the condition or disease. In some instances, suitable subjects include, for example, subjects who have or had a condition or disease but that resolved the disease or an aspect thereof, present reduced symptoms of disease (e.g., relative to other subjects (e.g., the majority of subjects) with the same condition or disease), and/or that survive for extended periods of time with the condition or disease (e.g., relative to other subjects (e.g., the majority of subjects) with the same condition or disease), e.g., in an asymptomatic state (e.g., relative to other subjects (e.g., the majority of subjects) with the same condition or disease). In some instances, subjects can be selected if they have been vaccinated (e.g., previously vaccinated and/or vaccinated and re-vaccinated (e.g., received a booster vaccine)) against a condition or disease.

In some instances, subject selection can include obtaining a sample from a subject (e.g., a candidate subject) and testing the sample for an indication that the subject is suitable for selection. In some instances, the subject can be confirmed or identified, e.g. by a health care professional, as having had or having a condition or disease. In some instances, exhibition of a positive immune response towards a condition or disease can be made from patient records, family history, and/or detecting an indication of a positive immune response. In some instances multiple parties can be included in subject selection. For example, a first party can obtain a sample from a candidate subject and a second party can test the sample. In some instances, subjects can be selected and/or referred by a medical practitioner (e.g., a general practitioner). In some instances, subject selection can include obtaining a sample from a selected subject and storing the sample and/or using the in the methods disclosed herein. Samples can include, for example, cells or populations of cells.

Provided herein are methods for treating and/or preventing cancer or symptoms of cancer in a subject comprising administering to the subject a therapeutically effective amount of a composition comprising an anti-MICA and/or anti-MICB antibody or antigen binding fragment thereof disclosed herein.

In some embodiments the cancer is a cancer associated with overexpression of MICA. In some embodiments, the cancer is melanoma, lung, breast, kidney, ovarian, prostate, pancreatic, gastric, and colon carcinoma, lymphoma or leukemia. In some embodiments, the cancer is melanoma. In some embodiments, the cancer is a plasma cell malignancy, for example, multiple myeloma (MM) or pre-malignant condition of plasma cells. In some embodiments the subject has been diagnosed as having a cancer or as being predisposed to cancer.

Symptoms of cancer are well-known to those of skill in the art and include, without limitation, unusual mole features, a change in the appearance of a mole, including asymmetry, border, color and/or diameter, a newly pigmented skin area, an abnormal mole, darkened area under nail, breast lumps, nipple changes, breast cysts, breast pain, death, weight loss, weakness, excessive fatigue, difficulty eating, loss of appetite, chronic cough, worsening breathlessness, coughing up blood, blood in the urine, blood in stool, nausea, vomiting, liver metastases, lung metastases, bone metastases, abdominal fullness, bloating, fluid in peritoneal cavity, vaginal bleeding, constipation, abdominal distension, perforation of colon, acute peritonitis (infection, fever, pain), pain, vomiting blood, heavy sweating, fever, high blood pressure, anemia, diarrhea, jaundice, dizziness, chills, muscle spasms, colon metastases, lung metastases, bladder metastases, liver metastases, bone metastases, kidney metastases, and pancreatic metastases, difficulty swallowing, and the like.

The methods disclosed herein can be applied to a wide range of species, e.g., humans, non-human primates (e.g., monkeys), horses, cattle, pigs, sheep, deer, elk, goats, dogs, cats, mustelids, rabbits, guinea pigs, hamsters, rats, and mice.

By way of example, an anti-cancer agent promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms in the patient. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount or dosage of the drug preferably inhibits cell growth or tumor growth by at least about 20%, more preferably by at least about 40%, even more preferably by at least about 60%, and still more preferably by at least about 80% relative to untreated subjects. In the most preferred embodiments, a therapeutically effective amount or dosage of the drug completely inhibits cell growth or tumor growth, i.e., preferably inhibits cell growth or tumor growth by 100%. The ability of a compound to inhibit tumor growth can be evaluated using the assays described infra. Alternatively, this property of a composition can be evaluated by examining the ability of the compound to inhibit cell growth, such inhibition can be measured in vitro by assays known to the skilled practitioner. In other preferred embodiments of the invention, tumor regression may be observed and continue for a period of at least about 20 days, more preferably at least about 40 days, or even more preferably at least about 60 days.

In general, methods include selecting a subject at risk for or with a condition or disease. In some instances, the subject's condition or disease can be treated with a pharmaceutical composition disclosed herein. For example, in some instances, methods include selecting a subject with cancer, e.g., wherein the subject's cancer can be treated by targeting MICA.

In some instances, treatments methods can include a single administration, multiple administrations, and repeating administration as required for the prophylaxis or treatment of the disease or condition from which the subject is suffering. In some instances treatment methods can include assessing a level of disease in the subject prior to treatment, during treatment, and/or after treatment. In some instances, treatment can continue until a decrease in the level of disease in the subject is detected.

The terms "administer," "administering," or "administration," as used herein refers to implanting, absorbing, ingesting, injecting, or inhaling, the inventive peptide, regardless of form. In some instances, one or more of the peptides disclosed herein can be administered to a subject topically (e.g., nasally) and/or orally. For example, the methods herein include administration of an effective amount of compound or compound composition to achieve the desired or stated effect. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

For example, dosage regimens are adjusted to provide the optimum desired response (e.g., a therapeutic response). A single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. "Dosage unit form" as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For administration of an anti-MICA and/or anti-MICB antibody or antibody fragment, the dosage ranges from about 0.0001 to 100 mg/kg, and more usually 0.01 to 5 mg/kg, of the host body weight. For example dosages can be 0.3 mg/kg body weight, 1 mg/kg body weight, 3 mg/kg body weight, 5 mg/kg body weight or 10 mg/kg body weight or within the range of 1-10 mg/kg. An exemplary treatment regime entails administration once per week, once every two weeks, once every three weeks, once every four weeks, once a month, once every 3 months or once every three to 6 months. Preferred dosage regimens for an anti-MICA and/or anti-MICB antibody of the invention include 1 mg/kg body weight or 3 mg/kg body weight via intravenous administration, with the antibody being given using one of the following dosing schedules: (i) every four weeks for six dosages, then every three months; (ii) every three weeks; (iii) 3 mg/kg body weight once followed by 1 mg/kg body weight every three weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, pharmaceutical compositions can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

Following administration, the subject can be evaluated to detect, assess, or determine their level of disease. In some instances, treatment can continue until a change (e.g., reduction) in the level of disease in the subject is detected.

Upon improvement of a patient's condition (e.g., a change (e.g., decrease) in the level of disease in the subject), a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

In some instances, the disclosure provides methods for detecting immune cells e.g., B cells and/or memory B cells, from a human subject. Such methods can be used, for example, to monitor the levels of immune cells e.g., B cells and/or memory B cells, in a human subject, e.g., following an event. Exemplary events can include, but are not limited to, detection of diseases, infection; administration of a therapeutic composition disclosed herein, administration of a therapeutic agent or treatment regimen, administration of a vaccine, induction of an immune response. Such methods can be used clinically and/or for research.

Combination Therapies

In some instances, the anti-MICA and/or anti-MICB antibodies and/or antigen binding fragments disclosed herein can be administered in combination with compounds, drugs, and/or agents used for the treatment of cancer. Such compounds, drugs, and/or agents can include, for example, chemotherapy drugs, small molecule drugs or antibodies that stimulate the immune response to a given cancer. In some instances, the anti-MICA and/or anti-MICB antibodies and/or antigen binding fragments may be administered, for example, concurrently or sequentially with one or more of an anti-CTLA-4 antibody or peptide, an anti-PD-1 antibody or peptide, an anti-PDL-1 antibody or peptide, an anti-OX40 (also known as CD134, TNFRSF4, ACT35 and/or TXGP1L) antibody or peptide, an anti-GITR (also known as TNFRSF18, AITR, and/or CD357) antibody or peptide, an anti-LAG-3 antibody or peptide, and/or an anti-TIM-3 antibody or peptide. For example, in some instances, therapeutic methods disclosed herein can include administration of one or more (e.g., one, two, three, four, five, or less than ten) compounds.

In some instances, the anti-MICA and/or anti-MICB antibodies and/or antigen binding fragments disclosed herein disclosed herein can be administered with other compounds including histone deacetylase inhibitors ("HDAC") inhibitors. Examples of HDAC inhibitors include, for example, hydroxamic acid, Vorinostat (Zolinza); suberoylanilide hydroxamic acid (SAHA) (Merck), Trichostatin A (TSA), LAQ824 (Novartis), Panobinostat (LBH589) (Novartis), Belinostat (PXD101) (CuraGen), ITF2357 Italfarmaco SpA (Cinisello), Cyclic tetrapeptide; Depsipeptide (romidepsin, FK228) (Gloucester Pharmaceuticals), Benzamide; Entinostat (SNDX-275/MS-275) (Syndax Pharmaceuticals), MGCD0103 (Celgene), Short-chain aliphatic acids, Valproic acid, Phenyl butyrate, AN-9, pivanex (Titan Pharmaceutical), CHR-3996 (Chroma Therapeutics), and CHR-2845 (Chroma Therapeutics).

In some instances, the anti-MICA and/or anti-MICB antibodies and/or antigen binding fragments disclosed herein can be administered with other compounds including proteasome inhibitors, including, for example, bortezomib, (Millennium Pharmaceuticals), NPI-0052 (Nereus Pharmaceuticals), carfilzomib (PR-171) (Onyx Pharmaceuticals), CEP 18770, and MLN9708.

In some instances, the anti-MICA and/or anti-MICB antibodies and/or antigen binding fragments disclosed herein can be administered with alkylating agents such as mephalan and topoisomerase inhibitors such as Adriamycin (doxorubicin) which have been shown to increase MICA and/or MICB expression and could enhance efficacy of an anti-MICA and/or anti-MICB monoclonal antibody.

In some instances, the anti-MICA and/or anti-MICB antibodies and/or antigen binding fragments disclosed herein can be administered with one or more other agents, such as chemotherapy, radiation therapy, cytokines, chemokines and other biologic signaling molecules, tumor specific vaccines, cellular cancer vaccines (e.g., GM-CSF transduced cancer cells), tumor specific monoclonal antibodies, autologous and allogeneic stem cell rescue (e.g., to augment graft versus tumor effects), other therapeutic antibodies, molecular targeted therapies, anti-angiogenic therapy, infectious agents with therapeutic intent (such as tumor localizing bacteria) and gene therapy.

In some instances, the anti-MICA and/or anti-MICB antibodies and/or antigen binding fragments disclosed herein can be administered with one or a combination e.g., two or more different) of additional (antibodies, antigen-binding portions, immunoconjugates or bispecific molecules which bind to MICA and/or MICB (e.g., that to different epitopes on the target antigen or that have complementary activities). Examples of anti-MICA and/or anti-MICB antibodies are discloses, for example, in WO 2013/049517, WO 2014/144791 and WO 2015/085210).

Accordingly, therapeutic compositions provided herein can include other compounds, drugs, and/or agents used for the treatment of cancer as disclosed herein. For example, in some instances, therapeutic compositions disclosed herein can be combined with one or more (e.g., one, two, three, four, five, or less than ten) compounds.

EXAMPLES

The invention is further described in the following examples, which do not limit the scope of the invention described in the claims.

Example 1—Materials and Methods for Examples 2-7

Experimental Design

ELISA assays for antibody binding and Bead assays for NKG2D binding were all done with one single replicate per sample, repeated either three times or twice, respectively. All the in vitro experiments with cells were done with at least 3 replicates per condition, and repeated at least three times. In vitro experiments with human NK cells were performed with at least three independent NK cell donors. In vitro experiments with mouse NK cells were done three times, each time with different batches of mice. All in vivo tumor experiments were performed with at least 4 mice per group and repeated at least twice. Each experiment in the human metastasis model was done twice, with different NK cell donors at each time. All the mice were adult, gender and age matched. No outliers were removed.

Expression of MICA α3 Domain for Immunization and Hybridoma Generation

The MICA α3 domain (allele 002) was expressed using the Baculovirus system. Seven of eight N-linked glycosylation sites were mutated to reduce the complexity of the protein. An N-terminal signal peptide was added to target the protein to the secretory pathway, and a C-terminal HA tag was added to facilitate downstream purification. The synthesized, codon-optimized gene was cloned into pAcDB3 Baculovirus expression vector, and the protein was expressed in Sf9 insect cells infected with the recombinant Baculovirus at a multiplicity of infection of 10. Cells were grown in Sf900 serum free media (Life Technologies) for three days following infection. The supernatants were concentrated and the protein was purified by HA affinity chromatography, followed by size exclusion chromatography using a Superose 6 column (GE Healthcare). The purified proteins were buffer exchanged into PBS using PD-10 desalting columns (GE) and concentrated to 1 mg/ml using Amicon Ultra 10 kDa ultrafiltration systems. Protein purity and size were confirmed by SDS-PAGE.

Mice

C57BL/6 wild type, $Rag1^{-/-}$, $Rag2^{-/-}$, $Il2rg^{-/-}$, $Prf1^{-/-}$, $Ifng^{-/-}$, $Klrk1^{-/-}$, $Fcgr3a^{-/-}$, $Igh^{-/-}$, Balb/c wild type, and NOD Scid $Il2rg^{-/-}$ mice were all obtained from The Jackson Laboratory (JAX®). $Klrk1^{-/-}$ $Fcgr3a^{-/-}$ mice were obtained by crossing of individual knockouts strains. All mice were genotyped by PCR, according to JAX® protocol, and were kept in the 'specific pathogen free' animal facility at Dana-Farber Cancer Institute. $Rag2^{-/-}$ $Il2rg^{-/-}$ mice were phenotyped by flow cytometry. All the breeding and experimental procedures were in accordance with and approved by the Institutional Care and Use Committee (IACUC).

Cell Lines

A375, HCT-116, SK-N-SH, K562, A2058, B16F10, CT26, and Neuro-2a cell lines were all obtained from American Type Culture Collection (ATCC). HEPG2 and MDA-MB-231 cell lines were kindly provided by Drs. Chandan Sharma and Martin Hemler, Dana-Farber Cancer Institute, Boston. The EL4 and RMA-S cell lines were generous gifts from Dr. Mark Smyth, QIMR Berghofer Medical Research Institute, Herston, Australia. The short-term human melanoma cell lines CY.21A-S1, CY36-S1, and CY048-S were obtained from patients following surgical resection of metastatic lesions as previously described (27). All cell lines were *mycoplasma* free, as tested by MycoProbe *Mycoplasma* Detection Kit (R&D Systems). Human and murine cell lines were cultivated in RPMI-1640 or DMEM media, respectively, supplemented with 10% fetal bovine serum (FBS), 1× Glutamax® (Gibco), and 1× Penicillin and Streptomycin (Gibco). Cells were cultivated at 37° C., 5% $CO_2$. Cells were kept at low passages (~3-5 passages) once obtained from vendors or collaborators.

Cell Line Transduction with Lentiviral Vectors

B16F10, CT26, Neuro-2a, EL4 and RMA-S cell lines were transduced with lentiviral vector pHAGE-CMV-full EF1α. MICA (allele 009) cDNA or other inserts were placed between NotI and BamHI cloning sites, 3' to the EF1α promoter and 5' to the IRES. ZsGreen or luciferase cDNAs were cloned 3' to the IRES as fluorescence or bioluminescence reporters, respectively. The vector with the ZsGreen reporter was used to compare expression of cDNAs encoding full length MICA, full-length MICB and secreted MICA (Neuro-2a, RMA-S and/or B16F10 cell lines). CT26, EL4 and B16F10 cell lines were transduced with the vector that supported expression of the luciferase reporter. Lentiviruses were produced in 293T cells by transient expression of the pHAGE vector plasmid plus packaging plasmid (pCMV-DR8.9.1) and envelope plasmid (pCMV-VSV-G) using the TransIT®-293 Transfection Reagent (Minis). Tumor cells were transduced with lentiviruses at a multiplicity of infection (MOI) of 5:1 to 20:1, depending on the cell line. Polybrene (5 µg/ml) was used to enhance the infection rate. Transduced cells were sorted by flow cytometry based on MICA or ZsGreen expression. Cells were resorted 1 week later, expanded and frozen. Cells were retested for *mycoplasma* and used at low passages.

ELISA for Antibody Binding to MICA

ELISA experiments were performed in DELFIA® 96-well plates (Perkin Elmer) or in Nunc Maxisorp 96-wells plates (Thermo Scientific). Wells were coated with antigens by overnight incubation at 4° C. using 100 ng of protein in 100 µl of carbonate buffer, pH 7.4. Plates were subsequently washed with 1× Tris-buffered saline-Tween buffer and incubated for 2 hours with 2% bovine serum albumin (BSA) in phosphate buffered saline (PBS), pH 7.4, or DELFIA® Assay Buffer (Perkin Elmer) at room temperature. MICA antibodies were used at 1 µg/ml, unless indicated otherwise. Isotype controls were MPC-11 (mIgG2b) and MOPC-21 (mIgG1), but only MPC-11 is shown in the figures, given that no differences were observed between these controls. Human isotype control was a recombinant human IgG1 antibody (BE0096, BioXcell). Biotinylated goat anti-mouse IgG (Poly4053—Biolegend) was used as the secondary antibody which was followed by streptavidin-Europium (Perkin Elmer) and DELFIA® Enhancement Solution (Perkin Elmer). Europium fluorescence was quantified using an EnVision® microplate reader (Perkin Elmer). The HRP-conjugated secondary antibodies were Novex® Goat anti-human IgG (A24470, Life Technologies), Goat anti-mouse IgG1 (1070-05), IgG2a (1080-08), IgG2b (1090-05), and IgG3 (1100-05), and Goat anti-mouse IgG (31430, Thermo Scientific). For peroxidase-based assays, reactions were revealed by TMB substrate and stopped by 1 N sulfuric acid. Absorbance was read at 450 nm.

Bead Assays for NKG2D Receptor Binding and Detection of Endogenous MICA Antibodies Streptavidin-conjugated C4 beads (BD Pharmingen) were incubated for 2 hours with MICA biotinylated at a C-terminal BirA site (200 ng of MICA per 10,000 beads). Beads were then washed with PBS containing 1% FBS. For the NKG2D receptor binding assay, chimeric human NKG2D-Fc dimer (1299-NK-050, R&D Systems) was conjugated with Alexa$^{488}$ (A10468, Molecular Probes) and used at 10 µg/ml. Binding of murine NKG2D to human MICA was measured using NKG2D-Fc dimers (10 µg/ml) followed by an Alexa$^{488}$-conjugated anti-human IgG (Molecular Probes) that bound to the Fc region of the NKG2D-Fc dimer. MICA antibodies were also used as competitors for NKG2D dimer binding at concentrations of 10, 30 and 100 µg/ml. In these assays, NKG2D dimer and MICA antibodies were co-incubated with biotinylated MICA*008-conjugated beads.

Endogenous MICA antibodies were detected by incubating mouse sera (at 1:100 dilution with 10,000 MICA-coated beads), and binding of murine antibodies was detected using PE-conjugated anti-mouse IgG antibody (Poly4053, Biolegend) or a PE-conjugated anti-mouse IgM antibody (M31504, Invitrogen). All the samples were acquired using a BD LSR Fortessa flow cytometer and analyzed by FlowJo V10 software.

In Vitro Assays for NKG2D Binding to B16F10 Cells $1×10^5$ B16F10-MICA cells or control B16F10 cells transduced with a control lentiviral vector were stained with 10 µg/ml human NKG2D-Fc chimera plus 10 µg/ml of MICA or isotype control antibodies for 1 hour on ice (FIG. 9B-C). Subsequently, cells were washed and stained with an APC-conjugated anti-human IgG antibody (Life Technologies, catalog number A21445) at a 1:1,000 dilution for thirty minutes (detection of bound NKG2D-Fc) as well as Zombie Near Infra-Red dye (viability marker). Cells were washed and analyzed using a CytoFLEX flow cytometer (Beckman Coulter). Data were analyzed using FlowJo V10 software.

In Vitro Assays of Antibody Binding to CD16a Fc Receptor

In assays examining human CD16a binding to antibodies, 7C6-hIgG1 and 7C6-hIgG1-DANA antibodies were coated in ELISA plates at 0.1 µg/well. Wells were subsequently blocked with 1% BSA in PBS. His-tagged recombinant human CD16a (R&D Systems) was added to wells at different concentrations, and bound CD16a was detected with a HRP-conjugated anti-HIS tag secondary antibody (652504, Biolegend) and 3,3',5,5'-tetramethylbenzidine (TMB) as the substrate. Reactions were stopped using 1 N sulfuric acid, and absorbance was read at 450 nm.

In the assays evaluating antibody binding to murine CD16a, recombinant mouse CD16a (R&D Systems) was coated in ELISA plates at 0.1 µg/well, and wells were subsequently blocked with 1% BSA in PBS. 7C6-mIgG2b and 7C6-mIgG2b-DANA antibodies were then added to wells at different concentrations. Bound antibodies were detected using a HRP-conjugated anti-mouse IgG antibody (31430, Thermo Scientific) with TMB as the substrate; reactions were stopped using 1 N sulfuric acid, and absorbance was read at 450 nm.

In Vitro Assay for Inhibition of MICA Shedding

Tumor cells ($5×10^4$ or $1×10^5$ per well, depending on the cell line) were cultured for 24 to 72 hours in 96-well plates (flat-bottom plates for adherent cell lines, U-bottom plates for suspension cell lines). Human and murine cell lines were cultivated in RPMI-1640 or DMEM media, respectively, supplemented with 10% fetal bovine serum (FBS), 1× Glutamax® (Gibco), and 1× Penicillin and Streptomycin (Gibco). MICA or control antibodies were added at different concentrations, and shed MICA/B was then detected in supernatants by ELISA using the Human MICA ELISA kit (Ab59569, Abcam) or Human MICB DuoSet ELISA kit (DY1599, R&D Systems), using the procedures recommended by the manufacturers. For both assays, standard curves were generated using recombinant MICA*008 or MICB*005 extracellular domain proteins that had been expressed using the Baculovirus system. It was found that the standard samples included in the kits overestimated the amount of MICA/B proteins.

This MICA ELISA assay was also used to examine whether MICA α3 domain specific antibodies interfere with detection of shed MICA. Recombinant soluble MICA (allele 008) was incubated with different concentrations of either MICA α3 domain specific antibodies or the 6D4 antibody specific for the MICA α1-α2 domains. Soluble MICA was then quantified as described above.

Detection of Surface MICA/B

MICA and MICB were detected on the cell surface by the PE-conjugated anti-MICA/B antibody (clone 6D4, 320906, Biolegend). The isotype control is a PE-conjugated mouse IgG2a (400211, Biolegend). For the processing of adherent tumor cells, cells were detached by incubation with Versene® (15040-066, Gibco), which preserves the integrity of MICA/B on the cell surface. Prior to anti-MICA/B antibody incubation, Fc receptors were blocked with Mouse or Human TruStain FcX™ (101320 and 422302, respectively, Biolegend) diluted 1:100 in 1% FBS 2 mM EDTA PBS. All samples were acquired in a BD LSR Fortessa flow cytometer, and analyzed by FlowJo V10 software.

Inhibition of MICA Shedding by Macrophages

PBMC were isolated from a leukapheresis collar obtained from a healthy donor, and monocytes were isolated by adherence to tissue culture plates (2 hour incubation). Non-adherent cells were then washed away and M-CSF was added at 100 ng/ml in RPMI-1640 media supplemented with 10% FBS, Glutamax and Penicillin/Streptomycin. Visual inspection of cell morphology on day 5 confirmed that monocytes had differentiated into macrophages. Macrophages were treated for 24 hours in 96-well plates with different concentrations of acetylated LDL as well as MICA antibodies (10 μg/ml). Shed MICA in supernatants was examined by ELISA (Abcam) and cell surface density of MICA/B was quantified by flow cytometry.

Human NK Cell Isolation

Human NK cells were isolated from fresh leukapheresis blood collars that had been generated by Brigham & Women's Hospital, Boston, from healthy donors. Samples were diluted with an equal volume of PBS and blood mononuclear cells were isolated by Ficoll density gradient centrifugation. Cells were washed with PBS, and NK cells were isolated by negative selection using the Human NK Cell Isolation Kit (130-092-657, Miltenyi Biotech) using an autoMACS system (Miltenyi Biotech). Enriched NK cells (purity of 50-90%) were then incubated with anti-CD56 (PE or APC conjugated) and anti-CD3 (FITC or Pacific Blue conjugated) (Biolegend) and sorted using a BD FACS Aria. Following sorting, NK cell purity was ~99%. These cells were cultured for twelve hours in complete RPMI media supplemented with 300-1000 U/ml of recombinant human IL-2 (BD Pharmingen).

Isolation of Murine NK Cells

Murine NK cells were isolated from the spleen of C57BL/6 Rag1$^{-/-}$ mice. These cells were enriched by negative selection using a Mouse NK Cell Isolation Kit (130-096-892, Miltenyi Biotech). Cells were then incubated with PE-conjugated anti-NK1.1 and Pacific Blue-conjugated anti-CD3 (Biolegend), and NK cells were sorted using a BD FACS Aria. Purity after sorting was ~99%. NK cells used for cytotoxicity assays were isolated from mice that had received an intraperitoneal injection of 200 μg Poly(I:C) (InvivoGen) 1 day prior to NK cell isolation.

NK Cell Cytotoxicity Assays

Target cells were labeled for 1 hour with 100 μCi of $^{51}$[Cr] per 2×10$^6$ cells in 0.2 ml of media. Subsequently, cells were washed and plated in V-bottom 96-wells plates (5,000 target cells per well). To determine the experimental release, NK cells were added in an equal volume, but at different ratios. To determine maximum and spontaneous release, target cells were mixed with an equal volume of 2% Triton-X100 in PBS or an equal volume of media, respectively. Antibodies were added at a final concentration of 10 μg/ml.

Figure 1:
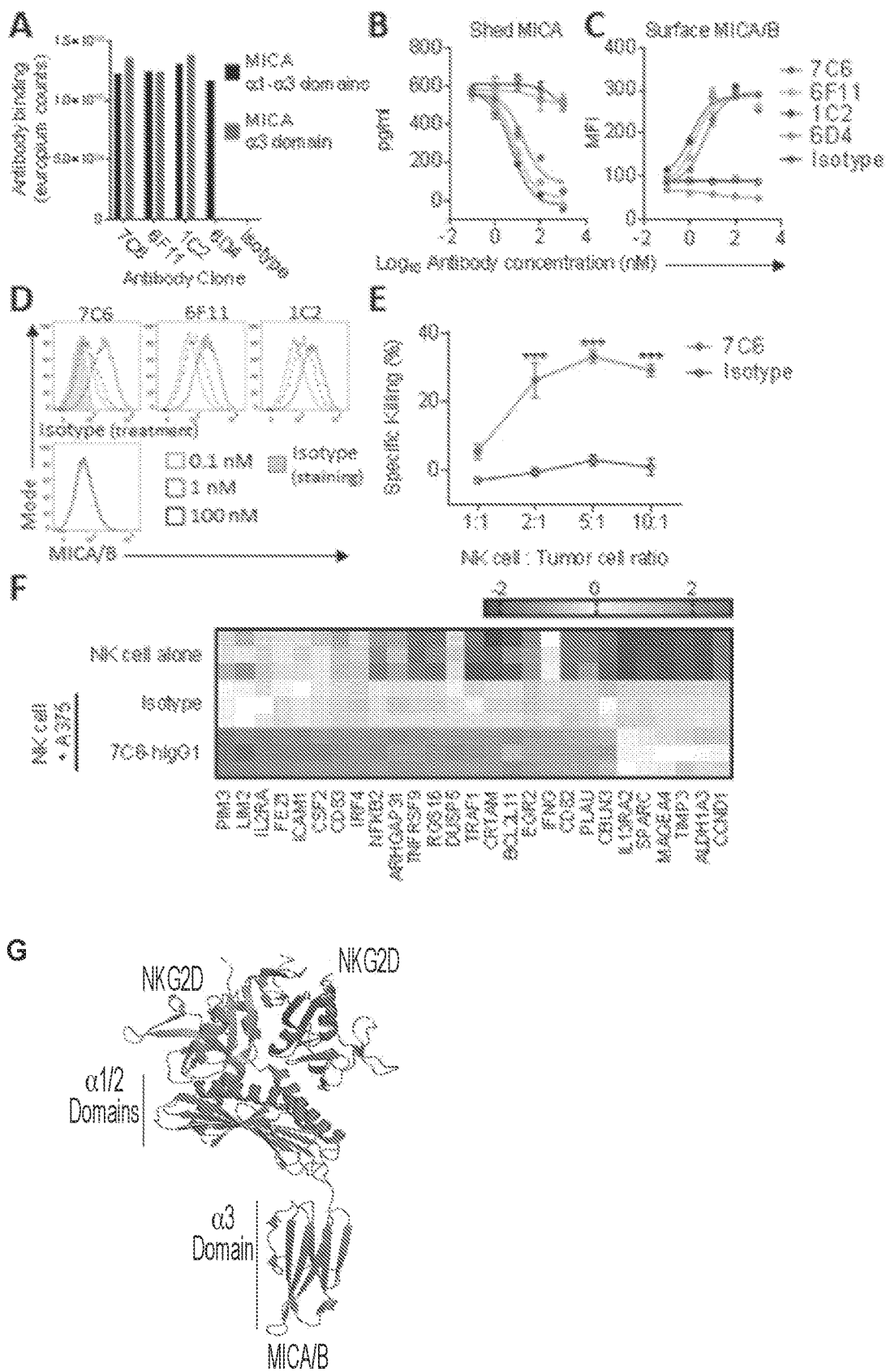
FIG. 1. Depicts data demonstrating that MICA/B α3 domain specific antibodies inhibit shedding and stabilize the protein on the surface of human tumor cells for recognition by NK cells. (A) Binding of mAbs to immobilized MICA α3 domain or MICA α1-α3 domains using a fluorescence-based ELISA (one representative of three independent experiments). (B-D, and F) Human A375 melanoma cells were treated for 24 hours with the indicated antibodies. (B) MICA α3 domain antibodies (7C6, 1C2, 6F11) inhibit MICA release into the supernatant as quantified with sandwich ELISA; mAb 6D4 binds to MICA α1-α2 domains and thus does not inhibit shedding. Data show mean±SD for triplicate measurements from one representative of three independent experiments. (C and D) MICA α3 domain-specific mAbs stabilize MICA surface expression as determined by flow cytometry using PE-labeled 6D4 mAb. MFI=Mean Fluorescence Intensity. Data show mean±SD for triplicate measurements from one representative of three independent experiments. (E) Human NK cells exhibit cytotoxicity against A375 cells in the presence of 7C6-hIgG1 antibody (66.7 nM) but not isotype control antibody. Mean±standard deviation for quadruplicate measurements. ***p<0.001 calculated by two-way Analysis of Variance (ANOVA), Bonferroni's post-hoc test. Representative of three independent experiments (each experiment was done with different human NK cell donors). (F) Human NK cells have changes in gene expression after co-culture with tumor cells that were pre-treated with the antibodies, as determined by RNA-sequencing. (G) Illustration of MICA protein bound to a NKG2D homodimer (Protein Data Bank 1HYR). MICA is labeled-and the NKG2D homodimer is labeled. The NKG2D dimer binds to the α1 and α2 domains; the α3 domain is the site of proteolytic cleavage.
Figure 10:
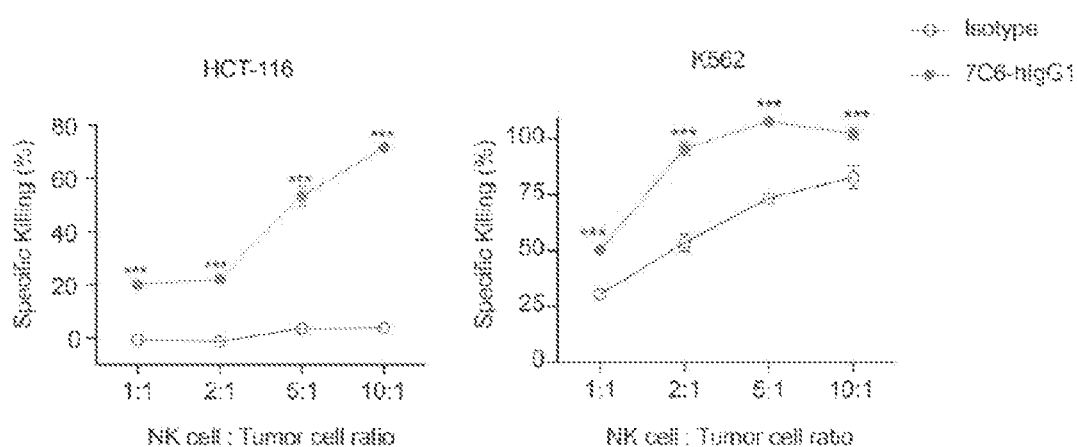
FIG. 10. Depicts data demonstrating that the 7C6 antibody increases NK cell cytotoxicity and cytokine production. (A, B) Human NK cells from healthy donors were isolated and activated with 300 U/ml IL-2 overnight. 7C6-hIgG1 or isotype control antibodies were added to cultures at a concentration of 10 μg/ml. (A) The indicated tumor cells were used as target cells for NK cell mediated killing in a $^{51}$Cr release assay. Data are mean±SEM of four replicates per condition; data representative of three independent experiments. *$p<0.001$ calculated by two-way ANOVA, Bonferroni's post-hoc test. (B) Following co-culture with tumor cells, interferon-γ was detected in NK cells by intracellular staining followed by FACS analysis. Data are mean±stdev of three replicates per group; data representative of three independent experiments. *$p<0.001$ calculated by two-way ANOVA, Bonferroni's post-hoc test.

For experiments shown in FIGS. 1E, 10, and 13E antibodies were added at the time of the killing assay. For FIGS. 3A-B, antibodies were added to tumor cells 48 hours prior to labelling with $^{51}$[Cr] to inhibit MICAS shedding. The isotype control antibody for assays with human NK cells was recombinant human IgG1 Fc (BE0096, BioXcell). NKG2D blocking antibody (1D11, Biolegend) or control IgG (MOPC-21, BioXcell) was added at the initiation of killing assays to a final concentration of 20 μg/ml. Plates were then spun for 1 minute at 1,000 rpm. NK cells and target cells were incubated for 2 hours (assays with K562 target cells), or 4 hours (all other target cells) at 37° C. 5% $CO_2$. At the end of the incubation period, plates were centrifuged (2000 rpm, 5 minutes), part of the supernatant was collected, mixed with scintillation fluid, and radioactivity was quantified using a MicroBeta2 reader (Perkin Elmer). Specific killing was calculated using the following formula: 100×(Experimental release−Spontaneous release)/(Maximum release−Spontaneous release).

Intracellular Interferon-γ Production by NK Cells

NK cells were co-cultured for 6 hours at a ratio of 5:1 with tumor cells in the presence of Brefeldin-A (Biolegend). After the incubation time, Fc receptors were blocked, cells stained with NK cell markers, stained further with a dead cell marker (Zombie Yellow, Biolegend), and subsequently processed for intracellular interferon-γ labeling. Briefly, cells were fixed with BD Cytofix/Cytoperm™ Fixation and Permeabilization Solution (BD Pharmingen), permeabilized with Permeabilization Wash Buffer (Biolegend), and stained with APC-conjugated anti-human interferon-γ (4S.B3, Biolegend) or appropriate isotype control. Fluorescence spectra were acquired using a LSR Fortessa flow cytometer and analyzed by FlowJo.

NK Cell RNA-Sequencing

Human NK cells were isolated from a healthy volunteer to ~99% purity. These cells were pre-activated with 1,000 U/ml IL-2 overnight. A375 tumor cells were pre-treated with 10 μg/ml of 7C6-hIgG1 or isotype control (BioXcell BE0096) antibodies for 48 hours. Cells were then washed and NK cells were co-cultured with tumor cells for 6 hours in a 5:1 ratio. Subsequently, human NK cells were re-sorted and total RNA isolated with genomic DNA digestion with QIAGEN RNeasy RNA isolation kit (74134). RNA sequencing libraries were generated using the Kapa mRNAseq kit (KapaBiosystems). The libraries were analyzed by Next-Generation Sequencing and pooled barcoded samples were subjected to VIPER analysis. RNA levels were compared for NK cells from co-cultures treated with 7C6-hIgG1 versus isotype control antibodies. A cut-off of at least 1 Log$_2$ fold change was applied to select genes that were differentially expressed. Gene set enrichment analysis (GSEA) was also performed in order to identify relevant molecular pathways for differentially expressed mRNAs.

B16F10 Metastasis Model in Immunocompetent Mice

The B16F10 cells were transduced with the luciferase-based lentiviral vector to express MICA. B16F10-MICA cells (5×10$^5$) were injected intravenously into C57BL/6 mice through the tail vein. Fewer tumor cells (4×10$^5$) were injected into NK cell-deficient mice given that the absence of NK cells results in a very large number of metastases. 7C6 or isotype control antibodies (MPC-11 or C1184, BioXcell, which have mIgG2b and mIgG2a isotypes, respectively)

were administered intraperitoneally on days 1, 2, 7 and 10 at a dose of 200 µg per mouse. Antibody blockade and depletion were performed as described previously (24). For antibody-based depletion of CD8 T cells or NK cells, 100 µg per mouse of anti-CD8 (5358, BioXcell), anti-NK1.1 (PK136, BioXcell), and anti-asialo(as)GM1 (Wako Chemicals) were given on days −1, 0, and 7. For antibody blockade, anti-NKG2D (HMG2D, BioXcell) or control IgG (MOPC-21) were given at 200 µg per mouse on days −1, 0, 5, 7 and 10. Blood samples were collected at multiple time points by retro-orbital bleeding under isoflurane anesthesia. Mice were euthanized by $CO_2$ inhalation, lungs were perfused with PBS and fixed in formalin solution, and the number of superficial metastases was counted under a stereomicroscope. Histology was performed by the Rodent Histopathology Core of the Dana-Farber/Harvard Cancer Center using lungs that had not been perfused with PBS.

B16F10-MICA Metastasis Model in $Igh^{-/-}$ Mice $Igh^{-/-}$ mice were injected intravenously with $8 \times 10^5$ B16F10-MICA cells that had been transduced with the lentiviral vector that drives MICA and ZsGreen expression. Seven days following tumor cell inoculation, a group of mice was euthanized for analysis of metastases, both by visual inspection of lung surfaces under a stereo microscope as well as by Fontana-Masson and H&E staining of tissue sections. A second group of mice was treated until day 14, and at this time point metastases were quantified and lung-resident group 1 ILC were analyzed by flow cytometry.

CT26 Metastasis Model

Balb/c wild type mice were injected intravenously with $1 \times 10^6$ CT26-MICA, and treated with 7C6-mIgG2b or MPC-11 (isotype) administered intraperitoneally on days 1, 2, 7, and 14. Euthanasia was performed on day 21, followed by lung perfusion with 30% Indian ink through the trachea and fixation in Fekete's fixative. That procedure stains the lungs in black, while the metastases remain white, enabling counting of metastases under a stereomicroscope (24).

Subcutaneous B16F10-MICA Model

C57BL/6 mice were injected subcutaneously with $1 \times 10^6$ B16F10 cells that had been transduced with different lentiviral vectors (ZsGreen reporter). Five days later, treatment was initiated with 7C6-mIgG2a, 7C6-mIgG2b-DANA, or isotype control (C1184) antibodies (200 µg/mouse). Treatment was continued as indicated in the relevant figures. For antibody blockade, $Igh^{-/-}$ mice were given 200 µg/mouse of anti-NKG2D (HMG2D) or control IgG (MOPC-21) on days −1, 0, 5, 9, 14, and 19. Mice were bled on day 9. Tumor size was monitored with a digital caliper and the tumor area was calculated by multiplying the two largest diameters. To minimize suffering, the end point was defined as a tumor size of 200 mm2.

Mouse NK Cell Transfer and B16F10-MICA Metastases in $Rag2^{-/-}$ $Il2rg^{-/-}$ Mice NK cell adoptive transfer was done as described previously (25). Briefly, NK cells from mice of indicated genotypes were isolated from the spleen, enriched by negative selection, and sorted to achieve an NK cell purity of ~99%. Subsequently, $2 \times 10^5$ NK cells were injected intravenously into $Rag2^{-/-}$ $IL2rg^{-/-}$ mice. Three days later, reconstitution was checked in blood samples by flow cytometry, and no differences in NK cell frequency were observed among the NK cell genotypes. Subsequently, $4 \times 10^5$ B16F10-MICA cells (with luciferase reporter) were injected intravenously (day 0). On days 1, 2, 7, and 10, mice received 200 µg 7C6-mIgG2b or MPC-11 (isotype control) by intraperitoneal injection. Mice were bled at the indicated time points. Euthanasia by $CO_2$ inhalation was performed on day 14 followed by counting of superficial lung metastases as described above.

Flow Cytometry-Based Analysis of Immune and Tumor Cells in Lung Tissue

Wild-type mice were injected with $1 \times 10^6$ B16F10 cells that were previously transduced with ZsGreen-based lentiviral vectors (full-length MICA, secreted MICA or empty vector). In some experiments, mice received a lower dose of B16F10-MICA tumor cells ($7 \times 10^5$). On days 1, 2, 7 and 10 following B16F10-MICA cell injection, mice received 200 µg of 7C6-mIgG2a or isotype control (C1184) antibodies by intraperitoneal injection. Prior to euthanasia, mice received an intravenous injection of 50 µl of APC-conjugated anti-CD45.2 (clone104, Biolegend) to label intravascular immune cells. Approximately 5 minutes later, mice were euthanized by $CO_2$ inhalation and cell suspensions were generated from lung tissue. Lungs were cut into small pieces which were re-suspended in 10 ml of RPMI-1640 supplemented with 1 mg/ml collagenase type IV, 0.1 mg/ml hyaluronidase, and 20 U/ml DNase type IV. Samples were dissociated in a gentleMACS instrument (Miltenyi) using the program 37C_m_LDK_1 which digests the tissue by incubation with 37° C. followed by mechanical dissociation. Cells were then washed with PBS, Fc receptors were blocked with Mouse True Stain FcX (Biolegend), and cells were stained with PE-Cy7 or v450-conjugated anti-CD45.2 (104), PE or BV785-NK1.1 (PK136), PerCP-Cy5.5 or $Alexa^{700}$-NKp46 (29A1.4), APC or APC-Cy7-CD3ε (145.2C11), APC or BV511-TCRβ, PE-Cy5 or $Alexa^{488}$-CD69 (H1.2F3), BV421-NKG2D (CX5), BV510-Ly49C (5E6), BV570-CD62L (MEL-14), BV605-CD49a (Ha31/8), $Alexa^{488}$-EOMES (Dan11mag), PE-Granzyme A (GzA-3G8.5), PE or PERCP-Cy5.5-CD16/CD32 (93), PE-Cy7-Granzyme B (NGZB), BV510-DNAM-1 (10E5), $Alexa^{488}$-KLRG1 (2F1), PE-CXCR6 (SA051D1), PERCP-Cy5.5 or PE-Cy7-CD127 (A7R34), BV510-CXCR3 (CXCR3-173), Zombie NIR, Zombie Yellow or Zombie UV (all from Biolegend, BD Pharmigen or eBiosciences). For transcription factor staining, cells were fixed and permeabilized by a Transcription Factor Buffer kit (BDB562574). For Fc receptor staining, small aliquots of cells from the lung suspensions were separated and stained with PE or PerCP-Cy5.5-CD16/32 antibody (the incubation with Mouse True Stain FcX was skipped in that aliquot of cells). Tumor cells were stained with APC-conjugated anti-H2-Kb (AF6-88.5, Biolegend) and BV650-activated Caspase-3 (C92-605, BD Pharmingen) following permeabilization. Even though the CD45.2 antibody given intravenously and the anti-H2-Kb antibody were conjugated to the same fluorophore (APC), B16F10 cells could be identified based on their larger size, ZsGreen expression as well as the absence of CD45.2 expression. Samples were acquired using a LSR Fortessa, CytoFLEX or a Sony Spectral Analyzer and analyzed by FlowJo V10 software.

Single Cell RNA-Sequencing

C57BL/6 mice were injected i.v. with 7×105 B16F10-MICA cells and treated with 200 µg 7C6-mIgG2a or isotype control antibodies on days 1 and 2 after tumor cell inoculation. On day 7, mice received an intravenous injection of 50 µl APC-CD45.2 to label intravascular leukocytes and approximately five minutes later mice were euthanized and the lungs were removed. Cell suspensions from lung tissue were generated as described above. Cell suspensions from nine mice and eight mice were pooled for isotype and 7C6-mIgG2a groups, respectively. Group 1 ILCs were then enriched by negative selection in an autoMACS (130-096-

892, Miltenyi Biotec) and cells were stained with PE-Cy7-CD45.2, PE-NK1.1, PerCP-Cy5.5-NKp46, APC-Cy7-CD3 E, APC-Cy7-TCRβ, and Zombie Yellow. Cells that were positively stained for PE-Cy7-CD45.2, NK1.1 and NKp46, but not stained by Zombie Yellow, APC-CD45.2, CD3E and TCRβ were sorted using a FACS Aria flow cytometer. Immediately after cell sorting, the cell suspension was washed in 0.04% RNase-free BSA in PBS (ThermoFisher Scientific). A total of 5,000 cells from isotype or 7C6-mIgG2a groups were targeted for the 10× Genomics 3' V2 single cell assay (10× Genomics). Reverse transcription, cDNA amplification and library preparation were all performed according to the manufacturer's instructions. Libraries were sequenced using an Illumina HiSeq 2500 on rapid-run mode, which yielded >25,000 reads per cell. These procedures were later repeated for lung-specific group 1 ILC from age-matched naïve mice that did not receive B16F10-MICA cells.

Sequencing data were processed using the Cell Ranger Single-Cell Software Suite provided by 10× Genomics (available on the World Wide Web at support.10xgenomics.com/single-cell-gene-expression/software/downloads/latest). This pipeline includes read alignment and barcode demultiplexing, followed by UMI and barcode filtering and correction. The resulting gene expression matrix was then filtered to exclude genes with less than one UMI count in at least one cell. UMI counts were normalized by dividing the raw counts by the total counts in each cell. Subsequent clustering and visualization were conducted on a reduced expression matrix, retaining only the 1,000 genes exhibiting the highest dispersion values (defined as the variance over the mean expression). For each remaining gene, UMI counts were log-transformed and z-score normalized. Clustering and visualization were then performed using k-means and tSNE, respectively, on the first 50 principal components obtained from PCA analysis. Differentially expressed genes for each cluster were identified through the MAST R package, using zlm.SingleCellAssay function with method="glm". GSEA for single cell data was performed by Hypergeometric overlap statistic tool (available on the World Wide Web at software.broadinstitute.org/gsea/msigdb/annotate.jsp). For this analysis, the top 30 genes that were significantly overexpressed in each cell cluster were used.

CT26 Metastasis Model

Balb/c wild type mice were injected intravenously with $1\times10^6$ CT26-MICA, and treated with 7C6-mIgG2b or MPC-11 (isotype) administered intraperitoneally on days 1, 2, 7, and 14. Euthanasia was performed on day 21, followed by lung perfusion with 30% Indian ink through the trachea and fixation in Fekete's fixative. That procedure stains the lungs in black, while the metastases remain white, enabling counting of metastases under a stereomicroscope.

Subcutaneous B16F10-MICA Model

C57BL/6 mice were injected subcutaneously with $1\times10^6$ B16F10 cells that had been transduced with different lentiviral vectors (ZsGreen reporter). Five days later, treatment was initiated with 7C6-mIgG2a, 7C6-mIgG2b-DANA, or isotype control (C1184) antibodies (200 μg/mouse). Treatment was continued as indicated in the relevant Figures. For antibody blockade, $Igh^{-/-}$ mice were given 200 μg/mouse of anti-NKG2D (HMG2D) or control IgG (MOPC-21) on days −1, 0, 5, 9, 14, and 19. Mice were bled on day 9. Tumor size was monitored with a digital caliper and the area was calculated by multiplying the two largest diameters. To minimize suffering, the end point was defined as the time point when tumors reached a size of 200 mm².

Flow Cytometry Analyses of Subcutaneous B16F10-MICA Tumors $Igh^{-/-}$ mice were injected subcutaneously with $1\times10^6$ B16F10-MICA cells that had been transduced with a ZsGreen-based lentiviral vector that drives MICA expression. On days 5, 7 and 9 after tumor cell inoculation, mice were treated with 200 μg 7C6-mIgG2a or isotype control antibodies. On days 7 and 14, sets of mice were euthanized and tumors were removed. Tumors were then mechanically dissociated to preserve MICA integrity on the cell surface. Next, Fc receptors were blocked using Mouse True Stain FcX (Biolegend). Cells were subsequently stained with a PE-conjugated anti-mouse IgG antibody (Poly4053, Biolegend). Cells were then washed and stained with APC-conjugated anti-MICAS antibody (6D4), PE-Cy7-CD45.2 and Zombie NIR (all from Biolegend). Viable tumor cells were identified by flow cytometry based on size, ZsGreen fluorescence and absence of CD45.2 expression. Samples were examined using a Sony Spectral Analyzer or Beckman Coulter CytoFLEX, and data were analyzed by FlowJo.

A2058 Metastasis Model

Human NK cell reconstitution of NSG mice was done similar to a previous report (26). Briefly, human NK cells were obtained from fresh blood collars, as described above. Cells were treated overnight with 300 U/ml of recombinant human IL-2 (BD Pharmingen), and $1.5\times10^6$NK cells were injected intravenously into NSG mice. NK cell survival was supported by intraperitoneal injection of 75,000 U of IL-2 (Peprotech) every other day. Human NK cells survived in NSG mice for approximately one week under these conditions (data not shown) and therefore the last IL-2 injection was given 7 days following NK cell transfer. Furthermore, one day after NK cell inoculation and the first injection of IL-2, NSG mice were also injected intravenously with $1\times10^6$ A2058 melanoma cells. Two days later, mice were treated with 200 μg 7C6-hIgG1 or isotype control (BioXcell) and again once per week. Mice were bled at multiple time points to measure shed MICA and other serum markers. Euthanasia was performed on day 30 following tumor cell inoculation, lungs were perfused with Indian ink (as described above), fixed in Fekete's solution, and the number of lung metastases was counted. Lungs processed for histology were not perfused but fixed in formalin. Livers were also collected, fixed in formalin solution and the number of metastases was counted, or processed for histology. Following removal of these tissues, mice were fixed in Bouin fixative and processed for necropsy by the Rodent Histopathology Core (Dana-Farber/Harvard Cancer Center). The analysis was performed by a pathologist unaware of the different experimental groups.

Analysis of Serum Alanine Transaminase Activity

Serum alanine transaminase activity was analyzed in the blood of NSG mice injected with A2058 cells. The Alanine Transaminase Assay Kit (Bioassays Systems) was used according to the manufacturer's instructions.

Analysis of Liver Macrophages in Humanized Metastasis Model

NSG mice were injected i.v with A2058 cells and treated with 7C6-hgG1 or isotype control antibodies as described above. Three weeks following tumor cell inoculation, mice were euthanized and livers were perfused with PBS through the portal vein. Livers were mechanically dissociated and cell suspensions passed through a 70□ filter. Leukocytes were separated from hepatocytes by centrifugation in 37.5% Percoll, and Fc receptors were blocked with both Mouse and Human TrueStain FcXTM (BioLegend). Antibodies used for subsequent labeling were APC-CD45.2, APC-CD45.1, BV785-CD11b, BV421-F4/80, BV650-CD80, PE-CD86, FITC-Ly6C, PE-Cy7-Ly6G, PERCP-Cy5.5-CD16/CD32 and Zombie NIR. Cells were acquired in a Sony Spectral Analyzer and data were analyzed by FlowJo.

Macrophage Depletion

Macrophages were depleted by intravenous injection of 0.2 ml clodronate liposomes (Encapsula NanoSciences LLC). In the humanized and B16F10-MICA metastasis models, 0.2 ml of clodronate liposomes or control liposomes were injected i.v. (on the same day of tumor cell inoculation and then once weekly).

Statistical Analysis

All statistical analyses were performed using GraphPad Prism 7 software, with exception of the Rag2$^{-/-}$ Il2gr$^{-/-}$ experiments, which were performed using Microsoft Excel 2013. The statistical analysis performed were: 1) non-linear regression; 2) two-tailed unpaired Student's t test, with Welch's correction for unequal variances, 3) one-way Analysis of Variance (ANOVA) with Dunnett's multiple comparison test, and 4) two-way ANOVA with Bonferroni's multiple comparison test, or with Dunnett's multiple comparison test. Statistical significance was considered when p<0.05. All the figures have data that are representative of (or pooled from) at least two independent in vivo experiments, or at least three independent in vitro experiments. All graphs show mean±stdev, unless otherwise indicated in the figure legends.

Example 2—Isolation of Anti-MICA Antibodies

The membrane-proximal MICA and MICB α3 domain is the site of proteolytic shedding, whereas the membrane-distal α1 and α2 domains bind to the NKG2D receptor (FIG. 1G). Antibodies were generated to determine whether MICA shedding could be inhibited in a highly specific manner with antibodies that bind to the key epitopes of the MICA/B α3 domain, and that such antibodies would not interfere with NKG2D recognition of these proteins. It was further hypothesized that the Fc segment of such antibodies could contribute to the therapeutic efficacy by enabling engagement of a second activating receptors on NK cells, the CD16 Fc receptor.

Figure 6:
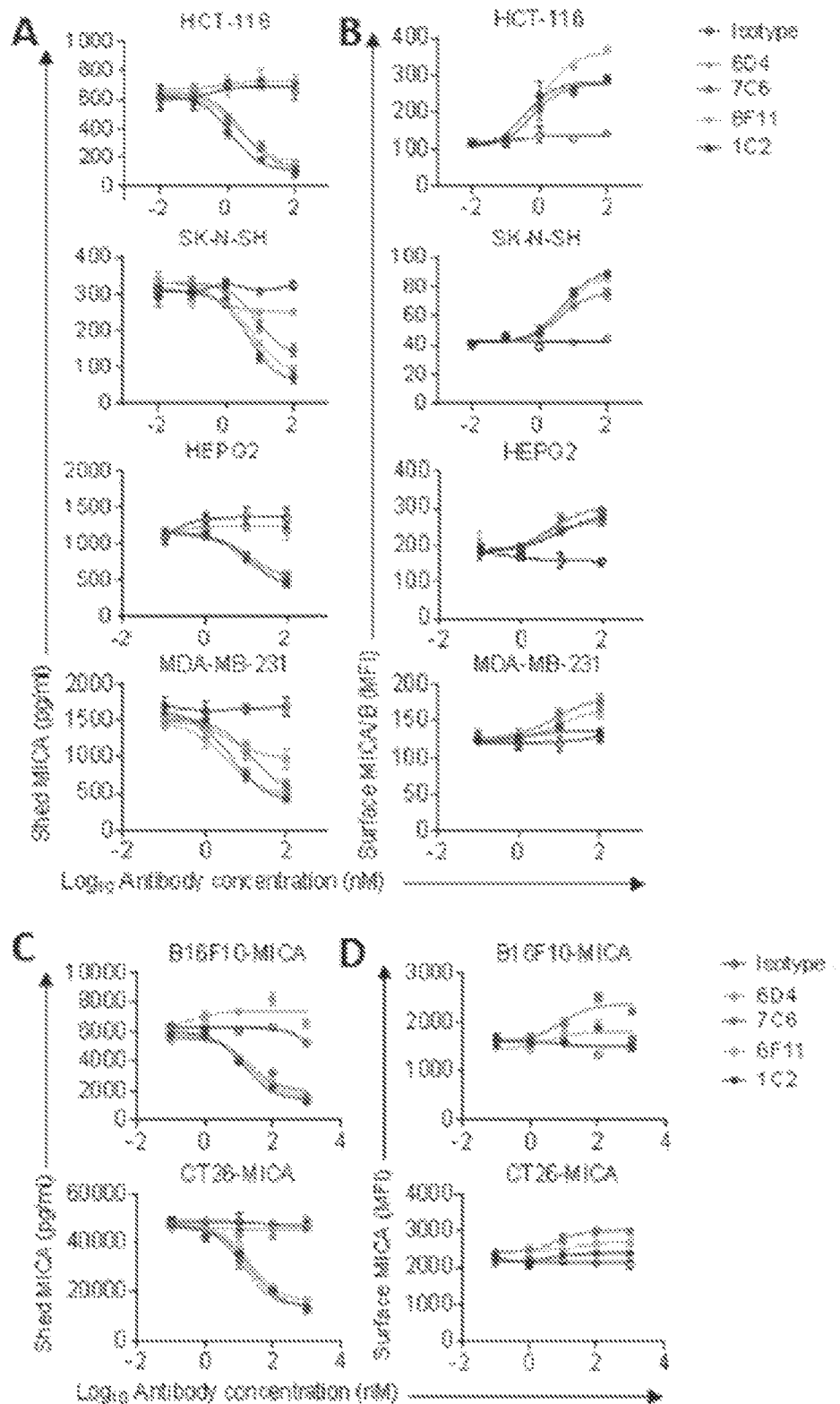
FIG. 6. Depicts data demonstrating that antibodies specific for the MICA α3 domain inhibit shedding and increase the cell surface density of MICA/B. (A, B) A panel of human tumor cell lines was treated for 24 hours with the indicated concentrations of MICA or isotype control antibodies. Shed MICA was quantified in the supernatant by sandwich ELISA (A), and surface MICA/B was measured by flow cytometry using a PE-labeled 6D4 antibody (B). Data are mean+/−SD of triplicate measurements; data representative of three independent experiments. (C, D) Murine B16F10 and CT26 tumor cell lines were transduced with a lentiviral vector to drive MICA expression. Shed MICA (C) and surface MICA (D) were then measured as described above. Mean±stdev for triplicates per condition; data representative of three independent experiments.

Mice were immunized with the recombinant MICA α3 domain and obtained three monoclonal antibodies (mAbs 7C6, 6F11, and 1C2) that bound to the MICA α3 domain and also the full-length extracellular domain (FIG. 1A, FIG. 5A-C). MICA and MICB genes are polymorphic, but the α3 domain is more conserved than the α1 and α2 domains, explaining why these antibodies bound to all tested MICA variants and also MICB (FIGS. 5B and D). The MICA and MICB α3 domain-specific antibodies strongly inhibited MICA shedding by the human A375 melanoma cell line and substantially increased the density of MICA on the cell surface (FIG. 1B-D). A similar activity was observed against a diverse panel of human tumor cell lines (FIG. 6A, B). In contrast, the previously reported 6D4 mAb (17) bound outside the MICA α3 domain and did not inhibit MICA shedding (FIG. 1A-C, and FIG. 6A-B). The antibodies also reduced MICA or MICB shedding by murine tumor cell lines that had been transduced by lentiviral vector with cDNAs for full-length MICA or MICB under the control of a lentiviral vector (FIG. 6C, D, FIG. 7A-C, and FIG. 8B), but did not affect levels of MICA secreted by cell lines transfected with a construct for the MICA extracellular domain (FIG. 8A-B). These antibodies minimally affected detection of recombinant soluble MICA by enzyme-linked immunosorbent assay (ELISA) (FIG. 8C and FIG. 8D). It was also confirmed that antibodies specific for the α3 domain did not interfere with NKG2D binding to MICA (FIG. 9).

These results confirmed that antibody-mediated targeting of the MICAS α3 domain could specifically inhibit proteolytic shedding of these NKG2D ligands.

Example 3—Expression of Recombinant MICA Antibodies

Recombinant anti-MICA antibodies were expressed in CHO-S cells as stable lines using the UCOE Hu-P vector (EMD Millipore) and puromycin selection. cDNAs for the heavy and light chains of the 7C6 mAb were ligated into the vector as one segment separated by a viral 2A peptide, which enabled stoichiometric expression from a single plasmid and efficient antibody assembly. The following oligos were used:

```
Oligos used in #4853 7C6MICA-mIgG2a-F (primes
both heavy and light chains)
                                 (SEQ ID NO: 26)
5' AAAAAAGGCCGGCCG CCGCCACCAT GGTACCGTGC A 3'

#4854 7C6MICA-mIgG2a-2A-R
                                 (SEQ ID NO: 27)
5' TACCATGGGG CCGGGGTTCT CCTCCACGTC GCCGCAGGTC
AGCAGGCTGC CTCTGCCCTC TTTACCCGGA GTCCGGGAGA 3'

#4855 7C6MICA-LC-2A-F
                                 (SEQ ID NO: 28)
5' AGAGGG CAGAGGCAGC CTGCTGACCT GCGGCGACGT
GGAGGAGAAC CCCGGCCCCA TGGTACCGTG CACGCTGCT 3'

#4856 7C6MICA-LC-R
                                 (SEQ ID NO: 29)
5' AAAAAAGCTAGCTCAA CACTCATTCC TGTTGAAGCT 3'

#4878 UCOE Hu-P_F1
                                 (SEQ ID NO: 30)
5' AG AGCGGAATTC GAGCTCCCTG CAGGTTAGTT 3'
```

The Fc segment of the parental mIgG2b antibody was replaced with either murine IgG2a (mIgG2a) or human IgG1 (hIgG1); in addition the Fc segment of mIgG2b and of a batch of hIgG1 were mutated to abrogate Fc receptor binding (D265A and N297A, abbreviated as DANA mutant). Selection was performed with puromycin (InvivoGen) at concentrations up to 50 µg/ml. Expression was scaled up in Freestyle CHO medium supplemented with 40 ml Gluta-MAX and 10 ml Anti-Clumping Agent (Life Technologies) per liter. Cells were split to 0.25 million/ml in 5 L Optimum Growth shaker flasks (Thompson Scientific) and incubated in a Multitron incubation shaker (Infors HT) at 37° C., 8% $CO_2$, 120 rpm. Supernatant containing the antibody was collected after 8-10 days and purified over Protein G Sepharose affinity columns (GE Healthcare). Expression of stable lines was 50-100 mg per liter. Antibody was concentrated in Amicon spin columns (Millipore), exchanged into PBS, and filtered prior to injection.

The nucleotide and amino acid sequences are provided in FIGS. 20-23.

Figure 7:
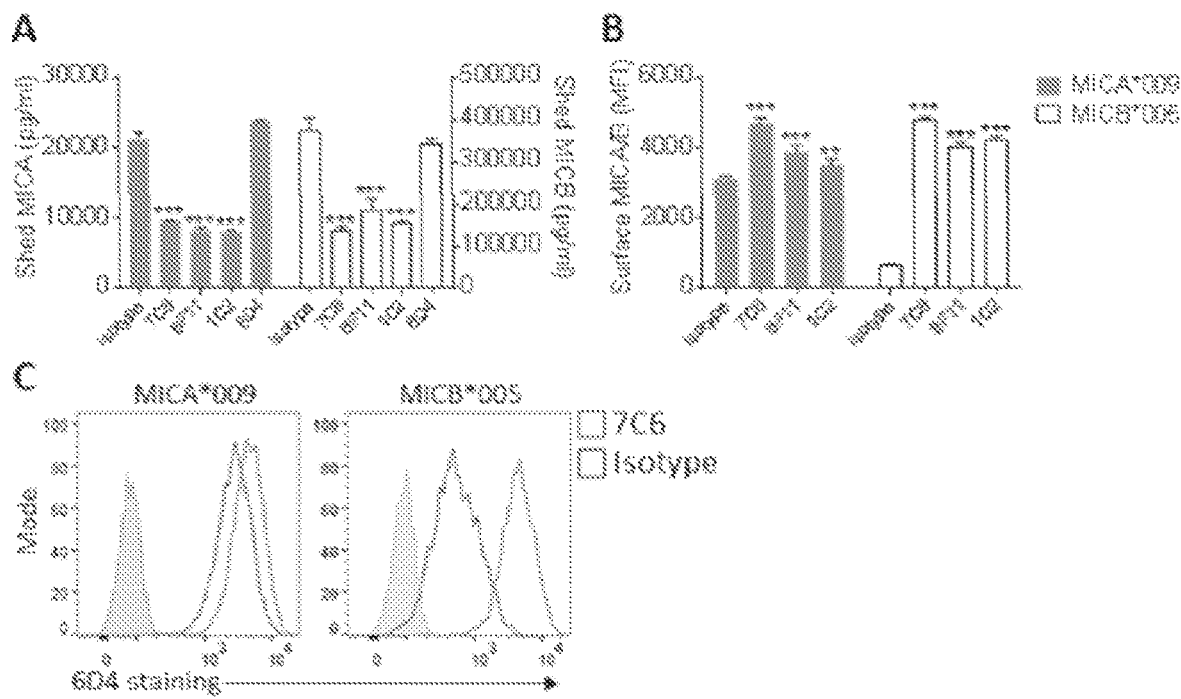
FIG. 7. Depicts data demonstrating that antibodies inhibit shedding of both MICA and MICB. (A-B) B16F10 cells expressing MICA allele or MICB (alleles 009 and 005, respectively) were treated with indicated MICA/B or isotype control antibodies for 24 hours. Shed MICA and MICB in supernatants were quantified by sandwich ELISA (A). Surface levels of both proteins were measured by flow cytometry following staining with PE-labeled 6D4 antibody; mean fluorescence intensities (MFI) are shown (B). Data are mean+/−SD of triplicate measurements; data representative of three independent experiments. (C) Histograms demonstrating surface levels of MICA or MICB following treatment with 7C6 or isotype control antibodies.
Figure 8:
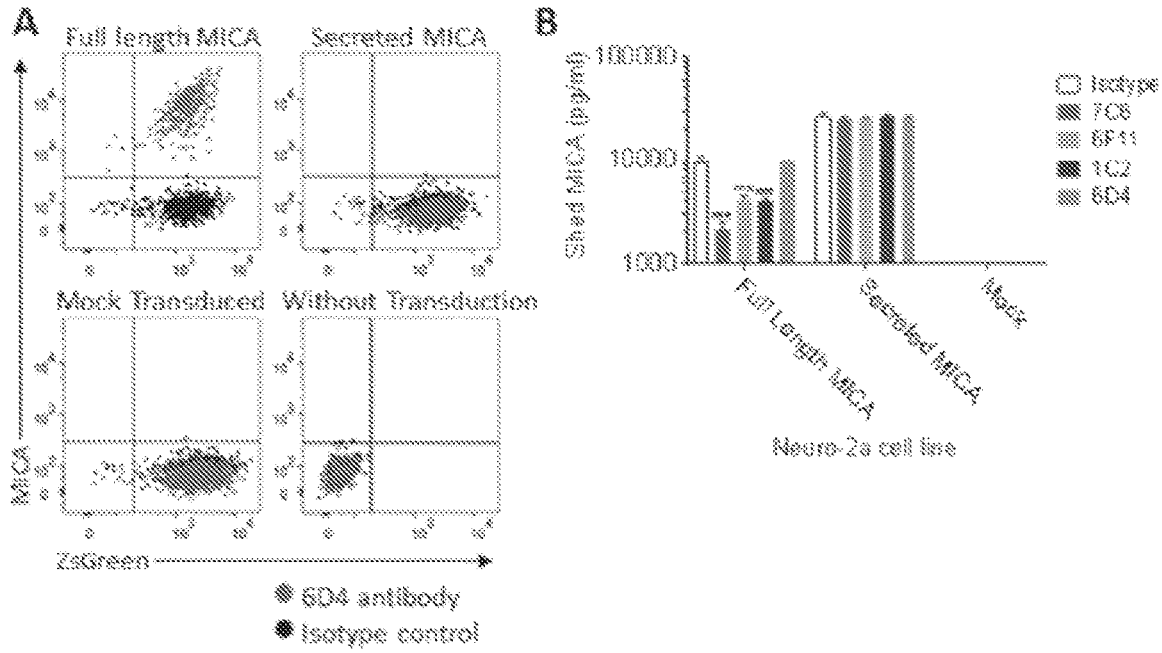
FIG. 8. Depicts the characterization of tumor cell lines that shed membrane-anchored MICA or release MICA by exocytosis. (A) The murine neuroblastoma cell line Neuro-2a was transduced with lentiviral vectors to enable expression of full-length membrane-anchored MICA or secreted MICA (stop codon preceding TM domain); the empty vector was used as a control. ZsGreen was expressed from the same vector downstream of an IRES. Each dot plot contains two pooled samples, which are the indicated cell lines stained with either 6D4 (red) or isotype control (black) antibodies. (B) Quantification of shed MICA in the supernatant following 24 hour treatment with MICA or isotype control antibodies. The supernatants were diluted 1:20 for shed MICA quantification, and thus in the isotype control group the supernatant of the secreted MICA cell line was measured at approximately 1,250 pg/ml, which is below the limit of detection for this ELISA. MICA antibodies inhibit shedding but do not affect levels of secreted MICA. Mean±stdev from triplicates per condition; data representative of three independent experiments. ***$p<0.001$, calculated by a two-way ANOVA followed by Dunnett's post-hoc test for each cell lines. (C) Dose-response for recombinant soluble MICA (allele 008) in ELISA assay. Data representative of three independent experiments. (D) Testing of potential interference of α3 domain-specific antibodies for detection of shed MICA by ELISA. MICA ELISA was performed with 2,000 pg/ml of soluble, recombinant MICA and indicated concentrations of α3 domain antibodies (7C6, 6F11 and 1C2) as well as α1-α2 antibody (6D4). Data representative of three independent experiments.

Example 4—Enhancement of NK Anti-Tumor Activity mAb 7C6 was selected for further experiments because it was most effective in stabilizing MICAS on the surface of tumor cells (FIG. 7B and FIG. 7C). NKG2D is an important receptor for NK cell mediated cytotoxicity, and it was observed that the 7C6 mAb (with human IgG1 Fc region, hIgG1) enabled strong NK cell mediated killing of human tumor cells, including tumor cell lines that were not killed by NK cells in the absence of this antibody (FIG. 1E, FIG. 10A, FIG. 13E). Human NK cells also produced higher levels of IFNγ when co-cultured with tumor cells in the presence of the 7C6-hIgG1 mAb (FIG. 10B). The 7C6 antibody also inhibited MICA and MICB shedding by short-term human melanoma (27) cell lines generated from metastatic lesions (FIG. 24A-C). These results demonstrated that a MICA α3 domain specific antibody could enhance the anti-tumor activity of human NK cells.

Example 5—Anti-MICA Activity in Immunocompetent Tumor Model

Figure 2:
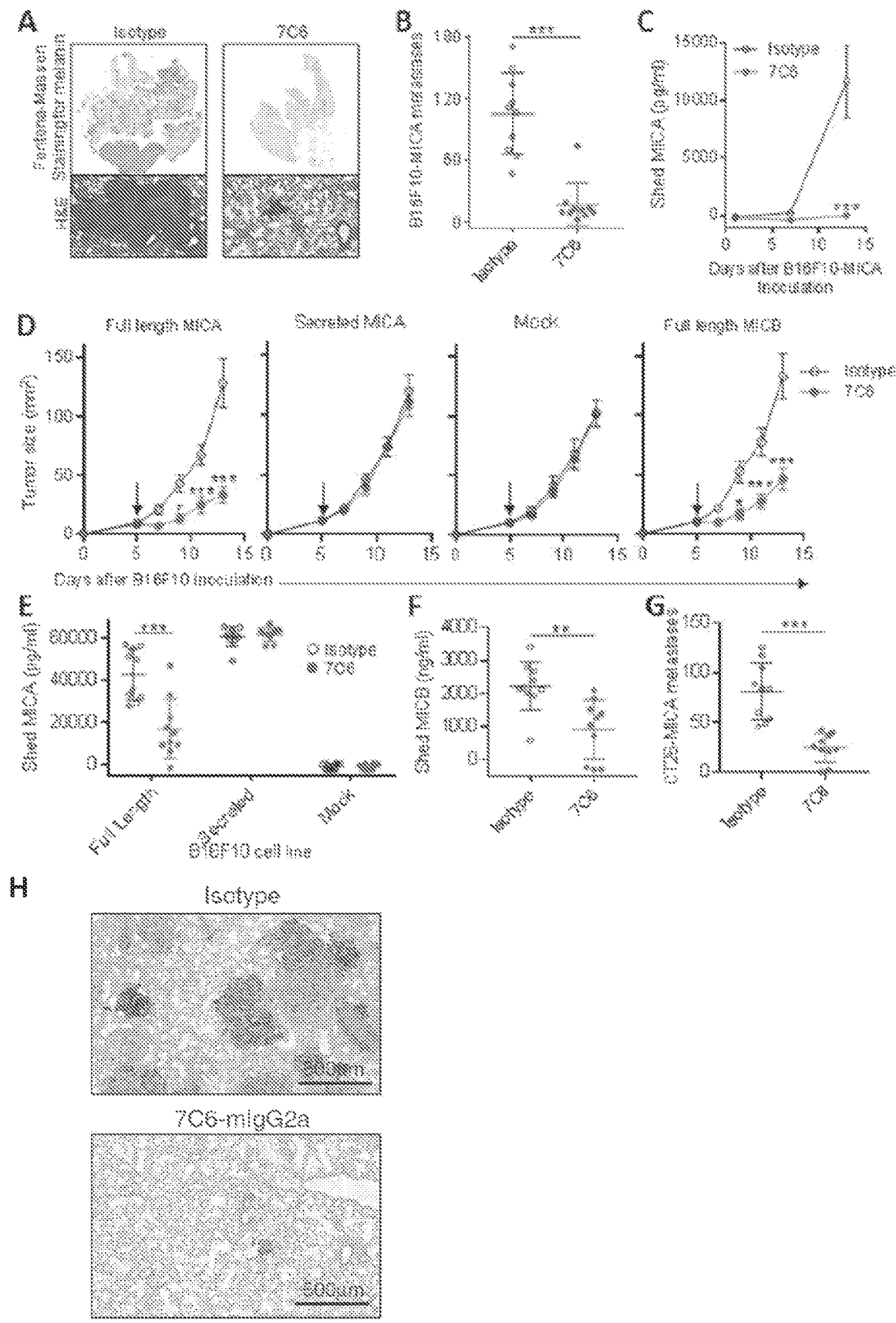
FIG. 2. Depicts the anti-tumor activity of antibodies that inhibit MICA/B shedding. (A-C) C57BL/6 mice were injected intravenously with B16F10-MICA cells and treated with 7C6-mIgG2a, 7C6-mIgG2b, or isotype control antibodies (200 μg) on days 1, 2, 7, and 10. On day 14, lungs were processed for histology. (A) Fontana-Masson staining for melanin to visualize lung metastases (top). H & E staining of metastases (bottom). Representative of five mice per group. (B) MICA antibody treatment reduced number of superficial lung metastases (day 14) counted by stereomicroscopy. Data indicate mean±SD of pooled data from two independent experiments. (C) Serum concentrations of shed MICA. Data show mean±SEM for five mice per group and one representative of two independent experiments. (D) 7C6-mIgG2a antibody has therapeutic activity against subcutaneous B16F10 tumors that express full-length MICA or MICB, but not tumors that secrete MICA. Tumor cells were inoculated into Igh$^{-/-}$ mice; treatment with 7C6-mIgG2a or isotype started on day 5 (arrow) and was repeated at every tumor measurement. Data show mean±SEM for 10 mice per group pooled from two independent experiments. (E-F) Analysis of serum MICAS on day 9 for experiment shown in (D). Data are mean±SD from pooled data of two independent experiments. (G) 7C6-IgG2b antibody has activity against CT26-MICA tumor cells inoculated intravenously into Balb/c mice (antibody injection on days 1, 2, 7 and 14, lung metastasis count on day 21). Data indicate mean±SD of pooled data from two independent experiments. *p<0.05, p<0.01, and *p<0.001, calculated by Mantel-Cox test (A), unpaired Student's t test (B, F, and G), and two-way ANOVA, Bonferroni's post-hoc test (C, D, and E). (H) Histology analysis (Fontana-Masson staining) of the lung tissue revealed an apparent reduction in the number and size of lung metastases in mice that were treated with MICA antibody (representative of five mice).
Figure 11:
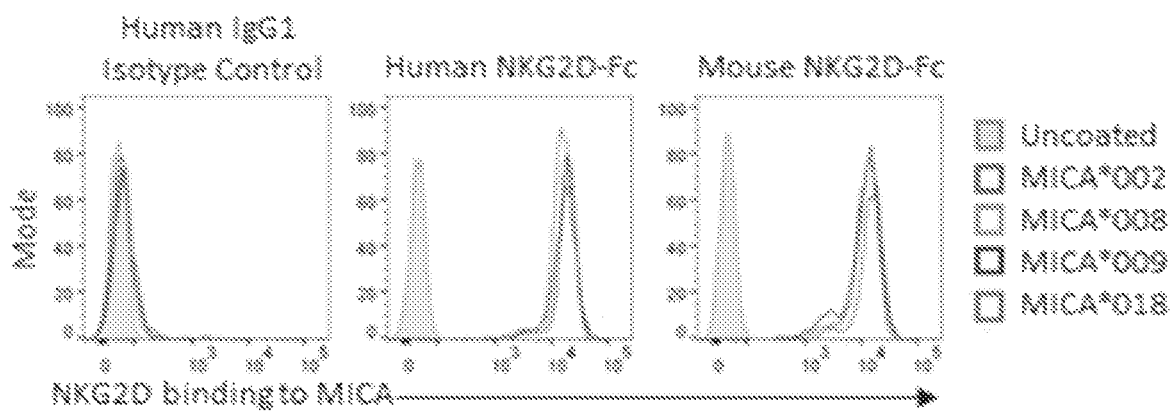
FIG. 11. Depicts data showing that the murine NKG2D receptor binds to human MICA. Mono-biotinylated MICA (alleles 002, 008, 009 or 018) was bound to streptavidin-conjugated beads. Beads were then incubated with human or murine NKG2D-Fc fusion proteins or a human IgG1 control antibody (10 μg/ml), as indicated. NKG2D-Fc fusion protein binding was quantified by flow cytometry following incubation with an Alexa$^{488}$-conjugated anti-human IgG secondary antibody. Data representative of two independent experiments.
Figure 12:
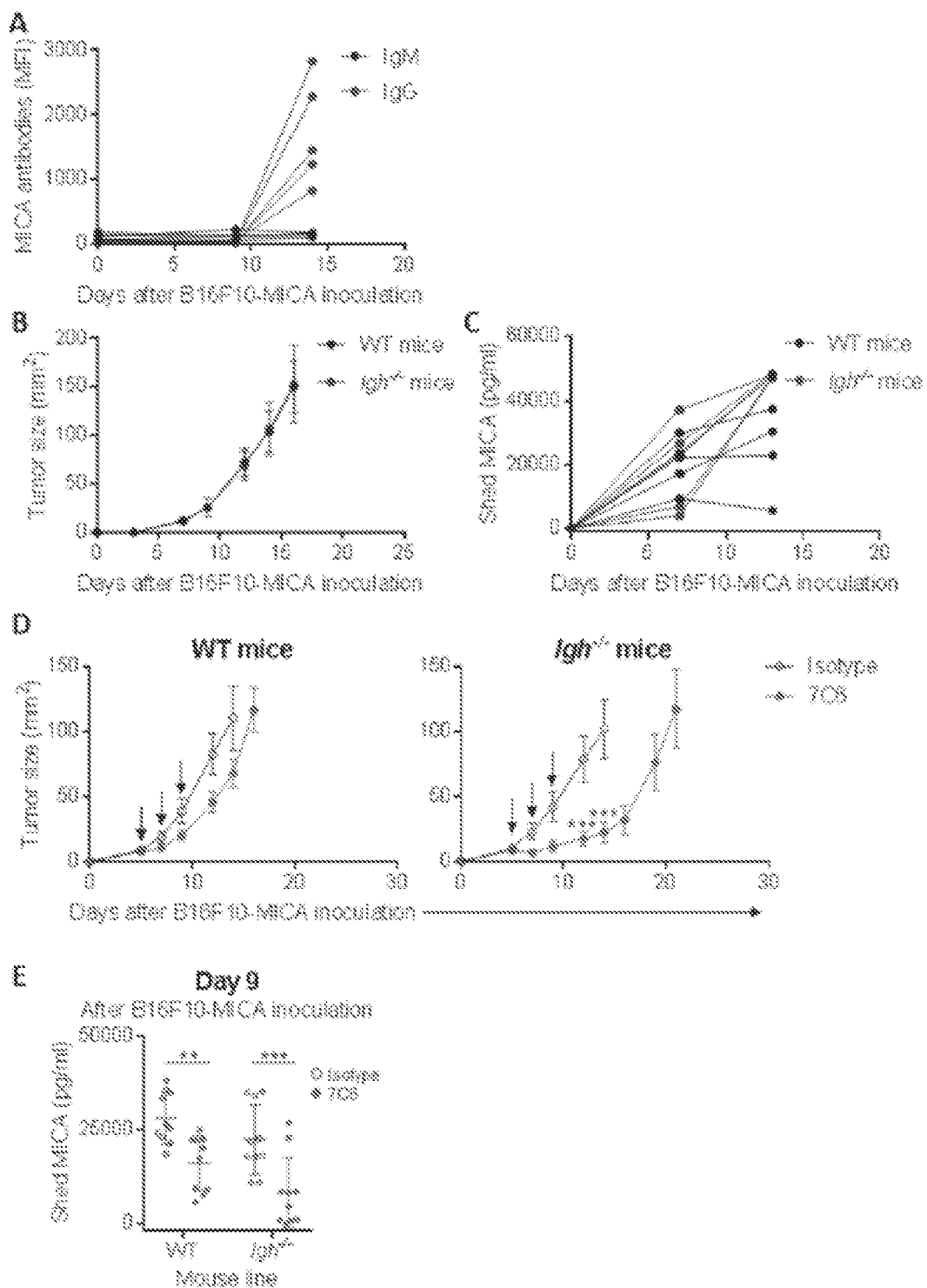
FIG. 12. Depicts the in vivo evidence for inhibition of MICA shedding and the analysis of endogenous MICA antibodies. B16F10-MICA tumor cells were implanted subcutaneously and tumor growth as well as MICA shedding were examined. (A) Endogenous MICA IgG antibodies were detected in the sera of tumor-bearing mice using a bead assay (day 14). Data representative of two independent experiments. (B) B16F10-MICA tumor growth in C57BL/6 wild-type mice and B cell deficient (Igh$^{-/-}$) mice. Data representative of two independent experiments. (C) Quantification of shed MICA for experiment shown in (B). Data representative of two independent experiments. (D) MICA antibody (7C6-mIgG2a) has greater efficacy in Igh$^{-/-}$ mice that lack endogenous MICA antibodies; MICA or isotype control antibodies were administered (200 μg) on indicated days (arrows). Data are mean+/−SEM of 10 mice per treatment condition. Data are pooled from two independent experiments. (E) Analysis of shed MICA on day 9 for experiment shown in (D). Data are mean+/−SD; data are pooled from two independent experiments. (F-H) In vivo inhibition of MICA shedding by 7C6-mIgG2a antibody. Igh$^{-/-}$ mice were injected subcutaneously with B16F10-MICA cells and treated with 7C6-mIgG2a or isotype control antibodies on days 5, 7, and 9. Tumors were dissociated without use of proteolytic enzymes to preserve surface MICA protein. (F) MICA antibody treatment does not affect ZsGreen fluorescence by tumor cells (driven by lentiviral vector). Data are mean+/−SD; data representative of two independent experiments. (G) MICA antibody detection within tumors. Tumor surface bound IgG was detected with a PE-conjugated anti-mouse IgG antibody from mice treated with isotype control or 7C6-mIgG2a antibodies. Data are mean+/−SD; data representative of two independent experiments. (H) 7C6-mIgG2a treatment increases surface MICA levels. Surface MICA on tumor cells was detected with an APC-labeled 6D4 antibody following treatment of mice with isotype control or 7C6-mIgG2a antibody. Data are mean+/−SD; data representative of two independent experiments. (I)

Only primates have MICA and MICB genes (1). However, human MICA is recognized by the murine NKG2D receptor (FIG. 11), which enabled testing of this therapeutic concept in fully immunocompetent mouse models. MICA cDNA with a lentiviral vector was introduced into the murine B16F10 melanoma and CT26 colon cancer cell lines, and tested the activity of the 7C6 antibody in lung metastasis models. 7C6 antibody treatment (mouse IgG2a Fc region) strongly reduced the number of lung metastases formed by B16F10-MICA tumor cells (FIG. 2A-B, FIG. 2H). Shed MICA levels were high in the sera of mice treated with an isotype control antibody, but undetectable in mice treated with 7C6 mAb (FIG. 2C). The 7C6 mAb also demonstrated efficacy in a lung metastasis model with the CT26 colon cancer cells that expressed MICA (FIG. 2G) and could be detected on the surface of B16F10-MICA cells in subcutaneous tumors (FIG. 12F and FIG. 12G). Also, increased MICA expression was detected on the surface of B16F10-MICA tumor cells when mice were treated with 7C6-mIgG2a compared to isotype control antibody (FIG. 12H). Interestingly, endogenous anti-MICA antibodies naturally arose in mice inoculated with MICA-expressing tumor cells (FIG. 12A). Murine IgG1 was the predominant isotype for these antibodies (FIG. 12I), an isotype associated with poor antitumor activity (21). These endogenous antibodies did not affect detection of recombinant MICA by ELSA (FIG. 12J), did not slow tumor growth (FIG. 12B), and moderately inhibited detection of shed MICA in serum samples (FIG. 12C).

Accordingly, 7C6 treatment inhibited growth of subcutaneous B16F10-MICA melanomas more effectively in B cell deficient mice (Igh$^{-/-}$) that were unable to mount such an antibody response (Fig. S8D, E). The efficacy of the 7C6 mAb was restricted to subcutaneous tumors that expressed full-length MICA or MICB; no therapeutic effect was observed for tumor cells that secreted the extracellular domain of MICA or that lacked these NKG2D ligands (FIG. 2D). Furthermore, 7C6 mAb inhibited MICA and MICB shedding, but did not promote clearance of secreted MICA protein (FIG. 2E). These results demonstrated that a mAb that inhibits MICA and MICB shedding had therapeutic efficacy in fully immunocompetent mouse models.

Antibody-mediated depletion revealed that NK cells, but not CD8 T cells, were essential for the therapeutic activity of 7C6 mAb against lung metastases (FIG. 13A, B). Furthermore, therapeutic efficacy was lost in perforin (Prf1) but not IFNγ (Ifng) deficient mice, indicating that NK cell-mediated cytotoxicity represented an essential mechanism (FIG. 13C-D). NK cell populations in lung tissue were then investigated by gating out blood leukocytes that had been labeled by a CD45 mAb injected i.v. prior to tissue harvest. Lung-infiltrating NK cells (NK1.1$^+$, NKp46$^+$) expressed CD69, a marker of tissue residency, while blood NK cells were negative (FIG. 14A). NK cell numbers were significantly higher in lung tissue of mice injected with MICA-expressing tumor cells compared to B16F10 control cells (FIG. 14B). However, NKG2D expression was strongly downregulated on tissue-resident NK cells, regardless of whether tumor cells expressed MICA (FIG. 14C).

These results indicated that NKG2D downregulation was not specifically caused by soluble MICA in this model, as previously reported in other systems (18, 19). Importantly, 7C6 antibody treatment restored NKG2D levels by lung NK cells (FIG. 15A). This was associated with massive tumor cell apoptosis (FIGS. 15B and C), MHC class I upregulation (FIG. 15D), and a substantial reduction of tumor cell load within lung tissue (FIGS. 15E and F). These results demonstrated that 7C6 antibody treatment activated important pathways for NK cell-mediated cytotoxicity. The MICA antibody also had activity against established metastases. Treatment was delayed until day 7, when metastases were detectable, and 7C6-mIgG2a reduced serum MICA concentrations and the number of lung metastases while enhancing infiltration of lung tissue by activated NK cells (FIG. 25, A to D).

Figure 3:
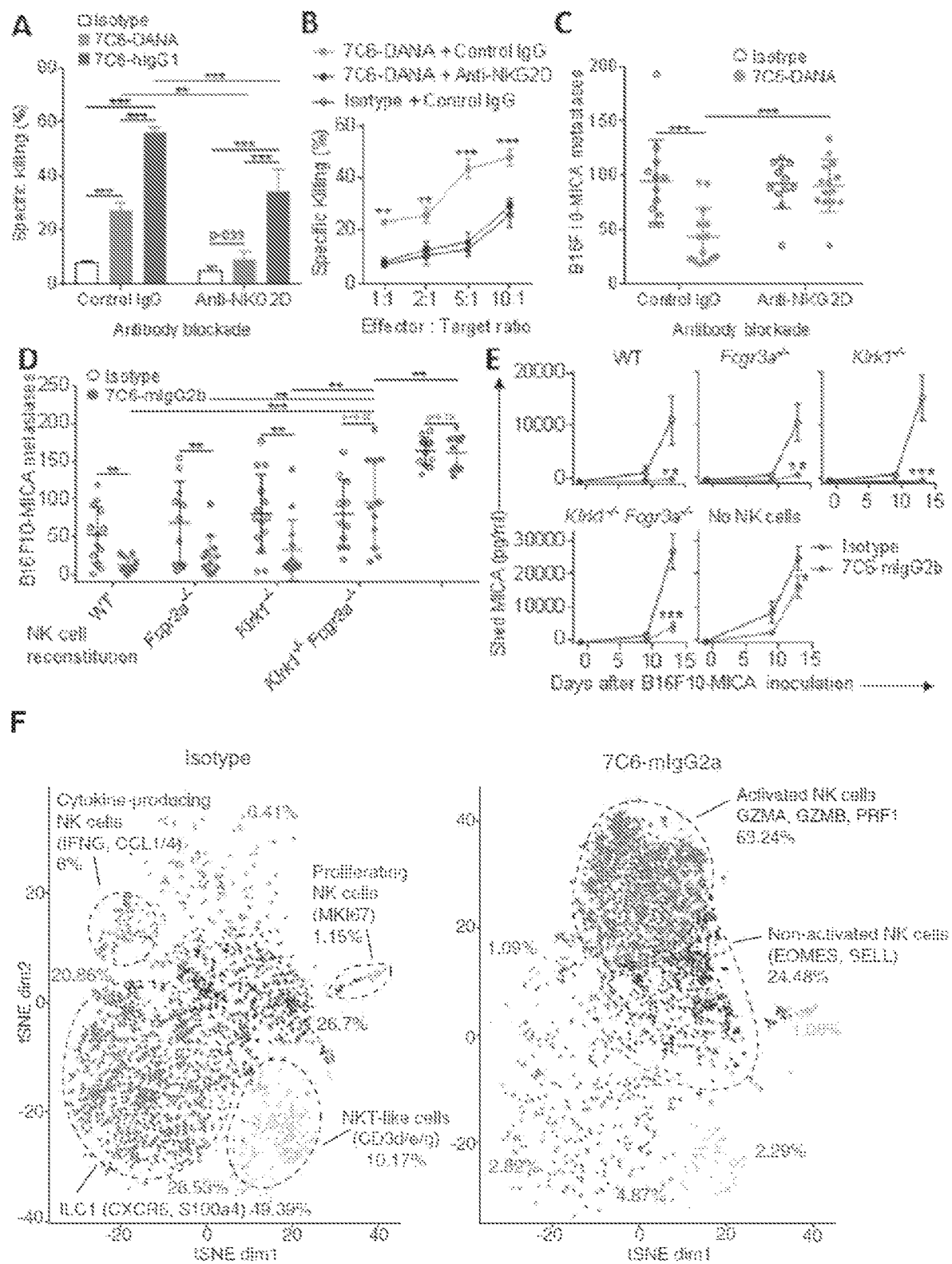
FIG. 3. Depicts data demonstrating that CD16 engagement enhances tumor immunity mediated by NKG2D receptor recognition. (A, B) Contribution of the NKG2D receptor and Fc region to anti-tumor activity of MICA antibody. A375 cells were treated for 48 hours with 7C6-hIgG1, 7C6-hIgG1-DANA or isotype control antibodies and then cocultured for 4 hours with human NK cells in a $^{51}$Cr-release assay. The 7C6-hIgG1-DANA mutant lacked Fc receptor binding. NKG2D recognition was blocked with mAb 1D11. Data indicate mean±SD and one representative of three independent experiments. (C) MICA antibody with mutant Fc segment retains anti-tumor activity. B16F10-MICA lung metastases were quantified following treatment with 7C6-mIgG2b-DANA or isotype control antibodies; NKG2D receptor recognition was blocked with antibody HMG2D, as indicated. (D and E) Both NKG2D and CD16 receptors contribute to therapeutic activity of MICA antibody. Rag2$^{-/-}$ Il2rg$^{-/-}$ mice were reconstituted with WT NK cells or NK cells mutant for NKG2D [Klrk1] and/or CD16 [Fcgr3a] genes. Mice were then injected intravenously with B16F10-MICA cells, and treated with 7C6-mIgG2b or isotype control antibodies, and lung metastases were quantified on day 14. Quantification of lung metastases (D) and serum shed MICA (E) for five mice per group. (A, C and D) Mean±stdev. (B and E) Mean±SEM. *p<0.05, p<0.01, and *p<0.001, calculated by (A, B, C, and E) two-way ANOVA with Bonferroni's post-hoc test, and (D) multiple unpaired Student's t tests. (F and G) Single-cell RNA-seq analysis of lung-infiltrating group 1 ILCs. On day 7 after intravenous injection of B16F10-MICA tumor cells, lung-infiltrating group 1 ILCs were isolated on the basis of NK1.1 and NKp46 staining (cells pooled from nine mice for isotype control and eight mice for 7C6-mIgG2a groups). Natural killer T-like cells that expressed both T cell and NK cell markers were also identified (even though TCRβ and CD3ε positive cells had been excluded), likely because the T cell receptor (TCR) is internalized after T cell activation. (F) t-distributed stochastic neighbor embedding (tSNE) plots illustrating identified cell populations in isotype control (left)- and 7C6-mIgG2a (right)-treated mice. Major populations and key markers are indicated. (G) Expression of key genes in group 1 ILCs on pooled data from isotype- and 7C6-mIgG2a-treated groups. FCER1G, Fc epsilon receptor gamma chain. (H) Fluorescence-activated cell sorting analysis of lung-infiltrating activated NK cells (EOMES$^+$ GZMA$^+$) across indicated time points relative to tumor burden (five mice per group and time point). Data indicate mean±SEM; days 7 and 14 are representative of two independent experiments.

The changes in gene expression by NK cells induced by MICA antibodies were next examined. Human NK cells cocultured with 7C6-hIgG1-pretreated human A375 melanoma cells upregulated genes associated with NK cell activation and effector functions (FIGS. 26, A and B). It was previously reported that tumors are infiltrated by group 1 innate lymphoid cells (ILCs), which are composed of NK cells and innate lymphoid cells 1 (ILC1) (26). Group 1 ILCs from metastatic lung tissue were sorted by flow cytometry for single-cell RNA sequencing (RNA-seq); these tissue-infiltrating group 1 ILCs expressed CD69, a tissue residency marker, whereas blood group 1 ILCs (likely NK cells) were low in CD69 (FIG. 14A). Single-cell RNA-seq demonstrated major differences in the composition and activation state of group 1 ILCs between 7C6-mIgG2a and isotype control treatment groups. In 7C6-mIgG2a-antibody treated mice, most group 1 ILCs (63.2%) were NK cells with a gene expression signature associated with activation and cytotoxicity, including expression of eomesodermin (EOMES), granzymeA (GZMA), granzyme B (GZMB), and perforin 1 (PRF1) (FIGS. 3, F and G, and FIGS. 27, A and B). By notable contrast, a large fraction of cells (49.4%) in isotype control antibody-treated mice were ILC1 with a gene expression signature associated with cytokine and chemokine signaling and inflammation, including expression of the CXCR3 and CXCR6 chemokine receptors and lymphotoxin b (LTB) (FIGS. 3, F and G, and FIGS. 28, A and B) (30). ILC1 were also identified in lung tissue of naïve mice that had not been injected with tumor cells (FIGS. 29, A and B), indicating that ILC1 originated from a lung-resident cell population. Taken together, these data indicated that treatment with this MICA antibody resulted in a notable activation of tissue-infiltrating NK cells and expression of cytotoxicity genes. Using flow cytometry, key findings from the single-cell RNA-seq study were validated. Lung infiltrating NK cells were identified using EOMES and CD49b as markers, whereas lung-resident ILC1 were positive for CD49a, CD226, CXCR3, and CXCR6 (FIG. 520A). Staining for GZMA allowed identification of activated NK cells that also expressed EOMES and CD49b (FIG. 30A). Quantification of EOMES GZMA$^+$ cells demonstrated an approximately fourfold increase of these activated NK cells (adjusted for tumor burden) on days 4, 7, and 11 in 7C6-mIgG2a-treated mice compared to isotype control antibody-treated mice with lung metastases (FIG. 3H and FIG. 30C). Also, the presence of lung metastases increased absolute numbers of lung-resident NK cells and ILC1 as shown by comparison of naïve mice and isotype control antibody-treated mice with lung metastases (FIGS. 26B and 30B). ILC1 expressed higher amounts of NKG2D at the protein level, but not at the mRNA level, compared to NK cells (FIG. 3G and FIG. 30A). Also, surface levels of NKG2D were higher among tissue-infiltrating NK cells than blood NK cells (FIGS. 14C and 31A). However, NKG2D surface levels were substantially reduced among tissue-resident NK cells and ILC1 in tumor-bearing mice compared to naïve mice, even when tumor cells did not express MICA (FIGS. 31A and B, and 14C), suggesting that signals from the tumor microenvironment (such as transforming growth factor-$\beta$) contributed to lower NKG2D levels within metastases (31, 32).

Example 6—NK and CD16 Receptor Activation in Absence of Fc Receptor Engagement

The activity of NK cells is regulated by multiple activating and inhibitory receptors, and both NKG2D and CD16 Fc receptors are important activating receptors for NK cells (20). Two mutations were introduced into the 7C6 heavy chain (D265A and N297A, abbreviated as DANA) to abrogate its ability to interact with activating Fc receptors, like reported previously for other antibodies (21). 7C6-DANA mutant antibodies did not bind to the activating Fc receptor expressed by NK cells (CD16a) but retained MICA binding (FIG. 32, A to D). This 7C6-DANA mutant antibody had an identical ability to inhibit MICA shedding compared to the non-mutated mIgG2b and mIgG2a forms (FIG. 16A). Pretreatment of human A375 melanoma cells with the 7C6-DANA mutant mAb induced killing by human NK cells, and this effect was blocked with an NKG2D mAb. This result demonstrated that inhibition of MICA shedding could induce NK cell-mediated cytotoxicity in the absence of Fc receptor engagement (FIG. 3A, B). The 7C6-DANA mutant antibody also had therapeutic activity in the B16F10-MICA lung metastasis model, and therapeutic benefit was lost when a NKG2D blocking antibody was administered (FIG. 3C, FIG. 16B). These results demonstrated that 7C6-mediated inhibition of MICAS shedding could restore NKG2D-mediated tumor immunity.

Engagement of multiple activating receptors strengthens NK cell functions (20, 42). 7C6 antibody with a fully functional Fc region (human IgG1, hIgG1) triggered stronger NK cell-mediated cytotoxicity than the 7C6-hIgG1-DANA mutant (FIG. 3A). This result suggested that the 7C6-hIgG1 mAb caused simultaneous activation of NKG2D and Fc receptors.

The contribution of the NKG2D and CD16 Fc receptors also was addressed by transfer of WT or mutant NK cells into $Rag2^{-/-}$ $Il2rg^{-/-}$ mice that were T cell and NK cell deficient. The most consistent reduction in the number of lung metastases was observed following transfer of WT NK cells. The therapeutic effect was maintained (but more variable) following transfer of NK cells deficient in either NKG2D (Klrk1) or CD16 (Fcgr3a). In striking contrast, antibody therapy was ineffective following transfer of NK cells that lacked both NKG2D and CD16 receptors, although shed MICA was still reduced (FIG. 3D-E). NKG2D and CD16 Fc receptors were also both required for inhibition of subcutaneous tumor growth (FIG. 17A, B). These data demonstrated that 7C6 mAb activated NK cells through two important receptors, the NKG2D and CD16 Fc receptors.

Example 7—Reduced Metastases in Endogenously Activated Tumor Model

In the syngeneic tumor models described above, MICA/B gene expression was induced by a heterologous promoter. However, in human cancers MICA/B gene expression is endogenously activated in response to malignant transformation (1). To test this therapeutic concept with human cancer and NK cells, NSG mice were reconstituted with human NK cells, followed by injection of human A2058 melanoma cells (FIG. 4A). IL-2 was injected every other day for 7 days to support NK cell survival; control experiments demonstrated that NK cells were rapidly lost without IL-2 injection.

Inoculation of human A2058 melanoma cells by an intravenous route resulted not only in lung metastases, but surprisingly also in widespread metastases in many other organs (which may be caused by secondary spread of tumor cells from initial lung lesions) (FIG. 18A). Mice reconstituted with human NK cells and treated with 7C6-hIgG1 mAb had fewer lung metastases (FIG. 4B, and FIG. 18D). Antibody treatment also reduced the number of organs with metastases (FIG. 18A-C). Metastases were particularly prominent in the liver, and 7C6-hIgG1 treatment substantially reduced the number of liver metastases even without NK cell transfer (FIG. 4C and FIG. 19A). Liver-resident $F4/80^{high}$ macrophages (Kupffer cells) that expressed activating Fc receptors (FIG. 19B) had higher surface levels of the CD80 activation marker in 7C6-hIgG1 treated mice (FIG. 19C). Macrophage depletion with clodronate liposomes abrogated the therapeutic activity of 7C6-hIgG1 antibody against liver metastases (FIG. 4E) but had no negative effect on therapeutic efficacy in the lung metastasis model in immunocompetent mice (FIG. 33). Human macrophages cultured in vitro express MICA and MICB, and treatment with acetylated low-density lipoproteins, a model of foam cells present in atherosclerotic lesions, increased MICA and MICB expression (28). Treatment with 7C6-hIgG1 antibody inhibited MICA shedding and increased MICA and MICB surface levels on macrophages (FIG. 34, A to C). These mechanisms account for the significant survival benefit of 7C6-hIgG1 treatment in this humanized metastasis model (FIG. 4D). These data demonstrate the therapeutic activity of a MICA α3 domain-specific antibody in a humanized metastasis model by activating NK cells and macrophages in an organ-dependent manner.

The results demonstrated that MICA and MICB α3 domain-specific antibodies substantially increased the density of the stimulatory MICA and MICB ligands on the surface of tumor cells, reduced shed MICA amounts, and induced NK cell-mediated tumor immunity. This therapeutic strategy restores the function of an activating immune pathway that promotes clearance of stressed and transformed cells (FIG. 4F). The association between MICA and MICB shedding and cancer progression is primarily due to the loss of immunostimulatory NKG2D ligands on the tumor cell surface, although shed MICA may also be a relevant contributing factor. Interestingly, shedding of the high-affinity murine MULT-1 ligand of NKG2D enhances anti-tumor immunity by inhibiting chronic NKG2D engagement of intratumoral NK cells by myeloid cells that express RAE-1, a murine NKG2D ligand (29). Soluble MICA and MICB have a substantially lower affinity for the NKG2D receptor than MULT-1, which may explain why shed MICA and MICB do not have such a stimulatory function (1). MICA/B expression is widespread in human cancers (16) and, accordingly, the antibodies provide herein provide useful therapies for both hematological malignancies (such as multiple myeloma) and solid tumors (such as prostate cancer) (11, 22, 43, 44). Moreover, these antibodies are particularly useful in combination with established therapies that induce or enhance MICA and MICB expression through genomic damage pathways, including local radiation therapy or antibody drug conjugates that deliver toxic payloads to tumor cells (23). For example, Dacarbazine synergizes with MICA/B antibody in vitro against melanoma (FIG. 35 A-B). Antibody-mediated inhibition of MICA/B shedding synergizes with proteasome inhibitor against multiple myeloma (FIG. 36 A-C). MICA antibodies are also of considerable interest as a combination partner with other immunotherapies to activate NK cells and enhance cytotoxic T cell function for protective antitumor immunity.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control. Also incorporated by reference in their entirety are any polynucleotide and polypeptide sequences which reference an accession number correlating to an entry in a public database, such as those maintained by The Institute for Genomic Research (TIGR) on the World Wide Web at tigr.org and/or the National Center for Biotechnology Information (NCBI) on the World Wide Web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

REFERENCES

1. D. H. Raulet, S. Gasser, B. G. Gowen, W. Deng, H. Jung, Regulation of ligands for the NKG2D activating receptor. *Annual review of immunology* 31, 413 (2013).
2. Y. Hayakawa et al., Cutting edge: tumor rejection mediated by NKG2D receptor-ligand interaction is dependent upon perforin. *The Journal of Immunology* 169, 5377 (2002).
3. C. Chan, M. Smyth, L. Martinet, Molecular mechanisms of natural killer cell activation in response to cellular stress. *Cell Death & Differentiation* 21, 5 (2014).
4. S. Bauer et al., Activation of NK cells and T cells by NKG2D, a receptor for stress-inducible MICA. *Science* 285, 727 (1999).
5. V. Groh et al., Costimulation of CD8αβ T cells by NKG2D via engagement by MIC induced on virus-infected cells. *Nature immunology* 2, 255 (2001).
6. N. Guerra et al., NKG2D-deficient mice are defective in tumor surveillance in models of spontaneous malignancy. *Immunity* 28, 571 (2008).
7. B. K. Kaiser et al., Disulphide-isomerase-enabled shedding of tumour-associated NKG2D ligands. *Nature* 447, 482 (2007).
8. H. R. Salih, H.-G. Rammensee, A. Steinle, Cutting edge: down-regulation of MICA on human tumors by proteolytic shedding. *The Journal of Immunology* 169, 4098 (2002).
9. P. Boutet et al., Cutting edge: the metalloproteinase ADAM17/TNF-α-converting enzyme regulates proteolytic shedding of the MHC class I-related chain B protein. *The Journal of Immunology* 182, 49 (2009).
10. S. Holdenrieder et al., Soluble MICA in malignant diseases. *International journal of cancer* 118, 684 (2006).
11. G. Liu et al., Perturbation of NK cell peripheral homeostasis accelerates prostate carcinoma metastasis. *The Journal of clinical investigation* 123, 4410 (2013).
12. M. Jinushi et al., MHC class I chain-*related protein A antibodies and shedding are associated with the progression of multiple myeloma. Proceedings of the National Academy of Sciences* 105, 1285 (2008).
13. L. Raffaghello et al., Downregulation and/or release of NKG2D ligands as immune evasion strategy of human neuroblastoma. *Neoplasia* 6, 558 (2004).
14. Y. Koguchi et al., Serum immunoregulatory proteins as predictors of overall survival of metastatic melanoma patients treated with ipilimumab. *Cancer research* 75, 5084 (2015).
15. X. Wang et al., An six-amino acid motif in the α3 domain of MICA is the cancer therapeutic target to inhibit shedding. *Biochemical and biophysical research communications* 387, 476 (2009).
16. P. Li et al., Complex structure of the activating immunoreceptor NKG2D and its MHC class I-like ligand MICA. *Nature immunology* 2, 443 (2001).
17. V. Groh, A. Steinle, S. Bauer, T. Spies, Recognition of stress-induced MHC molecules by intestinal epithelial γδ T cells. *Science* 279, 1737 (1998).
18. K. Wiemann et al., Systemic NKG2D down-regulation impairs NK and CD8 T cell responses in vivo. *The Journal of Immunology* 175, 720 (2005).
19. M. von Lilienfeld-Toal et al., Reduced immune effector cell NKG2D expression and increased levels of soluble NKG2D ligands in multiple myeloma may not be causally linked. *Cancer immunology, immunotherapy* 59, 829 (2010).
20. E. O. Long, H. Sik Kim, D. Liu, M. E. Peterson, S. Rajagopalan, Controlling natural killer cell responses: integration of signals for activation and inhibition. *Annual review of immunology* 31, 227 (2013).
21. F. Nimmerjahn, J. V. Ravetch, Divergent immunoglobulin g subclass activity through selective Fc receptor binding. *Science* 310, 1510 (2005).
22. J. Zhang, F. Basher, J. D. Wu, NKG2D ligands in tumor immunity: two sides of a coin. *Frontiers in immunology* 6, 97 (2015).
23. S. Gasser, S. Orsulic, E. J. Brown, D. H. Raulet, The DNA damage pathway regulates innate immune system ligands of the NKG2D receptor. *nature* 436, 1186 (2005).
24. L. Ferrari de Andrade et al., Natural killer cells are essential for the ability of BRAF inhibitors to control BRAFV600E-mutant metastatic melanoma. *Cancer research* 74, 7298-7308 (2014).
25. L. Martinet et al., DNAM-1 expression marks an alternative program of NK cell maturation. *Cell reports* 11, 85-97 (2015).
26. J. W. Leong et al., Preactivation with IL-12, IL-15, and IL-18 induces CD25 and a functional high-affinity IL-2 receptor on human cytokine-induced memory-like natural killer cells. *Biology of Blood and Marrow Transplantation* 20, 463-473 (2014).
27. B. Izar, C. E. Joyce, S. Goff, N. L. Cho, P. M. Shah, G. Sharma, J. Li, N. Ibrahim, J. Gold, F. S. Hodi, L. A. Garraway, C. D. Novina, M. M. Bertagnolli, C. H. Yoon, Bidirectional cross talk between patient-derived melanoma and cancer-associated fibroblasts promotes invasion and proliferation. *Pigment Cell Melanoma Res.* 29, 656-668 (2016).
28. S. Ikeshita, Y. Miyatake, N. Otsuka, M. Kasahara, MICA/B expression in macrophage foam cells infiltrating atherosclerotic plaques. *Exp. Mol. Pathol.* 97, 171-175 (2014).
29. W. Deng, B. G. Gowen, L. Zhang, L. Wang, S. Lau, A. Iannello, J. Xu, T. L. Rovis, N. Xiong, D. H. Raulet, A shed NKG2D ligand that promotes natural killer cell activation and tumor rejection. *Science* 348, 136-139 (2015).
30. Y. Gao, F. Souza-Fonseca-Guimaraes, T. Bald, S. S. Ng, A. Young, S. F. Ngiow, J. Rautela, J. Straube, N. Waddell, S. J. Blake, J. Yan, L. Bartholin, J. S. Lee, E. Vivier, K. Takeda, M. Messaoudene, L. Zitvogel, M. W. L. Teng, G. T. Belz, C. R. Engwerda, N. D. Huntington, K. Nakamura, M. Hölzel, M. J. Smyth, Tumor immunoevasion by the conversion of effector NK cells into type 1 innate lymphoid cells. *Nat. Immunol.* 18, 1004-1015 (2017).
31. J.-C. Lee, K.-M. Lee, D.-W. Kim, D. S. Heo, Elevated TGF-β1 secretion and downmodulation of NKG2D underlies impaired NK cytotoxicity in cancer patients. *J. Immunol.* 172, 7335-7340 (2004).
32. A. Clayton, J. P. Mitchell, J. Court, S. Linnane, M. D. Mason, Z. Tabi, Human tumor-derived exosomes downmodulate NKG2D expression. *J. Immunol.* 180, 7249-7258 (2008).
33. P. Vantourout, C. Willcox, A. Turner, C. M. Swanson, Y. Hague, O. Sobolev, A. Grigoriadis, A. Tutt, A. Hayday, Immunological visibility: Posttranscriptional regulation of human NKG2D ligands by the EGF receptor pathway. *Sci. Transl. Med.* 6, 231ra49 (2014).
34. L. L. Lanier, NKG2D receptor and its ligands in host defense. *Cancer Immunol. Res.* 3, 575-582 (2015).
35. S. Bauer, V. Groh, J. Wu, A. Steinle, J. H. Phillips, L. L. Lanier, T. Spies, Activation of NK cells and T cells by NKG2D, a receptor for stress-inducible MICA. *Science* 285, 727-729 (1999).
36. V. Groh, J. Wu, C. Yee, T. Spies, Tumour-derived soluble MIC ligands impair expression of NKG2D and T-cell activation. *Nature* 419, 734-738 (2002).
37. I. Waldhauer, D. Goehlsdorf, F. Gieseke, T. Weinschenk, M. Wittenbrink, A. Ludwig, S. Stevanovic, H.-G. Rammensee, A. Steinle, Tumor-associated MICA is shed by ADAM proteases. *Cancer Res.* 68, 6368-6376 (2008).
38. J. D. Wu, L. M. Higgins, A. Steinle, D. Cosman, K. Haugk, S. R. Plymate, Prevalent expression of the immunostimulatory MHC class I chain-related molecule is counteracted by shedding in prostate cancer. *J. Clin. Invest.* 114, 560-568 (2004).
39. G. Chitadze, M. Lettau, J. Bhat, D. Wesch, A. Steinle, D. Furst, J. Mytilineos, H. Kalthoff, O. Janssen, H.-H. Oberg, D. Kabelitz, Shedding of endogenous MHC class I-related chain molecules A and B from different human tumor entities: Heterogeneous involvement of the "a disintegrin and metalloproteases" 10 and 17. *Int. J. Cancer* 133, 1557-1566 (2013).
40. F. Q. Yang, M. Liu, F. P. Yang, X. L. Zhang, B. Yang, C. C. Guo, J. H. Huang, J. P. Che, Y. Yan, J. H. Zheng, Matrix metallopeptidase 2 (MMP2) mediates MHC class I polypeptiderelated sequence A (MICA) shedding in renal cell carcinoma. *Actas Urol. Esp.* 38, 172-178 (2014).
41. L. Huergo-Zapico, A. P. Gonzalez-Rodriguez, J. Contesti, E. Gonzalez, A. López-Soto, A. Fernandez-Guizan, A. Acebes-Huerta, J. R. de Los Toyos, C. Lopez-Larrea, V. Groh, T. Spies, S. Gonzalez, Expression of ERp5 and GRP78 on the membrane of chronic lymphocytic leukemia cells: Association with soluble MICA shedding. *Cancer Immunol. Immunother.* 61, 1201-1210 (2012).
42. Y. T. Bryceson, M. E. March, H.-G. Ljunggren, E. O. Long, Synergy among receptors on resting NK cells for the activation of natural cytotoxicity and cytokine secretion. *Blood* 107, 159-166 (2006).
43. C. S. Vetter, V. Groh, P. thor Straten, T. Spies, E.-B. Brocker, J. C. Becker, Expression of stress-induced MHC class I related chain molecules on human melanoma. *J. Invest. Dermatol.* 118, 600-605 (2002).
44. D. Pende, P. Rivera, S. Marcenaro, C. C. Chang, R. Biassoni, R. Conte, M. Kubin, D. Cosman, S. Ferrone, L. Moretta, A. Moretta, Major histocompatibility complex class Irelated chain A and UL16-binding protein expression on tumor cell lines of different histotypes: Analysis of tumor susceptibility to NKG2D-dependent natural killer cell cytotoxicity. *Cancer Res.* 62, 6178-6186 (2002)

TABLE 2

| SEQUENCE SUMMARY |
|---|
| Heavy chain CDR1 amino acid sequence<br>SEQ ID NO: 1 NYAMN |
| Heavy chain CDR1 nucleotide sequence<br>SEQ ID NO: 9 AACTATGCAATGAAC |
| Heavy chain CDR2 amino acid sequence<br>SEQ ID NO: 2 WINTHTGDPTYADDFKG |
| Heavy chain CDR2 nucleotide sequence<br>SEQ ID NO: 10<br>TGGATAAACACCCACACTGGAGACCCAACATATGCTGATGACTTCAAGG<br>GA |
| Heavy chain CDR3 amino acid sequence<br>SEQ ID NO: 3 TYGNYAMDY |
| Heavy chain CDR3 nucleotide sequence<br>SEQ ID NO: 11 ACTTATGGTAATTACGCTATGGACTAC |
| Light chain CDR1 amino acid sequence<br>SEQ ID NO: 4 SASQDISNYLN |
| Light chain CDR1 nucleotide sequence<br>SEQ ID NO: 12 AGTGCAAGTCAGGACATTAGCAATTATTTAAAC |
| Light chain CDR2 amino acid sequence<br>SEQ ID NO: 5 DTSILHL |
| Light chain CDR2 nucleotide sequence<br>SEQ ID NO: 13 GACACATCAATTTTACACTTA |
| Light chain CDR3 amino acid sequence<br>SEQ ID NO: 6 QQYSKFPRT |
| Light chain CDR3 nucleotide sequence<br>SEQ ID NO: 14 CAGCAGTATAGTAAATTTCCTCGGACG |
| Heavy chain variable region amino acid sequence<br>SEQ ID NO: 7<br>QIQLVQSGPELKKPGETVKVSCKASGYMFTNYAMNWVKQAPEKGLKWMG<br>WINTHTGDPTYADDFKGRIAFSLETSASTAYLQINNLKNEDTATYFCVR<br>TYGNYAMDYWGQGTSVTVSSAKTTAPSVYPLAPVCGDTTGSSVTLGCLV<br>KGYFPEPVTLTWNSGSLSSGVHTFPAVLQSDLYTLSSSVTVTSS |
| Heavy chain variable region nucleotide sequence<br>SEQ ID NO: 15<br>CAGATCCAGTTGGTGCAGTCTGGACCTGAGCTGAAGAAGCCTGGAGAGA<br>CAGTCAAGGTCTCCTGCAAGGCTTCTGGGTATATGTTCACAAACTATGC<br>AATGAACTGGGTGAAGCAGGCTCCAGAAAAGGGTTTAAAGTGGATGGGC<br>TGGATAAACACCCACACTGGAGACCCAACATATGCTGATGACTTCAAGG<br>GACGAATTGCCTTCTCTTTGGAAACCTCTGCCAGCACTGCCTATTTGCA<br>GATCAACAACCTCAAAAATGAGGACACGGCTACATATTTCTGTGTAAGA<br>ACTTATGGTAATTACGCTATGGACTACTGGGGTCAAGGAACCTCAGTCA |

TABLE 2-continued

SEQUENCE SUMMARY

CCGTCTCCTCAGCCAAAACAACAGCCCCATCGGTCTATCCACTGGCCCC
TGTGTGTGGAGATACAACTGGCTCCTCGGTGACTCTAGGATGCCTGGTC
AAGGGTTATTTCCCTGAGCCAGTGACCTTGACCTGGAACTCTGGATCCC
TGTCCAGTGGTGTGCACACCTTCCCAGCTGTCCTGCAGTCTGACCTCTA
CACCCTCAGCAGCTCAGTGACTGTAACCTCGAGC

Light chain variable region amino acid sequence
SEQ ID NO: 8
DIQMTQTTSSLSASLGDRVTISCSASQDISNYLNWYQQKPDGTVKLLIY
DTSILHLGVPSRFSGSGSGTDYSLTISNLEPEDIATYYCQQYSKFPRTF
GGGTTLEIK TABLE 2-continued

SEQUENCE SUMMARY

Light chain variable region nucleotide sequence
SEQ ID NO: 16
GATATCCAGATGACACAGACCACATCCTCCCTGTCTGCCTCTCTGGGAG
ACAGAGTCACCATCAGTTGCAGTGCAAGTCAGGACATTAGCAATTATTT
AAACTGGTATCAGCAGAAACCAGATGGAACTGTTAAACTCCTGATCTAT
GACACATCAATTTTACACTTAGGAGTCCCATCAAGGTTCAGTGGCAGTG
GGTCTGGGACAGATTATTCTCTCACCATCAGTAACCTGGAACCTGAAGA
TATTGCCACTTACTATTGTCAGCAGTATAGTAAATTTCCTCGGACGTTC
GGTGGAGGCACCACGCTGGAAATCAAA

What is claimed is:

1. A monoclonal antibody, or antigen-binding fragment thereof, wherein the monoclonal antibody comprises:
   a heavy chain with three CDRs comprising amino acid sequences SEQ ID NO: 1, SEQ ID NO: 2, and SEQ ID NO: 3; and
   a light chain with three CDRs comprising amino acid SEQ ID NO: 4, SEQ ID NO: 5, and SEQ ID NO: 6.

2. The monoclonal antibody, or antigen-binding fragment thereof, of claim 1, wherein
   (a) the monoclonal antibody, or antigen-binding fragment thereof, is chimeric, humanized, composite, murine, or human,
   (b) the monoclonal antibody, or antigen-binding fragment thereof, is detectably labeled, comprises an effector domain, comprises an Fe domain, and/or is selected from the group consisting of Fv, Fav, F(ab')2), Fab', dsFv, scFv, sc(Fv)2, and diabodies fragments,
   (c) the monoclonal antibody, or antigen-binding fragment thereof, inhibits the shedding of MICA and/or MICB,
   (d) the monoclonal antibody, or antigen-binding fragment thereof, increases the cell surface density of MICA and/or MICB, optionally wherein the cell is a cancer cell,
   (e) the monoclonal antibody, or antigen-binding fragment thereof, reduces serum concentrations of shed MICA and/or MICB,
   (f) the monoclonal antibody, or antigen-binding fragment thereof, restores immune activation by stress molecules that activate cytotoxic lymphocytes, optionally the cytotoxic lymphocytes are NK cells or macrophages,
   (g) the monoclonal antibody, or antigen-binding fragment thereof, enhances the tumor immunity mediated by cytotoxic lymphocytes, optionally the cytotoxic lymphocytes are NK cells or macrophages,
   (h) the monoclonal antibody, or antigen-binding fragment thereof, enhances the tumor immunity through activation of NKG2D receptor and/or CD16 Fc receptor on cytotoxic lymphocytes, optionally the cytotoxic lymphocytes are NK cells or macrophages,
   (i) the monoclonal antibody, or antigen-binding fragment thereof, specifically binds MICA α3 domain and/or MICB α3 domain,
   (j) the monoclonal antibody, or antigen-binding fragment thereof, does not interfere with NKG2D binding to MICA and/or MICB,
   (k) the monoclonal antibody, or antigen-binding fragment thereof, does not bind to Fc receptors, and/or
   (l) the monoclonal antibody, or antigen-binding fragment thereof, binds to one or more FcγRs, optionally wherein the FcγRs are activating or inhibitory FcγRs.

3. A device or kit comprising at least one monoclonal antibody, or antigen-binding fragment thereof, according to claim 1, said device or kit optionally comprising a label to detect the at least one monoclonal antibody, or antigen-binding fragment thereof, or a complex comprising the monoclonal antibody, or antigen-binding fragment thereof.

4. A composition comprising at least one monoclonal antibody, or antigen-binding fragment thereof, according to claim 1, and a carrier.

5. A method of producing at least one monoclonal antibody, or antigen-binding fragment thereof, according to claim 1, which method comprises the steps of: (i) culturing a transformed host cell which has been transformed by a nucleic acid comprising a sequence encoding at least one monoclonal antibody according to claim 1 under conditions suitable to allow expression of said monoclonal antibody, or antigen-binding fragment thereof; and (ii) recovering the expressed monoclonal antibody, or antigen-binding fragment thereof.

6. An immune-conjugate comprising at least one monoclonal antibody, or antigen-binding fragment thereof, according to claim 1, linked to an agent, optionally wherein the agent is a cytotoxic agent, optionally, wherein the cytotoxic agent is selected form the group consisting of a chemotherapeutic agent, a biologic agent, a toxin, and a radioactive isotope.

7. A method of increasing NK cell cytotoxicity and cytokine production comprising contacting a T-cell with at least one monoclonal antibody, or antigen-binding fragment thereof, according to claim 1, such that NK cell cytotoxicity and cytokine production is increased.

8. A method of detecting the presence or level of a MICA and/or MICB polypeptide comprising obtaining a sample and detecting said polypeptide in the sample by contacting said sample with at least one monoclonal antibody, or antigen-binding fragment thereof, according to claim 1, optionally wherein (a) the at least one monoclonal antibody, or antigen-binding fragment thereof, forms a complex with a MICA and/or MICB polypeptide and the complex is detected in the form of an enzyme linked immunosorbent assay (ELISA), radioimmune assay (RIA), immunochemically, Western blot, or using an intracellular flow assay, and/or (b) wherein the sample comprises cells, serum, peritumoral tissue, and/or intratumoral tissue obtained from the subject.

9. A method of treating a subject afflicted with cancer that expresses MICA and/or MICB comprising administering to the subject at least one monoclonal antibody, or antigen-binding fragment thereof, according to claim 1.

10. The method of claim 9,
   (a) wherein the at least one monoclonal antibody, or antigen-binding fragment thereof, is conjugated to a cytotoxic agent, optionally wherein the cytotoxic agent is selected from the group consisting of a chemotherapeutic agent, a biologic agent, a toxin, and a radioactive isotope,
   (b) wherein the at least one monoclonal antibody, or antigen-binding fragment thereof, reduces the number of proliferating cells in the cancer and/or reduces the volume or size of a tumor of the cancer,
   (c) wherein the at least one monoclonal antibody, or antigen-binding fragment thereof, reduces the metastases of cancer cells,
   (d) wherein the at least monoclonal antibody, or antigen-binding fragment thereof, enhances the infiltration of NK cells into a tumor, optionally (i) wherein the infiltrating NK cells are activated and cytotoxic, or (ii) wherein the infiltrating NK cells express cytotoxicity genes selected from the group consisting of eomesodermin, granzyme A, granzyme B, and perforin 1,
   (e) wherein the at least one monoclonal antibody, or antigen-binding fragment thereof, is administered in a pharmaceutically acceptable formulation,
   (f) further comprising administering to the subject a therapeutic agent or regimen for treating cancer,
   (g) further comprising administering to the subject an additional therapy selected from the group consisting of immunotherapy, checkpoint blockade, cancer vaccines, chimeric antigen receptors, chemotherapy, radiation, target therapy, and surgery,
   (h) wherein the cancer is selected from the group consisting of bladder cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and virus-related cancer, optionally wherein the cancer is a metastatic cancer, refractory cancer, or recurrent cancer,
- (i) wherein the subject is an animal model of cancer, optionally wherein the animal model is a mouse model, optionally wherein the mouse model is a humanized mouse model, and/or
- (j) wherein the subject is a mammal, optionally wherein the mammal is a humanized mouse or a human, optionally wherein the mammal is a human.

11. A method of treating a subject afflicted with cancer that expresses MICA and/or MICB comprising administering to the subject at least one monoclonal antibody, or antigen-binding fragment thereof, according to claim 1, in combination with an agent that enhances MICA and/or MICB expression.

12. The method of claim 11,
- (a) wherein the agent enhances MICA and/or MICB expression through genomic damage pathways,
- (b) wherein the agent is selected from the group consisting of radiation therapy, antibody-drug conjugate, HDAC inhibitor, proteasome inhibitor, chemotherapy, alkylating agent, and topoisomerase inhibitor, optionally (i) wherein the HDAC inhibitor is selected from the group consisting of hydroxamic acid, vorinostat, suberoylanilide hydroxamic acid, trichostatin A, LAO824, panobinostat, belinostat, ITF2357, cyclic tetrapeptide, depsipeptide, benzamide, Eetinostat, MGCD0103, short-chain aliphatic acids, valproic acid, phenyl butyrate, AN-9, pivanex, CHR-3996, and CHR-2845, (ii) wherein the proteasome inhibitor is selected from the group consisting of bortezomib, NPI-0052, carfilzomib, CEP 18770, and MLN9708, optionally wherein the proteasome inhibitor is bortezomib, or (iii) wherein the chemotherapy agent is dacarbazine,
- (c) wherein the agent administered before, after, or concurrently with the at least one monoclonal antibody, or antigen-binding fragment thereof,
- (d) wherein the at least one monoclonal antibody, or antigen-binding fragment thereof, is conjugated to a cytotoxic agent, optionally wherein the cytotoxic agent is selected from the group consisting of a chemotherapeutic agent, a biologic agent, a toxin, and a radioactive isotope,
- (e) wherein the at least one monoclonal antibody, or antigen-binding fragment thereof, and the agent, have a synergistic effect on reducing the number of proliferating cells in the cancer and/or reduces the volume or size of a tumor of the cancer,
- (f) wherein the at least one monoclonal antibody, or antigen-binding fragment thereof, and the agent, have a synergistic effect on reducing the metastases of cancer cells,
- (g) wherein the at least monoclonal antibody, or antigen-binding fragment thereof, and the agent, have a synergistic effect on enhancing the infiltration of NK cells into a tumor, optionally (i) wherein the infiltrating NK cells are activated and cytotoxic, or (ii) wherein the infiltrating NK cells express cytotoxicity genes selected from the group consisting of eomesodermin, granzyme A, granzyme B, and perforin 1,
- (h) wherein the at least one monoclonal antibody, or antigen-binding fragment thereof, and/or the agent is administered in a pharmaceutically acceptable formulation,
- (i) further comprising administering to the subject a therapeutic agent or regimen for treating cancer,
- (j) further comprising administering to the subject an additional therapy selected from the group consisting of immunotherapy, checkpoint blockade, cancer vaccines, chimeric antigen receptors, chemotherapy, radiation, target therapy, and surgery,
- (k) wherein the cancer is selected from the group consisting of bladder cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and virus-related cancer, optionally wherein the cancer is a metastatic cancer, refractory cancer, or recurrent cancer,
- (l) wherein the subject is an animal model of cancer, optionally wherein the animal model is a mouse model, optionally wherein the mouse model is a humanized mouse model, and/or
- (m) wherein the subject is a mammal, optionally wherein the mammal is a humanized mouse or a human, optionally wherein the mammal is a human.

13. An immunoglobulin comprising a variable heavy chain amino acid sequence consisting of SEQ ID NO: 7, and variable light chain amino acid sequence consisting of SEQ ID NO: 8.

14. An isolated nucleic acid molecule that hybridizes with the complement of a nucleic acid sequence selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16, or a nucleic acid sequence selected from the group consisting of SEQ ID NO: 9, SEQ ID NO: 10, SEQ ID NO: 11, SEQ ID NO: 12, SEQ ID NO: 13, SEQ ID NO: 14, SEQ ID NO: 15, and SEQ ID NO: 16.

15. A vector comprising the isolated nucleic acid of claim 14.

16. An isolated host cell which comprises the isolated nucleic acid of claim 14.

\* \* \* \* \*

SEQUENCE LISTING

<160> NUMBER OF SEQ ID NOS: 33

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb 7C6 CDR-H1 amino

<400> SEQUENCE: 1

Asn Tyr Ala Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb 7C6 CDR-H2 amino acid sequence

<400> SEQUENCE: 2

Trp Ile Asn Thr His Thr Gly Asp Pro Thr Tyr Ala Asp Asp Phe Lys
1               5                   10                  15
Gly

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb 7C6 CDR-H3 amino

<400> SEQUENCE: 3

Thr Tyr Gly Asn Tyr Ala Met Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:

<223> OTHER INFORMATION: mAb 7C6 CDR-L1 amino

<400> SEQUENCE: 4

Ser Ala Ser Gln Asp Ile Ser Asn Tyr Leu Asn
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb 7C6 CDR-L2 amino

<400> SEQUENCE: 5

Asp Thr Ser Ile Leu His Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: mAb 7C6 CDR-L3 amino acid sequence

<400> SEQUENCE: 6

Gln Gln Tyr Ser Lys Phe Pro Arg Thr
1               5

<210> SEQ ID NO 7
<211> LENGTH: 191
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: mAb 7C6 heavy chain amino acid sequence

<400> SEQUENCE: 7

Gln Ile Gln Leu Val Gln Ser Gly Pro Glu Leu Lys Lys Pro Gly Glu
1               5                   10                  15

Thr Val Lys Val Ser Cys Lys Ala Ser Gly Tyr Met Phe Thr Asn Tyr
            20                  25                  30

Ala Met Asn Trp Val Lys Gln Ala Pro Glu Lys Gly Leu Lys Trp Met
        35                  40                  45

Gly Trp Ile Asn Thr His Thr Gly Asp Pro Thr Tyr Ala Asp Asp Phe
    50                  55                  60

Lys Gly Arg Ile Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Val Arg Thr Tyr Gly Asn Tyr Ala Met Asp Tyr Trp Gly Gln Gly Thr
            100                 105                 110

Ser Val Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

```
Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
            165                 170                 175

Ser Asp Leu Tyr Thr Leu Ser Ser Ser Val Thr Val Thr Ser Ser
        180                 185                 190

<210> SEQ ID NO 8
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: mAb 7C6 light chain amino acid sequence

<400> SEQUENCE: 8

Asp Ile Gln Met Thr Gln Thr Thr Ser Ser Leu Ser Ala Ser Leu Gly
1               5                   10                  15

Asp Arg Val Thr Ile Ser Cys Ser Ala Ser Gln Asp Ile Ser Asn Tyr
            20                  25                  30

Leu Asn Trp Tyr Gln Gln Lys Pro Asp Gly Thr Val Lys Leu Leu Ile
        35                  40                  45

Tyr Asp Thr Ser Ile Leu His Leu Gly Val Pro Ser Arg Phe Ser Gly
50                  55                  60

Ser Gly Ser Gly Thr Asp Tyr Ser Leu Thr Ile Ser Asn Leu Glu Pro
65                  70                  75                  80

Glu Asp Ile Ala Thr Tyr Tyr Cys Gln Gln Tyr Ser Lys Phe Pro Arg
                85                  90                  95

Thr Phe Gly Gly Gly Thr Thr Leu Glu Ile Lys
            100                 105

<210> SEQ ID NO 9
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: mAb 7C6 CDR-H1 cDNA

<400> SEQUENCE: 9
aactatgcaa tgaac                                                      15

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: mAb 7C6 CDR-H2 cDNA sequence

<400> SEQUENCE: 10
tggataaaca cccacactgg agacccaaca tatgctgatg acttcaaggg a              51

<210> SEQ ID NO 11
<211> LENGTH: 27
<212> TYPE: DNA
<213> ORGANISM: Artificial Sequence
<220> FEATURE:
```

<223> OTHER INFORMATION: Description of Artificial Sequence: Synthetic
      oligonucleotide
<220> FEATURE:
<223> OTHER INFORMATION: mAb 7C6 CDR-H3 cDNA

<400> SEQUENCE: 11
acttatggta attacgctat ggactac                                        27

<210> SEQ ID NO 12
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: mAb 7C6 CDR-L1 cDNA

<400> SEQUENCE: 12
agtgcaagtc aggacattag caattattta aac                                 33

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: mAb 7C6 CDR-L2 cDNA sequence

<400> SEQUENCE: 13
gacacatcaa ttttacactt a                                              21

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: mAb 7C6 CDR-L1 cDNA sequence

<400> SEQUENCE: 14
cagcagtata gtaaatttcc tcggacg                                        27

<210> SEQ ID NO 15
<211> LENGTH: 573
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: mAb 7C6 heavy chain cDNA sequence

<400> SEQUENCE: 15
cagatccagt tggtgcagtc tggacctgag ctgaagaagc ctggagagac agtcaaggtc     60
tcctgcaagg cttctgggta tatgttcaca aactatgcaa tgaactgggt gaagcaggct    120
ccagaaaagg gtttaaagtg gatgggctgg ataaacaccc acactggaga cccaacatat    180
gctgatgact tcaagggacg aattgccttc tctttggaaa cctctgccag cactgcctat    240
ttgcagatca acaacctcaa aaatgaggac acggctacat atttctgtgt aagaacttat    300
ggtaattacg ctatggacta ctgggggtcaa ggaacctcag tcaccgtctc ctcagccaaa    360

```
acaacagccc catcggtcta tccactggcc cctgtgtgtg gagatacaac tggctcctcg    420
gtgactctag gatgcctggt caagggttat tccctgagcc agtgaccttt gacctggaac    480
tctggatccc tgtccagtgg tgtgcacacc ttcccagctg tcctgcagtc tgacctctac    540
accctcagca gctcagtgac tgtaacctcg agc                                 573
```

```
<210> SEQ ID NO 16
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: mAb 7C6 light chain cDNA sequence

<400> SEQUENCE: 16
gatatccaga tgacacagac cacatcctcc ctgtctgcct ctctgggaga cagagtcacc    60
atcagttgca gtgcaagtca ggacattagc aattatttaa actggtatca gcagaaacca    120
gatggaactg ttaaactcct gatctatgac acatcaattt tacacttagg agtcccatca    180
aggttcagtg gcagtgggtc tgggacagat tattctctca ccatcagtaa cctggaacct    240
gaagatattg ccacttacta ttgtcagcag tatagtaaat ttcctcggac gttcggtgga    300
ggcaccacgc tggaaatcaa a                                              321
```

```
<210> SEQ ID NO 17
<211> LENGTH: 102
<212> TYPE: PRT
<213> ORGANISM: Homo sapiens

<400> SEQUENCE: 17

Val Pro Pro Met Val Asn Val Thr Arg Ser Glu Ala Ser Glu Gly Asn
1               5                   10                  15

Ile Thr Val Thr Cys Arg Ala Ser Gly Phe Tyr Pro Trp Asn Ile Thr
            20                  25                  30

Leu Ser Trp Arg Gln Asp Gly Val Ser Leu Ser His Asp Thr Gln Gln
        35                  40                  45

Trp Gly Asp Val Leu Pro Asp Gly Asn Gly Thr Tyr Gln Thr Trp Val
    50                  55                  60

Ala Thr Arg Ile Cys Gln Gly Glu Glu Gln Arg Phe Thr Cys Tyr Met
65                  70                  75                  80

Glu His Ser Gly Asn His Ser Thr His Pro Val Pro Ser Gly Lys Val
                85                  90                  95

Leu Val Leu Gln Ser His
            100
```

```
<210> SEQ ID NO 18
<211> LENGTH: 102
<212> TYPE: PRT
<213> ORGANISM: Homo sapiens

<400> SEQUENCE: 18

Val Pro Pro Met Val Asn Val Thr Arg Ser Glu Ala Ser Glu Gly Asn
1               5                   10                  15

Ile Thr Val Thr Cys Arg Ala Ser Ser Phe Tyr Pro Arg Asn Ile Ile
            20                  25                  30

Leu Thr Trp Arg Gln Asp Gly Val Ser Leu Ser His Asp Thr Gln Gln
        35                  40                  45
```

```
Trp Gly Asp Val Leu Pro Asp Gly Asn Gly Thr Tyr Gln Thr Trp Val
        50                  55                  60

Ala Thr Arg Ile Cys Arg Gly Glu Glu Gln Arg Phe Thr Cys Tyr Met
 65                  70                  75                  80

Glu His Ser Gly Asn His Ser Thr His Pro Val Pro Ser Gly Lys Val
                 85                  90                  95

Leu Val Leu Gln Ser His
            100

<210> SEQ ID NO 19
<211> LENGTH: 102
<212> TYPE: PRT
<213> ORGANISM: Homo sapiens

<400> SEQUENCE: 19

Val Pro Pro Met Val Asn Val Thr Arg Ser Glu Ala Ser Glu Gly Asn
 1               5                  10                  15

Ile Thr Val Thr Cys Arg Ala Ser Ser Phe Tyr Pro Arg Asn Ile Thr
                20                  25                  30

Leu Thr Trp Arg Gln Asp Gly Val Ser Leu Ser His Asp Thr Gln Gln
            35                  40                  45

Trp Gly Asp Val Leu Pro Asp Gly Asn Gly Thr Tyr Gln Thr Trp Val
        50                  55                  60

Ala Thr Arg Ile Cys Gln Gly Glu Glu Gln Arg Phe Thr Cys Tyr Met
 65                  70                  75                  80

Glu His Ser Gly Asn His Ser Thr His Pro Val Pro Ser Gly Lys Val
                 85                  90                  95

Leu Val Leu Gln Ser His
            100

<210> SEQ ID NO 20
<211> LENGTH: 102
<212> TYPE: PRT
<213> ORGANISM: Homo sapiens

<400> SEQUENCE: 20

Val Pro Pro Met Val Asn Val Thr Arg Ser Glu Ala Ser Glu Gly Asn
 1               5                  10                  15

Ile Thr Val Thr Cys Arg Ala Ser Gly Phe Tyr Pro Trp Asn Ile Thr
                20                  25                  30

Leu Ser Trp Arg Gln Asp Gly Val Ser Leu Ser His Asp Thr Gln Gln
            35                  40                  45

Trp Gly Asp Val Leu Pro Asp Gly Asn Gly Thr Tyr Gln Thr Trp Val
        50                  55                  60

Ala Thr Arg Ile Cys Gln Gly Glu Glu Gln Arg Phe Thr Cys Tyr Met
 65                  70                  75                  80

Glu His Ser Gly Asn His Ser Thr His Pro Val Pro Ser Gly Lys Val
                 85                  90                  95

Leu Val Leu Gln Ser His
            100

<210> SEQ ID NO 21
<211> LENGTH: 102
<212> TYPE: PRT
<213> ORGANISM: Homo sapiens
```

<400> SEQUENCE: 21

```
Val Pro Pro Met Val Asn Val Thr Cys Ser Glu Tyr Ser Glu Gly Asn
1               5                   10                  15

Ile Thr Val Thr Cys Arg Ala Ser Gly Phe Tyr Pro Trp Asn Ile Thr
            20                  25                  30

Leu Thr Trp Arg Gln Asp Gly Val Ser Leu Ser His Asn Thr Gln Gln
        35                  40                  45

Trp Gly Asp Val Leu Pro Asp Gly Asn Gly Thr Tyr Gln Thr Trp Val
    50                  55                  60

Ala Thr Arg Ile Arg Gln Gly Glu Glu Gln Arg Phe Thr Cys Tyr Met
65                  70                  75                  80

Glu His Ser Gly Asn His Gly Thr His Pro Val Pro Ser Gly Lys Ala
                85                  90                  95

Leu Val Leu Gln Ser Gln
            100
```

<210> SEQ ID NO 22
<211> LENGTH: 2240
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 7C6-mIg2A-2A-LC vector insert sequence

<400> SEQUENCE: 22

```
agccgggcag agcggaattc gagctccctg caggttagtt aagttaacgg ccggccgccg      60
ccaccatggt accgtgcacg ctgctcctgc tgttggcggc cgccctggct ccgactcaga     120
cccgcgcgca gatccagttg gtgcagtctg gacctgagct gaagaagcct ggagagacag     180
tcaaggtctc ctgcaaggct tctgggtata tgttcacaaa ctatgcaatg aactgggtga     240
agcaggctcc agaaaagggt ttaaagtgga tgggctggat aaacacccac actggagacc     300
caacatatgc tgatgacttc aagggacgaa ttgccttctc tttggaaacc tctgccagca     360
ctgcctattt gcagatcaac aacctcaaaa atgaggacac ggctacatat ttctgtgtaa     420
gaacttatgg taattacgct atggactact ggggtcaagg aacctcagtc accgtctcct     480
cagccaaaac aacagcccca tcggtctatc cactggcccc tgtgtgtgga gatacaactg     540
gctcctcggt gactctagga tgcctggtca agggttattt ccctgagcca gtgaccttga     600
cctggaactc tggatccctg tccagtggtg tgcacacctt cccagctgtc ctgcagtctg     660
acctctacac cctcagcagc tcagtgactg taacctcgag cacctggccc agccagtcca     720
tcacctgcaa tgtggcccac ccggcaagca gcaccaaggt ggacaagaaa attgagccca     780
gagggcccac aatcaagccc tgtcctccat gcaaatgccc agcacctaac ctcttgggtg     840
gaccatccgt cttcatcttc cctccaaaga tcaaggatgt actcatgatc tccctgagcc     900
ccatagtcac atgtgtggtg gtggatgtga gcgaggatga cccagatgtc cagatcagct     960
ggtttgtgaa caacgtggaa gtacacacag ctcagacaca aacccataga gaggattaca    1020
acagtactct ccgggtggtc agtgccctcc ccatccagca ccaggactgg atgagtggca    1080
aggagttcaa atgcaaggtc aacaacaaag acctcccagc gcccatcgag agaaccatct    1140
caaaacccaa agggtcagta agagctccac aggtatatgt cttgcctcca ccagaagaag    1200
agatgactaa gaaacaggtc actctgacct gcatggtcac agacttcatg cctgaagaca    1260
```

-continued

```
tttacgtgga gtggaccaac aacgggaaaa cagagctaaa ctacaagaac actgaaccag    1320
tcctggactc tgatggttct tacttcatgt acagcaagct gagagtggaa aagaagaact    1380
gggtggaaag aaatagctac tcctgttcag tggtccacga gggtctgcac aatcaccaca    1440
cgactaagag cttctcccgg actccgggta aagagggcag aggcagcctg ctgacctgcg    1500
gcgacgtgga ggagaacccc ggccccatgg taccgtgcac gctgctcctg ctgttggcgg    1560
ccgcccctgg ctccgactca gacccgcgcg atatccagat gacacagacc acatcctccc    1620
tgtctgcctc tctgggagac agagtcacca tcagttgcag tgcaagtcag gacattagca    1680
attatttaaa ctggtatcag cagaaaccag atggaactgt taaactcctg atctatgaca    1740
catcaatttt acacttagga gtcccatcaa ggttcagtgg cagtgggtct gggacagatt    1800
attctctcac catcagtaac ctggaacctg aagatattgc cacttactat tgtcagcagt    1860
atagtaaatt tcctcggacg ttcggtggag gcaccacgct ggaaatcaaa cgggctgatg    1920
ctgcaccaac tgtatccatc ttcccaccat ccagtgagca gttaacatct ggaggtgcct    1980
cagtcgtgtg cttcttgaac aacttctacc ccaaagacat caatgtcaag tggaagattg    2040
atggcagtga acgacaaaat ggcgtcctga acagttggac tgatcaggac agcaaagaca    2100
gcacctacag catgagcagc accctcacgt tgaccaagga cgagtatgaa cgacataaca    2160
gctatacctg tgaggccact cacaagacat caacttcacc cattgtcaag agcttcaaca    2220
ggaatgagtg ttgagctagc                                                2240
```

<210> SEQ ID NO 23
<211> LENGTH: 2169
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 7C6-mIg2A-2A-LC vector insert cDNA sequence
<220> FEATURE:
<221> NAME/KEY: CDS
<222> LOCATION: (1)..(2169)

<400> SEQUENCE: 23

```
atg gta ccg tgc acg ctg ctc ctg ctg ttg gcg gcc gcc ctg gct ccg     48
Met Val Pro Cys Thr Leu Leu Leu Leu Ala Ala Ala Leu Ala Pro
1               5                   10                  15 act cag acc cgc gcg cag atc cag ttg gtg cag tct gga cct gag ctg     96
Thr Gln Thr Arg Ala Gln Ile Gln Leu Val Gln Ser Gly Pro Glu Leu
            20                  25                  30 aag aag cct gga gag aca gtc aag gtc tcc tgc aag gct tct ggg tat    144
Lys Lys Pro Gly Glu Thr Val Lys Val Ser Cys Lys Ala Ser Gly Tyr
        35                  40                  45 atg ttc aca aac tat gca atg aac tgg gtg aag cag gct cca gaa aag    192
Met Phe Thr Asn Tyr Ala Met Asn Trp Val Lys Gln Ala Pro Glu Lys
    50                  55                  60 ggt tta aag tgg atg ggc tgg ata aac acc cac act gga gac cca aca    240
Gly Leu Lys Trp Met Gly Trp Ile Asn Thr His Thr Gly Asp Pro Thr
65                  70                  75                  80 tat gct gat gac ttc aag gga cga att gcc ttc tct ttg gaa acc tct    288
Tyr Ala Asp Asp Phe Lys Gly Arg Ile Ala Phe Ser Leu Glu Thr Ser
                85                  90                  95 gcc agc act gcc tat ttg cag atc aac aac ctc aaa aat gag gac acg    336
Ala Ser Thr Ala Tyr Leu Gln Ile Asn Asn Leu Lys Asn Glu Asp Thr
            100                 105                 110
```

| | | |
|---|---|---|
| gct aca tat ttc tgt gta aga act tat ggt aat tac gct atg gac tac<br>Ala Thr Tyr Phe Cys Val Arg Thr Tyr Gly Asn Tyr Ala Met Asp Tyr<br>115                        120                      125 | | 384 |
| tgg ggt caa gga acc tca gtc acc gtc tcc tca gcc aaa aca aca gcc<br>Trp Gly Gln Gly Thr Ser Val Thr Val Ser Ser Ala Lys Thr Thr Ala<br>130                        135                      140 | | 432 |
| cca tcg gtc tat cca ctg gcc cct gtg tgt gga gat aca act ggc tcc<br>Pro Ser Val Tyr Pro Leu Ala Pro Val Cys Gly Asp Thr Thr Gly Ser<br>145                        150                      155                      160 | | 480 |
| tcg gtg act cta gga tgc ctg gtc aag ggt tat ttc cct gag cca gtg<br>Ser Val Thr Leu Gly Cys Leu Val Lys Gly Tyr Phe Pro Glu Pro Val<br>                  165                      170                      175 | | 528 |
| acc ttg acc tgg aac tct gga tcc ctg tcc agt ggt gtg cac acc ttc<br>Thr Leu Thr Trp Asn Ser Gly Ser Leu Ser Ser Gly Val His Thr Phe<br>                180                      185                      190 | | 576 |
| cca gct gtc ctg cag tct gac ctc tac acc ctc agc agc tca gtg act<br>Pro Ala Val Leu Gln Ser Asp Leu Tyr Thr Leu Ser Ser Ser Val Thr<br>                  195                      200                      205 | | 624 |
| gta acc tcg agc acc tgg ccc agc cag tcc atc acc tgc aat gtg gcc<br>Val Thr Ser Ser Thr Trp Pro Ser Gln Ser Ile Thr Cys Asn Val Ala<br>210                        215                      220 | | 672 |
| cac ccg gca agc agc acc aag gtg gac aag aaa att gag ccc aga ggg<br>His Pro Ala Ser Ser Thr Lys Val Asp Lys Lys Ile Glu Pro Arg Gly<br>225                        230                      235                      240 | | 720 |
| ccc aca atc aag ccc tgt cct cca tgc aaa tgc cca gca cct gaa ctc<br>Pro Thr Ile Lys Pro Cys Pro Pro Cys Lys Cys Pro Ala Pro Glu Leu<br>                          245                      250                      255 | | 768 |
| ctg ggg gga ccg tca gtc ttc ctc ttc ccc cca aaa ccc aag gac acc<br>Leu Gly Gly Pro Ser Val Phe Leu Phe Pro Pro Lys Pro Lys Asp Thr<br>                260                      265                      270 | | 816 |
| ctc atg atc tcc cgg acc cct gag gtc aca tgc gtg gtg gtg gac gtg<br>Leu Met Ile Ser Arg Thr Pro Glu Val Thr Cys Val Val Val Asp Val<br>                275                      280                      285 | | 864 |
| agc cac gaa gac cct gag gtc aag ttc aac tgg tac gtg gac ggc gtg<br>Ser His Glu Asp Pro Glu Val Lys Phe Asn Trp Tyr Val Asp Gly Val<br>          290                      295                      300 | | 912 |
| gag gtg cat aat gcc aag aca aag ccg cgg gag gag cag tac aac agc<br>Glu Val His Asn Ala Lys Thr Lys Pro Arg Glu Glu Gln Tyr Asn Ser<br>305                        310                      315                      320 | | 960 |
| acg tac cgt gtg gtc agc gtc ctc acc gtc ctg cac cag gac tgg ctg<br>Thr Tyr Arg Val Val Ser Val Leu Thr Val Leu His Gln Asp Trp Leu<br>                          325                      330                      335 | | 1008 |
| aat ggc aag gag tac aag tgc aag gtc tcc aac aaa gcc ctc cca gcc<br>Asn Gly Lys Glu Tyr Lys Cys Lys Val Ser Asn Lys Ala Leu Pro Ala<br>                    340                      345                      350 | | 1056 |
| ccc atc gag aaa acc atc tcc aaa gcc aaa ggg cag ccc cga gaa cca<br>Pro Ile Glu Lys Thr Ile Ser Lys Ala Lys Gly Gln Pro Arg Glu Pro<br>                355                      360                      365 | | 1104 |
| cag gtg tac acc ctg ccc cca tcc cgg gat gag ctg acc aag aac cag<br>Gln Val Tyr Thr Leu Pro Pro Ser Arg Asp Glu Leu Thr Lys Asn Gln<br>          370                      375                      380 | | 1152 |
| gtc agc ctg acc tgc ctg gtc aaa ggc ttc tat ccc agc gac atc gcc<br>Val Ser Leu Thr Cys Leu Val Lys Gly Phe Tyr Pro Ser Asp Ile Ala<br>385                        390                      395                      400 | | 1200 |
| gtg gag tgg gag agc aat ggg cag ccg gag aac aac tac aag acc acg<br>Val Glu Trp Glu Ser Asn Gly Gln Pro Glu Asn Asn Tyr Lys Thr Thr<br>                    405                      410                      415 | | 1248 |

```
cct ccc gtg ctg gac tcc gac ggc tcc ttc ttc ctc tac agc aag ctc    1296
Pro Pro Val Leu Asp Ser Asp Gly Ser Phe Phe Leu Tyr Ser Lys Leu
            420             425                 430 acc gtg gac aag agc agg tgg cag cag ggg aac gtc ttc tca tgc tcc    1344
Thr Val Asp Lys Ser Arg Trp Gln Gln Gly Asn Val Phe Ser Cys Ser
            435             440                 445 gtg atg cat gag gct ctg cac aac cac tac acg cag aag agc ctc tcc    1392
Val Met His Glu Ala Leu His Asn His Tyr Thr Gln Lys Ser Leu Ser
450             455                 460 ctg tct ccg ggt aaa gag ggc aga ggc agc ctg ctc acc tgc ggc gac    1440
Leu Ser Pro Gly Lys Glu Gly Arg Gly Ser Leu Leu Thr Cys Gly Asp
465             470                 475                 480 gtg gag gag aac ccc ggc ccc atg gta ccg tgc acg ctg ctc ctg ctg    1488
Val Glu Glu Asn Pro Gly Pro Met Val Pro Cys Thr Leu Leu Leu Leu
                485             490                 495 ttg gcg gcc gcc ctg gct ccg act cag acc cgc gcg gat atc cag atg    1536
Leu Ala Ala Ala Leu Ala Pro Thr Gln Thr Arg Ala Asp Ile Gln Met
                500             505                 510 aca cag acc aca tcc tcc ctg tct gcc tct ctg gga gac aga gtc acc    1584
Thr Gln Thr Thr Ser Ser Leu Ser Ala Ser Leu Gly Asp Arg Val Thr
            515                 520             525 atc agt tgc agt gca agt cag gac att agc aat tat tta aac tgg tat    1632
Ile Ser Cys Ser Ala Ser Gln Asp Ile Ser Asn Tyr Leu Asn Trp Tyr
        530                 535                 540 cag cag aaa cca gat gga act gtt aaa ctc ctg atc tat gac aca tca    1680
Gln Gln Lys Pro Asp Gly Thr Val Lys Leu Leu Ile Tyr Asp Thr Ser
545                 550                 555                 560 att tta cac tta gga gtc cca tca agg ttc agt ggc agt ggg tct ggg    1728
Ile Leu His Leu Gly Val Pro Ser Arg Phe Ser Gly Ser Gly Ser Gly
                565             570                 575 aca gat tat tct ctc acc atc agt aac ctg gaa cct gaa gat att gcc    1776
Thr Asp Tyr Ser Leu Thr Ile Ser Asn Leu Glu Pro Glu Asp Ile Ala
                580             585                 590 act tac tat tgt cag cag tat agt aaa ttt cct cgg acg ttc ggt gga    1824
Thr Tyr Tyr Cys Gln Gln Tyr Ser Lys Phe Pro Arg Thr Phe Gly Gly
            595                 600             605 ggc acc acg ctg gaa atc aaa cgg gct gat gct gca cca act gta tcc    1872
Gly Thr Thr Leu Glu Ile Lys Arg Ala Asp Ala Ala Pro Thr Val Ser
            610             615                 620 atc ttc cca cca tcc agt gag cag tta aca tct gga ggt gcc tca gtc    1920
Ile Phe Pro Pro Ser Ser Glu Gln Leu Thr Ser Gly Gly Ala Ser Val
625             630                 635                 640 gtg tgc ttc ttg aac aac ttc tac ccc aaa gac atc aat gtc aag tgg    1968
Val Cys Phe Leu Asn Asn Phe Tyr Pro Lys Asp Ile Asn Val Lys Trp
                645             650                 655 aag att gat ggc agt gaa cga caa aat ggc gtc ctg aac agt tgg act    2016
Lys Ile Asp Gly Ser Glu Arg Gln Asn Gly Val Leu Asn Ser Trp Thr
                660             665                 670 gat cag gac agc aaa gac agc acc tac agc atg agc agc acc ctc acg    2064
Asp Gln Asp Ser Lys Asp Ser Thr Tyr Ser Met Ser Ser Thr Leu Thr
            675                 680             685 ttg acc aag gac gag tat gaa cga cat aac agc tat acc tgt gag gcc    2112
Leu Thr Lys Asp Glu Tyr Glu Arg His Asn Ser Tyr Thr Cys Glu Ala
            690             695                 700 act cac aag aca tca act tca ccc att gtc aag agc ttc aac agg aat    2160
Thr His Lys Thr Ser Thr Ser Pro Ile Val Lys Ser Phe Asn Arg Asn
705             710                 715                 720 gag tgt tga                                                        2169
Glu Cys
```

<210> SEQ ID NO 24
<211> LENGTH: 2258
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<223> OTHER INFORMATION: 7C6-mIg2b-DANA-2A-LC vector insert sequence

<400> SEQUENCE: 24

| | | | | | |
|---|---|---|---|---|---|
| agccgggcag | agcggaattc | gagctccctg | caggttagtt | aagttaacgg | ccggccgccg | 60 |
| ccaccatggt | accgtgcacg | ctgctcctgc | tgttggcggc | cgccctggct | ccgactcaga | 120 |
| cccgcgcgca | gatccagttg | gtgcagtctg | gacctgagct | gaagaagcct | ggagagacag | 180 |
| tcaaggtctc | ctgcaaggct | tctgggtata | tgttcacaaa | ctatgcaatg | aactgggtga | 240 |
| agcaggctcc | agaaaagggt | ttaaagtgga | tgggctggat | aaacacccac | actggagacc | 300 |
| caacatatgc | tgatgacttc | aagggacgaa | ttgccttctc | tttggaaacc | tctgccagca | 360 |
| ctgcctattt | gcagatcaac | aacctcaaaa | tgaggacac | ggctacatat | ttctgtgtaa | 420 |
| gaacttatgg | taattacgct | atggactact | ggggtcaagg | aacctcagtc | accgtctcct | 480 |
| cagccaaaac | aacacccca | tcagtctatc | cactggcccc | tgggtgtgga | gatacaactg | 540 |
| gttcctccgt | gactctggga | tgcctggtca | agggctactt | ccctgagtca | gtgactgtga | 600 |
| cttggaactc | tggatccctg | tccagcagtg | tgcacacctt | cccagctctc | ctgcagtctg | 660 |
| gactctacac | tatgagcagc | tcagtgactg | tcccctccag | cacctggcca | agtcagaccg | 720 |
| tcacctgcag | cgttgctcac | ccagccagca | gcaccacggt | ggacaaaaaa | cttgagccca | 780 |
| gcgggcccat | ttcaacaatc | aaccctgtc | tccatgcaa | ggagtgtcac | aaatgcccag | 840 |
| ctcctaacct | cgagggtgga | ccatccgtct | tcatcttccc | tccaaatatc | aaggatgtac | 900 |
| tcatgatctc | cctgacaccc | aaggtcacgt | gtgtggtggt | ggcagtgagc | gaggatgacc | 960 |
| cagacgtcca | gatcagctgg | tttgtgaaca | acgtggaagt | acacacagct | cagacacaaa | 1020 |
| cccatagaga | ggattacgca | agtactatcc | gggtggtcag | cacccteccc | atccagcacc | 1080 |
| aggactggat | gagtggcaag | gagttcaaat | gcaaggtcaa | caacaaagac | ctcccatcac | 1140 |
| ccatcgagag | aaccatctca | aaaattaaag | ggctagtcag | agctccacaa | gtatacatct | 1200 |
| tgccgccacc | agcagagcag | ttgtccagga | agatgtcag | tctcacttgc | ctggtcgtgg | 1260 |
| gcttcaaccc | tggagacatc | agtgtggagt | ggaccagcaa | tgggcataca | gaggagaact | 1320 |
| acaaggacac | cgcaccagtc | ctggactctg | acggttctta | cttcatatat | agcaagctca | 1380 |
| atatgaaaac | aagcaagtgg | gagaaaacag | attccttctc | atgcaacgtg | agacacgagg | 1440 |
| gtctgaaaaa | ttactacctg | aagaagacca | tctcccggtc | tccgggtaaa | gagggcagag | 1500 |
| gcagcctgct | gacctgcggc | gacgtggagg | agaaccccgg | ccccatggta | ccgtgcacgc | 1560 |
| tgctcctgct | gttggcggcc | gccctggctc | cgactcagac | ccgcgcggat | atccagatga | 1620 |
| cacagaccac | atcctccctg | tctgcctctc | tgggagacag | agtcaccatc | agttgcagtg | 1680 |
| caagtcagga | cattagcaat | tatttaaact | ggtatcagca | gaaaccagat | ggaactgtta | 1740 |
| aactcctgat | ctatgacaca | tcaatttac | acttaggagt | cccatcaagg | ttcagtggca | 1800 |
| gtgggtctgg | gacagattat | tctctcacca | tcagtaacct | ggaacctgaa | gatattgcca | 1860 |
| cttactattg | tcagcagtat | agtaaatttc | ctcggacgtt | cggtggaggc | accacgctgg | 1920 |
| aaatcaaacg | ggctgatgct | gcaccaactg | tatccatctt | cccaccatcc | agtgagcagt | 1980 |

-continued

```
taacatctgg aggtgcctca gtcgtgtgct tcttgaacaa cttctacccc aaagacatca    2040
atgtcaagtg aagattgat ggcagtgaac gacaaaatgg cgtcctgaac agttggactg     2100
atcaggacag caaagacagc acctacagca tgagcagcac cctcacgttg accaaggacg    2160
agtatgaacg acataacagc tatacctgtg aggccactca caagacatca acttcaccca    2220
ttgtcaagag cttcaacagg aatgagtgtt gagctagc                            2258
```

<210> SEQ ID NO 25
<211> LENGTH: 2169
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<223> OTHER INFORMATION: 7C6-mIg2b-DANA-2A-LC vector insert cDNA sequence
<220> FEATURE:
<221> NAME/KEY: CDS
<222> LOCATION: (1)..(2169)

<400> SEQUENCE: 25

```
atg gta ccg tgc acg ctg ctc ctg ctg ttg gcg gcc gcc ctg gct ccg       48
Met Val Pro Cys Thr Leu Leu Leu Leu Leu Ala Ala Ala Leu Ala Pro
1               5                   10                  15 act cag acc cgc gcg cag atc cag ttg gtg cag tct gga cct gag ctg       96
Thr Gln Thr Arg Ala Gln Ile Gln Leu Val Gln Ser Gly Pro Glu Leu
                20                  25                  30 aag aag cct gga gag aca gtc aag gtc tcc tgc aag gct tct ggg tat      144
Lys Lys Pro Gly Glu Thr Val Lys Val Ser Cys Lys Ala Ser Gly Tyr
            35                  40                  45 atg ttc aca aac tat gca atg aac tgg gtg aag cag gct cca gaa aag      192
Met Phe Thr Asn Tyr Ala Met Asn Trp Val Lys Gln Ala Pro Glu Lys
        50                  55                  60 ggt tta aag tgg atg ggc tgg ata aac acc cac act gga gac cca aca      240
Gly Leu Lys Trp Met Gly Trp Ile Asn Thr His Thr Gly Asp Pro Thr
65                  70                  75                  80 tat gct gat gac ttc aag gga cga att gcc ttc tct ttg gaa acc tct      288
Tyr Ala Asp Asp Phe Lys Gly Arg Ile Ala Phe Ser Leu Glu Thr Ser
                85                  90                  95 gcc agc act gcc tat ttg cag atc aac aac ctc aaa aat gag gac acg      336
Ala Ser Thr Ala Tyr Leu Gln Ile Asn Asn Leu Lys Asn Glu Asp Thr
            100                 105                 110 gct aca tat ttc tgt gta aga act tat ggt aat tac gct atg gac tac      384
Ala Thr Tyr Phe Cys Val Arg Thr Tyr Gly Asn Tyr Ala Met Asp Tyr
        115                 120                 125 tgg ggt caa gga acc tca gtc acc gtc tcc tca gcc aaa aca aca gcc      432
Trp Gly Gln Gly Thr Ser Val Thr Val Ser Ser Ala Lys Thr Thr Ala
    130                 135                 140 cca tcg gtc tat cca ctg gcc cct gtg tgt gga gat aca act ggc tcc      480
Pro Ser Val Tyr Pro Leu Ala Pro Val Cys Gly Asp Thr Thr Gly Ser
145                 150                 155                 160 tcg gtg act cta gga tgc ctg gtc aag ggt tat ttc cct gag cca gtg      528
Ser Val Thr Leu Gly Cys Leu Val Lys Gly Tyr Phe Pro Glu Pro Val
                165                 170                 175 acc ttg acc tgg aac tct gga tcc ctg tcc agt ggt gtg cac acc ttc      576
Thr Leu Thr Trp Asn Ser Gly Ser Leu Ser Ser Gly Val His Thr Phe
            180                 185                 190 cca gct gtc ctg cag tct gac ctc tac acc ctc agc agc tca gtt act      624
Pro Ala Val Leu Gln Ser Asp Leu Tyr Thr Leu Ser Ser Ser Val Thr
        195                 200                 205
```

```
gta acc tcg agc acc tgg ccc agc cag tcc atc acc tgc aat gtg gcc      672
Val Thr Ser Ser Thr Trp Pro Ser Gln Ser Ile Thr Cys Asn Val Ala
    210                 215                 220 cac ccg gca agc agc acc aag gtg gac aag aaa att gag ccc aga ggg      720
His Pro Ala Ser Ser Thr Lys Val Asp Lys Lys Ile Glu Pro Arg Gly
225                 230                 235                 240 ccc aca atc aag ccc tgt cct cca tgc aaa tgc cca gca cct gaa ctc      768
Pro Thr Ile Lys Pro Cys Pro Pro Cys Lys Cys Pro Ala Pro Glu Leu
                245                 250                 255 ctg ggg gga ccg tca gtc ttc ctc ttc ccc cca aaa ccc aag gac acc      816
Leu Gly Gly Pro Ser Val Phe Leu Phe Pro Pro Lys Pro Lys Asp Thr
                260                 265                 270 ctc atg atc tcc cgg acc cct gag gtc aca tgc gtg gtg gtg gca gtg      864
Leu Met Ile Ser Arg Thr Pro Glu Val Thr Cys Val Val Val Ala Val
            275                 280                 285 agc cac gaa gac cct gag gtc aag ttc aac tgg tac gtg gac ggc gtg      912
Ser His Glu Asp Pro Glu Val Lys Phe Asn Trp Tyr Val Asp Gly Val
290                 295                 300 gag gtg cat aat gcc aag aca aag ccg cgg gag gag cag tac gca agc      960
Glu Val His Asn Ala Lys Thr Lys Pro Arg Glu Glu Gln Tyr Ala Ser
305                 310                 315                 320 acg tac cgt gtg gtc agc gtc ctc acc gtc ctg cac cag gac tgg ctg     1008
Thr Tyr Arg Val Val Ser Val Leu Thr Val Leu His Gln Asp Trp Leu
                325                 330                 335 aat ggc aag gag tac aag tgc aag gtc tcc aac aaa gcc ctc cca gcc     1056
Asn Gly Lys Glu Tyr Lys Cys Lys Val Ser Asn Lys Ala Leu Pro Ala
                340                 345                 350 ccc atc gag aaa acc atc tcc aaa gcc aaa ggg cag ccc cga gaa cca     1104
Pro Ile Glu Lys Thr Ile Ser Lys Ala Lys Gly Gln Pro Arg Glu Pro
                355                 360                 365 cag gtg tac acc ctg ccc cca tcc cgg gag gag atg acc aag aac cag     1152
Gln Val Tyr Thr Leu Pro Pro Ser Arg Glu Glu Met Thr Lys Asn Gln
370                 375                 380 gtc agc ctg acc tgc ctg gtc aaa ggc ttc tat ccc agc gac atc gcc     1200
Val Ser Leu Thr Cys Leu Val Lys Gly Phe Tyr Pro Ser Asp Ile Ala
385                 390                 395                 400 gtg gag tgg gag agc aat ggg cag ccg gag aac aac tac aag acc acg     1248
Val Glu Trp Glu Ser Asn Gly Gln Pro Glu Asn Asn Tyr Lys Thr Thr
                405                 410                 415 cct ccc gtg ctg gac tcc gac ggc tcc ttc ttc ctc tac agc aag ctc     1296
Pro Pro Val Leu Asp Ser Asp Gly Ser Phe Phe Leu Tyr Ser Lys Leu
                420                 425                 430 acc gtg gac aag agc agg tgg cag cag ggg aac gtc ttc tca tgc tcc     1344
Thr Val Asp Lys Ser Arg Trp Gln Gln Gly Asn Val Phe Ser Cys Ser
                435                 440                 445 gtg atg cat gag gct ctg cac aac cac tac acg cag aag agc ctc tcc     1392
Val Met His Glu Ala Leu His Asn His Tyr Thr Gln Lys Ser Leu Ser
450                 455                 460 ctg tct ccg ggt aaa gag ggc aga ggc agc ctg ctg acc tgc ggc gac     1440
Leu Ser Pro Gly Lys Glu Gly Arg Gly Ser Leu Leu Thr Cys Gly Asp
465                 470                 475                 480 gtg gag gag aac ccc ggc ccc atg gta ccg tgc acg ctg ctc ctg ctg     1488
Val Glu Glu Asn Pro Gly Pro Met Val Pro Cys Thr Leu Leu Leu Leu
                485                 490                 495 ttg gcg gcc gcc ctg gct ccg act cag acc cgc gcg gat atc cag atg     1536
Leu Ala Ala Ala Leu Ala Pro Thr Gln Thr Arg Ala Asp Ile Gln Met
                500                 505                 510
```

```
aca cag acc aca tcc tcc ctg tct gcc tct ctg gga gac aga gtc acc    1584
Thr Gln Thr Thr Ser Ser Leu Ser Ala Ser Leu Gly Asp Arg Val Thr
            515                 520                 525 atc agt tgc agt gca agt cag gac att agc aat tat tta aac tgg tat    1632
Ile Ser Cys Ser Ala Ser Gln Asp Ile Ser Asn Tyr Leu Asn Trp Tyr
530                 535                 540 cag cag aaa cca gat gga act gtt aaa ctc ctg atc tat gac aca tca    1680
Gln Gln Lys Pro Asp Gly Thr Val Lys Leu Leu Ile Tyr Asp Thr Ser
545                 550                 555                 560 att tta cac tta gga gtc cca tca agg ttc agt ggc agt ggg tct ggg    1728
Ile Leu His Leu Gly Val Pro Ser Arg Phe Ser Gly Ser Gly Ser Gly
                565                 570                 575 aca gat tat tct ctc acc atc agt aac ctg gaa cct gaa gat att gcc    1776
Thr Asp Tyr Ser Leu Thr Ile Ser Asn Leu Glu Pro Glu Asp Ile Ala
            580                 585                 590 act tac tat tgt cag cag tat agt aaa ttt cct cgg acg ttc ggt gga    1824
Thr Tyr Tyr Cys Gln Gln Tyr Ser Lys Phe Pro Arg Thr Phe Gly Gly
        595                 600                 605 ggc acc acg ctg gaa atc aaa cgg gct gat gct gca cca act gta tcc    1872
Gly Thr Thr Leu Glu Ile Lys Arg Ala Asp Ala Ala Pro Thr Val Ser
    610                 615                 620 atc ttc cca cca tcc agt gag cag tta aca tct gga ggt gcc tca gtc    1920
Ile Phe Pro Pro Ser Ser Glu Gln Leu Thr Ser Gly Gly Ala Ser Val
625                 630                 635                 640 gtg tgc ttc ttg aac aac ttc tac ccc aaa gac atc aat gtc aag tgg    1968
Val Cys Phe Leu Asn Asn Phe Tyr Pro Lys Asp Ile Asn Val Lys Trp
                645                 650                 655 aag att gat ggc agt gaa cga caa aat ggc gtc ctg aac agt tgg act    2016
Lys Ile Asp Gly Ser Glu Arg Gln Asn Gly Val Leu Asn Ser Trp Thr
            660                 665                 670 gat cag gac agc aaa gac agc acc tac agc atg agc agc acc ctc acg    2064
Asp Gln Asp Ser Lys Asp Ser Thr Tyr Ser Met Ser Ser Thr Leu Thr
        675                 680                 685 ttg acc aag gac gag tat gaa cga cat aac agc tat acc tgt gag gcc    2112
Leu Thr Lys Asp Glu Tyr Glu Arg His Asn Ser Tyr Thr Cys Glu Ala
    690                 695                 700 act cac aag aca tca act tca ccc att gtc aag agc ttc aac agg aat    2160
Thr His Lys Thr Ser Thr Ser Pro Ile Val Lys Ser Phe Asn Arg Asn
705                 710                 715                 720 gag tgt tga                                                         2169
Glu Cys <210> SEQ ID NO 26
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
aaaaaaggcc ggccgccgcc accatggtac cgtgca                             36

<210> SEQ ID NO 27
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 27
taccatgggg ccggggttct cctccacgtc gccgcaggtc agcaggctgc ctctgccctc     60
tttacccgga gtccgggaga                                                 80

<210> SEQ ID NO 28
<211> LENGTH: 75
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 28
agagggcaga ggcagcctgc tgacctgcgg cgacgtggag gagaaccccg gccccatggt     60
accgtgcacg ctgct                                                      75

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
aaaaaagcta gctcaacact cattcctgtt gaagct                               36

<210> SEQ ID NO 30
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
agagcggaat tcgagctccc tgcaggttag tt                                   32

<210> SEQ ID NO 31
<211> LENGTH: 102
<212> TYPE: PRT
<213> ORGANISM: Homo sapiens

<400> SEQUENCE: 31

Val Pro Pro Met Val Asn Val Thr Cys Ser Glu Val Ser Glu Gly Asn
1               5                   10                  15

Ile Thr Val Thr Cys Arg Ala Ser Ser Phe Tyr Pro Arg Asn Ile Thr
            20                  25                  30

Leu Thr Trp Arg Gln Asp Gly Val Ser Leu Ser His Asn Thr Gln Gln
        35                  40                  45

Trp Gly Asp Val Leu Pro Asp Gly Asn Gly Thr Tyr Gln Thr Trp Val
    50                  55                  60

Ala Thr Arg Ile Arg Gln Gly Glu Glu Gln Arg Phe Thr Cys Tyr Met
65                  70                  75                  80

Glu His Gly Gly Asn His Gly Thr His Pro Val Pro Ser Gly Lys Val
                85                  90                  95

Leu Ala Leu Gln Ser Gln
            100

<210> SEQ ID NO 32

<211> LENGTH: 722
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: 7C6-mIg2A-2A-LC vector insert sequence

<400> SEQUENCE: 32

```
Met Val Pro Cys Thr Leu Leu Leu Leu Ala Ala Ala Leu Ala Pro
1               5                   10                  15

Thr Gln Thr Arg Ala Gln Ile Gln Leu Val Gln Ser Gly Pro Glu Leu
            20                  25                  30

Lys Lys Pro Gly Glu Thr Val Lys Val Ser Cys Lys Ala Ser Gly Tyr
                35                  40                  45

Met Phe Thr Asn Tyr Ala Met Asn Trp Val Lys Gln Ala Pro Glu Lys
 50                  55                  60

Gly Leu Lys Trp Met Gly Trp Ile Asn Thr His Thr Gly Asp Pro Thr
 65                  70                  75                  80

Tyr Ala Asp Asp Phe Lys Gly Arg Ile Ala Phe Ser Leu Glu Thr Ser
                85                  90                  95

Ala Ser Thr Ala Tyr Leu Gln Ile Asn Asn Leu Lys Asn Glu Asp Thr
            100                 105                 110

Ala Thr Tyr Phe Cys Val Arg Thr Tyr Gly Asn Tyr Ala Met Asp Tyr
            115                 120                 125

Trp Gly Gln Gly Thr Ser Val Thr Val Ser Ser Ala Lys Thr Thr Ala
        130                 135                 140

Pro Ser Val Tyr Pro Leu Ala Pro Val Cys Gly Asp Thr Thr Gly Ser
145                 150                 155                 160

Ser Val Thr Leu Gly Cys Leu Val Lys Gly Tyr Phe Pro Glu Pro Val
                165                 170                 175

Thr Leu Thr Trp Asn Ser Gly Ser Leu Ser Ser Gly Val His Thr Phe
            180                 185                 190

Pro Ala Val Leu Gln Ser Asp Leu Tyr Thr Leu Ser Ser Ser Val Thr
        195                 200                 205

Val Thr Ser Ser Thr Trp Pro Ser Gln Ser Ile Thr Cys Asn Val Ala
    210                 215                 220

His Pro Ala Ser Ser Thr Lys Val Asp Lys Lys Ile Glu Pro Arg Gly
225                 230                 235                 240

Pro Thr Ile Lys Pro Cys Pro Pro Cys Lys Cys Pro Ala Pro Glu Leu
                245                 250                 255

Leu Gly Gly Pro Ser Val Phe Leu Phe Pro Pro Lys Pro Lys Asp Thr
            260                 265                 270

Leu Met Ile Ser Arg Thr Pro Glu Val Thr Cys Val Val Val Asp Val
        275                 280                 285

Ser His Glu Asp Pro Glu Val Lys Phe Asn Trp Tyr Val Asp Gly Val
    290                 295                 300

Glu Val His Asn Ala Lys Thr Lys Pro Arg Glu Glu Gln Tyr Asn Ser
305                 310                 315                 320

Thr Tyr Arg Val Val Ser Val Leu Thr Val Leu His Gln Asp Trp Leu
                325                 330                 335

Asn Gly Lys Glu Tyr Lys Cys Lys Val Ser Asn Lys Ala Leu Pro Ala
            340                 345                 350

Pro Ile Glu Lys Thr Ile Ser Lys Ala Lys Gly Gln Pro Arg Glu Pro
        355                 360                 365
```

Gln Val Tyr Thr Leu Pro Pro Ser Arg Asp Glu Leu Thr Lys Asn Gln
            370                 375                 380

Val Ser Leu Thr Cys Leu Val Lys Gly Phe Tyr Pro Ser Asp Ile Ala
385                 390                 395                 400

Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
450                 455                 460

Leu Ser Pro Gly Lys Glu Gly Arg Gly Ser Leu Leu Thr Cys Gly Asp
465                 470                 475                 480

Val Glu Glu Asn Pro Gly Pro Met Val Pro Cys Thr Leu Leu Leu Leu
            485                 490                 495

Leu Ala Ala Ala Leu Ala Pro Thr Gln Thr Arg Ala Asp Ile Gln Met
            500                 505                 510

Thr Gln Thr Thr Ser Ser Leu Ser Ala Ser Leu Gly Asp Arg Val Thr
            515                 520                 525

Ile Ser Cys Ser Ala Ser Gln Asp Ile Ser Asn Tyr Leu Asn Trp Tyr
            530                 535                 540

Gln Gln Lys Pro Asp Gly Thr Val Lys Leu Leu Ile Tyr Asp Thr Ser
545                 550                 555                 560

Ile Leu His Leu Gly Val Pro Ser Arg Phe Ser Gly Ser Gly Ser Gly
            565                 570                 575

Thr Asp Tyr Ser Leu Thr Ile Ser Asn Leu Glu Pro Glu Asp Ile Ala
            580                 585                 590

Thr Tyr Tyr Cys Gln Gln Tyr Ser Lys Phe Pro Arg Thr Phe Gly Gly
            595                 600                 605

Gly Thr Thr Leu Glu Ile Lys Arg Ala Asp Ala Ala Pro Thr Val Ser
            610                 615                 620

Ile Phe Pro Pro Ser Ser Glu Gln Leu Thr Ser Gly Gly Ala Ser Val
625                 630                 635                 640

Val Cys Phe Leu Asn Asn Phe Tyr Pro Lys Asp Ile Asn Val Lys Trp
            645                 650                 655

Lys Ile Asp Gly Ser Glu Arg Gln Asn Gly Val Leu Asn Ser Trp Thr
            660                 665                 670

Asp Gln Asp Ser Lys Asp Ser Thr Tyr Ser Met Ser Ser Thr Leu Thr
            675                 680                 685

Leu Thr Lys Asp Glu Tyr Glu Arg His Asn Ser Tyr Thr Cys Glu Ala
            690                 695                 700

Thr His Lys Thr Ser Thr Ser Pro Ile Val Lys Ser Phe Asn Arg Asn
705                 710                 715                 720

Glu Cys

<210> SEQ ID NO 33
<211> LENGTH: 722
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: 7C6-mIg2b-DANA-2A-LC vector insert sequence

<400> SEQUENCE: 33

| | | | | | | | | | | | | | | |
|---|---|---|---|---|---|---|---|---|---|---|---|---|---|---|
|Met|Val|Pro|Cys|Thr|Leu|Leu|Leu|Leu|Ala|Ala|Leu|Ala|Pro| |
|1| | | |5| | | | |10| | | | |15|

Thr Gln Thr Arg Ala Gln Ile Gln Leu Val Gln Ser Gly Pro Glu Leu
                 20                 25               30

Lys Lys Pro Gly Glu Thr Val Lys Val Ser Cys Lys Ala Ser Gly Tyr
         35              40              45

Met Phe Thr Asn Tyr Ala Met Asn Trp Val Lys Gln Ala Pro Glu Lys
     50                55              60

Gly Leu Lys Trp Met Gly Trp Ile Asn Thr His Thr Gly Asp Pro Thr
65              70                75              80

Tyr Ala Asp Asp Phe Lys Gly Arg Ile Ala Phe Ser Leu Glu Thr Ser
             85               90              95

Ala Ser Thr Ala Tyr Leu Gln Ile Asn Asn Leu Lys Asn Glu Asp Thr
         100             105           110

Ala Thr Tyr Phe Cys Val Arg Thr Tyr Gly Asn Tyr Ala Met Asp Tyr
         115             120           125

Trp Gly Gln Gly Thr Ser Val Thr Val Ser Ser Ala Lys Thr Thr Ala
    130              135             140

Pro Ser Val Tyr Pro Leu Ala Pro Val Cys Gly Asp Thr Thr Gly Ser
145             150             155            160

Ser Val Thr Leu Gly Cys Leu Val Lys Gly Tyr Phe Pro Glu Pro Val
         165             170           175

Thr Leu Thr Trp Asn Ser Gly Ser Leu Ser Ser Gly Val His Thr Phe
        180             185           190

Pro Ala Val Leu Gln Ser Asp Leu Tyr Thr Leu Ser Ser Ser Val Thr
         195             200           205

Val Thr Ser Ser Thr Trp Pro Ser Gln Ser Ile Thr Cys Asn Val Ala
    210            215             220

His Pro Ala Ser Ser Thr Lys Val Asp Lys Lys Ile Glu Pro Arg Gly
225             230            235           240

Pro Thr Ile Lys Pro Cys Pro Pro Cys Lys Cys Pro Ala Pro Glu Leu
         245             250           255

Leu Gly Gly Pro Ser Val Phe Leu Phe Pro Pro Lys Pro Lys Asp Thr
        260             265           270

Leu Met Ile Ser Arg Thr Pro Glu Val Thr Cys Val Val Val Ala Val
        275             280           285

Ser His Glu Asp Pro Glu Val Lys Phe Asn Trp Tyr Val Asp Gly Val
    290            295             300

Glu Val His Asn Ala Lys Thr Lys Pro Arg Glu Glu Gln Tyr Ala Ser
305             310            315           320

Thr Tyr Arg Val Val Ser Val Leu Thr Val Leu His Gln Asp Trp Leu
         325             330           335

Asn Gly Lys Glu Tyr Lys Cys Lys Val Ser Asn Lys Ala Leu Pro Ala
        340             345           350

Pro Ile Glu Lys Thr Ile Ser Lys Ala Lys Gly Gln Pro Arg Glu Pro
        355             360           365

Gln Val Tyr Thr Leu Pro Pro Ser Arg Glu Glu Met Thr Lys Asn Gln
    370            375             380

Val Ser Leu Thr Cys Leu Val Lys Gly Phe Tyr Pro Ser Asp Ile Ala
385             390            395           400

```
Val Glu Trp Glu Ser Asn Gly Gln Pro Glu Asn Asn Tyr Lys Thr Thr
            405                 410                 415

Pro Pro Val Leu Asp Ser Asp Gly Ser Phe Phe Leu Tyr Ser Lys Leu
            420                 425                 430

Thr Val Asp Lys Ser Arg Trp Gln Gln Gly Asn Val Phe Ser Cys Ser
            435                 440                 445

Val Met His Glu Ala Leu His Asn His Tyr Thr Gln Lys Ser Leu Ser
            450                 455                 460

Leu Ser Pro Gly Lys Glu Gly Arg Gly Ser Leu Leu Thr Cys Gly Asp
465                 470                 475                 480

Val Glu Glu Asn Pro Gly Pro Met Val Pro Cys Thr Leu Leu Leu Leu
            485                 490                 495

Leu Ala Ala Ala Leu Ala Pro Thr Gln Thr Arg Ala Asp Ile Gln Met
            500                 505                 510

Thr Gln Thr Thr Ser Ser Leu Ser Ala Ser Leu Gly Asp Arg Val Thr
            515                 520                 525

Ile Ser Cys Ser Ala Ser Gln Asp Ile Ser Asn Tyr Leu Asn Trp Tyr
            530                 535                 540

Gln Gln Lys Pro Asp Gly Thr Val Lys Leu Leu Ile Tyr Asp Thr Ser
545                 550                 555                 560

Ile Leu His Leu Gly Val Pro Ser Arg Phe Ser Gly Ser Gly Ser Gly
            565                 570                 575

Thr Asp Tyr Ser Leu Thr Ile Ser Asn Leu Glu Pro Glu Asp Ile Ala
            580                 585                 590

Thr Tyr Tyr Cys Gln Gln Tyr Ser Lys Phe Pro Arg Thr Phe Gly Gly
            595                 600                 605

Gly Thr Thr Leu Glu Ile Lys Arg Ala Asp Ala Ala Pro Thr Val Ser
            610                 615                 620

Ile Phe Pro Pro Ser Ser Glu Gln Leu Thr Ser Gly Gly Ala Ser Val
625                 630                 635                 640

Val Cys Phe Leu Asn Asn Phe Tyr Pro Lys Asp Ile Asn Val Lys Trp
            645                 650                 655

Lys Ile Asp Gly Ser Glu Arg Gln Asn Gly Val Leu Asn Ser Trp Thr
            660                 665                 670

Asp Gln Asp Ser Lys Asp Ser Thr Tyr Ser Met Ser Ser Thr Leu Thr
            675                 680                 685

Leu Thr Lys Asp Glu Tyr Glu Arg His Asn Ser Tyr Thr Cys Glu Ala
            690                 695                 700

Thr His Lys Thr Ser Thr Ser Pro Ile Val Lys Ser Phe Asn Arg Asn
705                 710                 715                 720

Glu Cys
```